US010036050B2

(12) United States Patent
Wogulis

(10) Patent No.: US 10,036,050 B2
(45) Date of Patent: Jul. 31, 2018

(54) CELLOBIOHYDROLASE VARIANTS AND POLYNUCLEOTIDES ENCODING SAME

(71) Applicant: Novozymes, Inc., Davis, CA (US)

(72) Inventor: Mark Wogulis, Davis, CA (US)

(73) Assignee: Novozymes, Inc., Davis, CA (US)

( * ) Notice: Subject to any disclaimer, the term of this patent is extended or adjusted under 35 U.S.C. 154(b) by 382 days.

(21) Appl. No.: 14/367,182

(22) PCT Filed: Dec. 20, 2012

(86) PCT No.: PCT/US2012/070905

§ 371 (c)(1),
(2) Date: Jun. 19, 2014

(87) PCT Pub. No.: WO2013/096603

PCT Pub. Date: Jun. 27, 2013

(65) Prior Publication Data

US 2015/0004655 A1 Jan. 1, 2015

Related U.S. Application Data

(60) Provisional application No. 61/578,062, filed on Dec. 20, 2011.

(51) Int. Cl.

| | |
|---|---|
| ***C12P 19/14*** | (2006.01) |
| ***G01N 31/22*** | (2006.01) |
| ***C12N 9/42*** | (2006.01) |
| ***C12P 19/02*** | (2006.01) |
| ***C12P 7/14*** | (2006.01) |

(52) U.S. Cl.

CPC ............ *C12P 19/14* (2013.01); *C12N 9/2437* (2013.01); *C12P 7/14* (2013.01); *C12P 19/02* (2013.01); *C12Y 302/01091* (2013.01); *C12Y 302/01176* (2013.01); *G01N 31/226* (2013.01); *C12P 2203/00* (2013.01)

(58) Field of Classification Search

None

See application file for complete search history.

(56) References Cited

U.S. PATENT DOCUMENTS

| | | | |
|---|---|---|---|
| RE32,153 | E | 5/1986 | Tamura |
| 6,916,782 | B1 | 7/2005 | Lamberty et al. |
| 9,080,161 | B2 | 7/2015 | Spodsberg |
| 2009/0186381 | A1 | 7/2009 | Lavigne et al. |
| 2009/0193541 | A1 | 7/2009 | Miles |
| 2011/0111453 | A1 | 5/2011 | McBrayer |
| 2015/0004655 | A1 | 1/2015 | Wogulis |

FOREIGN PATENT DOCUMENTS

| | | | | |
|---|---|---|---|---|
| WO | 03/012071 A2 | 2/2003 | | |
| WO | 2004056981 A2 | 7/2004 | | |
| WO | 2009/045627 A2 | 4/2009 | | |
| WO | 2009/138877 A2 | 11/2009 | | |
| WO | 2010/055533 A1 | 1/2010 | | |
| WO | 2010141779 A1 | 12/2010 | | |
| WO | WO 2010/141779 A1 * | 12/2010 | .......... | C12N 9/2437 |
| WO | 2011050037 A1 | 4/2011 | | |
| WO | 2011/057140 A2 | 5/2011 | | |
| WO | 2011/059740 A2 | 5/2011 | | |
| WO | 2011123450 A1 | 10/2011 | | |
| WO | 2012101206 A2 | 8/2012 | | |
| WO | 2012103350 A1 | 8/2012 | | |

OTHER PUBLICATIONS

Murray et al 2003, Biochemical and Biophysical Research Communications 301: 280-286.*
Tuohy et al 2002, Biochimica et Biophysica Acta 1596: 366-380.*
Panasik et al 2000, Biochimica et Biophysica Acta 1543: 189-201.*
WO 2012-101206 A2—EBI Access No. AZY42206.
WO 2004-056981 A2—Wu et al., 2004, EBI Access No. ADP84845.
US 2009-0193541—Miles S., 2009, EBI Access No. AXQ01297.
EP2245148—SEQ ID No. 41.
WO 2010-141779 A1—Wolfgang et al., 2011, Geneseq Access No. AYN21986.
Lavigne et al, 2010—EBI Access No. HI644825.
Lavigne et al, 2010—EPO Protein Access No. HI644863.
Broun et al, 1998, Sci 282, 1315-1317.
Chang et al, 2008, Geneseq Access No. ASR93964.
Chica et al, 2005, Curr Op Biotechnol 16, 378-384.
Devos et al, 2000, Prot—Struc Func Gene 41, 98-107.
Seffernick et al, 2001, J Bacteriol 183(8), 2405-2410.
Peterson et al, 2010, Mycologia 102(4), 847-864.
Sen et al, 2007, Appl Biochem Biotechnol 143, 212-223.
Witkowski et al, 1999, Biochem 38(36), 11643-11650.
Whisstock et al, 2003, Qtr Rev Biophys 36(3), 307-340.
WO 2008-095033 A2—Uniprot Acccess No. ASR93965.

* cited by examiner

*Primary Examiner* — David H Kruse
(74) *Attorney, Agent, or Firm* — Robert Starnes

(57) ABSTRACT

The present invention relates to cellobiohydrolase variants. The present invention also relates to polynucleotides encoding the variants; nucleic acid constructs, vectors, and host cells comprising the polynucleotides; and methods of producing and using the variants.

29 Claims, 2 Drawing Sheets

```
 M  R  N  I  L  A  L  V  P  A  A  F  L  L  G  A  A  E  A  Q
atgcgaaatattcttgctcttgtgccagcagcgttcctcctcggtgcagctgaagcgcag
 Q  S  V  W  G  Q
caatccgtctggggacaatgtgagagctcagctcgtgtctaaagaatttgaattgtactg
           C  G  G  S  G  Y  T  G  P  T  S  C  A  A  G  S  T
acagtcgttaggtggtggtagtgggtacactggaccgaccagctgtgccgcaggatcgac
  C  S  T  Q  N  A
gtgcagcacgcaaaatgcttgtacgtctgtgttctgcacctgatgagtgagatgtccact
              Y  Y  A  Q  C  V  P  A  T  A  T  P  T  T  L  T
gaccgctgcatagactacgcacaatgcgttcctgcaacggccacacccaccacgttgacg
 T  T  T  T  S  P  S  G  G  T  G  P  T  S  T  S  S  T  P  T
acgacgacgacgtcgccatcgggtggcactggtccaacaagcacctcgtccacgccgact
 G  T  T  S  T  P  T  I  T  A  S  A  S  G  N  P  F  E  G  Y
ggaacgacgtcgacgccaaccatcaccgcgtctgcttccggcaatccattcgagggctac
 Q  L  Y  A  N  P  Y  Y  S  S  E  V  Y  T  L  A  I  P  S  L
cagctctatgccaatccgtactattcgtctgaagtgtacactttggccattccgtcgctg
 T  G  T  L  A  A  K  A  T  E  V  A  K  V  P  S  F  V  W  L
accggcacgcttgctgcaaaggcgaccgaggtggccaaggtgccgtctttcgtctggctg
                                                      D  Q
taaaagatgactcttttcctcgttctttttatttttactaattttccacagcgaccaag
A  A  K  V  P  T  V  G  E  Y  L  A  D  I  R  S  Q  N  A  A
cagccaaggtgcctaccgtgggcgagtatctggccgacatccggtcccaaaacgccgccg
G  A  N  P  P  I  A  G  I  F  V  V  Y  D  L  P  D  R  D  C
gcgccaaccctccaattgcgggtatcttcgtcgtttacgacctgcctgatcgtgactgcg
A  A  A  A  S  N  G  E  F  S  I  A  D  N  G  V  A  L  Y  K
ctgcagcagccagcaatggagaattctccattgccgacaatggagtcgccttgtacaagc
Q  Y  I  D  N  I  T  E  W  L  V  T  Y  S  D  V  H  T  I  L
agtacatcgacaacattaccgagtggctggtgacgtattcggatgtccacaccatcctga
I  I                                                     E
tcattggtacgtcggctctcgctggttacaagatcatgtactgagacgagactctagaac
P  D  S  L  A  N  L  V  T  N  L  N  V  E  K  C  A  N  A  E
ccgacagcctggccaacttggtcaccaacctgaacgtcgagaaatgcgcgaacgcagaga
S  A  Y  L  E  C  I  N  Y  A  I  T  K  L  N  L  P  N  V  A
gcgcgtatttggagtgcatcaactatgcgataacgaagctcaacctgcccaatgtggcca
M  Y  L  D  A
tgtatcttgacgcgggtgagtccacctccattgtcgaactaccacctggattcaaactaa
               G  H  A  G  W  L  G  W  S  A  N  L  Q  P  A
tattgtattccacaggacacgccggatggttaggctggtcggcaaacctccagcccgcag
A  N  L  F  A  S  V  Y  K  N  A  S  S  P  A  S  V  R  G  L
ccaacctcttcgcttccgtgtacaagaacgcctcatcgccggcttccgtgcgcggtctgg
A  T  N  V  A  N  Y  N  A  W  T  V  S  P  C  P  S  Y  T  Q
ccaccaacgtcgctaactacaacgcctggaccgtcagtccgtgcccgtcgtacacgcagg
G  D  S  N  C  D  E  E  D  Y  V  N  A  L  G  P  L  V  A  A
gcgactccaactgcgatgaagaggactatgtgaatgccctgggaccactggtcgcggcgc
Q  G  F  N  A  H  F  I  T  D  T
agggctttaacgcgcactttatcaccgacacatgtaagtaccaccgtcaacactaactcc

aaacccaagccggaagccacatctttctctatggatatacatctaattgctgagctgttt
   S  R  N  G  V  Q  P  T  Q  Q  Q  Q  W  G  D  W  C  N  V
cagcccgcaacggtgtccaacccacccagcaacaacaatggggtgactggtgcaacgtga
I  G  T  G  F  G  V  R  P  T  T  N  T  G  N  S  L  E  D  A
tcggcaccggctttggcgtgcgtccgactaccaacacgggcaactctctcgaggacgcct
F  V  W  V  K  P  G  G  E  S  D  G  T  S  N  T  T  S  P  R
tcgtctgggtcaagcctggtggtgagagcgacggcacgtccaacacgacctcgcctcgtt
Y  D  Y  H  C  G  L  S  D  A  L  Q  P  A  P  E  A  G  T  W
acgactaccactgcgggctcagcgatgcgctgcagccggcaccggaggcggggacttggt
F  Q
tccaggtatgtagcagcttgctttcagggctgatgggataattgagctaatcatttgtga
     A  Y  F  E  Q  L  L  E  N  A  N  P  S  F  *
ataggcctacttcgagcaactcctcgagaacgccaatccgtcattctag
```

Fig. 1

CELLOBIOHYDROLASE VARIANTS AND POLYNUCLEOTIDES ENCODING SAME

CROSS-REFERENCE TO RELATED APPLICATIONS

This application is a 35 U.S.C. § 371 national application of PCT/US2012/070905 filed on Dec. 20, 2012, which claims priority or the benefit under 35 U.S.C. § 119 of U.S. Provisional Application No. 61/578,062 filed on Dec. 20, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to cellobiohydrolase variants, polynucleotides encoding the variants, and methods of producing and using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars can easily be fermented by yeast into ethanol.

WO 2011/050037 discloses *Thielavia terrestris* cellobiohydrolase variants with improved thermostability. WO 2011/050037 discloses *Aspergillus fumigatus* cellobiohydrolase variants with improved thermostability.

The present invention provides cellobiohydrolase variants with increased thermostability.

SUMMARY OF THE INVENTION

The present invention relates to isolated cellobiohydrolase variants, comprising a substitution at one or more (e.g., several) positions corresponding to positions 112, 154, 197, 228, 261, 306, and 375 of the mature polypeptide of SEQ ID NO: 2, wherein the variants have cellobiohydrolase activity.

The present invention also relates to isolated polynucleotides encoding the variants; nucleic acid constructs, vectors, and host cells comprising the polynucleotides; and methods of producing the variants.

The present invention also relates to processes for degrading or converting a cellulosic material, comprising: treating the cellulosic material with an enzyme composition in the presence of a cellobiohydrolase variant of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a cellobiohydrolase variant of the present invention. In one aspect, the fermenting of the cellulosic material produces a fermentation product. In another aspect, the processes further comprise recovering the fermentation product from the fermentation.

BRIEF DESCRIPTION OF THE FIGURES

FIG. 1 shows the genomic DNA sequence (SEQ ID NO: 1) and the deduced amino acid sequence (SEQ ID NO: 2) of a *Talaromyces byssochlamydoides* gene encoding a GH6 polypeptide having cellobiohydrolase activity.

DEFINITIONS

Figure 2:
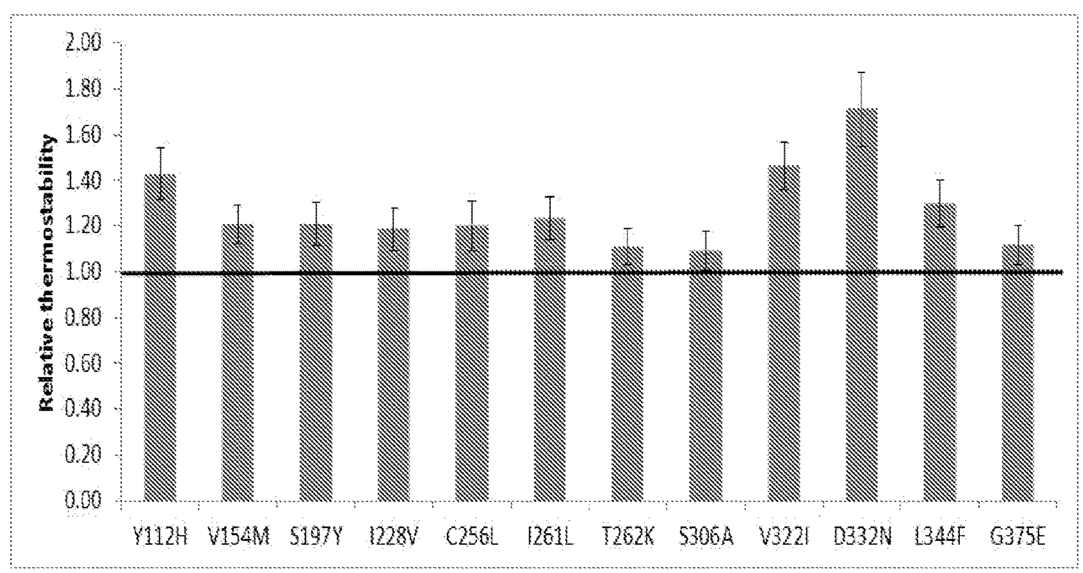
FIG. 2 shows the thermostability of *Talaromyces byssochlamydoides* Family GH6A cellobiohydrolase variants.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha- L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed pretreated corn stover (PCS), 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnol-*

*ogy*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of the mature polypeptide thereof, wherein the fragment has cellobiohydrolase activity. In one aspect, a fragment contains at least 85% of the amino acid residues, e.g., at least 90% of the amino acid residues or at least 95% of the amino acid residues of the mature polypeptide of a cellobiohydrolase.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property includes, but is not limited to, increased thermostability.

Increased thermostability: The term "increased thermostability" means a higher retention of cellobiohydrolase activity of a variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 67° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability" herein.

The increased thermostability of the variant relative to the parent can be determined by differential scanning calorimetry (DSC) using methods standard in the art (see, for example, Sturtevant, 1987, *Annual Review of Physical Chemistry* 38: 463-488). The increased thermostability of the variant relative to the parent can also be determined using protein thermal unfolding analysis. The increased thermostability of the variant relative to the parent can also be determined using any application assay for the variant where the performance of the variant is compared to the parent. For example, the application assay described in Example 8 can be used.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 456 of SEQ ID NO: 2 based on the SignalP program (Nielsen et al., 1997, Protein Engineering 10:1-6) that predicts amino acids 1 to 19 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellobiohydrolase activity. In one aspect, the mature polypeptide coding sequence is nucleotides 58 to 1786 of SEQ ID NO: 1 or the cDNA sequence thereof based on the SignalP program (Nielsen et al., 1997, supra) that predicts nucleotides 1 to 57 of SEQ ID NO: 1 encode a signal peptide.

The term "mature polypeptide coding sequence" herein shall be understood to include the cDNA sequence of the genomic DNA sequence or the genomic DNA sequence of the cDNA sequence.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent cellobiohydrolase: The term "parent" or "parent cellobiohydrolase" means a cellobiohydrolase to which an alteration is made to produce the cellobiohydrolase variants of the present invention. The parent may be a naturally occurring (wild-type) polypeptide or a variant or fragment thereof.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide having cellulolytic enhancing activity for 1-7 days at a suitable temperature, such as 40° C.-80° C., e.g., 50° C., 55° C., 60° C., 65° C., or 70° C., and a suitable pH, such as 4-9, e.g., 5.0, 5.5, 6.0, 6.5, or 7.0, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

Another assay for determining the cellulolytic enhancing activity of a GH61 polypeptide is to incubate the GH61 polypeptide with 0.5% phosphoric acid swollen cellulose (PASO), 100 mM sodium acetate pH 5, 1 mM $MnSO_4$, 0.1% gallic acid, 0.025 mg/ml of *Aspergillus fumigatus* beta-glucosidase, and 0.01% TRITON® X100 for 24-96 hours at 40° C. followed by determination of the glucose released from the PASC.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence, wherein the subsequence encodes a fragment having cellobiohydrolase activity. In one aspect, a subsequence contains at least 85% of the nucleotides, e.g., at least 90% of the nucleotides or at least 95% of the nucleotides of the mature polypeptide coding sequence of a cellobiohydrolase.

Variant: The term "variant" means a polypeptide having cellobiohydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellobiohydrolase activity of their parent cellobiohydrolases.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type cellobiohydrolase: The term "wild-type" cellobiohydrolase means a cellobiohydrolase expressed by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Conventions for Designation of Variants

For purposes of the present invention, the mature polypeptide disclosed in SEQ ID NO: 2 is used to determine the corresponding amino acid residue in another cellobiohydrolase. The amino acid sequence of another cellobiohydrolase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 2 wherein position 1 is the first amino acid of the signal peptide (e.g., Met).

Identification of the corresponding amino acid residue in another cellobiohydrolase can be determined by alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, Nucleic Acids Research 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another cellobiohydrolase has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the cellobiohydrolase variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411 Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple Substitutions.

Variants comprising multiple substitutions are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Substitutions.

Where different substitutions can be introduced at a position, the different substitutions are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated cellobiohydrolase variants, comprising a substitution at one or more (e.g., several) positions corresponding to positions 112, 154, 197, 228, 261, 306, and 375 of the mature polypeptide of SEQ ID NO: 2, wherein the variants have cellobiohydrolase activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

In one aspect, the number of substitutions in the variants of the present invention is 1-7, e.g., 1, 2, 3, 4, 5, 6, or 7 substitutions.

In another aspect, a variant comprises a substitution at one or more (e.g., several) positions corresponding to positions 112, 154, 197, 228, 261, 306, and 375. In another aspect, a variant comprises a substitution at two positions corresponding to any of positions 112, 154, 197, 228, 261, 306, and 375. In another aspect, a variant comprises a substitution at three positions corresponding to any of positions 112, 154, 197, 228, 261, 306, and 375. In another aspect, a variant comprises a substitution at four positions corresponding to any of positions 112, 154, 197, 228, 261, 306, and 375. In another aspect, a variant comprises a substitution at five positions corresponding to any of positions 112, 154, 197, 228, 261, 306, and 375. In another aspect, a variant comprises a substitution at six positions corresponding to any of positions 112, 154, 197, 228, 261, 306, and 375. In another aspect, a variant comprises a substitution at each position corresponding to positions 112, 154, 197, 228, 261, 306, and 375.

In another aspect, the variant comprises or consists of a substitution at a position corresponding to position 112. In another aspect, the amino acid at a position corresponding to position 112 is substituted with Ala, Arg, Asn, Asp, Cys, Gln, Glu, Gly, His, Ile, Leu, Lys, Met, Phe, Pro, Ser, Thr, Trp, Tyr, or Val, preferably with His. In another aspect, the variant comprises or consists of the substitution Y112H of the mature polypeptide of SEQ ID NO: 2.

In another aspect, the variant comprises or consists of a substitution at a position corresponding to position 154. In another aspect, the amino acid at a position corresponding to position 154 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met. In another aspect, the variant comprises or consists of the substitution V154M of the mature polypeptide of SEQ ID NO: 2.

In another aspect, the variant comprises or consists of a substitution at a position corresponding to position 197. In another aspect, the amino acid at a position corresponding to position 197 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr. In another aspect, the variant comprises or consists of the substitution S197Y of the mature polypeptide of SEQ ID NO: 2.

In another aspect, the variant comprises or consists of a substitution at a position corresponding to position 228. In another aspect, the amino acid at a position corresponding to position 228 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant comprises or consists of the substitution I228V of the mature polypeptide of SEQ ID NO: 2.

In another aspect, the variant comprises or consists of a substitution at a position corresponding to position 261. In another aspect, the amino acid at a position corresponding to position 261 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution I261L of the mature polypeptide of SEQ ID NO: 2.

In another aspect, the variant comprises or consists of a substitution at a position corresponding to position 306. In another aspect, the amino acid at a position corresponding to position 306 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution S306A of the mature polypeptide of SEQ ID NO: 2.

In another aspect, the variant comprises or consists of a substitution at a position corresponding to position 375. In another aspect, the amino acid at a position corresponding to position 375 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu. In another aspect, the variant comprises or consists of the substitution G375E of the mature polypeptide of SEQ ID NO: 2.

In another aspect, the variant comprises or consists of substitutions at positions corresponding to positions 112 and 154, such as those described above. In another aspect, the variant comprises or consists of substitutions at positions corresponding to positions 112 and 197, such as those described above. In another aspect, the variant comprises or consists of substitutions at positions corresponding to positions 112 and 228, such as those described above. In another aspect, the variant comprises or consists of substitutions at positions corresponding to positions 112 and 261, such as those described above. In another aspect, the variant comprises or consists of substitutions at positions corresponding to positions 112 and 306, such as those described above. In another aspect, the variant comprises or consists of substitutions at positions corresponding to positions 112 and 375, such as those described above. In another aspect, the variant comprises or consists of substitutions at positions corresponding to positions 154 and 197, such as those described above. In another aspect, the variant comprises or consists of substitutions at positions corresponding to positions 154 and 228, such as those described above. In another aspect, the variant comprises or consists of substitutions at positions corresponding to positions 154 and 261, such as those described above. In another aspect, the variant comprises or consists of substitutions at positions corresponding to positions 154 and 306, such as those described above. In another aspect, the variant comprises or consists of substitutions at positions corresponding to positions 154 and 375, such as those described above. In another aspect, the variant comprises or consists of substitutions at positions corresponding to positions 197 and 228, such as those described above. In another aspect, the variant comprises or consists of substitutions at positions corresponding to positions 197 and 261, such as those described above. In another aspect, the variant comprises or consists of substitutions at positions corresponding to positions 197 and 306, such as those described above. In another aspect, the variant comprises or consists of substitutions at positions corresponding to positions 197 and 375, such as those described above. In another aspect, the variant comprises or consists of substitutions at positions corresponding to positions 228 and 261, such as those described above. In another aspect, the variant comprises or consists of substitutions at positions corresponding to positions 228 and 306, such as those described above. In another aspect, the variant comprises or consists of substitutions at positions corresponding to positions 228 and 375, such as those described above. In another aspect, the variant comprises or consists of substitutions at positions corresponding to positions 261 and 306, such as those described above. In another aspect, the variant comprises or consists of substitutions at positions corresponding to positions 261 and 375, such as those described above. In another aspect, the variant comprises or consists of substitutions at positions corresponding to positions 306 and 375, such as those described above.

In another aspect, the variant comprises or consists of substitutions at positions corresponding to positions 112, 154, and 197, such as those described above. In another aspect, the variant comprises or consists of substitutions at positions corresponding to positions 112, 154, and 228, such as those described above. In another aspect, the variant comprises or consists of substitutions at positions corresponding to positions 112, 154, and 261, such as those described above. In another aspect, the variant comprises or consists of substitutions at positions corresponding to positions 112, 154, and 306, such as those described above. In another aspect, the variant comprises or consists of substitutions at positions corresponding to positions 112, 154, and 375, such as those described above. In another aspect, the variant comprises or consists of substitutions at positions corresponding to positions 112, 197, and 228, such as those described above. In another aspect, the variant comprises or consists of substitutions at positions corresponding to positions 112, 197, and 261, such as those described above. In another aspect, the variant comprises or consists of substitutions at positions corresponding to positions 112, 197, and 306, such as those described above. In another aspect, the variant comprises or consists of substitutions at positions corresponding to positions 112, 197, and 375, such as those described above. In another aspect, the variant comprises or consists of substitutions at positions corresponding to positions 112, 228, and 261, such as those described above. In another aspect, the variant comprises or consists of substitutions at positions corresponding to positions 112, 228, and 306, such as those described above. In another aspect, the variant comprises or consists of substitutions at positions corresponding to positions 112, 228, and 375, such as those described above. In another aspect, the variant comprises or consists of substitutions at positions corresponding to positions 112, 261, and 306, such as those described above. In another aspect, the variant comprises or consists of substitutions at positions corresponding to positions 112, 261, and 375, such as those described above. In another aspect, the variant comprises or consists of substitutions at positions corresponding to positions 112, 306, and 375, such as those described above. In another aspect, the variant comprises or consists of substitutions at positions corresponding to positions 154, 197, and 228, such as those described above. In another aspect, the variant comprises or consists of substitutions at positions corresponding to positions 154, 197, and 261, such as those described above. In another aspect, the variant comprises or consists of substitutions at positions corresponding to positions 154, 197, and 306, such as those described above. In another aspect, the variant comprises or consists of substitutions at positions corresponding to positions 154, 197, and 375, such as those described above. In another aspect, the variant comprises or consists of substitutions at positions corresponding to positions 154, 228, and 261, such as those described above. In another aspect, the variant comprises or consists of substitutions at positions corresponding to positions 154, 228, and 306, such as those described above. In another aspect, the variant comprises or consists of substitutions at positions corresponding to positions 154, 228, and 375, such as those described above. In another aspect, the variant comprises or consists of substitutions at positions corresponding to positions 154, 261, and 306, such as those described above. In another aspect, the variant comprises or consists of substitutions at positions corresponding to positions 154, 261, and 375, such as those described above. In another aspect, the variant comprises or consists of substitutions at positions corresponding to positions 154, 306, and 375, such as those described above. In another aspect, the variant comprises or consists of substitutions at positions corresponding to positions 197, 228, and 261, such as those described above. In another aspect, the variant comprises or consists of substitutions at positions corresponding to positions 197, 228, and 306, such as those described above. In another aspect, the variant comprises or consists of substitutions at positions corresponding to positions 197, 228, and 375, such as those described above. In another aspect, the variant comprises or consists of substitutions at positions corresponding to positions 197, 261, and 306, such as those described above. In another aspect, the variant comprises or consists of substitutions at positions corresponding to positions 197, 261, and 375, such as those described above. In another aspect, the variant comprises or consists of substitutions at positions corresponding to positions 197, 306, and 375, such as those described above. In another aspect, the variant comprises or consists of substitutions at positions corresponding to positions 228, 261, and 306, such as those described above. In another aspect, the variant comprises or consists of substitutions at positions corresponding to positions 228, 261, and 375, such as those described above. In another aspect, the variant comprises or consists of substitutions at positions corresponding to positions 228, 306, and 375, such as those described above. In another aspect, the variant comprises or consists of substitutions at positions corresponding to positions 261, 306, and 375, such as those described above.

In another aspect, the variant comprises or consists of substitutions at positions corresponding to positions 112, 154, 197, and 228, such as those described above. In another aspect, the variant comprises or consists of substitutions at positions corresponding to positions 112, 154, 197, and 261, such as those described above. In another aspect, the variant comprises or consists of substitutions at positions corresponding to positions 112, 154, 197, and 306, such as those described above. In another aspect, the variant comprises or consists of substitutions at positions corresponding to positions 112, 154, 197, and 375, such as those described above. In another aspect, the variant comprises or consists of substitutions at positions corresponding to positions 112, 154, 228, and 261, such as those described above. In another aspect, the variant comprises or consists of substitutions at positions corresponding to positions 112, 154, 228, and 306, such as those described above. In another aspect, the variant comprises or consists of substitutions at positions corresponding to positions 112, 154, 228, and 375, such as those described above. In another aspect, the variant comprises or consists of substitutions at positions corresponding to positions 112, 154, 261, and 306, such as those described above. In another aspect, the variant comprises or consists of substitutions at positions corresponding to positions 112, 154, 261, and 375, such as those described above. In another aspect, the variant comprises or consists of substitutions at positions corresponding to positions 112, 154, 306, and 375, such as those described above. In another aspect, the variant comprises or consists of substitutions at positions corresponding to positions 112, 197, 228, and 261, such as those described above. In another aspect, the variant comprises or consists of substitutions at positions corresponding to positions 112, 197, 228, and 306, such as those described above. In another aspect, the variant comprises or consists of substitutions at positions corresponding to positions 112, 197, 228, and 375, such as those described above. In another aspect, the variant comprises or consists of substitutions at positions corresponding to positions 112, 197, 261, and 306, such as those described above. In another aspect, the variant comprises or consists of substitutions at positions corresponding to positions 112, 197, 261, and 375, such as those described above. In another aspect, the variant comprises or consists of substitutions at positions corresponding to positions 112, 197, 306, and 375, such as those described above. In another aspect, the variant comprises or consists of substitutions at positions corresponding to positions 112, 228, 261, and 306, such as those described above. In another aspect, the variant comprises or consists of substitutions at positions corresponding to positions 112, 228, 261, and 375, such as those described above. In another aspect, the variant comprises or consists of substitutions at positions corresponding to positions 112, 228, 306, and 375, such as those described above. In another aspect, the variant comprises or consists of substitutions at positions corresponding to positions 112, 261, 306, and 375, such as those described above. In another aspect, the variant comprises or consists of substitutions at positions corresponding to positions 154, 197, 228, and 261, such as those described above. In another aspect, the variant comprises or consists of substitutions at positions corresponding to positions 154, 197, 228, and 306, such as those described above. In another aspect, the variant comprises or consists of substitutions at positions corresponding to positions 154, 197, 228, and 375, such as those described above. In another aspect, the variant comprises or consists of substitutions at positions corresponding to positions 154, 197, 261, and 306, such as those described above. In another aspect, the variant comprises or consists of substitutions at positions corresponding to positions 154, 197, 261, and 375, such as those described above. In another aspect, the variant comprises or consists of substitutions at positions corresponding to positions 154, 197, 306, and 375, such as those described above. In another aspect, the variant comprises or consists of substitutions at positions corresponding to positions 154, 228, 261, and 306, such as those described above. In another aspect, the variant comprises or consists of substitutions at positions corresponding to positions 154, 228, 261, and 375, such as those described above. In another aspect, the variant comprises or consists of substitutions at positions corresponding to positions 154, 228, 306, and 375, such as those described above. In another aspect, the variant comprises or consists of substitutions at positions corresponding to positions 154, 261, 306, and 375, such as those described above. In another aspect, the variant comprises or consists of substitutions at positions corresponding to positions 197, 228, 261, and 306, such as those described above. In another aspect, the variant comprises or consists of substitutions at positions corresponding to positions 197, 228, 261, and 375, such as those described above. In another aspect, the variant comprises or consists of substitutions at positions corresponding to positions 197, 228, 306, and 375, such as those described above. In another aspect, the variant comprises or consists of substitutions at positions corresponding to positions 197, 261, 306, and 375, such as those described above. In another aspect, the variant comprises or consists of substitutions at positions corresponding to positions 228, 261, 306, and 375, such as those described above.

In another aspect, the variant comprises or consists of substitutions at positions corresponding to positions 112, 154, 197, 228, and 261, such as those described above. In another aspect, the variant comprises or consists of substitutions at positions corresponding to positions 112, 154, 197, 228, and 306, such as those described above. In another aspect, the variant comprises or consists of substitutions at positions corresponding to positions 112, 154, 197, 228, and 375, such as those described above. In another aspect, the variant comprises or consists of substitutions at positions corresponding to positions 112, 154, 197, 261, and 306, such as those described above. In another aspect, the variant comprises or consists of substitutions at positions corresponding to positions 112, 154, 197, 261, and 375, such as those described above. In another aspect, the variant comprises or consists of substitutions at positions corresponding to positions 112, 154, 197, 306, and 375, such as those described above. In another aspect, the variant comprises or consists of substitutions at positions corresponding to positions 112, 154, 228, 261, and 306, such as those described above. In another aspect, the variant comprises or consists of substitutions at positions corresponding to positions 112, 154, 228, 261, and 375, such as those described above. In another aspect, the variant comprises or consists of substitutions at positions corresponding to positions 112, 154, 228, 306, and 375, such as those described above. In another aspect, the variant comprises or consists of substitutions at positions corresponding to positions 112, 154, 261, 306, and 375, such as those described above. In another aspect, the variant comprises or consists of substitutions at positions corresponding to positions 112, 197, 228, 261, and 306, such as those described above. In another aspect, the variant comprises or consists of substitutions at positions corresponding to positions 112, 197, 228, 261, and 375, such as those described above. In another aspect, the variant comprises or consists of substitutions at positions corresponding to positions 112, 197, 228, 306, and 375, such as those described above. In another aspect, the variant comprises or consists of substitutions at positions corresponding to positions 112, 197, 261, 306, and 375, such as those described above. In another aspect, the variant comprises or consists of substitutions at positions corresponding to positions 112, 228, 261, 306, and 375, such as those described above. In another aspect, the variant comprises or consists of substitutions at positions corresponding to positions 154, 197, 228, 261, and 306, such as those described above. In another aspect, the variant comprises or consists of substitutions at positions corresponding to positions 154, 197, 228, 261, and 375, such as those described above. In another aspect, the variant comprises or consists of substitutions at positions corresponding to positions 154, 197, 228, 306, and 375, such as those described above. In another aspect, the variant comprises or consists of substitutions at positions corresponding to positions 154, 197, 261, 306, and 375, such as those described above. In another aspect, the variant comprises or consists of substitutions at positions corresponding to positions 154, 228, 261, 306, and 375, such as those described above. In another aspect, the variant comprises or consists of substitutions at positions corresponding to positions 197, 228, 261, 306, and 375, such as those described above.

In another aspect, the variant comprises or consists of substitutions at positions corresponding to positions 112, 154, 197, 228, 261, and 306, such as those described above. In another aspect, the variant comprises or consists of substitutions at positions corresponding to positions 112, 154, 197, 228, 261, and 375, such as those described above.

In another aspect, the variant comprises or consists of substitutions at positions corresponding to positions 112, 154, 197, 228, 306, and 375, such as those described above. In another aspect, the variant comprises or consists of substitutions at positions corresponding to positions 112, 154, 197, 261, 306, and 375, such as those described above. In another aspect, the variant comprises or consists of substitutions at positions corresponding to positions 112, 154, 228, 261, 306, and 375, such as those described above. In another aspect, the variant comprises or consists of substitutions at positions corresponding to positions 112, 197, 228, 261, 306, and 375, such as those described above. In another aspect, the variant comprises or consists of substitutions at positions corresponding to positions 154, 197, 228, 261, 306, and 375, such as those described above.

In another aspect, the variant comprises or consists of substitutions at positions corresponding to positions 112, 154, 197, 228, 261, 306, and 375, such as those described above.

In another aspect, the variant comprises or consists of one or more (e.g., several) substitutions selected from the group consisting of Y112H, V154M, S197Y, I228V, I261L, S306A, and G375E, or the one or more (e.g., several) substitutions selected from the group consisting of Y112H, V154M, S197Y, I228V, I261L, S306A, and G375E at positions corresponding to SEQ ID NO: 2 in other cellobiohydrolases such as those described herein.

In each of the aspects below, the variant comprises or consists of the one or more (e.g., several) substitutions described below at positions corresponding to SEQ ID NO: 2 in other cellobiohydrolases such as those described herein.

In another aspect, the variant comprises or consists of the substitutions Y112H+V154M of the mature polypeptide of SEQ ID NO: 2. In another aspect, the variant comprises or consists of the substitutions Y112H+S197Y of the mature polypeptide of SEQ ID NO: 2. In another aspect, the variant comprises or consists of the substitutions Y112H+I228V of the mature polypeptide of SEQ ID NO: 2. In another aspect, the variant comprises or consists of the substitutions Y112H+I261L of the mature polypeptide of SEQ ID NO: 2. In another aspect, the variant comprises or consists of the substitutions Y112H+S306A of the mature polypeptide of SEQ ID NO: 2. In another aspect, the variant comprises or consists of the substitutions Y112H+G375E of the mature polypeptide of SEQ ID NO: 2. In another aspect, the variant comprises or consists of the substitutions V154M+S197Y of the mature polypeptide of SEQ ID NO: 2. In another aspect, the variant comprises or consists of the substitutions V154M+I228V of the mature polypeptide of SEQ ID NO: 2. In another aspect, the variant comprises or consists of the substitutions V154M+I261L of the mature polypeptide of SEQ ID NO: 2. In another aspect, the variant comprises or consists of the substitutions V154M+S306A of the mature polypeptide of SEQ ID NO: 2. In another aspect, the variant comprises or consists of the substitutions V154M+G375E of the mature polypeptide of SEQ ID NO: 2. In another aspect, the variant comprises or consists of the substitutions S197Y+I228V of the mature polypeptide of SEQ ID NO: 2. In another aspect, the variant comprises or consists of the substitutions S197Y+I261L of the mature polypeptide of SEQ ID NO: 2. In another aspect, the variant comprises or consists of the substitutions S197Y+S306A of the mature polypeptide of SEQ ID NO: 2. In another aspect, the variant comprises or consists of the substitutions S197Y+G375E of the mature polypeptide of SEQ ID NO: 2. In another aspect, the variant comprises or consists of the substitutions I228V+I261L of the mature polypeptide of SEQ ID NO: 2. In another aspect, the variant comprises or consists of the substitutions I228V+S306A of the mature polypeptide of SEQ ID NO: 2. In another aspect, the variant comprises or consists of the substitutions I228V+G375E of the mature polypeptide of SEQ ID NO: 2. In another aspect, the variant comprises or consists of the substitutions I261L+S306A of the mature polypeptide of SEQ ID NO: 2. In another aspect, the variant comprises or consists of the substitutions I261L+G375E of the mature polypeptide of SEQ ID NO: 2. In another aspect, the variant comprises or consists of the substitutions S306A+G375E of the mature polypeptide of SEQ ID NO: 2.

In another aspect, the variant comprises or consists of the substitutions Y112H+V154M+S197Y of the mature polypeptide of SEQ ID NO: 2. In another aspect, the variant comprises or consists of the substitutions Y112H+V154M+I228V of the mature polypeptide of SEQ ID NO: 2. In another aspect, the variant comprises or consists of the substitutions Y112H+V154M+I261L of the mature polypeptide of SEQ ID NO: 2. In another aspect, the variant comprises or consists of the substitutions Y112H+V154M+S306A of the mature polypeptide of SEQ ID NO: 2. In another aspect, the variant comprises or consists of the substitutions Y112H+V154M+G375E of the mature polypeptide of SEQ ID NO: 2. In another aspect, the variant comprises or consists of the substitutions Y112H+S197Y+I228V of the mature polypeptide of SEQ ID NO: 2. In another aspect, the variant comprises or consists of the substitutions Y112H+S197Y+I261L of the mature polypeptide of SEQ ID NO: 2. In another aspect, the variant comprises or consists of the substitutions Y112H+S197Y+S306A of the mature polypeptide of SEQ ID NO: 2. In another aspect, the variant comprises or consists of the substitutions Y112H+S197Y+G375E of the mature polypeptide of SEQ ID NO: 2. In another aspect, the variant comprises or consists of the substitutions Y112H+I228V+I261L of the mature polypeptide of SEQ ID NO: 2. In another aspect, the variant comprises or consists of the substitutions Y112H+I228V+S306A of the mature polypeptide of SEQ ID NO: 2. In another aspect, the variant comprises or consists of the substitutions Y112H+I228V+G375E of the mature polypeptide of SEQ ID NO: 2. In another aspect, the variant comprises or consists of the substitutions Y112H+I261L+S306A of the mature polypeptide of SEQ ID NO: 2. In another aspect, the variant comprises or consists of the substitutions Y112H+I261L+G375E of the mature polypeptide of SEQ ID NO: 2. In another aspect, the variant comprises or consists of the substitutions Y112H+S306A+G375E of the mature polypeptide of SEQ ID NO: 2. In another aspect, the variant comprises or consists of the substitutions V154M+S197Y+I228V of the mature polypeptide of SEQ ID NO: 2. In another aspect, the variant comprises or consists of the substitutions V154M+S197Y+I261L of the mature polypeptide of SEQ ID NO: 2. In another aspect, the variant comprises or consists of the substitutions V154M+S197Y+S306A of the mature polypeptide of SEQ ID NO: 2. In another aspect, the variant comprises or consists of the substitutions V154M+S197Y+G375E of the mature polypeptide of SEQ ID NO: 2. In another aspect, the variant comprises or consists of the substitutions V154M+I228V+I261L of the mature polypeptide of SEQ ID NO: 2. In another aspect, the variant comprises or consists of the substitutions V154M+I228V+S306A of the mature polypeptide of SEQ ID NO: 2. In another aspect, the variant comprises or consists of the substitutions V154M+I228V+G375E of the mature polypeptide of SEQ ID NO: 2. In another aspect, the variant comprises or consists of the substitutions V154M+I261L+S306A of the mature polypeptide of SEQ ID NO: 2. In another aspect, the variant comprises or consists of the substitutions V154M+I261L+G375E of the mature polypeptide of SEQ ID NO: 2. In another aspect, the variant comprises or consists of the substitutions V154M+S306A+G375E of the mature polypeptide of SEQ ID NO: 2. In another aspect, the variant comprises or consists of the substitutions S197Y+I228V+I261L of the mature polypeptide of SEQ ID NO: 2. In another aspect, the variant comprises or consists of the substitutions S197Y+I228V+S306A of the mature polypeptide of SEQ ID NO: 2. In another aspect, the variant comprises or consists of the substitutions S197Y+I228V+G375E of the mature polypeptide of SEQ ID NO: 2. In another aspect, the variant comprises or consists of the substitutions S197Y+I261L+S306A of the mature polypeptide of SEQ ID NO: 2. In another aspect, the variant comprises or consists of the substitutions S197Y+I261L+G375E of the mature polypeptide of SEQ ID NO: 2. In another aspect, the variant comprises or consists of the substitutions S197Y+S306A+G375E of the mature polypeptide of SEQ ID NO: 2. In another aspect, the variant comprises or consists of the substitutions I228V+I261L+S306A of the mature polypeptide of SEQ ID NO: 2. In another aspect, the variant comprises or consists of the substitutions I228V+I261L+G375E of the mature polypeptide of SEQ ID NO: 2. In another aspect, the variant comprises or consists of the substitutions I228V+S306A+G375E of the mature polypeptide of SEQ ID NO: 2. In another aspect, the variant comprises or consists of the substitutions I261L+S306A+G375E of the mature polypeptide of SEQ ID NO: 2.

In another aspect, the variant comprises or consists of the substitutions Y112H+V154M+S197Y+I228V of the mature polypeptide of SEQ ID NO: 2. In another aspect, the variant comprises or consists of the substitutions Y112H+V154M+S197Y+I261L of the mature polypeptide of SEQ ID NO: 2. In another aspect, the variant comprises or consists of the substitutions Y112H+V154M+S197Y+S306A of the mature polypeptide of SEQ ID NO: 2. In another aspect, the variant comprises or consists of the substitutions Y112H+V154M+S197Y+G375E of the mature polypeptide of SEQ ID NO: 2. In another aspect, the variant comprises or consists of the substitutions Y112H+V154M+I228V+I261L of the mature polypeptide of SEQ ID NO: 2. In another aspect, the variant comprises or consists of the substitutions Y112H+V154M+I228V+S306A of the mature polypeptide of SEQ ID NO: 2. In another aspect, the variant comprises or consists of the substitutions Y112H+V154M+I228V+G375E of the mature polypeptide of SEQ ID NO: 2. In another aspect, the variant comprises or consists of the substitutions Y112H+V154M+I261L+S306A of the mature polypeptide of SEQ ID NO: 2. In another aspect, the variant comprises or consists of the substitutions Y112H+V154M+I261L+G375E of the mature polypeptide of SEQ ID NO: 2. In another aspect, the variant comprises or consists of the substitutions Y112H+V154M+S306A+G375E of the mature polypeptide of SEQ ID NO: 2. In another aspect, the variant comprises or consists of the substitutions Y112H+S197Y+I228V+I261L of the mature polypeptide of SEQ ID NO: 2. In another aspect, the variant comprises or consists of the substitutions Y112H+S197Y+I228V+S306A of the mature polypeptide of SEQ ID NO: 2. In another aspect, the variant comprises or consists of the substitutions Y112H+S197Y+I228V+G375E of the mature polypeptide of SEQ ID NO: 2. In another aspect, the variant comprises or consists of the substitutions Y112H+S197Y+I261L+S306A of the mature polypeptide of SEQ ID NO: 2. In another aspect, the variant comprises or consists of the substitutions Y112H+S197Y+I261L+G375E of the mature polypeptide of SEQ ID NO: 2. In another aspect, the variant comprises or consists of the substitutions Y112H+S197Y+S306A+G375E of the mature polypeptide of SEQ ID NO: 2. In another aspect, the variant comprises or consists of the substitutions Y112H+I228V+I261L+S306A of the mature polypeptide of SEQ ID NO: 2. In another aspect, the variant comprises or consists of the substitutions Y112H+I228V+I261L+G375E of the mature polypeptide of SEQ ID NO: 2. In another aspect, the variant comprises or consists of the substitutions Y112H+I228V+S306A+G375E of the mature polypeptide of SEQ ID NO: 2. In another aspect, the variant comprises or consists of the substitutions Y112H+I261L+S306A+G375E of the mature polypeptide of SEQ ID NO: 2. In another aspect, the variant comprises or consists of the substitutions V154M+S197Y+I228V+I261L of the mature polypeptide of SEQ ID NO: 2. In another aspect, the variant comprises or consists of the substitutions V154M+S197Y+I228V+S306A of the mature polypeptide of SEQ ID NO: 2. In another aspect, the variant comprises or consists of the substitutions V154M+S197Y+I228V+G375E of the mature polypeptide of SEQ ID NO: 2. In another aspect, the variant comprises or consists of the substitutions V154M+S197Y+I261L+S306A of the mature polypeptide of SEQ ID NO: 2. In another aspect, the variant comprises or consists of the substitutions V154M+S197Y+I261L+G375E of the mature polypeptide of SEQ ID NO: 2. In another aspect, the variant comprises or consists of the substitutions V154M+S197Y+S306A+G375E of the mature polypeptide of SEQ ID NO: 2. In another aspect, the variant comprises or consists of the substitutions V154M+I228V+I261L+S306A of the mature polypeptide of SEQ ID NO: 2. In another aspect, the variant comprises or consists of the substitutions V154M+I228V+I261L+G375E of the mature polypeptide of SEQ ID NO: 2. In another aspect, the variant comprises or consists of the substitutions V154M+I228V+S306A+G375E of the mature polypeptide of SEQ ID NO: 2. In another aspect, the variant comprises or consists of the substitutions V154M+I261L+S306A+G375E of the mature polypeptide of SEQ ID NO: 2. In another aspect, the variant comprises or consists of the substitutions S197Y+I228V+I261L+S306A of the mature polypeptide of SEQ ID NO: 2. In another aspect, the variant comprises or consists of the substitutions S197Y+I228V+I261L+G375E of the mature polypeptide of SEQ ID NO: 2. In another aspect, the variant comprises or consists of the substitutions S197Y+I228V+S306A+G375E of the mature polypeptide of SEQ ID NO: 2. In another aspect, the variant comprises or consists of the substitutions S197Y+I261L+S306A+G375E of the mature polypeptide of SEQ ID NO: 2. In another aspect, the variant comprises or consists of the substitutions I228V+I261L+S306A+G375E of the mature polypeptide of SEQ ID NO: 2.

In another aspect, the variant comprises or consists of the substitutions Y112H+ V154M+S197Y+I228V+I261L of the mature polypeptide of SEQ ID NO: 2. In another aspect, the variant comprises or consists of the substitutions Y112H+V154M+S197Y+I228V+S306A of the mature polypeptide of SEQ ID NO: 2. In another aspect, the variant comprises or consists of the substitutions Y112H+V154M+S197Y+I228V+G375E of the mature polypeptide of SEQ ID NO: 2. In another aspect, the variant comprises or consists of the substitutions Y112H+V154M+S197Y+I261L+S306A of the mature polypeptide of SEQ ID NO: 2. In another aspect, the variant comprises or consists of the substitutions Y112H+V154M+S197Y+I261L+G375E of the mature polypeptide of SEQ ID NO: 2. In another aspect, the variant comprises or consists of the substitutions Y112H+V154M+S197Y+S306A+G375E of the mature polypeptide of SEQ ID NO: 2. In another aspect, the variant comprises or consists of the substitutions Y112H+V154M+I228V+I261L+S306A of the mature polypeptide of SEQ ID NO: 2. In another aspect, the variant comprises or consists of the substitutions Y112H+V154M+I228V+I261L+G375E of the mature polypeptide of SEQ ID NO: 2. In another aspect, the variant comprises or consists of the substitutions Y112H+V154M+I228V+S306A+G375E of the mature polypeptide of SEQ ID NO: 2. In another aspect, the variant comprises or consists of the substitutions Y112H+V154M+I261L+S306A+G375E of the mature polypeptide of SEQ ID NO: 2. In another aspect, the variant comprises or consists of the substitutions Y112H+S197Y+I228V+I261L+S306A of the mature polypeptide of SEQ ID NO: 2. In another aspect, the variant comprises or consists of the substitutions Y112H+S197Y+I228V+I261L+G375E of the mature polypeptide of SEQ ID NO: 2. In another aspect, the variant comprises or consists of the substitutions Y112H+S197Y+I228V+S306A+G375E of the mature polypeptide of SEQ ID NO: 2. In another aspect, the variant comprises or consists of the substitutions Y112H+S197Y+I261L+S306A+G375E of the mature polypeptide of SEQ ID NO: 2. In another aspect, the variant comprises or consists of the substitutions Y112H+I228V+I261L+S306A+G375E of the mature polypeptide of SEQ ID NO: 2. In another aspect, the variant comprises or consists of the substitutions V154M+S197Y+I228V+I261L+S306A of the mature polypeptide of SEQ ID NO: 2. In another aspect, the variant comprises or consists of the substitutions V154M+S197Y+I228V+I261L+G375E of the mature polypeptide of SEQ ID NO: 2. In another aspect, the variant comprises or consists of the substitutions V154M+S197Y+I228V+S306A+G375E of the mature polypeptide of SEQ ID NO: 2. In another aspect, the variant comprises or consists of the substitutions V154M+S197Y+I261L+S306A+G375E of the mature polypeptide of SEQ ID NO: 2. In another aspect, the variant comprises or consists of the substitutions V154M+I228V+I261L+S306A+G375E of the mature polypeptide of SEQ ID NO: 2. In another aspect, the variant comprises or consists of the substitutions S197Y+I228V+I261L+S306A+G375E of the mature polypeptide of SEQ ID NO: 2.

In another aspect, the variant comprises or consists of the substitutions Y112H+V154M+S197Y+I228V+I261L+S306A of the mature polypeptide of SEQ ID NO: 2. In another aspect, the variant comprises or consists of the substitutions Y112H+V154M+S197Y+I228V+I261L+G375E of the mature polypeptide of SEQ ID NO: 2. In another aspect, the variant comprises or consists of the substitutions Y112H+V154M+S197Y+I228V+S306A+G375E of the mature polypeptide of SEQ ID NO: 2. In another aspect, the variant comprises or consists of the substitutions Y112H+V154M+S197Y+I261L+S306A+G375E of the mature polypeptide of SEQ ID NO: 2. In another aspect, the variant comprises or consists of the substitutions Y112H+V154M+I228V+I261L+S306A+G375E of the mature polypeptide of SEQ ID NO: 2. In another aspect, the variant comprises or consists of the substitutions Y112H+S197Y+I228V+I261L+S306A+G375E of the mature polypeptide of SEQ ID NO: 2. In another aspect, the variant comprises or consists of the substitutions V154M+S197Y+I228V+I261L+S306A+G375E of the mature polypeptide of SEQ ID NO: 2.

In another aspect, the variant comprises or consists of the substitutions Y112H+ V154M+S197Y+I228V+I261L+S306A+G375E of the mature polypeptide of SEQ ID NO: 2.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

The variants of the present invention may further or even further comprise a substitution at one or more (e.g., several) positions corresponding to positions 247, 262, 300, 322, 332, 338, and 439 of the mature polypeptide of SEQ ID NO: 2, wherein the variants have cellobiohydrolase activity (WO 2010/141325).

In one aspect, the number of additional substitutions in the variants of the present invention is 1-7, such as 1, 2, 3, 4, 5, 6, or 7 substitutions.

In another aspect, the variant further comprises a substitution at one or more (e.g., several) positions corresponding to positions 247, 262, 300, 322, 332, 338, and 439. In another aspect, the variant further comprises a substitution at two positions corresponding to any of positions 262, 287, 322, and 332. In another aspect, the variant further comprises a substitution at three positions corresponding to any of positions 247, 262, 300, 322, 332, 338, and 439. In another aspect, the variant further comprises a substitution at four positions corresponding to any of positions 247, 262, 300, 322, 332, 338, and 439. In another aspect, the variant further comprises a substitution at five positions corresponding to any of positions 247, 262, 300, 322, 332, 338, and 439. In another aspect, the variant further comprises a substitution at six positions corresponding to any of positions 247, 262, 300, 322, 332, 338, and 439. In another aspect, the variant further comprises a substitution at each position corresponding to positions 247, 262, 300, 322, 332, 338, and 439.

In another aspect, the variant further comprises a substitution at a position corresponding to position 247. In another aspect, the amino acid at a position corresponding to position 247 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant further comprises the substitution A247S of the mature polypeptide of SEQ ID NO: 2.

In another aspect, the variant further comprises a substitution at a position corresponding to position 262. In another aspect, the amino acid at a position corresponding to position 262 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another aspect, the variant further comprises or consists of the substitution T262K of the mature polypeptide of SEQ ID NO: 2.

In another aspect, the variant further comprises a substitution at a position corresponding to position 300. In another aspect, the amino acid at a position corresponding to position 300 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant further comprises the substitution N300D of the mature polypeptide of SEQ ID NO: 2.

In another aspect, the variant further comprises a substitution at a position corresponding to position 322. In another aspect, the amino acid at a position corresponding to position 322 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further comprises the substitution V322I of the mature polypeptide of SEQ ID NO: 2.

In another aspect, the variant further comprises a substitution at a position corresponding to position 332. In another aspect, the amino acid at a position corresponding to position 332 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant further comprises the substitution D332N of the mature polypeptide of SEQ ID NO: 2.

In another aspect, the variant further comprises a substitution at a position corresponding to position 338. In another aspect, the amino acid at a position corresponding to position 338 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another aspect, the variant further comprises the substitution E338K of the mature polypeptide of SEQ ID NO: 2.

In another aspect, the variant further comprises a substitution at a position corresponding to position 439. In another aspect, the amino acid at a position corresponding to position 439 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant further comprises the substitution T439Q of the mature polypeptide of SEQ ID NO: 2.

In another aspect, the variant further comprises substitutions at positions corresponding to positions 247 and 262, such as those described above. In another aspect, the variant further comprises substitutions at positions corresponding to positions 247 and 300, such as those described above. In another aspect, the variant further comprises substitutions at positions corresponding to positions 247 and 322, such as those described above. In another aspect, the variant further comprises substitutions at positions corresponding to positions 247 and 332, such as those described above. In another aspect, the variant further comprises substitutions at positions corresponding to positions 247 and 338, such as those described above. In another aspect, the variant further comprises substitutions at positions corresponding to positions 247 and 439, such as those described above. In another aspect, the variant further comprises substitutions at positions corresponding to positions 262 and 300, such as those described above. In another aspect, the variant further comprises substitutions at positions corresponding to positions 262 and 322, such as those described above. In another aspect, the variant further comprises substitutions at positions corresponding to positions 262 and 332, such as those described above. In another aspect, the variant further comprises substitutions at positions corresponding to positions 262 and 338, such as those described above. In another aspect, the variant further comprises substitutions at positions corresponding to positions 262 and 439, such as those described above. In another aspect, the variant further comprises substitutions at positions corresponding to positions 300 and 322, such as those described above. In another aspect, the variant further comprises substitutions at positions corresponding to positions 300 and 332, such as those described above. In another aspect, the variant further comprises substitutions at positions corresponding to positions 300 and 338, such as those described above. In another aspect, the variant further comprises substitutions at positions corresponding to positions 300 and 439, such as those described above. In another aspect, the variant further comprises substitutions at positions corresponding to positions 322 and 332, such as those described above. In another aspect, the variant further comprises substitutions at positions corresponding to positions 322 and 338, such as those described above. In another aspect, the variant further comprises substitutions at positions corresponding to positions 322 and 439, such as those described above. In another aspect, the variant further comprises substitutions at positions corresponding to positions 332 and 338, such as those described above. In another aspect, the variant further comprises substitutions at positions corresponding to positions 332 and 439, such as those described above. In another aspect, the variant further comprises substitutions at positions corresponding to positions 338 and 439, such as those described above.

In another aspect, the variant further comprises substitutions at positions corresponding to positions 247, 262, and 300, such as those described above. In another aspect, the variant further comprises substitutions at positions corresponding to positions 247, 262, and 322, such as those described above. In another aspect, the variant further comprises substitutions at positions corresponding to positions 247, 262, and 332, such as those described above. In another aspect, the variant further comprises substitutions at positions corresponding to positions 247, 262, and 338, such as those described above. In another aspect, the variant further comprises substitutions at positions corresponding to positions 247, 262, and 439, such as those described above. In another aspect, the variant further comprises substitutions at positions corresponding to positions 247, 300, and 322, such as those described above. In another aspect, the variant further comprises substitutions at positions corresponding to positions 247, 300, and 332, such as those described above. In another aspect, the variant further comprises substitutions at positions corresponding to positions 247, 300, and 338, such as those described above. In another aspect, the variant further comprises substitutions at positions corresponding to positions 247, 300, and 439, such as those described above. In another aspect, the variant further comprises substitutions at positions corresponding to positions 247, 322, and 332, such as those described above. In another aspect, the variant further comprises substitutions at positions corresponding to positions 247, 322, and 338, such as those described above. In another aspect, the variant further comprises substitutions at positions corresponding to positions 247, 322, and 439, such as those described above. In another aspect, the variant further comprises substitutions at positions corresponding to positions 247, 332, and 338, such as those described above. In another aspect, the variant further comprises substitutions at positions corresponding to positions 247, 332, and 439, such as those described above. In another aspect, the variant further comprises substitutions at positions corresponding to positions 247, 338, and 439, such as those described above. In another aspect, the variant further comprises substitutions at positions corresponding to positions 262, 300, and 322, such as those described above. In another aspect, the variant further comprises substitutions at positions corresponding to positions 262, 300, and 332, such as those described above. In another aspect, the variant further comprises substitutions at positions corresponding to positions 262, 300, and 338, such as those described above. In another aspect, the variant further comprises substitutions at positions corresponding to positions 262, 300, and 439, such as those described above. In another aspect, the variant further comprises substitutions at positions corresponding to positions 262, 322, and 332, such as those described above. In another aspect, the variant further comprises substitutions at positions corresponding to positions 262, 322, and 338, such as those described above. In another aspect, the variant further comprises substitutions at positions corresponding to positions 262, 322, and 439, such as those described above. In another aspect, the variant further comprises substitutions at positions corresponding to positions 262, 332, and 338, such as those described above. In another aspect, the variant further comprises substitutions at positions corresponding to positions 262, 332, and 439, such as those described above. In another aspect, the variant further comprises substitutions at positions corresponding to positions 262, 338, and 439, such as those described above. In another aspect, the variant further comprises substitutions at positions corresponding to positions 300, 322, and 332, such as those described above. In another aspect, the variant further comprises substitutions at positions corresponding to positions 300, 322, and 338, such as those described above. In another aspect, the variant further comprises substitutions at positions corresponding to positions 300, 322, and 439, such as those described above. In another aspect, the variant further comprises substitutions at positions corresponding to positions 300, 332, and 338, such as those described above. In another aspect, the variant further comprises substitutions at positions corresponding to positions 300, 332, and 439, such as those described above. In another aspect, the variant further comprises substitutions at positions corresponding to positions 300, 338, and 439, such as those described above. In another aspect, the variant further comprises substitutions at positions corresponding to positions 322, 332, and 338, such as those described above. In another aspect, the variant further comprises substitutions at positions corresponding to positions 322, 332, and 439, such as those described above. In another aspect, the variant further comprises substitutions at positions corresponding to positions 322, 338, and 439, such as those described above. In another aspect, the variant further comprises substitutions at positions corresponding to positions 332, 338, and 439, such as those described above.

In another aspect, the variant further comprises substitutions at positions corresponding to positions 247, 262, 300, and 322, such as those described above. In another aspect, the variant further comprises substitutions at positions corresponding to positions 247, 262, 300, and 332, such as those described above. In another aspect, the variant further comprises substitutions at positions corresponding to positions 247, 262, 300, and 338, such as those described above. In another aspect, the variant further comprises substitutions at positions corresponding to positions 247, 262, 300, and 439, such as those described above. In another aspect, the variant further comprises substitutions at positions corresponding to positions 247, 262, 322, and 332, such as those described above. In another aspect, the variant further comprises substitutions at positions corresponding to positions 247, 262, 322, and 338, such as those described above. In another aspect, the variant further comprises substitutions at positions corresponding to positions 247, 262, 322, and 439, such as those described above. In another aspect, the variant further comprises substitutions at positions corresponding to positions 247, 262, 332, and 338, such as those described above. In another aspect, the variant further comprises substitutions at positions corresponding to positions 247, 262, 332, and 439, such as those described above. In another aspect, the variant further comprises substitutions at positions corresponding to positions 247, 262, 338, and 439, such as those described above. In another aspect, the variant further comprises substitutions at positions corresponding to positions 247, 300, 322, and 332, such as those described above. In another aspect, the variant further comprises substitutions at positions corresponding to positions 247, 300, 322, and 338, such as those described above. In another aspect, the variant further comprises substitutions at positions corresponding to positions 247, 300, 322, and 439, such as those described above. In another aspect, the variant further comprises substitutions at positions corresponding to positions 247, 300, 332, and 338, such as those described above. In another aspect, the variant further comprises substitutions at positions corresponding to positions 247, 300, 332, and 439, such as those described above. In another aspect, the variant further comprises substitutions at positions corresponding to positions 247, 300, 338, and 439, such as those described above. In another aspect, the variant further comprises substitutions at positions corresponding to positions 247, 322, 332, and 338, such as those described above. In another aspect, the variant further comprises substitutions at positions corresponding to positions 247, 322, 332, and 439, such as those described above. In another aspect, the variant further comprises substitutions at positions corresponding to positions 247, 322, 338, and 439, such as those described above. In another aspect, the variant further comprises substitutions at positions corresponding to positions 247, 332, 338, and 439, such as those described above. In another aspect, the variant further comprises substitutions at positions corresponding to positions 262, 300, 322, and 332, such as those described above. In another aspect, the variant further comprises substitutions at positions corresponding to positions 262, 300, 322, and 338, such as those described above. In another aspect, the variant further comprises substitutions at positions corresponding to positions 262, 300, 322, and 439, such as those described above. In another aspect, the variant further comprises substitutions at positions corresponding to positions 262, 300, 332, and 338, such as those described above. In another aspect, the variant further comprises substitutions at positions corresponding to positions 262, 300, 332, and 439, such as those described above. In another aspect, the variant further comprises substitutions at positions corresponding to positions 262, 300, 338, and 439, such as those described above. In another aspect, the variant further comprises substitutions at positions corresponding to positions 262, 322, 332, and 338, such as those described above. In another aspect, the variant further comprises substitutions at positions corresponding to positions 262, 322, 332, and 439, such as those described above. In another aspect, the variant further comprises substitutions at positions corresponding to positions 262, 322, 338, and 439, such as those described above. In another aspect, the variant further comprises substitutions at positions corresponding to positions 262, 332, 338, and 439, such as those described above. In another aspect, the variant further comprises substitutions at positions corresponding to positions 300, 322, 332, and 338, such as those described above. In another aspect, the variant further comprises substitutions at positions corresponding to positions 300, 322, 332, and 439, such as those described above. In another aspect, the variant further comprises substitutions at positions corresponding to positions 300, 322, 338, and 439, such as those described above. In another aspect, the variant further comprises substitutions at positions corresponding to positions 300, 332, 338, and 439, such as those described above. In another aspect, the variant further comprises substitutions at positions corresponding to positions 322, 332, 338, and 439, such as those described above.

In another aspect, the variant further comprises substitutions at positions corresponding to positions 247, 262, 300, 322, and 332, such as those described above. In another aspect, the variant further comprises substitutions at positions corresponding to positions 247, 262, 300, 322, and 338, such as those described above. In another aspect, the variant further comprises substitutions at positions corresponding to positions 247, 262, 300, 322, and 439, such as those described above. In another aspect, the variant further comprises substitutions at positions corresponding to positions 247, 262, 300, 332, and 338, such as those described above. In another aspect, the variant further comprises substitutions at positions corresponding to positions 247, 262, 300, 332, and 439, such as those described above. In another aspect, the variant further comprises substitutions at positions corresponding to positions 247, 262, 300, 338, and 439, such as those described above. In another aspect, the variant further comprises substitutions at positions corresponding to positions 247, 262, 322, 332, and 338, such as those described above. In another aspect, the variant further comprises substitutions at positions corresponding to positions 247, 262, 322, 332, and 439, such as those described above. In another aspect, the variant further comprises substitutions at positions corresponding to positions 247, 262, 322, 338, and 439, such as those described above. In another aspect, the variant further comprises substitutions at positions corresponding to positions 247, 262, 332, 338, and 439, such as those described above. In another aspect, the variant further comprises substitutions at positions corresponding to positions 247, 300, 322, 332, and 338, such as those described above. In another aspect, the variant further comprises substitutions at positions corresponding to positions 247, 300, 322, 332, and 439, such as those described above. In another aspect, the variant further comprises substitutions at positions corresponding to positions 247, 300, 322, 338, and 439, such as those described above. In another aspect, the variant further comprises substitutions at positions corresponding to positions 247, 300, 332, 338, and 439, such as those described above. In another aspect, the variant further comprises substitutions at positions corresponding to positions 247, 322, 332, 338, and 439, such as those described above. In another aspect, the variant further comprises substitutions at positions corresponding to positions 262, 300, 322, 332, and 338, such as those described above. In another aspect, the variant further comprises substitutions at positions corresponding to positions 262, 300, 322, 332, and 439, such as those described above. In another aspect, the variant further comprises substitutions at positions corresponding to positions 262, 300, 322, 338, and 439, such as those described above. In another aspect, the variant further comprises substitutions at positions corresponding to positions 262, 300, 332, 338, and 439, such as those described above. In another aspect, the variant further comprises substitutions at positions corresponding to positions 262, 322, 332, 338, and 439, such as those described above. In another aspect, the variant further comprises substitutions at positions corresponding to positions 300, 322, 332, 338, and 439, such as those described above.

In another aspect, the variant further comprises substitutions at positions corresponding to positions 247, 262, 300, 322, 332, and 338, such as those described above. In another aspect, the variant further comprises substitutions at positions corresponding to positions 247, 262, 300, 322, 332, and 439, such as those described above. In another aspect, the variant further comprises substitutions at positions corresponding to positions 247, 262, 300, 322, 338, and 439, such as those described above. In another aspect, the variant further comprises substitutions at positions corresponding to positions 247, 262, 300, 332, 338, and 439, such as those described above. In another aspect, the variant further comprises substitutions at positions corresponding to positions 247, 262, 322, 332, 338, and 439, such as those described above. In another aspect, the variant further comprises substitutions at positions corresponding to positions 247, 300, 322, 332, 338, and 439, such as those described above. In another aspect, the variant further comprises substitutions at positions corresponding to positions 262, 300, 322, 332, 338, and 439, such as those described above.

In another aspect, the variant further comprises substitutions at positions corresponding to positions 247, 262, 300, 322, 332, 338, and 439, such as those described above.

In another aspect, the variant further comprises one or more (e.g., several) substitutions selected from the group consisting of A247S, T262K, N300D, V322I, D332N, E338K, and T439Q, or the one or more (e.g., several) substitutions selected from the group consisting of A247S, T262K, N300D, V322I, D332N, E338K, and T439Q at positions corresponding to SEQ ID NO: 2 in other cellobiohydrolases such as those described herein.

In each of the aspects below, the variant further comprises the one or more (e.g., several) substitutions described below at positions corresponding to SEQ ID NO: 2 in other cellobiohydrolases such as those described herein.

In another aspect, the variant further comprises the substitutions A247S+T262K of the mature polypeptide of SEQ ID NO: 2. In another aspect, the variant further comprises the substitutions A247S+N300D of the mature polypeptide of SEQ ID NO: 2. In another aspect, the variant further comprises the substitutions A247S+V322I of the mature polypeptide of SEQ ID NO: 2. In another aspect, the variant further comprises the substitutions A247S+D332N of the mature polypeptide of SEQ ID NO: 2. In another aspect, the variant further comprises the substitutions A247S+E338K of the mature polypeptide of SEQ ID NO: 2. In another aspect, the variant further comprises the substitutions A247S+T439Q of the mature polypeptide of SEQ ID NO: 2. In another aspect, the variant further comprises the substitutions T262K+N300D of the mature polypeptide of SEQ ID NO: 2. In another aspect, the variant further comprises the substitutions T262K+V322I of the mature polypeptide of SEQ ID NO: 2. In another aspect, the variant further comprises the substitutions T262K+D332N of the mature polypeptide of SEQ ID NO: 2. In another aspect, the variant further comprises the substitutions T262K+E338K of the mature polypeptide of SEQ ID NO: 2. In another aspect, the variant further comprises the substitutions T262K+T439Q of the mature polypeptide of SEQ ID NO: 2. In another aspect, the variant further comprises the substitutions N300D+V322I of the mature polypeptide of SEQ ID NO: 2. In another aspect, the variant further comprises the substitutions N300D+D332N of the mature polypeptide of SEQ ID NO: 2. In another aspect, the variant further comprises the substitutions N300D+E338K of the mature polypeptide of SEQ ID NO: 2. In another aspect, the variant further comprises the substitutions N300D+T439Q of the mature polypeptide of SEQ ID NO: 2. In another aspect, the variant further comprises the substitutions V322I+D332N of the mature polypeptide of SEQ ID NO: 2. In another aspect, the variant further comprises the substitutions V322I+E338K of the mature polypeptide of SEQ ID NO: 2. In another aspect, the variant further comprises the substitutions V322I+T439Q of the mature polypeptide of SEQ ID NO: 2. In another aspect, the variant further comprises the substitutions D332N+E338K of the mature polypeptide of SEQ ID NO: 2. In another aspect, the variant further comprises the substitutions D332N+T439Q of the mature polypeptide of SEQ ID NO: 2. In another aspect, the variant further comprises the substitutions E338K+T439Q of the mature polypeptide of SEQ ID NO: 2.

In another aspect, the variant further comprises the substitutions A247S+T262K+N300D of the mature polypeptide of SEQ ID NO: 2. In another aspect, the variant further comprises the substitutions A247S+T262K+V322I of the mature polypeptide of SEQ ID NO: 2. In another aspect, the variant further comprises the substitutions A247S+T262K+D332N of the mature polypeptide of SEQ ID NO: 2. In another aspect, the variant further comprises the substitutions A247S+T262K+E338K of the mature polypeptide of SEQ ID NO: 2. In another aspect, the variant further comprises the substitutions A247S+T262K+T439Q of the mature polypeptide of SEQ ID NO: 2. In another aspect, the variant further comprises the substitutions A247S+N300D+V322I of the mature polypeptide of SEQ ID NO: 2. In another aspect, the variant further comprises the substitutions A247S+N300D+D332N of the mature polypeptide of SEQ ID NO: 2. In another aspect, the variant further comprises the substitutions A247S+N300D+E338K of the mature polypeptide of SEQ ID NO: 2. In another aspect, the variant further comprises the substitutions A247S+N300D+T439Q of the mature polypeptide of SEQ ID NO: 2. In another aspect, the variant further comprises the substitutions A247S+V322I+D332N of the mature polypeptide of SEQ ID NO: 2. In another aspect, the variant further comprises the substitutions A247S+V322I+E338K of the mature polypeptide of SEQ ID NO: 2. In another aspect, the variant further comprises the substitutions A247S+V322I+T439Q of the mature polypeptide of SEQ ID NO: 2. In another aspect, the variant further comprises the substitutions A247S+D332N+E338K of the mature polypeptide of SEQ ID NO: 2. In another aspect, the variant further comprises the substitutions A247S+D332N+T439Q of the mature polypeptide of SEQ ID NO: 2. In another aspect, the variant further comprises the substitutions A247S+E338K+T439Q of the mature polypeptide of SEQ ID NO: 2. In another aspect, the variant further comprises the substitutions T262K+N300D+V322I of the mature polypeptide of SEQ ID NO: 2. In another aspect, the variant further comprises the substitutions T262K+N300D+D332N of the mature polypeptide of SEQ ID NO: 2. In another aspect, the variant further comprises the substitutions T262K+N300D+E338K of the mature polypeptide of SEQ ID NO: 2. In another aspect, the variant further comprises the substitutions T262K+N300D+T439Q of the mature polypeptide of SEQ ID NO: 2. In another aspect, the variant further comprises the substitutions T262K+V322I+D332N of the mature polypeptide of SEQ ID NO: 2. In another aspect, the variant further comprises the substitutions T262K+V322I+E338K of the mature polypeptide of SEQ ID NO: 2. In another aspect, the variant further comprises the substitutions T262K+V322I+T439Q of the mature polypeptide of SEQ ID NO: 2. In another aspect, the variant further comprises the substitutions T262K+D332N+E338K of the mature polypeptide of SEQ ID NO: 2. In another aspect, the variant further comprises the substitutions T262K+D332N+T439Q of the mature polypeptide of SEQ ID NO: 2. In another aspect, the variant further comprises the substitutions T262K+E338K+T439Q of the mature polypeptide of SEQ ID NO: 2. In another aspect, the variant further comprises the substitutions N300D+V322I+D332N of the mature polypeptide of SEQ ID NO: 2. In another aspect, the variant further comprises the substitutions N300D+V322I+E338K of the mature polypeptide of SEQ ID NO: 2. In another aspect, the variant further comprises the substitutions N300D+V322I+T439Q of the mature polypeptide of SEQ ID NO: 2. In another aspect, the variant further comprises the substitutions N300D+D332N+E338K of the mature polypeptide of SEQ ID NO: 2. In another aspect, the variant further comprises the substitutions N300D+D332N+T439Q of the mature polypeptide of SEQ ID NO: 2. In another aspect, the variant further comprises the substitutions N300D+E338K+T439Q of the mature polypeptide of SEQ ID NO: 2. In another aspect, the variant further comprises the substitutions V322I+D332N+E338K of the mature polypeptide of SEQ ID NO: 2. In another aspect, the variant further comprises the substitutions V322I+D332N+T439Q of the mature polypeptide of SEQ ID NO: 2. In another aspect, the variant further comprises the substitutions V322I+E338K+T439Q of the mature polypeptide of SEQ ID NO: 2. In another aspect, the variant further comprises the substitutions D332N+E338K+T439Q of the mature polypeptide of SEQ ID NO: 2.

In another aspect, the variant further comprises the substitutions A247S+T262K+N300D+V322I of the mature polypeptide of SEQ ID NO: 2. In another aspect, the variant further comprises the substitutions A247S+T262K+N300D+D332N of the mature polypeptide of SEQ ID NO: 2. In another aspect, the variant further comprises the substitutions A247S+T262K+N300D+E338K of the mature polypeptide of SEQ ID NO: 2. In another aspect, the variant further comprises the substitutions A247S+T262K+N300D+T439Q of the mature polypeptide of SEQ ID NO: 2. In another aspect, the variant further comprises the substitutions A247S+T262K+V322I+D332N of the mature polypeptide of SEQ ID NO: 2. In another aspect, the variant further comprises the substitutions A247S+T262K+V322I+E338K of the mature polypeptide of SEQ ID NO: 2. In another aspect, the variant further comprises the substitutions A247S+T262K+V322I+T439Q of the mature polypeptide of SEQ ID NO: 2. In another aspect, the variant further comprises the substitutions A247S+T262K+D332N+E338K of the mature polypeptide of SEQ ID NO: 2. In another aspect, the variant further comprises the substitutions A247S+T262K+D332N+T439Q of the mature polypeptide of SEQ ID NO: 2. In another aspect, the variant further comprises the substitutions A247S+T262K+E338K+T439Q of the mature polypeptide of SEQ ID NO: 2. In another aspect, the variant further comprises the substitutions A247S+N300D+V322I+D332N of the mature polypeptide of SEQ ID NO: 2. In another aspect, the variant further comprises the substitutions A247S+N300D+V322I+E338K of the mature polypeptide of SEQ ID NO: 2. In another aspect, the variant further comprises the substitutions A247S+N300D+V322I+T439Q of the mature polypeptide of SEQ ID NO: 2. In another aspect, the variant further comprises the substitutions A247S+N300D+D332N+E338K of the mature polypeptide of SEQ ID NO: 2. In another aspect, the variant further comprises the substitutions A247S+N300D+D332N+T439Q of the mature polypeptide of SEQ ID NO: 2. In another aspect, the variant further comprises the substitutions A247S+N300D+E338K+T439Q of the mature polypeptide of SEQ ID NO: 2. In another aspect, the variant further comprises the substitutions A247S+V322I+D332N+E338K of the mature polypeptide of SEQ ID NO: 2. In another aspect, the variant further comprises the substitutions A247S+V322I+D332N+T439Q of the mature polypeptide of SEQ ID NO: 2. In another aspect, the variant further comprises the substitutions A247S+V322I+E338K+T439Q of the mature polypeptide of SEQ ID NO: 2. In another aspect, the variant further comprises the substitutions A247S+D332N+E338K+T439Q of the mature polypeptide of SEQ ID NO: 2. In another aspect, the variant further comprises the substitutions T262K+N300D+V322I+D332N of the mature polypeptide of SEQ ID NO: 2. In another aspect, the variant further comprises the substitutions T262K+N300D+V322I+E338K of the mature polypeptide of SEQ ID NO: 2. In another aspect, the variant further comprises the substitutions T262K+N300D+V322I+T439Q of the mature polypeptide of SEQ ID NO: 2. In another aspect, the variant further comprises the substitutions T262K+N300D+D332N+E338K of the mature polypeptide of SEQ ID NO: 2. In another aspect, the variant further comprises the substitutions T262K+N300D+D332N+T439Q of the mature polypeptide of SEQ ID NO: 2. In another aspect, the variant further comprises the substitutions T262K+N300D+E338K+T439Q of the mature polypeptide of SEQ ID NO: 2. In another aspect, the variant further comprises the substitutions T262K+V322I+D332N+E338K of the mature polypeptide of SEQ ID NO: 2. In another aspect, the variant further comprises the substitutions T262K+V322I+D332N+T439Q of the mature polypeptide of SEQ ID NO: 2. In another aspect, the variant further comprises the substitutions T262K+V322I+E338K+T439Q of the mature polypeptide of SEQ ID NO: 2. In another aspect, the variant further comprises the substitutions T262K+D332N+E338K+T439Q of the mature polypeptide of SEQ ID NO: 2. In another aspect, the variant further comprises the substitutions N300D+V322I+D332N+E338K of the mature polypeptide of SEQ ID NO: 2. In another aspect, the variant further comprises the substitutions N300D+V322I+D332N+T439Q of the mature polypeptide of SEQ ID NO: 2. In another aspect, the variant further comprises the substitutions N300D+V322I+E338K+T439Q of the mature polypeptide of SEQ ID NO: 2. In another aspect, the variant further comprises the substitutions N300D+D332N+E338K+T439Q of the mature polypeptide of SEQ ID NO: 2. In another aspect, the variant further comprises the substitutions V322I+D332N+E338K+T439Q of the mature polypeptide of SEQ ID NO: 2.

In another aspect, the variant further comprises the substitutions A247S+T262K+N300D+V322I+D332N of the mature polypeptide of SEQ ID NO: 2. In another aspect, the variant further comprises the substitutions A247S+T262K+N300D+V322I+E338K of the mature polypeptide of SEQ ID NO: 2. In another aspect, the variant further comprises the substitutions A247S+T262K+N300D+V322I+T439Q of the mature polypeptide of SEQ ID NO: 2. In another aspect, the variant further comprises the substitutions A247S+T262K+N300D+D332N+E338K of the mature polypeptide of SEQ ID NO: 2. In another aspect, the variant further comprises the substitutions A247S+T262K+N300D+D332N+T439Q of the mature polypeptide of SEQ ID NO: 2. In another aspect, the variant further comprises the substitutions A247S+T262K+N300D+E338K+T439Q of the mature polypeptide of SEQ ID NO: 2. In another aspect, the variant further comprises the substitutions A247S+T262K+V322I+D332N+E338K of the mature polypeptide of SEQ ID NO: 2. In another aspect, the variant further comprises the substitutions A247S+T262K+V322I+D332N+T439Q of the mature polypeptide of SEQ ID NO: 2. In another aspect, the variant further comprises the substitutions A247S+T262K+V322I+E338K+T439Q of the mature polypeptide of SEQ ID NO: 2. In another aspect, the variant further comprises the substitutions A247S+T262K+D332N+E338K+T439Q of the mature polypeptide of SEQ ID NO: 2. In another aspect, the variant further comprises the substitutions A247S+N300D+V322I+D332N+E338K of the mature polypeptide of SEQ ID NO: 2. In another aspect, the variant further comprises the substitutions A247S+N300D+V322I+D332N+T439Q of the mature polypeptide of SEQ ID NO: 2. In another aspect, the variant further comprises the substitutions A247S+N300D+V322I+E338K+T439Q of the mature polypeptide of SEQ ID NO: 2. In another aspect, the variant further comprises the substitutions A247S+N300D+D332N+E338K+T439Q of the mature polypeptide of SEQ ID NO: 2. In another aspect, the variant further comprises the substitutions A247S+V322I+D332N+E338K+T439Q of the mature polypeptide of SEQ ID NO: 2. In another aspect, the variant further comprises the substitutions T262K+N300D+V322I+D332N+E338K of the mature polypeptide of SEQ ID NO: 2. In another aspect, the variant further comprises the substitutions T262K+N300D+V322I+D332N+T439Q of the mature polypeptide of SEQ ID NO: 2. In another aspect, the variant further comprises the substitutions T262K+N300D+V322I+E338K+T439Q of the mature polypeptide of SEQ ID NO: 2. In another aspect, the variant further comprises the substitutions T262K+N300D+D332N+E338K+T439Q of the mature polypeptide of SEQ ID NO: 2. In another aspect, the variant further comprises the substitutions T262K+V322I+D332N+E338K+T439Q of the mature polypeptide of SEQ ID NO: 2. In another aspect, the variant further comprises the substitutions N300D+V322I+D332N+E338K+T439Q of the mature polypeptide of SEQ ID NO: 2.

In another aspect, the variant further comprises the substitutions A247S+T262K+N300D+V322I+D332N+E338K of the mature polypeptide of SEQ ID NO: 2. In another aspect, the variant further comprises the substitutions A247S+T262K+N300D+V322I+D332N+T439Q of the mature polypeptide of SEQ ID NO: 2. In another aspect, the variant further comprises the substitutions A247S+T262K+N300D+V322I+E338K+T439Q of the mature polypeptide of SEQ ID NO: 2. In another aspect, the variant further comprises the substitutions A247S+T262K+N300D+D332N+E338K+T439Q of the mature polypeptide of SEQ ID NO: 2. In another aspect, the variant further comprises the substitutions A247S+T262K+V322I+D332N+E338K+T439Q of the mature polypeptide of SEQ ID NO: 2. In another aspect, the variant further comprises the substitutions A247S+N300D+V322I+D332N+E338K+T439Q of the mature polypeptide of SEQ ID NO: 2. In another aspect, the variant further comprises the substitutions T262K+N300D+V322I+D332N+E338K+T439Q of the mature polypeptide of SEQ ID NO: 2.

In another aspect, the variant further comprises the substitutions A247S+T262K+N300D+V322I+D332N+E338K+T439Q of the mature polypeptide of SEQ ID NO: 2.

The variants of the present invention may further or even further comprise a substitution at one or more (e.g., several) positions corresponding to positions 256, 287, and 344 of the mature polypeptide of SEQ ID NO: 2, wherein the variants have cellobiohydrolase activity (WO 2011/123450).

In one aspect, the number of additional substitutions in the variants of the present invention is 1-3, such as 1, 2, or 3 substitutions.

In another aspect, the variant further comprises a substitution at one or more (e.g., several) positions corresponding to positions 256, 287, and 344. In another aspect, a variant comprises a substitution at two positions corresponding to any of positions 256, 287, and 344. In another aspect, a variant comprises a substitution at each position corresponding to positions 256, 287, and 344.

In another aspect, the variant further comprises a substitution at a position corresponding to position 256. In another aspect, the amino acid at a position corresponding to position 256 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant further comprises the substitution C256L of the mature polypeptide of SEQ ID NO: 2.

In another aspect, the variant further comprises a substitution at a position corresponding to position 287. In another aspect, the amino acid at a position corresponding to position 287 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further comprises the substitution L287I of the mature polypeptide of SEQ ID NO: 2.

In another aspect, the variant further comprises a substitution at a position corresponding to position 344. In another aspect, the amino acid at a position corresponding to position 344 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant further comprises the substitution L344F of the mature polypeptide of SEQ ID NO: 2.

In another aspect, the variant further comprises substitutions at positions corresponding to positions 256 and 287, such as those described above. In another aspect, the variant further comprises substitutions at positions corresponding to positions 256 and 344, such as those described above. In another aspect, the variant further comprises substitutions at positions corresponding to positions 287 and 344, such as those described above.

In another aspect, the variant further comprises substitutions at positions corresponding to positions 256, 287, and 344, such as those described above.

In another aspect, the variant further comprises one or more (e.g., several) substitutions selected from the group consisting of C256L, L287I, and L344F, or the one or more (e.g., several) substitutions selected from the group consisting of C256L, L287I, and L344F at positions corresponding to SEQ ID NO: 2 in other cellobiohydrolases such as those described herein.

In each of the aspects below, the variant further comprises the one or more (e.g., several) substitutions described below at positions corresponding to SEQ ID NO: 2 in other cellobiohydrolases such as those described herein.

In another aspect, the variant further comprises the substitutions C256L+L287I of the mature polypeptide of SEQ ID NO: 2. In another aspect, the variant further comprises the substitutions C256L+L344F of the mature polypeptide of SEQ ID NO: 2. In another aspect, the variant further comprises the substitutions L287I+L344 of the mature polypeptide of SEQ ID NO: 2.

In another aspect, the variant further comprises the substitutions C256L+L287I+L344F of the mature polypeptide of SEQ ID NO: 2.

The variants may consist of at least 85% of the amino acid residues, e.g., at least 90% of the amino acid residues or at least 95% of the amino acid residues of the mature polypeptides of the corresponding parent cellobiohydrolases.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in cellobiohydrolases correspond to positions 22, 107, 194, and/or 196 of the mature polypeptide of SEQ ID NO: 2.

In an embodiment, the variants have increased thermostability compared to their parent cellobiohydrolases.

In one aspect, the thermostability of the variant relative to the parent is determined at pH 3.0 and 45° C. In another aspect, the thermostability of the variant relative to the parent is determined at pH 3.0 and 50° C. In another aspect, the thermostability of the variant relative to the parent is determined at pH 3.0 and 55° C. In another aspect, the thermostability of the variant relative to the parent is determined at pH 3.0 and 60° C. In another aspect, the thermostability of the variant relative to the parent is determined at pH 3.0 and 65° C. In another aspect, the thermostability of the variant relative to the parent is determined at pH 3.0 and 70° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C. In another aspect, the thermostability of the variant relative to the parent is determined at pH 3.0 and 95° C.

In another aspect, the thermostability of the variant relative to the parent is determined at pH 3.5 and 45° C. In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 65° C. In another aspect, the thermostability of the variant relative to the parent is determined at pH 3.5 and 70° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90° C. In another aspect, the thermostability of the variant relative to the parent is determined at pH 3.5 and 95° C.

In another aspect, the thermostability of the variant relative to the parent is determined at pH 4.0 and 45° C. In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 65° C. In another aspect, the thermostability of the variant relative to the parent is determined at pH 4.0 and 70° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C. In another aspect, the thermostability of the variant relative to the parent is determined at pH 4.0 and 95° C.

In another aspect, the thermostability of the variant relative to the parent is determined at pH 4.5 and 45° C. In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 65° C. In another aspect, the thermostability of the variant relative to the parent is determined at pH 4.5 and 70° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C. In another aspect, the thermostability of the variant relative to the parent is determined at pH 4.5 and 95° C.

In another aspect, the thermostability of the variant relative to the parent is determined at pH 5.0 and 45° C. In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 65° C. In another aspect, the thermostability of the variant relative to the parent is determined at pH 5.0 and 67° C. In another aspect, the thermostability of the variant relative to the parent is determined at pH 5.0 and 70° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C. In another aspect, the thermostability of the variant relative to the parent is determined at pH 5.0 and 95° C.

In another aspect, the thermostability of the variant relative to the parent is determined at pH 5.5 and 45° C. In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 65° C. In another aspect, the thermostability of the variant relative to the parent is determined at pH 5.5 and 70° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C. In another aspect, the thermostability of the variant relative to the parent is determined at pH 5.5 and 95° C.

In another aspect, the thermostability of the variant relative to the parent is determined at pH 6.0 and 45° C. In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 65° C. In another aspect, the thermostability of the variant relative to the parent is determined at pH 6.0 and 70° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C. In another aspect, the thermostability of the variant relative to the parent is determined at pH 6.0 and 95° C.

In another aspect, the thermostability of the variant relative to the parent is determined at pH 6.5 and 45° C. In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 65° C. In another aspect, the thermostability of the variant relative to the parent is determined at pH 6.5 and 70° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C. In another aspect, the thermostability of the variant relative to the parent is determined at pH 6.5 and 95° C.

In another aspect, the thermostability of the variant relative to the parent is determined at pH 7.0 and 45° C. In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 65° C. In another aspect, the thermostability of the variant relative to the parent is determined at pH 7.0 and 70° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C. In another aspect, the thermostability of the variant relative to the parent is determined at pH 7.0 and 95° C.

In another aspect, the thermostability of the variant relative to the parent is determined at pH 7.5 and 45° C. In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 65° C. In another aspect, the thermostability of the variant relative to the parent is determined at pH 7.5 and 70° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C. In another aspect, the thermostability of the variant relative to the parent is determined at pH 7.5 and 95° C.

In another aspect, the thermostability of the variant relative to the parent is determined at pH 8.0 and 45° C. In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 65° C. In another aspect, the thermostability of the variant relative to the parent is determined at pH 8.0 and 70° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C. In another aspect, the thermostability of the variant relative to the parent is determined at pH 8.0 and 95° C.

In another aspect, the thermostability of the variant relative to the parent is determined at pH 8.5 and 45° C. In another aspect, the thermostability of the variant relative to the parent is determined at pH 8.5 and 50° C. In another aspect, the thermostability of the variant relative to the parent is determined at pH 8.5 and 55° C. In another aspect, the thermostability of the variant relative to the parent is determined at pH 8.5 and 60° C. In another aspect, the thermostability of the variant relative to the parent is determined at pH 8.5 and 65° C. In another aspect, the thermostability of the variant relative to the parent is determined at pH 8.5 and 70° C. In another aspect, the thermostability of the variant relative to the parent is determined at pH 8.5 and 75° C. In another aspect, the thermostability of the variant relative to the parent is determined at pH 8.5 and 80° C. In another aspect, the thermostability of the variant relative to the parent is determined at pH 8.5 and 85° C. In another aspect, the thermostability of the variant relative to the parent is determined at pH 8.5 and 90° C. In another aspect, the thermostability of the variant relative to the parent is determined at pH 8.5 and 95° C.

In another aspect, the thermostability of the variant relative to the parent is determined at pH 9.0 and 45° C. In another aspect, the thermostability of the variant relative to the parent is determined at pH 9.0 and 50° C. In another aspect, the thermostability of the variant relative to the parent is determined at pH 9.0 and 55° C. In another aspect, the thermostability of the variant relative to the parent is determined at pH 9.0 and 60° C. In another aspect, the thermostability of the variant relative to the parent is determined at pH 9.0 and 65° C. In another aspect, the thermostability of the variant relative to the parent is determined at pH 9.0 and 70° C. In another aspect, the thermostability of the variant relative to the parent is determined at pH 9.0 and 75° C. In another aspect, the thermostability of the variant relative to the parent is determined at pH 9.0 and 80° C. In another aspect, the thermostability of the variant relative to the parent is determined at pH 9.0 and 85° C. In another aspect, the thermostability of the variant relative to the parent is determined at pH 9.0 and 90° C. In another aspect, the thermostability of the variant relative to the parent is determined at pH 9.0 and 95° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 20 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes. In each of the aspects above the thermostability of the variant relative to the parent can be determined by incubating the variant and parent for any suitable time.

In one aspect, the thermostability of the variant having cellobiohydrolase activity is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 50-fold, at least 75-fold, or at least 100-fold compared to the parent.

Parent Cellobiohydrolases

The parent cellobiohydrolase may be any cellobiohydrolase.

The parent cellobiohydrolase may be (a) a polypeptide having at least 60% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116; (b) a polypeptide encoded by a polynucleotide that hybridizes under low stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115, or (ii) the full-length complement of (i); or (c) a polypeptide encoded by a polynucleotide having at least 60% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

In one aspect, the parent has a sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity.

In another aspect, the amino acid sequence of the parent differs by up to 10 amino acids, e.g., 1, 2, 3, 4, 5, 6, 7, 8, 9, or 10 from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

In another aspect, the parent comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

In another aspect, the parent comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

In another aspect, the parent comprises or consists of amino acids 20 to 456 of SEQ ID NO: 2, amino acids 17 to 447 of SEQ ID NO: 4, amino acids 18 to 481 of SEQ ID NO: 6, amino acids 18 to 482 of SEQ ID NO: 8, amino acids 20 to 454 of SEQ ID NO: 10, amino acids 20 to 463 of SEQ ID NO: 12, amino acids 18 to 399 of SEQ ID NO: 14, amino acids 18 to 400 of SEQ ID NO: 16, amino acids 20 to 450 of SEQ ID NO: 18, amino acids 20 to 457 of SEQ ID NO: 20, amino acids 19 to 468 of SEQ ID NO: 22, amino acids 18 to 403 of SEQ ID NO: 24, amino acids 19 to 484 of SEQ ID NO: 26, amino acids 19 to 464 of SEQ ID NO: 28, amino acids 19 to 485 of SEQ ID NO: 30, amino acids 17 to 385 of SEQ ID NO: 32, amino acids 20 to 457 of SEQ ID NO: 34, amino acids 20 to 457 of SEQ ID NO: 36, amino acids 20 to 455 of SEQ ID NO: 38, amino acids 19 to 469 of SEQ ID NO: 40, amino acids 18 to 487 of SEQ ID NO: 42, amino acids 19 to 471 of SEQ ID NO: 44, amino acids 17 to 401 of SEQ ID NO: 46, amino acids 23 to 408 of SEQ ID NO: 48, amino acids 18 to 386 of SEQ ID NO: 50, amino acids 23 to 399 of SEQ ID NO: 52, amino acids 19 to 469 of SEQ ID NO: 54, amino acids 17 to 400 of SEQ ID NO: 56, amino acids 19 to 459 of SEQ ID NO: 58, amino acids 20 to 393 of SEQ ID NO: 60, amino acids 18 to 403 of SEQ ID NO: 62, amino acids 18 to 492 of SEQ ID NO: 64, amino acids 20 to 459 of SEQ ID NO: 66, amino acids 19 to 470 of SEQ ID NO: 68, amino acids 19 to 480 of SEQ ID NO: 70, amino acids 19 to 470 of SEQ ID NO: 110, amino acids 18 to 394 of SEQ ID NO: 112, amino acids 18 to 469 of SEQ ID NO: 114, or amino acids 19 to 464 of SEQ ID NO: 116.

In another aspect, the parent is a fragment containing at least 85% of the amino acid residues, e.g., at least 90% of the amino acid residues or at least 95% of the amino acid residues of the mature polypeptide of a cellobiohydrolase.

In another embodiment, the parent is an allelic variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115, or the full-length complements thereof (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115, or subsequences thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116, or fragments thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115, or subsequences thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115; (ii) the mature polypeptide coding sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

In another aspect, the nucleic acid probe is nucleotides 58 to 1786 of SEQ ID NO: 1, nucleotides 109 to 1401 of SEQ ID NO: 3, nucleotides 52 to 1443 of SEQ ID NO: 5, nucleotides 52 to 1809 of SEQ ID NO: 7, nucleotides 58 to 1710 of SEQ ID NO: 9, nucleotides 58 to 1392 of SEQ ID NO: 11, nucleotides 52 to 1197 of SEQ ID NO: 13, nucleotides 52 to 1200 of SEQ ID NO: 15, nucleotides 58 to 1350 of SEQ ID NO: 17, nucleotides 58 to 1371 of SEQ ID NO: 19, nucleotides 55 to 1404 of SEQ ID NO: 21, nucleotides 52 to 1209 of SEQ ID NO: 23, nucleotides 55 to 1452 of SEQ ID NO: 25, nucleotides 55 to 1392 of SEQ ID NO: 27, nucleotides 55 to 1455 of SEQ ID NO: 29, nucleotides 49 to 1155 of SEQ ID NO: 31, nucleotides 58 to 1371 of SEQ ID NO: 33, nucleotides 58 to 1371 of SEQ ID NO: 35, nucleotides 58 to 1365 of SEQ ID NO: 37, nucleotides 55 to 1407 of SEQ ID NO: 39, nucleotides 52 to 1461 of SEQ ID NO: 41, nucleotides 55 to 1413 of SEQ ID NO: 43, nucleotides 49 to 1203 of SEQ ID NO: 45, nucleotides 67 to 1224 of SEQ ID NO: 47, nucleotides 52 to 1158 of SEQ ID NO: 49, nucleotides 67 to 1197 of SEQ ID NO: 51, nucleotides 55 to 1407 of SEQ ID NO: 53, nucleotides 49 to 1200 of SEQ ID NO: 55, nucleotides 55 to 1377 of SEQ ID NO: 57, nucleotides 58 to 1179 of SEQ ID NO: 59, nucleotides 52 to 1209 of SEQ ID NO: 61, nucleotides 52 to 1476 of SEQ ID NO: 63, nucleotides 58 to 1377 of SEQ ID NO: 65, nucleotides 55 to 1410 of SEQ ID NO: 67, nucleotides 55 to 1440 of SEQ ID NO: 69, nucleotides 55 to 1575 of SEQ ID NO:109, nucleotides 52 to 1379 of SEQ ID NO: 111, nucleotides 52 to 1659 of SEQ ID NO: 113, or nucleotides 55 to 1895 of SEQ ID NO: 115.

In another aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116; the mature polypeptide thereof; or a fragment thereof.

In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

In another embodiment, the parent is encoded by a polynucleotide having a sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may also be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial cellobiohydrolase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* cellobiohydrolase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* cellobiohydrolase.

In one aspect, the parent is a *Bacillus alkalophilus, Bacillus amyloliquefaciens, Bacillus brevis, Bacillus circulans, Bacillus clausii, Bacillus coagulans, Bacillus firmus,*

*Bacillus lautus, Bacillus lentus, Bacillus licheniformis, Bacillus megaterium, Bacillus pumilus, Bacillus stearothermophilus, Bacillus subtilis*, or *Bacillus thuringiensis* cellobiohydrolase.

In another aspect, the parent is a *Streptococcus equisimilis, Streptococcus pyogenes, Streptococcus uberis*, or *Streptococcus equi* subsp. *Zooepidemicus* cellobiohydrolase.

In another aspect, the parent is a *Streptomyces achromogenes, Streptomyces avermitilis, Streptomyces coelicolor, Streptomyces griseus*, or *Streptomyces lividans* cellobiohydrolase.

The parent may be a fungal cellobiohydrolase. For example, the parent may be a yeast cellobiohydrolase such as a *Candida, Kluyveromyces, Pichia, Saccharomyces, Schizosaccharomyces*, or *Yarrowia* cellobiohydrolase; or a filamentous fungal cellobiohydrolase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* cellobiohydrolase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cellobiohydrolase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus lentulus, Aspergillus nidulans, Aspergillus niger, Aspergillus oryzae, Aspergillus terreus, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fennellia nivea, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium pinophilum, Penicillium purpurogenum, Phanerochaete chrysosporium, Talaromyces leycettanus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* cellobiohydrolase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a cellobiohydrolase variant, comprising: (a) introducing into a parent cellobiohydrolase a substitution at one or more (e.g., several) positions corresponding to positions 112, 154, 197, 228, 261, 306, and 375 of the mature polypeptide of SEQ ID NO: 2, wherein the variant has cellobiohydrolase activity; and (b) recovering the variant. In one aspect, the methods further or even further comprise introducing into the parent cellobiohydrolase a substitution at one or more (e.g., several) positions corresponding to positions 247, 262, 300, 322, 332, 338, and 439 of the mature polypeptide of SEQ ID NO: 2, wherein the variant has cellobiohydrolase activity. In another aspect, the methods further or even further comprise introducing into the parent cellobiohydrolase a substitution at one or more (e.g., several) positions corresponding to positions 256, 287, and 344 of the mature polypeptide of SEQ ID NO: 2, wherein the variant has cellobiohydrolase activity.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998,

*Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding cellobiohydrolase variants of the present invention.

Nucleic Acid Constructs

The present invention also relates to nucleic acid constructs comprising a polynucleotide encoding a cellobiohydrolase variant of the present invention operably linked to one or more control sequences that direct the expression of the coding sequence in a suitable host cell under conditions compatible with the control sequences.

The polynucleotide may be manipulated in a variety of ways to provide for expression of a cellobiohydrolase variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the cellobiohydrolase variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP),

*Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the cellobiohydrolase variant. Any terminator that is functional in the host cell may be used.

Preferred terminators for bacterial host cells are obtained from the genes for *Bacillus* clausii alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the cellobiohydrolase variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the cellobiohydrolase variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a cellobiohydrolase variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a cellobiohydrolase variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the cellobiohydrolase variant and the signal peptide sequence is positioned next to the N-terminus of the propeptide sequence.

It may also be desirable to add regulatory sequences that regulate expression of the cellobiohydrolase variant relative to the growth of the host cell. Examples of regulatory sequences are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a cellobiohydrolase variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the cellobiohydrolase variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a cellobiohydrolase variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a cellobiohydrolase variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a cellobiohydrolase variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis*

*rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a cellobiohydrolase variant, comprising: (a) cultivating a host cell of the present invention under conditions suitable for expression of the variant; and optionally (b) recovering the variant.

The host cells are cultivated in a nutrient medium suitable for production of the cellobiohydrolase variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The cellobiohydrolase variant may be detected using methods known in the art that are specific for the variant. These detection methods include, but are not limited to, use of specific antibodies, formation of an enzyme product, or disappearance of an enzyme substrate. For example, an enzyme assay may be used to determine the activity of the variant. See, for example, the assay described in Example 5.

The cellobiohydrolase variant may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The cellobiohydrolase variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the cellobiohydrolase variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a GH61 polypeptide having cellulolytic enhancing activity, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the cellobiohydrolase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, a GH61 polypeptide having cellulolytic enhancing activity, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the cellobiohydrolase variants, or compositions thereof.

The present invention also relates to processes for degrading or converting a cellulosic material, comprising: treating the cellulosic material with an enzyme composition in the presence of a cellobiohydrolase variant of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a cellobiohydrolase variant of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a cellobiohydrolase variant of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996*, Bioresource Technology* 855: 1-33; Galbe and Zacchi, 2002*, Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N.J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a cellobiohydrolase variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 80° C., e.g., about 30° C. to about 65° C., about 40° C. to about 60° C., or about 50° C. to about 55° C. The pH is in the range of preferably about 3 to about 9, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another preferred aspect, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and the cellobiohydrolase variants depend on several factors including, but not limited to, the mixture of component cellulolytic enzymes and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a cellobiohydrolase variant to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a cellobiohydrolase variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram-negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces* avermitilis, *Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), *Thermoascus crustaceus* (WO 2011/041504), *Aspergillus aculeatus* (WO 2012/0307990, and *Thermomyces lanuginosus* (WO 2012/113340). WO 2012/146171 discloses GH61 polypeptides having cellulolytic enhancing activity and the polynucleotides thereof from *Humicola insolens.*

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4- benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-6}$ to about 1, about $10^{-6}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis, and C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis.*

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophillia*. In another more preferred aspect, the yeast is *Candida pseudotropicalis*. In another more preferred aspect, the yeast is *Candida* scehatae. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum.*

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N.J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine.

In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly (glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to plants, e.g., a transgenic plant, plant part, or plant cell, comprising a polynucleotide of the present invention so as to express and produce a cellobiohydrolase variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988*, Plant Physiology* 86: 506.

For constitutive expression, the 35S-CaMV, the maize ubiquitin 1, or the rice actin 1 promoter may be used (Franck et al., 1980*, Cell* 21: 285-294; Christensen et al., 1992*, Plant Mol. Biol.* 18: 675-689; Zhang et al., 1991*, Plant Cell* 3: 1155-1165). Organ-specific promoters may be, for example, a promoter from storage sink tissues such as seeds, potato tubers, and fruits (Edwards and Coruzzi, 1990*, Ann. Rev. Genet.* 24: 275-303), or from metabolic sink tissues such as meristems (Ito et al., 1994*, Plant Mol. Biol.* 24: 863-878), a seed specific promoter such as the glutelin, prolamin, globulin, or albumin promoter from rice (Wu et al., 1998*, Plant Cell Physiol.* 39: 885-889), a *Vicia faba* promoter from the legumin B4 and the unknown seed protein gene from *Vicia faba* (Conrad et al., 1998*, J. Plant Physiol.* 152: 708-711), a promoter from a seed oil body protein (Chen et al., 1998*, Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993*, Plant Physiol.* 102: 991-1000), the *chlorella* virus adenine methyltransferase gene promoter (Mitra and Higgins, 1994*, Plant Mol. Biol.* 26: 85-93), the aldP gene promoter from rice (Kagaya et al., 1995*, Mol. Gen. Genet.* 248: 668-674), or a wound inducible promoter such as the potato pin2 promoter (Xu et al., 1993*, Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990*, Science* 244: 1293; Potrykus, 1990*, Bio/Technology* 8: 535; Shimamoto et al., 1989*, Nature* 338: 274).

*Agrobacterium tumefaciens*-mediated gene transfer is a method for generating transgenic dicots (for a review, see Hooykas and Schilperoort, 1992*, Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992*, Plant J.* 2: 275-281; Shimamoto, 1994*, Curr. Opin. Biotechnol.* 5: 158-162; Vasil et al., 1992*, Bio/Technology* 10: 667-674). An alternative method for transformation of monocots is based on protoplast transformation as described by Omirulleh et al., 1993*, Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Strains

*Talaromyces byssochlamydoides* CBS 413.71 was used as a source of a cellobiohydrolase gene. *Aspergillus oryzae* MT3568 was used as an expression host for the *Talaromyces byssochlamydoides* CBS 413.71 cellobiohydrolase. *Aspergillus oryzae* MT3568 is an amdS (acetamidase) gene disrupted derivative of *Aspergillus oryzae* JaL355 (WO 2002/40694) in which pyrG auxotrophy was restored in the process of knocking out the *Aspergillus oryzae* amdS gene. *Aspergillus oryzae* strain JaL250 (WO 99/61651) was used as an expression host for the cellobiohydrolase variants.

Media and Reagents

PDA plates were composed of 39 grams of potato dextrose agar and deionized water to 1 liter.

2XYT plates were composed of 16 g of tryptone, 10 g of yeast extract, 5 g of NaCl, 15 g of Bacto agar, and deionized water to 1 liter.

MDU2BP medium was composed of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, 0.5 ml of AMG trace metals solution, and deionized water to 1 liter; pH to 5.0.

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, 3 g of citric acid, and deionized water to 1 liter.

TAE buffer was composed of 4.84 g of Tris base, 1.14 ml of glacial acetic acid, 2 ml of 0.5 M EDTA pH 8.0, and deionized water to 1 liter.

Example 1: PCR Amplification of a Cellobiohydrolase Gene from the Genomic DNA of *Talaromyces byssochlamydoides* CBS 413.71

A cellobiohydrolase gene was amplified by PCR from the genomic DNA of *Talaromyces byssochlamydoides* CBS 413.71 in a two-step process. First, a central fragment of the gene was amplified using degenerate primers designed to match two conserved regions of sequence in genes coding for known Family GH6 cellobiohydrolase enzymes. After amplification of the internal fragment the sequence of the fragment was determined and used to design gene-specific primers for gene walking in both the 5' and 3' directions to obtain the entire coding sequence.

The internal gene fragment was amplified using the degenerate primers 859 and 860 shown below in a touchdown PCR protocol in which the initial annealing temperature of 67° C. was decreased by 1° C. in each successive cycle for a total of 10 cycles, until an annealing temperature of 57° C. was reached. The amplification was then completed with an additional 29 cycles utilizing a 57° C. annealing temperature.

```
Primer 859:
                                   (SEQ ID NO: 71)
TKCCYGAYCGYGAYTGYGC

Primer 860:
                                   (SEQ ID NO: 72)
TCRCCACCKGGCTTKAYCCA
```

The amplification was performed using a REDDYMIX™ PCR Master Mix (ABgene Ltd, Epsom, UK). The amplification reaction was composed of 1 μl of *T. byssochlamydoides* CBS 413.71 genomic DNA as template, 50 μmoles each of primers 859 and 860, and 12.5 μl of REDDYMIX™ PCR Master Mix in a final volume of 25 μl. *T. byssochlamydoides* genomic DNA was extracted from fresh mycelium using the protocol of a FASTDNA® SPIN Kit for Soil (Qbiogene, Inc., Carlsbad, Calif., USA). The amplification was performed in a thermal cycler programmed for an initial template denaturation step at 94° C. for 2 minutes; 11 cycles with denaturing at 94° C. for 45 seconds, annealing at 67° C. for 45 seconds, with a decrease of 1° C. for each subsequent cycle, and elongation at 72° C. for 1 minute; and 29 cycles with denaturing at 94° C. for 45 seconds, annealing at 57° C. for 45 seconds, and an extension at 72° C. for 1 minute. A final elongation was made at 72° C. for 7 minutes.

The reaction products were resolved by 1% agarose gel electrophoresis using TAE buffer where a PCR product band of approximately 700-800 bp was observed. The band was excised from the gel and the DNA purified using an ILLUSTRA™ GFX™ PCR DNA and Gel Band Purification Kit (GE Healthcare, Little Chalfont, UK). The purified PCR fragment was cloned into vector pCR®2.1-TOPO® (Invitrogen, Life Technologies, Carlsbad, Calif., USA) using a TOPO® TA CLONING® Kit (Invitrogen, Life Technologies, Carlsbad, Calif., USA) according to the manufacturer's instructions and then transformed into Chemically Competent *E. coli* cells (Invitrogen, Life Technologies, Carlsbad, Calif., USA) according to the manufacturer's instructions.

The sequence of the PCR product was determined directly with primers 859 and 860, and by sequencing 4 individual clones of the PCR product with M13 forward and M13 reverse vector primers shown below.

```
M13 forward:
                                        (SEQ ID NO: 73)
TGTAAAACGACGGCCAGT

M13 reverse:
                                        (SEQ ID NO: 74)
AGCGGATAACAATTTCACACAGG
```

The sequence was compared to known sequences using the BLAST search tool (Altschul et al., 1990, *J. Mol. Biol.* 215: 403-410) and confirmed to be similar to known cellobiohydrolase encoding genes.

The partial sequence of the *Talaromyces byssochlamydoides* cellobiohydrolase gene was used to design the gene specific primers 934, 935, 1044, and 1045 shown below to enable gene walking from both ends of the sequence.

```
Primer 934:
                                        (SEQ ID NO: 75)
AGAGTCTCGTCTCAGTACATG

Primer 935:
                                        (SEQ ID NO: 76)
CGAATACGTCACCAGCCAC

Primer 1044:
                                        (SEQ ID NO: 77)
AATTGCTGAGCTGTTTCAGC

Primer 1045:
                                        (SEQ ID NO: 78)
TGACTGGTGCAACGTGATCG
```

Gene walking was performed using a DNA Walking SPEEDUP™ Premix Kit (Seegene, Seoul, Korea) based on the manufacturer's protocol with some minor differences. Only the first two sets of PCR reactions described in the protocol were utilized, which included one initial set of amplifications with a gene-specific primer and four different return primers and one set of nested reactions with a second gene-specific primer. Half of the recommended reaction volumes were used for the first set of reactions.

For gene walking in the 5' direction, the first set of PCR reactions was performed with the gene-specific primer 934. After amplification, the reactions were diluted with 150 μl of water, and 5 μl of the dilutions were used as template in the second nested set of PCR reactions with the gene-specific primer 935. The second amplifications were performed as described by the DNA Walking SPEEDUP™ Premix Kit protocol with a 58° C. annealing temperature. Reaction products were resolved by 1% agarose gel electrophoresis using TAE buffer, where a faint single band was observed at approximately 1000 bp in one of the four nested reactions. The 1000 bp fragment was re-amplified twice, first by repeating the nested PCR reaction using 1 μl of the reaction including the 1000 bp product as template. The reaction products were resolved by 1% agarose gel electrophoresis using TAE buffer, and a second re-amplification was made from this reaction by removing a small piece of the 1000 bp band from the gel with a pipette tip, which was used as template in a PCR reaction under the same conditions. The reaction products were resolved by 1% agarose gel electrophoresis using TAE buffer and the 1000 bp band was excised from the gel and the DNA purified using an ILLUSTRA™ GFX™ PCR DNA and Gel Band Purification Kit. The sequence of the PCR product was determined using primer 935.

For gene walking in the 3' direction, the first set of PCR reactions was performed with the gene-specific primer 1044. After amplification, the reactions were diluted with 150 μl of water, and 5 μl of the dilutions were used as template in the second nested set of PCR reactions with the gene-specific primer 1045. The second amplifications were performed as described by the DNA Walking SPEEDUP™ Premix Kit protocol with a 56° C. annealing temperature. The reaction products were purified from the PCR reaction components using an ILLUSTRA™ GFX™ PCR DNA and Gel Band Purification Kit and concentrated by eluting in 10 μl of elution buffer supplied with the Kit. The products were analyzed by first cloning 4 μl of each purified PCR reaction directly into pCR®2.1-TOPO® using a TOPO® TA CLONING® Kit reaction and transforming the reactions into TOP10 Chemically Competent *E. coli* cells according to the manufacturers' instructions. The clones obtained were screened for inserts by restriction digestion, and those containing inserts were sequenced with M13 forward (SEQ ID NO: 73) and M13 reverse (SEQ ID NO: 74) vector primers. Four individual clones each of approximately 800 bp provided the 3' sequence for the *T. byssochlamydoides* cellobiohydrolase gene. All sequences were assembled into a single contig.

The genomic DNA sequence and deduced amino acid sequence of the *Talaromyces byssochlamydoides* cellobiohydrolase encoding sequence are shown in SEQ ID NO: 1 and SEQ ID NO: 2, respectively. The genomic DNA sequence of 1789 bp (including the stop codon) contains 7 introns located at nucleotides 80 to 131, 201 to 253, 540 to 592, 847 to 897, 1036 to 1095, 1354 to 1443, and 1686 to 1744 of SEQ ID NO: 1. The genomic DNA fragment encodes a polypeptide of 456 amino acids. The % G+C content of the mature polypeptide coding sequence is 56%. Using the SignalP software program (Nielsen et al., 1997, *Protein Engineering* 10:1-6), a signal peptide of 19 residues was predicted. The predicted mature protein contains 437 amino acids with a predicted molecular mass of 46 kDa and an isoelectric point of 4.0. The protein contains a carbohydrate binding module of the CBM1 type at the N terminus (amino acids 20 to 56 of SEQ ID NO: 2). The catalytic domain is amino acids 397 to 1786.

Example 2: Cloning of the *Talaromyces byssochlamydoides* Cellobiohydrolase Encoding Sequence into an *Aspergillus* Expression Vector The *T. byssochlamydoides* cellobiohydrolase encoding sequence was cloned into the *Aspergillus* expression vector pMStr57 (WO 2004/032648) by amplifying the protein coding sequence from genomic DNA using two synthetic oligonucleotide primers shown below. Vector pMStr57 contains sequences for selection and propagation in *E. coli*, and selection and expression in *Aspergillus*. Selection in *Aspergillus* is facilitated by the amdS gene of *Aspergillus nidulans*, which allows the use of acetamide as a sole nitrogen source. Expression in *Aspergillus* is mediated by a modified neutral amylase II (NA2) promoter from *Aspergillus niger* which is fused to the 5' leader sequence of the triose phosphate isomerase (tpi) encoding-gene from *Aspergillus nidulans*, and the terminator of the amyloglucosidase-encoding gene from *Aspergillus niger*.

```
Primer 1167:
                                        (SEQ ID NO: 79)
ACACAACTGGGGATCCTCACCATGCGAAATATTCTTG

Primer 1168:
                                        (SEQ ID NO: 80)
CCCTCTAGATCTCGAGCTAGAATGACGGATTGGCGTT
```

The amplification was performed using the IPROOF™ High Fidelity 2× Master Mix (Bio-Rad Laboratories, Inc., Hercules, Calif., USA) following the manufacturer's instructions. The amplification reaction was composed of *T.*

*byssochlamydoides* CBS 413.71 genomic DNA as template, 25 pmol each of primers 1167 and 1168, and 25 μl of IPROOF™ High Fidelity 2× Master Mix in a final volume of 50 μl. The amplification was performed in a thermal cycler programmed for an initial template denaturation step at 98° C. for 2 minutes; 5 cycles each with denaturing at 98° C. for 10 seconds, annealing at 65° C. for 10 seconds, and elongation at 72° C. for 1 minute; and 30 cycles each with denaturing at 98° C. for 10 seconds and a combined annealing extension at 72° C. for 1 minute. A final elongation was performed at 72° C. for 10 minutes.

A PCR product of approximately 2000 bp was separated from residual reaction components using an ILLUSTRA™ GFX™ PCR DNA and Gel Band Purification Kit according to the manufacturer's instructions. The purified PCR fragment was sequenced, and the sequence agreed with the sequence of SEQ. ID NO. 1.

The PCR fragment was cloned into Bam HI and Xho I digested pMStr57 using an IN-FUSION™ Dry-Down PCR Cloning Kit (Clontech Laboratories, Inc., Mountain View, Calif., USA) according to the manufacturer's instructions. The *Talaromyces byssochlamydoides* cellobiohydrolase encoding DNA of the resulting *Aspergillus* expression construct, pMStr215, was sequenced and the sequence agreed with the sequence of SEQ ID NO: 1.

Example 3: Expression of the *Talaromyces byssochlamydoides* Cellobiohydrolase Coding Sequence in *Aspergillus oryzae* MT3568

The fungal expression host *Aspergillus oryzae* strain MT3568 was transformed with pMStr215 according to Christensen et al., 1988, *Biotechnology* 6, 1419-1422 and WO 2004/032648. Eight transformants were each cultured for 4 days at 30° C. in 750 μl of DAP2C-1 medium (WO 2004/032648). Samples were analyzed by SDS-PAGE using E-PAGE™ 48 8% gels with SEEBLUE® Plus2 molecular weight standards (Invitrogen, Life Technologies, Carlsbad, Calif., USA) according to the manufacturer's instructions. The gel was stained with INSTANTBLUE™ (Expedeon Protein Solutions, Cambridge, UK). Six transformants produced a novel protein band at approximately 55 kDa.

Two of the transformants, designated *Aspergillus oryzae* MStr390 and MStr391, were isolated twice by dilution streaking conidia on selective medium (amdS) containing 0.01% TRITON® X-100 to limit colony size.

Example 4: Construction of a Plasmid for Expression of the *Talaromyces byssochlamydoides* Family GH6A Cellobiohydrolase II Gene in *Trichoderma reesei* Host Two synthetic oligonucleotide primers shown below were designed to amplify the full-length open reading frame of the *Talaromyces byssochlamydoides* GH6A cellobiohydrolase II coding sequence from pMStr215. An IN-FUSION™ Cloning Kit (Clontech Laboratories Inc., Mountain View, Calif., USA) was used to clone the fragment into plasmid pMJ09 (WO 2005/056772).

In-Fusion Forward primer:
(SEQ ID NO: 81)
5'-CAACCGCGGACTGCGCACCATGCGAAATATTCTTGCTCTTG-3'

In-Fusion Reverse primer:
(SEQ ID NO: 82)
5'-CAGGCTTTCGCCACGGAGCTTACTAGAATGACGGATTGGCG-3'

Bold letters represent coding sequence. The remaining sequence contains sequence identity to the insertion sites of plasmid pJM09.

Fifty picomoles of each of the primers above were used in a PCR reaction composed of approximately 150 ng of plasmid pMStr215, 1× EXPAND® High Fidelity PCR DNA polymerase buffer with 1.5 mM $MgCl_2$ (Roche Applied Science, Mannheim, Germany), 1.0 μl of a 10 mM blend of dATP, dTTP, dGTP, and dCTP, and 0.5 units of PHUSION® DNA polymerase (New England Biolabs Inc., Ipswich, Mass., USA) in a final volume of 50 μl. The amplification reaction was performed in an EPPENDORF® MASTERCYCLER® 5333 (Eppendorf Scientific, Inc., Westbury, N.Y., USA) programmed for 1 cycle at 94° C. for 2 minutes; and 30 cycles each at 98° C. for 10 seconds, 55° C. for 30 seconds, and 72° C. for 30 minutes. After the 30 cycles, the reaction was incubated at 72° C. for 10 minutes. The resulting PCR reaction product was restriction digested by adding 20 units of Dpn 1 (New England Biolabs, MA, USA) for 1 hour at 37° C. to digest any remaining plasmid pMStr215 and then purified using a NUCLEOSPIN® PCR Clean-up Kit (Macherey-Nagel, Duren, Germany), according to manufacturer's protocol.

Plasmid pMJ09 was linearized by digestion with Nco I and Pac I. The fragment was purified using a PCR Cleanup Kit (QIAGEN Inc., Valencia, Calif., USA) according to manufacturer's protocol. Cloning of the purified PCR fragment into the linearized and purified pMJ09 vector was performed using an IN-FUSION™ Cloning Kit. The reaction (10 μl) was composed of 1×IN-FUSION™ Buffer (Clontech Laboratories Inc., Mountain View, Calif., USA), 1×BSA (Clontech Laboratories Inc., Mountain View, Calif., USA), 1 μl of IN-FUSION™ enzyme (Clontech Laboratories Inc., Mountain View, Calif., USA), 145 ng of pMJ09 digested with Nco I and Pac I, and approximately 150 ng of the *Talaromyces byssochlamydoides* purified PCR product. The reaction was incubated at 50° C. for 15 minutes and 15 minutes at 37° C. A 2 μl sample of the reaction was used to transform XL-10 GOLD® *E. coli* competent cells (Stratagene, La Jolla, Calif., USA) according to the manufacturer's instructions. After a recovery period, 175 μl of the transformation reaction was spread onto 150 mm 2XYT plates supplemented with 100 μg of ampicillin per ml. The plates were incubated overnight at 37° C. Transformants were selected at random from the selection plates and plasmid DNA was prepared from each one using a BIOROBOT® 9600 (QIAGEN Inc., Valencia, Calif., USA. Clones were analyzed by Sac I restriction digestion. Clones with the expected restriction digestion pattern were sequenced using a 3130xl Genetic Analyzer (Applied Biosystems, Inc., Foster City, Calif., USA) to verify the changes and correct insertion into the pMJ09 plasmid. One of the plasmids was chosen and designated pAJ226.

Example 5: Construction of the *Talaromyces byssochlamydoides* Family GH6A Cellobiohydrolase II Gene Mutants Variants of the *Talaromyces byssochlamydoides* GH6A cellobiohydrolase II were constructed by performing site-directed mutagenesis on pAJ226 (Example 4) using a QUIKCHANGE® XL Site-Directed Mutagenesis Kit (Stratagene, La Jolla, Calif., USA). A summary of the oligos used for the site-directed mutagenesis and the variants obtained are shown in Table 1.

The resulting mutant plasmid DNAs were prepared using a BIOROBOT® 9600 and sequenced using a 3130xl Genetic Analyzer to verify the changes.

TABLE 1

| Amino acid changes | Primer name | Sequences | Cloning Plasmid Name |
|---|---|---|---|
| D332N | MaWo236 | cgtcgtacacgcagggcAactccaactgcgatg (SEQ ID NO: 83) | pMaWo92 |
| | MaWo237 | catcgcagttggagtTgccctgcgtgtacgacg (SEQ ID NO: 84) | |
| C256L | MaWo244 | cgcagagagcgcgtatttggagCTcatcaactatgcgataacgaagc (SEQ ID NO: 85) | pMaWo95 |
| | MaWo245 | gcttcgttatcgcatagttgatgAGctccaaatacgcgctctctgcg (SEQ ID NO: 86) | |
| V154M | MaWo250 | gccaaggtgcctaccAtgggcgagtatctgg (SEQ ID NO: 87) | pMaWo98 |
| | MaWo251 | ccagatactcgcccaTggtaggcaccttggc (SEQ ID NO: 88) | |
| I228V | MaWo252 | gtccacaccatcctgGtcattggtacgtcggc (SEQ ID NO: 89) | pMaWo99 |
| | MaWo253 | gccgacgtaccaatgaCcaggatggtgtggac (SEQ ID NO: 90) | |
| S306A | MaWo254 | ctcatcgccggctGccgtgcgcggtctgg (SEQ ID NO: 91) | pMaWo100 |
| | MaWo255 | ccagaccgcgcacggCagccggcgatgag (SEQ ID NO: 92) | |
| L344F | MaWo258 | ggactatgtgaatgccTtCggaccactggtcgcggcgc (SEQ ID NO: 93) | pMaWo102 |
| | MaWo259 | gcgccgcgaccagtggtccGaAggcattcacatagtcc (SEQ ID NO: 94) | |
| I261L | MaWo260 | ggagtgcatcaactatgcgCtaacgaagctcaacctgcc (SEQ ID NO: 95) | pMaWo103 |
| | MaWo261 | ggcaggttgagcttcgttaGcgcatagttgatgcactcc (SEQ ID NO: 96) | |
| T262K | MaWo264 | gtgcatcaactatgcgataaAgaagctcaacctgcccaatgtg (SEQ ID NO: 97) | pAJ235 |
| | MaWo265 | cacattgggcaggttgagcttcTttatcgcatagttgatgcac (SEQ ID NO: 98) | |
| V322I | MaWo266 | ctacaacgcctggaccAtcagtccgtgcccgtc (SEQ ID NO: 99) | pAJ234 |
| | MaWo267 | gacgggcacggactgaTggtccaggcgttgtag (SEQ ID NO: 100) | |
| Y112H | MaWo272 | ctaccagctctatgccaatccgCactattcgtctgaagtgtacactttg (SEQ ID NO: 101) | pMaWo105 |
| | MaWo273 | caaagtgtacacttcagacgaatagtGcggattggcatagagctggtag (SEQ ID NO: 102) | |

TABLE 1-continued

| Amino acid changes | Primer name | Sequences | Cloning Plasmid Name |
|---|---|---|---|
| G375E | MaWo274 | cccacccagcaacaacaatgggAGgactggtgcaacgtgatcggc (SEQ ID NO: 103) | pMaWo106 |
| | MaWo275 | gccgatcacgttgcaccagtcCTcccattgttgttgctgggtggg (SEQ ID NO: 104) | |
| S197Y | MaWo278 | agcagccagcaatggagaattctAcattgccgacaatggagtcgcc (SEQ ID NO: 105) | pMaWo108 |
| | MaWo279 | ggcgactccattgtcggcaatgTagaattctccattgctggctgct (SEQ ID NO: 106) | |

Example 6: Construction of Plasmids for Expression of *Talaromyces byssochlamydoides* Family GH6A Cellobiohydrolase II Gene Variants in *Aspergillus oryzae* Host Two synthetic oligonucleotide primers shown below were designed to amplify full-length open reading frames encoding the *Talaromyces byssochlamydoides* GH6A cellobiohydrolase II variants from Example 5. The templates used and the name of the resulting plasmids are shown in Table 2. An IN-FUSION™ Cloning Kit was used to clone each of the PCR products into pAlLo2 (WO 2004/099228).

In-Fusion Forward primer:
(SEQ ID NO: 107)
5'-ACTGGATTTACCATGCGAAATATTCTTGCTC-3'

In-Fusion Reverse primer:
(SEQ ID NO: 108)
5'-AGTCACCTCTAGTTACTAGAATGACGGATTGGC-3'

Bold letters represent coding sequence. The remaining sequence contains sequence identity to the insertion sites of pAlLo2 (WO 2005/074747).

Thirty-eight picomoles of each of the primers above were used in a PCR reaction composed of 40 ng of *Talaromyces byssochlamydoides* mutant DNA as indicated in Table 2, 1× PLATINUM® Pfx DNA polymerase buffer (Invitrogen, Carlsbad, Calif., USA), 1 mM magnesium sulfate, 1.5 μl of a 10 mM blend of dATP, dTTP, dGTP, and dCTP, and 2.5 units of PLATINUM® Pfx DNA polymerase (Invitrogen, Carlsbad, Calif., USA) in a final volume of 50 μl. The amplification reaction was performed in an EPPENDORF® MASTERCYCLER® 5333 programmed for 1 cycle at 94° C. for 2 minutes; and 30 cycles each at 94° C. for 15 seconds, 55° C. for 30 seconds, and 68° C. or 72° C. for 1.5 or 2 minutes. After the 30 cycles, the reaction was incubated at 68° C. for 10 minutes and then cooled at 4° C. until further processed. The resulting PCR reaction products were purified using a QIAGEN® PCR Cleanup Kit according to manufacturer's protocol. In some cases the PCR reaction product was restriction digested by adding 20 units of Dpn 1 for 1 hour at 37° C. to digest any remaining pAlLo2 and then purified using a NUCLEOSPIN® PCR Clean-up Kit according to manufacturer's protocol.

Plasmid pAlLo2 was linearized by digestion with Nco I and Pac I. The plasmid fragment was purified using a QIAGEN® PCR Cleanup Kit according to manufacturer's protocol. Cloning of each purified PCR fragment into the linearized and purified pAlLo2 vector was performed using an IN-FUSION™ Cloning Kit. The reaction (10 μl) was composed of 1×IN-FUSION™ Buffer, 1×BSA, 1 μl of IN-FUSION™ enzyme, 100 ng of pAlLo2 digested with Nco I and Pac I, and approximately 50 ng or 100 ng of each purified PCR product. The reactions were incubated at 50° C. for 15 minutes and 15 minutes at 37° C. A 2 μl sample of each reaction was used to transform XL-10 GOLD® or XL1-Blue *E. coli* competent cells (Stratagene, La Jolla, Calif., USA) according to the manufacturer's instructions. After a recovery period, 175 μl of the transformation reactions were spread onto 150 mm 2XYT plates supplemented with 100 μg of ampicillin per ml. The plates were incubated overnight at 37° C. Putative recombinant clones were selected at random from the selection plates and plasmid DNA was prepared from each one using a BIOROBOT® 9600. Clones were analyzed by Bam HI and Sna BI or Eco RI restriction digestion. Clones with the expected restriction digestion pattern were sequenced using a 3130xl Genetic Analyzer to verify the changes and correct insertion into pAlLo2. The resulting plasmids are summarized in Table 2.

TABLE 2

| Template | Resulting Plasmid |
|---|---|
| pMaWo92 | pMaWo92Ao |
| pMaWo95 | pMaWo95Ao |
| pMaWo98 | pMaWo98Ao |
| pMaWo99 | pMaWo99Ao |
| pMaWo100 | pMaWo100Ao |
| pMaWo102 | pMaWo102Ao |
| pMaWo103 | pMaWo103Ao |
| pAJ235 | pAJ238 |
| pAJ234 | pAJ240 |
| pMaWo105 | pMaWo105Ao |
| pMaWo106 | pMaWo106Ao |
| pMaWo108 | pMaWo108Ao |

Example 7: Expression of the *Talaromyces byssochlamydoides* Wild-Type GH6A Cellobiohydrolase II and Cellobiohydrolase II Variants Thereof in *Aspergillus oryzae* JaL250

*Aspergillus oryzae* JaL250 (WO 99/061651) protoplasts prepared according to the method of Christensen et al., 1988, Bio/Technology 6: 1419-1422, were transformed with 5 μg of pMaWo92Ao, pMaWo95Ao, pMaWo98Ao, pMaWo99Ao, pMaWo100Ao, pMaWo102Ao, pMaWo103Ao, pAJ238, pAJ240, pMaWo105Ao, pMaWo106Ao, or pMaWo108Ao, which yielded about 1-10 transformants for each vector. Up to ten transformants for each transformation were isolated to individual PDA plates.

Confluent PDA plates of the variant transformants and *Aspergillus oryzae* MStr391 (Example 3) were washed with 8 ml of 0.01% TWEEN® 20 and inoculated separately into 1 ml of MDU2BP medium in sterile 24 well tissue culture plates and incubated at 34° C. Three to five days after incubation, 20 μl of harvested broth from each culture were analyzed by SDS-PAGE using 8-16% Tris-Glycine gels (Invitrogen, Carlsbad, Calif., USA) according to the manufacturer's instructions. SDS-PAGE profiles of the cultures showed that several transformants had a new major band at approximately 75 kDa.

A confluent plate of one transformant for each transformation (grown on a PDA plate) was washed with 8 ml of 0.01% TWEEN® 20 and inoculated into 125 ml plastic shake flasks containing 25 ml of MDU2BP medium and incubated at 34° C., either stationary or at 200 rpm, to generate broth for characterization of the variants. The flasks were harvested on day 3 to 5 and filtered using a 0.22 μm STERICUP® Filter Unit (Millipore, Bedford, Mass., USA).

Example 8: Measuring Thermostability of *Talaromyces byssochlamydoides* Family GH6A Cellobiohydrolase II Variants Three ml of filtered broth for each of the cultures from Example 7 were desalted into 100 mM NaCl-50 mM sodium acetate pH 5.0 using ECONO-PAC® 10DG Desalting Columns (Bio-Rad Laboratories, Inc., Hercules, Calif., USA). Protein in the desalted broths was concentrated to a 0.5 ml volume using VIVASPIN® 6 (5 kDa cutoff) ultrafilters (Argos Technology, Elgin, Ill., USA).

The concentrated broths were diluted to 1 mg/ml protein concentration using 100 mM NaCl-50 mM sodium acetate pH 5.0. Protein concentration was determined at 280 nm (1.9 $A_{280}$=1 mg/ml). Two 25 μl aliquots of each 1 mg/ml protein sample were added to THERMOWELL® tube strip PCR tubes (Corning, Corning, N.Y., USA). One aliquot was kept on ice while the other aliquot was heated in an EPPENDORF® MASTERCYCLER® ep gradient S thermocycler (Eppendorf Scientific, Inc., Westbury, N.Y., USA) for 20 minutes at 67° C. and then cooled to 4° C. before being placed on ice. Both samples were then diluted with 175 μl of 0.0114% TWEEN® 20-100 mM NaCl-50 mM sodium acetate pH 5.0.

Residual activity of the heated samples was then measured by determining the activity of the heated samples and the samples kept on ice in the hydrolysis of phosphoric acid swollen cellulose (PASC). Ten microliters of each sample were added in triplicate to a 96 well PCR plate (Eppendorf Scientific, Inc., Westbury, N.Y., USA). Then 190 μl of 2.1 g/l PASC in 0.01% TWEEN®-20-50 mM sodium acetate pH 5.0 were added to 10 μl of sample and mixed. Glucose standards at 100, 75, 50, 25, 12.5 and 0 mg per liter in 50 mM sodium acetate pH 5.0 buffer were added in duplicate at 200 μl per well. The resulting mixtures were incubated for 30 minutes at 50° C. in an EPPENDORF® MASTERCYCLER® ep gradient S thermocycler. The reactions were stopped by addition of 50 μl of 0.5 M NaOH to each well, including the glucose standards. The plate was then centrifuged in a SORVALL® RT 6000D centrifuge (Thermo Scientific, Waltham, Mass., USA) with a SORVALL® 1000B rotor equipped with a microplate carrier (Thermo Scientific, Waltham, Mass., USA) for 2 minutes at 2,000 rpm.

Activity on PASC was determined by measuring reducing ends released during the minute hydrolysis at 50° C. One hundred microliters of each supernatant from the centrifuged plate were transferred to a separate 96-well PCR plate. Fifty microliters of 1.5% (w/v) PHBAH (4-hydroxy-benzhydride, Sigma Chemical Co., St. Louis, Mo., USA) in 0.5 M NaOH were added to each well. The plate was then heated in an EPPENDORF® MASTERCYCLER® ep gradient S thermocycler at 95° C. for 15 minutes and then 15° C. for 5 minutes. A total of 100 μl of each sample was transferred to a clear, flat-bottom 96-well plate (Corning, Inc., Corning, N.Y., USA). The absorbance at 410 nm was then measured using a SPECTRAMAX® 340pc spectrophotometric plate reader (Molecular Devices, Sunnyvale, Calif., USA). The concentration of reducing ends released was determined from a straight-line fit to the concentration of reducing ends released versus the absorbance at 410 nm for the glucose standards. Residual activity was then calculated by dividing the reducing ends released from PASC hydrolyzed by a heated sample by the reducing ends released from PASC hydrolyzed by a sample that was kept on ice. The ratio of the residual activity of a variant to the residual activity of the parent enzyme is a measure of thermostability of the enzyme. Variants having a value greater than 1 are more thermostable than the parent enzyme.

The results shown in FIG. 2 demonstrated an increase in thermostability by a higher residual activity for the indicated variants compared to the parent enzyme.

The present invention is further described by the following numbered paragraphs:

[1] A cellobiohydrolase variant, comprising a substitution at one or more positions corresponding to positions 112, 154, 197, 228, 261, 306, and 375 of the mature polypeptide of SEQ ID NO: 2, wherein the variant has cellobiohydrolase activity.

[2] The variant of paragraph 1, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100%, sequence identity to the amino acid sequence of a parent cellobiohydrolase.

[3] The variant of paragraph 1 or 2, which is a variant of a parent cellobiohydrolase selected from the group consisting of: (a) a polypeptide having at least 60% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116; (b) a polypeptide encoded by a polynucleotide that hybridizes under at least low stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115, or (ii) the full-length complement of (i); (c) a polypeptide encoded by a polynucleotide having at least 60% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115; and (d) a fragment of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116, which has cellobiohydrolase activity.

[4] The variant of paragraph 3, wherein the parent cellobiohydrolase has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99% or 100% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

[5] The variant of paragraph 3, wherein the parent cellobiohydrolase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115 or (ii) the full-length complement of (i).

[6] The variant of paragraph 3, wherein the parent cellobiohydrolase is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, at least 99%, or 100% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

[7] The variant of paragraph 3, wherein the parent cellobiohydrolase comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

[8] The variant of paragraph 3, wherein the parent cellobiohydrolase is a fragment of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116, wherein the fragment has cellobiohydrolase activity.

[9] The variant of any of paragraphs 1-8, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 95%, at least 96%, at least 97%, at least 98%, or at least 99%, but less than 100% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

[10] The variant of any of paragraphs 2-9, wherein the variant consists of at least 85% of the amino acid residues, e.g., at least 90% of the amino acid residues or at least 95% of the amino acid residues of the mature polypeptide of the parent cellobiohydrolase.

[11] The variant of any of paragraphs 1-10, wherein the number of substitutions is 1-7, e.g., 1, 2, 3, 4, 5, 6, or 7 substitutions.

[12] The variant of any of paragraphs 1-11, which comprises a substitution at a position corresponding to position 112.

[13] The variant of paragraph 12, wherein the substitution is His.

[14] The variant of any of paragraphs 1-13, which comprises a substitution at a position corresponding to position 154.

[15] The variant of paragraph 14, wherein the substitution is Met.

[16] The variant of any of paragraphs 1-15, which comprises a substitution at a position corresponding to position 197.

[17] The variant of paragraph 16, wherein the substitution is Tyr.

[18] The variant of any of paragraphs 1-17, which comprises a substitution at a position corresponding to position 228.

[19] The variant of paragraph 18, wherein the substitution is Val.

[20] The variant of any of paragraphs 1-19, which comprises a substitution at a position corresponding to position 261.

[21] The variant of paragraph 20, wherein the substitution is Leu.

[22] The variant of any of paragraphs 1-21, which comprises a substitution at a position corresponding to position 306.

[23] The variant of paragraph 22, wherein the substitution is Ala.

[24] The variant of any of paragraphs 1-23, which comprises a substitution at a position corresponding to position 375.

[25] The variant of paragraph 24, wherein the substitution is Glu.

[26] The variant of any of paragraphs 1-25, which comprises a substitution at two positions corresponding to any of positions 112, 154, 197, 228, 261, 306, and 375.

[27] The variant of any of paragraphs 1-25, which comprises a substitution at three positions corresponding to any of positions 112, 154, 197, 228, 261, 306, and 375.

[28] The variant of any of paragraphs 1-25, which comprises a substitution at four positions corresponding to any of positions 112, 154, 197, 228, 261, 306, and 375.

[29] The variant of any of paragraphs 1-25, which comprises a substitution at five positions corresponding to any of positions 112, 154, 197, 228, 261, 306, and 375.

[30] The variant of any of paragraphs 1-25, which comprises a substitution at six positions corresponding to any of positions 112, 154, 197, 228, 261, 306, and 375.

[31] The variant of any of paragraphs 1-25, which comprises a substitution at each position corresponding to positions 112, 154, 197, 228, 261, 306, and 375.

[32] The variant of any of paragraphs 1-31, which comprises one or more substitutions selected from the group consisting of Y112H, V154M, S197Y, I228V, I261L, S306A, and G375E.

[33] The variant of any of paragraphs 1-32, which further comprises a substitution at one or more positions corresponding to positions 247, 262, 300, 322, 332, 338, and 439 of the mature polypeptide of SEQ ID NO: 2, wherein the variant has cellobiohydrolase activity.

[34] The variant of paragraph 33, wherein the number of substitutions is 1-7, e.g., such as 1, 2, 3, 4, 5, 6, or 7 substitutions.

[35] The variant of paragraph 33 or 34, which further comprises a substitution at a position corresponding to position 247.

[36] The variant of paragraph 35, wherein the substitution is Ser.

[37] The variant of any of paragraphs 33-36, which further comprises a substitution at a position corresponding to position 262.

[38] The variant of paragraph 37, wherein the substitution is Lys.

[39] The variant of any of paragraphs 33-38, which further comprises a substitution at a position corresponding to position 300.

[40] The variant of paragraph 39, wherein the substitution is Asp.

[41] The variant of any of paragraphs 33-40, which further comprises a substitution at a position corresponding to position 322.

[42] The variant of paragraph 41, wherein the substitution is Ile.

[43] The variant of any of paragraphs 33-42, which further comprises a substitution at a position corresponding to position 332.

[44] The variant of paragraph 43, wherein the substitution is Asp.

[45] The variant of any of paragraphs 33-44, which further comprises a substitution at a position corresponding to position 338.

[46] The variant of paragraph 45, wherein the substitution is Lys.

[47] The variant of any of paragraphs 33-46, which further comprises a substitution at a position corresponding to position 439.

[48] The variant of paragraph 47, wherein the substitution is Gln.

[49] The variant of any of paragraphs 33-48, which further comprises a substitution at two positions corresponding to any of positions 247, 262, 300, 322, 332, 338, and 439.

[50] The variant of any of paragraphs 33-48, which further comprises a substitution at three positions corresponding to any of positions 247, 262, 300, 322, 332, 338, and 439.

[51] The variant of any of paragraphs 33-48, which further comprises a substitution at four positions corresponding to any of positions 247, 262, 300, 322, 332, 338, and 439.

[52] The variant of any of paragraphs 33-48, which further comprises a substitution at five positions corresponding to any of positions 247, 262, 300, 322, 332, 338, and 439.

[53] The variant of any of paragraphs 33-48, which further comprises a substitution at six positions corresponding to any of positions 247, 262, 300, 322, 332, 338, and 439.

[54] The variant of any of paragraphs 33-48, which further comprises a substitution at each position corresponding to positions 247, 262, 300, 322, 332, 338, and 439.

[55] The variant of any of paragraphs 33-54, which further comprises one or more substitutions selected from the group consisting of A247S, T262K, N300D, V322I, D332N, E338K, and T439.

[56] The variant of any of paragraphs 1-55, which further comprises a substitution at one or more positions corresponding to positions 256, 287, and 344 of the mature polypeptide of SEQ ID NO: 2, wherein the variant has cellobiohydrolase activity.

[57] The variant of paragraph 56, wherein the number of substitutions is 1-3, e.g., such as 1, 2, or 3 substitutions.

[58] The variant of paragraph 56 or 57, which further comprises a substitution at a position corresponding to position 256.

[59] The variant of paragraph 58, wherein the substitution is Leu.

[60] The variant of any of paragraphs 56-59, which further comprises a substitution at a position corresponding to position 287.

[61] The variant of paragraph 60, wherein the substitution is Ile.

[62] The variant of any of paragraphs 56-61, which further comprises a substitution at a position corresponding to position 344.

[63] The variant of paragraph 62, wherein the substitution is Phe.

[64] The variant of any of paragraphs 56-63, which further comprises a substitution at two positions corresponding to any of positions 256, 287, and 344.

[65] The variant of any of paragraphs 56-63, which further comprises a substitution at each position corresponding to positions 256, 287, and 344.

[66] The variant of any of paragraphs 56-65, which further comprises one or more substitutions selected from the group consisting of C256L, L287I, and L344F.

[67] The variant of any of paragraphs 1-66, which has an increased thermostability of at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 50-fold, at least 75-fold, or at least 100-fold compared to the parent.

[68] An isolated polynucleotide encoding the variant of any of paragraphs 1-67.

[69] A nucleic acid construct comprising the polynucleotide of paragraph 68.

[70] An expression vector comprising the polynucleotide of paragraph 68.

[71] A host cell comprising the polynucleotide of paragraph 68.

[72] A method of producing a cellobiohydrolase variant, comprising: cultivating the host cell of paragraph 71 under conditions suitable for expression of the variant.

[73] The method of paragraph 72, further comprising recovering the variant.

[74] A transgenic plant, plant part or plant cell transformed with the polynucleotide of paragraph 68.

[75] A method of producing a variant of any of paragraphs 1-67, comprising: cultivating a transgenic plant or a plant cell comprising a polynucleotide encoding the variant under conditions conducive for production of the variant.

[76] The method of paragraph 75, further comprising recovering the variant.

[77] A method for obtaining a cellobiohydrolase variant, comprising introducing into a parent cellobiohydrolase a substitution at one or more positions corresponding to positions 112, 154, 197, 228, 261, 306, and 375 of the mature polypeptide of SEQ ID NO: 2, wherein the variant has cellobiohydrolase activity; and recovering the variant.

[78] The method of paragraph 77, further comprising introducing into the parent cellobiohydrolase a substitution at one or more (e.g., several) positions corresponding to positions 247, 262, 300, 322, 332, 338, and 439 of the mature polypeptide of SEQ ID NO: 2, wherein the variant has cellobiohydrolase activity.

[79] The method of paragraph 77 or 78, further comprising introducing into the parent cellobiohydrolase a substitution at one or more (e.g., several) positions corresponding to positions 256, 287, and 344 of the mature polypeptide of SEQ ID NO: 2, wherein the variant has cellobiohydrolase activity.

[80] A process for degrading or converting a cellulosic material, comprising: treating the cellulosic material with an enzyme composition in the presence of the cellobiohydrolase variant of any of paragraphs 1-67.

[81] The process of paragraph 80, wherein the cellulosic material is pretreated.

[82] The process of paragraph 80 or 81, further comprising recovering the degraded cellulosic material.

[83] The process of any of paragraphs 80-82, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[84] The process of paragraph 83, wherein the cellulase is one or more enzymes selected from the group consisting of an endoglucanase, a cellobiohydrolase, and a beta-glucosidase.

[85] The process of paragraph 83, wherein the hemicellulase is one or more enzymes selected from the group consisting of a xylanase, an acetyxylan esterase, a feruloyl esterase, an arabinofuranosidase, a xylosidase, and a glucuronidase.

[86] The process of any of paragraphs 80-85, wherein the degraded cellulosic material is a sugar.

[87] The process of paragraph 86, wherein the sugar is selected from the group consisting of glucose, xylose, mannose, galactose, and arabinose.

[88] A process for producing a fermentation product, comprising: (a) saccharifying a cellulosic material with an enzyme composition in the presence of the cellobiohydrolase variant of any of paragraphs 1-67; (b) fermenting the saccharified cellulosic material with one or more fermenting microorganisms to produce the fermentation product; and (c) recovering the fermentation product from the fermentation.

[89] The process of paragraph 88, wherein the cellulosic material is pretreated.

[90] The process of paragraph 88 or 89, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[91] The process of paragraph 90, wherein the cellulase is one or more enzymes selected from the group consisting of an endoglucanase, a cellobiohydrolase, and a beta-glucosidase.

[92] The process of paragraph 90, wherein the hemicellulase is one or more enzymes selected from the group consisting of a xylanase, an acetyxylan esterase, a feruloyl esterase, an arabinofuranosidase, a xylosidase, and a glucuronidase.

[93] The process of any of paragraphs 88-92, wherein steps (a) and (b) are performed simultaneously in a simultaneous saccharification and fermentation.

[94] The process of any of paragraphs 88-93, wherein the fermentation product is an alcohol, an alkane, a cycloalkane, an alkene, an amino acid, a gas, isoprene, a ketone, an organic acid, or polyketide.

[95] A process of fermenting a cellulosic material, comprising: fermenting the cellulosic material with one or more fermenting microorganisms, wherein the cellulosic material is saccharified with an enzyme composition in the presence of the cellobiohydrolase variant of any of paragraphs 1-67.

[96] The process of paragraph 95, wherein the cellulosic material is pretreated before saccharification.

[97] The process of paragraph 95 or 96, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[98] The process of paragraph 97, wherein the cellulase is one or more enzymes selected from the group consisting of an endoglucanase, a cellobiohydrolase, and a beta-glucosidase.

[99] The process of paragraph 97, wherein the hemicellulase is one or more enzymes selected from the group consisting of a xylanase, an acetyxylan esterase, a feruloyl esterase, an arabinofuranosidase, a xylosidase, and a glucuronidase.

[100] The process of any of paragraphs 95-99, wherein the fermenting of the cellulosic material produces a fermentation product.

[101] The process of paragraph 100, further comprising recovering the fermentation product from the fermentation.

[102] The process of paragraph 100 or 101, wherein the fermentation product is an alcohol, an alkane, a cycloalkane, an alkene, an amino acid, a gas, isoprene, a ketone, an organic acid, or polyketide.

[103] A whole broth formulation or cell culture composition, comprising the variant of any of paragraphs 1-67.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated variant of a parent cellobiohydrolase, comprising a substitution at one or more positions corresponding to positions 112, 154, 197, 228, 261, 306, and 375 of the mature polypeptide of SEQ ID NO: 2, wherein the substitution at position 112 is with His, the substitution at position 154 is with Met, the substitution at position 197 is with Tyr, the substitution at position 228 is with Val, the substitution at position 261 is with Leu, the substitution at position 306 is with Ala, and the substitution at position 375 is with Glu, wherein the variant has cellobiohydrolase activity and an increased thermostability compared to the parent polypeptide, and wherein the parent cellobiohydrolase is selected from the group consisting of: (a) a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116; (b) a polypeptide encoded by a polynucleotide having at least 98% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115; and (c) a fragment of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116, which has cellobiohydrolase activity.

2. The variant of claim 1, which has at least 95%, but less than 100%, sequence identity to the amino acid sequence of the parent cellobiohydrolase.

3. The variant of claim 1, wherein the parent cellobiohydrolase comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116; or a fragment thereof having cellobiohydrolase activity.

4. The variant of claim 1, which comprises one or more substitutions selected from the group consisting of Y112H, V154M, S197Y, I228V, I261L, S306A, and G375E.

5. The variant of claim 1, which further comprises a substitution at one or more positions corresponding to positions 247, 262, 300, 322, 332, 338, and 439 of the mature polypeptide of SEQ ID NO: 2, wherein the variant has cellobiohydrolase activity.

6. The variant of claim 5, wherein the substitution at the one or more positions is selected from the group consisting of A247S, T262K, N300D, V322I, D332N, E338K, and T439Q.

7. The variant of claim 1, which further comprises a substitution at one or more positions corresponding to positions 256, 287, and 344 of the mature polypeptide of SEQ ID NO: 2, wherein the variant has cellobiohydrolase activity.

8. The variant of claim 7, wherein the substitution at the one or more positions is selected from the group consisting of C256L, L287I, and L344F.

9. The variant of claim 1, which has an increased thermostability of at least 1.01-fold compared to the parent.

10. An isolated polynucleotide encoding the variant of claim 1.

11. A method of producing a cellobiohydrolase variant, comprising: (a) cultivating a host cell comprising the polynucleotide of claim 10 for producing the variant; and optionally (b) recovering the variant.

12. A transgenic plant, plant part or plant cell transformed with the polynucleotide of claim 10.

13. A method of producing a variant of claim 1, comprising: (a) cultivating a transgenic plant or a plant cell comprising a polynucleotide encoding the variant for producing the variant; and optionally (b) recovering the variant.

14. A method for obtaining a cellobiohydrolase variant, comprising introducing into a parent cellobiohydrolase a substitution at one or more positions corresponding to positions 112, 154, 197, 228, 261, 306, and 375 of the mature polypeptide of SEQ ID NO: 2, wherein the variant has cellobiohydrolase activity; and recovering the variant.

15. A process for degrading or converting a cellulosic material, comprising: treating the cellulosic material with an enzyme composition in the presence of the cellobiohydrolase variant of claim 1.

16. A process for producing a fermentation product, comprising: (a) saccharifying a cellulosic material with an enzyme composition in the presence of the cellobiohydrolase variant of claim 1; (b) fermenting the saccharified cellulosic material with one or more fermenting microorganisms to produce the fermentation product; and (c) recovering the fermentation product from the fermentation.

17. A process of fermenting a cellulosic material, comprising: fermenting the cellulosic material with one or more fermenting microorganisms, wherein the cellulosic material is saccharified with an enzyme composition in the presence of the cellobiohydrolase variant of claim 1.

18. A whole broth formulation or cell culture composition, comprising the variant of claim 1.

19. The variant of claim 1, wherein the parent cellobiohydrolase is a polypeptide having at least 95% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

20. The variant of claim 1, wherein the parent cellobiohydrolase is a polypeptide having at least 96% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

21. The variant of claim 1, wherein the parent cellobiohydrolase is a polypeptide encoded by a polynucleotide having at least 98% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

22. The variant of claim 1, wherein the parent cellobiohydrolase is a polypeptide encoded by a polynucleotide having at least 99% sequence identity to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

23. The variant of claim 1, wherein the parent cellobiohydrolase is a fragment of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116, which has cellobiohydrolase activity.

24. The variant of claim 1, wherein the parent cellobiohydrolase is a polypeptide having at least 97% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

25. The variant of claim 1, wherein the parent cellobiohydrolase is a polypeptide having at least 98% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

26. The variant of claim 1, wherein the parent cellobiohydrolase is a polypeptide having at least 99% sequence identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

27. The variant of claim 1, wherein the parent cellobiohydrolase is a polypeptide encoded by the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 109, SEQ ID NO: 111, SEQ ID NO: 113, or SEQ ID NO: 115.

28. The variant of claim 1, wherein the parent cellobiohydrolase comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 110, SEQ ID NO: 112, SEQ ID NO: 114, or SEQ ID NO: 116.

29. The variant of claim 1, wherein the parent cellobiohydrolase comprises or consists of the mature polypeptide of SEQ ID NO: 2.

* * * * *

SEQUENCE LISTING

```
<160> NUMBER OF SEQ ID NOS: 116

<210> SEQ ID NO 1
<211> LENGTH: 1789
<212> TYPE: DNA
<213> ORGANISM: Talaromyces byssochlamydoides

<400> SEQUENCE: 1

atgcgaaata ttcttgctct tgtgccagca gcgttcctcc tcggtgcagc tgaagcgcag      60

caatccgtct ggggacaatg tgagagctca gctcgtgtct aaagaatttg aattgtactg     120
```

```
acagtcgtta ggtggtggta gtgggtacac tggaccgacc agctgtgccg caggatcgac    180

gtgcagcacg caaaatgctt gtacgtctgt gttctgcacc tgatgagtga gatgtccact    240

gaccgctgca tagactacgc acaatgcgtt cctgcaacgg ccacacccac cacgttgacg    300

acgacgacga cgtcgccatc gggtggcact ggtccaacaa gcacctcgtc cacgccgact    360

ggaacgacgt cgacgccaac catcaccgcg tctgcttccg gcaatccatt cgagggctac    420

cagctctatg ccaatccgta ctattcgtct gaagtgtaca ctttggccat tccgtcgctg    480

accggcacgc ttgctgcaaa ggcgaccgag gtggccaagg tgccgtcttt cgtctggctg    540

taaaagatga ctcttttcct cgttcttttt attttttact aattttccac agcgaccaag    600

cagccaaggt gcctaccgtg ggcgagtatc tggccgacat ccggtcccaa aacgccgccg    660

gcgccaaccc tccaattgcg ggtatcttcg tcgtttacga cctgcctgat cgtgactgcg    720

ctgcagcagc cagcaatgga gaattctcca ttgccgacaa tggagtcgcc ttgtacaagc    780

agtacatcga caacattacc gagtggctgg tgacgtattc ggatgtccac accatcctga    840

tcattggtac gtcggctctc gctggttaca agatcatgta ctgagacgag actctagaac    900

ccgacagcct ggccaacttg gtcaccaacc tgaacgtcga gaaatgcgcg aacgcagaga    960

gcgcgtattt ggagtgcatc aactatgcga taacgaagct caacctgccc aatgtggcca   1020

tgtatcttga cgcgggtgag tccacctcca ttgtcgaact accacctgga ttcaaactaa   1080

tattgtattc cacaggacac gccggatggt taggctggtc ggcaaacctc cagcccgcag   1140

ccaacctctt cgcttccgtg tacaagaacg cctcatcgcc ggcttccgtg cgcggtctgg   1200

ccaccaacgt cgctaactac aacgcctgga ccgtcagtcc gtgcccgtcg tacacgcagg   1260

gcgactccaa ctgcgatgaa gaggactatg tgaatgccct gggaccactg gtcgcggcgc   1320

agggctttaa cgcgcacttt atcaccgaca catgtaagta ccaccgtcaa cactaactcc   1380

aaacccaagc cggaagccac atctttctct atggatatac atctaattgc tgagctgttt   1440

cagcccgcaa cggtgtccaa cccacccagc aacaacaatg gggtgactgg tgcaacgtga   1500

tcggcaccgg ctttggcgtg cgtccgacta ccaacacggg caactctctc gaggacgcct   1560

tcgtctgggt caagcctggt ggtgagagcg acggcacgtc caacacgacc tcgcctcgtt   1620

acgactacca ctgcgggctc agcgatgcgc tgcagccggc accggaggcg gggacttggt   1680

tccaggtatg tagcagcttg ctttcagggc tgatgggata attgagctaa tcatttgtga   1740

ataggcctac ttcgagcaac tcctcgagaa cgccaatccg tcattctag               1789
```

```
<210> SEQ ID NO 2
<211> LENGTH: 456
<212> TYPE: PRT
<213> ORGANISM: Talaromyces byssochlamydoides

<400> SEQUENCE: 2

Met Arg Asn Ile Leu Ala Leu Val Pro Ala Ala Phe Leu Leu Gly Ala
1               5                   10                  15

Ala Glu Ala Gln Gln Ser Val Trp Gly Gln Cys Gly Gly Ser Gly Tyr
            20                  25                  30

Thr Gly Pro Thr Ser Cys Ala Ala Gly Ser Thr Cys Ser Thr Gln Asn
        35                  40                  45

Ala Tyr Tyr Ala Gln Cys Val Pro Ala Thr Ala Thr Pro Thr Thr Leu
    50                  55                  60

Thr Thr Thr Thr Thr Ser Pro Ser Gly Gly Thr Gly Pro Thr Ser Thr
65                  70                  75                  80
```

```
Ser Ser Thr Pro Thr Gly Thr Thr Ser Thr Pro Thr Ile Thr Ala Ser
                85                  90                  95

Ala Ser Gly Asn Pro Phe Glu Gly Tyr Gln Leu Tyr Ala Asn Pro Tyr
            100                 105                 110

Tyr Ser Ser Glu Val Tyr Thr Leu Ala Ile Pro Ser Leu Thr Gly Thr
        115                 120                 125

Leu Ala Ala Lys Ala Thr Glu Val Ala Lys Val Pro Ser Phe Val Trp
    130                 135                 140

Leu Asp Gln Ala Ala Lys Val Pro Thr Val Gly Glu Tyr Leu Ala Asp
145                 150                 155                 160

Ile Arg Ser Gln Asn Ala Ala Gly Ala Asn Pro Pro Ile Ala Gly Ile
                165                 170                 175

Phe Val Val Tyr Asp Leu Pro Asp Arg Asp Cys Ala Ala Ala Ala Ser
            180                 185                 190

Asn Gly Glu Phe Ser Ile Ala Asp Asn Gly Val Ala Leu Tyr Lys Gln
        195                 200                 205

Tyr Ile Asp Asn Ile Thr Glu Trp Leu Val Thr Tyr Ser Asp Val His
    210                 215                 220

Thr Ile Leu Ile Ile Glu Pro Asp Ser Leu Ala Asn Leu Val Thr Asn
225                 230                 235                 240

Leu Asn Val Glu Lys Cys Ala Asn Ala Glu Ser Ala Tyr Leu Glu Cys
                245                 250                 255

Ile Asn Tyr Ala Ile Thr Lys Leu Asn Leu Pro Asn Val Ala Met Tyr
            260                 265                 270

Leu Asp Ala Gly His Ala Gly Trp Leu Gly Trp Ser Ala Asn Leu Gln
        275                 280                 285

Pro Ala Ala Asn Leu Phe Ala Ser Val Tyr Lys Asn Ala Ser Ser Pro
    290                 295                 300

Ala Ser Val Arg Gly Leu Ala Thr Asn Val Ala Asn Tyr Asn Ala Trp
305                 310                 315                 320

Thr Val Ser Pro Cys Pro Ser Tyr Thr Gln Gly Asp Ser Asn Cys Asp
                325                 330                 335

Glu Glu Asp Tyr Val Asn Ala Leu Gly Pro Leu Val Ala Ala Gln Gly
            340                 345                 350

Phe Asn Ala His Phe Ile Thr Asp Thr Ser Arg Asn Gly Val Gln Pro
        355                 360                 365

Thr Gln Gln Gln Gln Trp Gly Asp Trp Cys Asn Val Ile Gly Thr Gly
    370                 375                 380

Phe Gly Val Arg Pro Thr Thr Asn Thr Gly Asn Ser Leu Glu Asp Ala
385                 390                 395                 400

Phe Val Trp Val Lys Pro Gly Gly Glu Ser Asp Gly Thr Ser Asn Thr
                405                 410                 415

Thr Ser Pro Arg Tyr Asp Tyr His Cys Gly Leu Ser Asp Ala Leu Gln
            420                 425                 430

Pro Ala Pro Glu Ala Gly Thr Trp Phe Gln Ala Tyr Phe Glu Gln Leu
        435                 440                 445

Leu Glu Asn Ala Asn Pro Ser Phe
    450                 455
```

<210> SEQ ID NO 3
<211> LENGTH: 1543
<212> TYPE: DNA
<213> ORGANISM: Trichophaea saccata

<400> SEQUENCE: 3

```
ggcacgaggg ctgccagcgt attcgcagca gatcgatcga ctcgaggacc acatcgcatc     60

atgaagaact tccttctggc gtccgcgctg atcgcggttg ccgcagctca gcagagtgct    120

tggggacagt gcggtggaat tggctggact ggcgcgacga cttgtatctc tggctacacg    180

tgctcaaaga tcaacgacta ctattcccag tgcattccgg gtacggcttc aaccaccact    240

caaggcggcg gcaatggcgg aggaaacggc ggtacaacga ctactcccac taccactcca    300

gcggccagta acaccaacaa cccgttctcc ggcaagaccc aatgggcgaa cccttactac    360

gcttccgagg tctcgagcat cgccatcccg tccctcgttg ccgccggaaa caccgcgctg    420

gcttccgccg cggccaaggt tgcccaggtc ccctccttca cctggttgga cacccgcgcc    480

aaagttccga gcgtgcgcac ctaccttcaa tccatcaagg acgccggcac caagaacgtg    540

atcgtcccga tcgtggtcta cgatctcccg gaacgagact gtgcagcggc cgcctccaac    600

ggagagctct cgctcgccaa caacggtacc gcaatttaca aggcagacta catcgaccag    660

atctacaaca tcctcgccga cttcccgaca attcccgtcg cgctgattat cgagccggat    720

tccctcgcta acttggttac gaacttgaat gtggccaagt gttcgaacgc tgagtccgcg    780

tataagacgc tcatcgctta tgcggtgcag aagtttggta ccctgtcgaa tgtggtgcag    840

tatctcgacg gcggccacgg tggatggctc ggatggcccg cgaatcttcc gcctgctgcg    900

cagctgttcg cccagatccg gcagagcgct ggaagtccgg cgaatctgag ggtttggct     960

actaacgttg ctaactacaa cgcttggtcc attgctacct gcccatctta cacttccccc   1020

aaccctaact gcgacgagaa acgatacata gccgctatgt cctccgcact cgccgcccag   1080

ggctggtcca acacccacta catcgtcgac caaggccgca gcggcaagca gccgaccggc   1140

cagctccagc agggcgattg gtgcaacgcc ctgggaaccg gctttggaat tcgtcctgat   1200

acaaccccgg atgatcccaa ccttgatgct ttcgtgtggg ttaagccggg tggtgaatcg   1260

gatggtacca gcaatacttc ctcgacccgc tatgattatc attgtggaca gagcgatgcg   1320

ctacaaccgg ccccggaggc gggaacgtgg ttccaggcgt attttgtgca gttgctgcag   1380

aatgctaatc ctagcttcac gtaagcttgg gagcgtgggg gttggaagat gtgtattgta   1440

tgtgtagata gagaaaaact gttggcctat tcaggactaa gtttggcgt ctgggttctg    1500

tttcttcgcg taggtagacg tgaacttgat gaacttgagc gtg                     1543
```

<210> SEQ ID NO 4
<211> LENGTH: 447
<212> TYPE: PRT
<213> ORGANISM: Trichophaea saccata

<400> SEQUENCE: 4

```
Met Lys Asn Phe Leu Leu Ala Ser Ala Leu Ile Ala Val Ala Ala Ala
1               5                   10                  15

Gln Gln Ser Ala Trp Gly Gln Cys Gly Gly Ile Gly Trp Thr Gly Ala
            20                  25                  30

Thr Thr Cys Ile Ser Gly Tyr Thr Cys Ser Lys Ile Asn Asp Tyr Tyr
        35                  40                  45

Ser Gln Cys Ile Pro Gly Thr Ala Ser Thr Thr Thr Gln Gly Gly Gly
    50                  55                  60

Asn Gly Gly Gly Asn Gly Gly Thr Thr Thr Thr Pro Thr Thr Thr Pro
65                  70                  75                  80

Ala Ala Ser Asn Thr Asn Asn Pro Phe Ser Gly Lys Thr Gln Trp Ala
                85                  90                  95
```

```
Asn Pro Tyr Tyr Ala Ser Glu Val Ser Ser Ile Ala Ile Pro Ser Leu
            100                 105                 110

Val Ala Ala Gly Asn Thr Ala Leu Ala Ser Ala Ala Ala Lys Val Ala
        115                 120                 125

Gln Val Pro Ser Phe Thr Trp Leu Asp Thr Arg Ala Lys Val Pro Ser
    130                 135                 140

Val Arg Thr Tyr Leu Gln Ser Ile Lys Asp Ala Gly Thr Lys Asn Val
145                 150                 155                 160

Ile Val Pro Ile Val Val Tyr Asp Leu Pro Glu Arg Asp Cys Ala Ala
                165                 170                 175

Ala Ala Ser Asn Gly Glu Leu Ser Leu Ala Asn Asn Gly Thr Ala Ile
            180                 185                 190

Tyr Lys Ala Asp Tyr Ile Asp Gln Ile Tyr Asn Ile Leu Ala Asp Phe
        195                 200                 205

Pro Thr Ile Pro Val Ala Leu Ile Ile Glu Pro Asp Ser Leu Ala Asn
    210                 215                 220

Leu Val Thr Asn Leu Asn Val Ala Lys Cys Ser Asn Ala Glu Ser Ala
225                 230                 235                 240

Tyr Lys Thr Leu Ile Ala Tyr Ala Val Gln Lys Phe Gly Thr Leu Ser
                245                 250                 255

Asn Val Val Gln Tyr Leu Asp Gly Gly His Gly Gly Trp Leu Gly Trp
            260                 265                 270

Pro Ala Asn Leu Pro Pro Ala Ala Gln Leu Phe Ala Gln Ile Arg Gln
        275                 280                 285

Ser Ala Gly Ser Pro Ala Asn Leu Arg Gly Leu Ala Thr Asn Val Ala
    290                 295                 300

Asn Tyr Asn Ala Trp Ser Ile Ala Thr Cys Pro Ser Tyr Thr Ser Pro
305                 310                 315                 320

Asn Pro Asn Cys Asp Glu Lys Arg Tyr Ile Ala Ala Met Ser Ser Ala
                325                 330                 335

Leu Ala Ala Gln Gly Trp Ser Asn Thr His Tyr Ile Val Asp Gln Gly
            340                 345                 350

Arg Ser Gly Lys Gln Pro Thr Gly Gln Leu Gln Gln Gly Asp Trp Cys
        355                 360                 365

Asn Ala Leu Gly Thr Gly Phe Gly Ile Arg Pro Asp Thr Thr Pro Asp
    370                 375                 380

Asp Pro Asn Leu Asp Ala Phe Val Trp Val Lys Pro Gly Gly Glu Ser
385                 390                 395                 400

Asp Gly Thr Ser Asn Thr Ser Ser Thr Arg Tyr Asp Tyr His Cys Gly
                405                 410                 415

Gln Ser Asp Ala Leu Gln Pro Ala Pro Glu Ala Gly Thr Trp Phe Gln
            420                 425                 430

Ala Tyr Phe Val Gln Leu Leu Gln Asn Ala Asn Pro Ser Phe Thr
        435                 440                 445
```

<210> SEQ ID NO 5
<211> LENGTH: 1446
<212> TYPE: DNA
<213> ORGANISM: Thielavia terrestris

<400> SEQUENCE: 5

```
atggctcaga agctccttct cgccgccgcc cttgcggcca gcgccctcgc tgctcccgtc      60

gtcgaggagc gccagaactg cggttccgtc tggagccaat gcggcggcat tggctggtcc     120

ggcgcgacct gctgcgcttc gggcaatacc tgcgttgagc tgaacccgta ctactcgcag     180
```

```
tgcctgccca acagccaggt gactacctcg accagcaaga ccacctccac caccaccagg    240

agcagcacca ccagccacag cagcggtccc accagcacga gcaccaccac caccagcagt    300

cccgtggtca ctaccccgcc gagtacctcc atccccggcg gtgcctcgtc aacggccagc    360

tggtccggca acccgttctc gggcgtgcag atgtgggcca acgactacta cgcctccgag    420

gtctcgtcgc tggccatccc cagcatgacg ggcgccatgg ccaccaaggc ggccgaggtg    480

gccaaggtgc ccagcttcca gtggcttgac cgcaacgtca ccatcgacac gctgttcgcc    540

cacacgctgt cgcagatccg cgcggccaac cagaaaggcg ccaacccgcc ctacgcgggc    600

atcttcgtgg tctacgacct tccggaccgc gactgcgccg ccgccgcgtc caacggcgag    660

ttctccatcg cgaacaacgg ggcggccaac tacaagacgt acatcgacgc gatccggagc    720

ctcgtcatcc agtactcaga catccgcatc atcttcgtca tcgagcccga ctcgctggcc    780

aacatggtga ccaacctgaa cgtggccaag tgcgccaacg ccgagtcgac ctacaaggag    840

ttgaccgtct acgcgctgca gcagctgaac ctgcccaacg tggccatgta cctggacgcc    900

ggccacgccg gctggctcgg ctggcccgcc aacatccagc cggccgccaa cctcttcgcc    960

gagatctaca cgagcgccgg caagccggcc gccgtgcgcg gcctcgccac caacgtggcc   1020

aactacaacg gctggagcct ggccacgccg ccctcgtaca cccagggcga ccccaactac   1080

gacgagagcc actacgtcca ggccctcgcc ccgctgctca ccgccaacgg cttccccgcc   1140

cacttcatca ccgacaccgg ccgcaacggc aagcagccga ccggacaacg gcaatgggga   1200

gactggtgca acgttatcgg aactggcttc ggcgtgcgcc cgacgacaaa caccggcctc   1260

gacatcgagg acgccttcgt ctgggtcaag cccggcggcg agtgcgacgg cacgagcaac   1320

acgacctctc cccgctacga ctaccactgc ggcctgtcgg acgcgctgca gcctgctccg   1380

gaggccggca cttggttcca ggcctacttc gagcagctcc tgaccaacgc caacccgccc   1440

ttttaa                                                               1446
```

```
<210> SEQ ID NO 6
<211> LENGTH: 481
<212> TYPE: PRT
<213> ORGANISM: Thielavia terrestris

<400> SEQUENCE: 6

Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140
```

```
Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
        435                 440                 445

His Cys Gly Leu Ser Asp Ala Leu Gln Pro Ala Pro Glu Ala Gly Thr
    450                 455                 460

Trp Phe Gln Ala Tyr Phe Glu Gln Leu Leu Thr Asn Ala Asn Pro Pro
465                 470                 475                 480

Phe
```

<210> SEQ ID NO 7
<211> LENGTH: 1812
<212> TYPE: DNA
<213> ORGANISM: Myceliophthora thermophila

<400> SEQUENCE: 7

```
atggccaaga agcttttcat caccgccgcc cttgcggctg ccgtgttggc ggcccccgtc      60

attgaggagc gccagaactg cggcgctgtg tggtaagaaa gcccggtctg agtttcccat     120

gactttctca tcgagtaatg gcataaggcc caccccttcg actgactgtg agaatcgatc     180
```

```
aaatccagga ctcaatgcgg cggcaacggg tggcagggtc ccacatgctg cgcctcgggc    240
tcgacctgcg ttgcgcagaa cgagtggtac tctcagtgcc tgcccaacaa tcaggtgacg    300
agttccaaca ctccgtcgtc gacttccacc tcgcagcgca gcagcagcac ctccagcagc    360
agcaccagga gcggcagctc ctcctcctcc accaccacgc cccctcccgt ctccagcccc    420
gtgactagca ttcccggcgg tgcgaccacc acggcgagct actctggcaa ccccttctcg    480
ggcgtccggc tcttcgccaa cgactactac aggtccgagg tccacaatct cgccattcct    540
agcatgaccg gtactctggc ggccaaggct tccgccgtcg ccgaagtccc tagcttccag    600
tggctcgacc ggaacgtcac catcgacacc ctgatggtcc agactctgtc ccagatccgg    660
gctgccaata atgccggtgc caatcctccc tatgctggtg agttacatgg cggcgacttg    720
ccttctcgtc ccccaccttt cttgacggga tcggttacct gacctggagg caaaacaaaa    780
ccagcccaac ttgtcgtcta cgacctcccc gaccgtgact gcgccgccgc tgcgtccaac    840
ggcgagtttt cgattgcaaa cggcggcgcc gccaactaca ggagctacat cgacgctatc    900
cgcaagcaca tcattgagta ctcggacatc cggatcatcc tggttatcga gcccgactcg    960
atggccaaca tggtgaccaa catgaacgtg gccaagtgca gcaacgccgc gtcgacgtac   1020
cacgagttga ccgtgtacgc gctcaagcag ctgaacctgc ccaacgtcgc catgtatctc   1080
gacgccggcc acgccggctg gctcggctgg cccgccaaca tccagcccgc cgccgacctg   1140
tttgccggca tctacaatga cgccggcaag ccggctgccg tccgcggcct ggccactaac   1200
gtcgccaact acaacgcctg gagtatcgct tcggccccgt cgtacacgtc ccctaaccct   1260
aactacgacg agaagcacta catcgaggcc ttcagcccgc tcctgaacgc ggccggcttc   1320
cccgcacgct tcattgtcga cactggccgc aacggcaaac aacctaccgg tatggttttt   1380
ttcttttttt ttctctgttc ccctccccct tccccttcag ttggcgtcca caaggtctct   1440
tagtcttgct tcttctcgga ccaaccttcc cccaccccca aaacgcaccg cccacaaccg   1500
ttcgactcta tactcttggg aatgggcgcc gaaactgacc gttcgacagg ccaacaacag   1560
tggggtgact ggtgcaatgt caagggcact ggctttggcg tgcgcccgac ggccaacacg   1620
ggccacgacc tggtcgatgc ctttgtctgg gtcaagcccg gcggcgagtc cgacggcaca   1680
agcgacacca gcgccgcccg ctacgactac cactgcggcc tgtccgatgc cctgcagcct   1740
gctccggagg ctggacagtg gttccaggcc tacttcgagc agctgctcac caacgccaac   1800
ccgcccttct aa                                                        1812
```

<210> SEQ ID NO 8
<211> LENGTH: 482
<212> TYPE: PRT
<213> ORGANISM: Myceliophthora thermophila

<400> SEQUENCE: 8

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80
```

```
Arg Ser Ser Ser Thr Ser Ser Ser Ser Thr Arg Ser Gly Ser Ser Ser
                85                  90                  95

Ser Ser Thr Thr Thr Pro Pro Pro Val Ser Ser Pro Val Thr Ser Ile
            100                 105                 110

Pro Gly Gly Ala Thr Thr Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe
```

<210> SEQ ID NO 9
<211> LENGTH: 1713
<212> TYPE: DNA
<213> ORGANISM: Aspergillus fumigatus

<400> SEQUENCE: 9

```
atgaagcacc ttgcatcttc catcgcattg actctactgt tgcctgccgt gcaggcccag     60
cagaccgtat ggggccaatg tatgttctgg ctgtcactgg aataagactg tatcaactgc    120
tgatatgctt ctaggtggcg gccaaggctg gtctggcccg acgagctgtg ttgccggcgc    180
agcctgtagc acactgaatc cctgtatgtt agatatcgtc ctgagtggag acttatactg    240
acttccttag actacgctca gtgtatcccg ggagccaccg cgacgtccac taccctcacg    300
acgacgacgg cggcgacgac gacatcccag accaccacca aacctaccac gactggtcca    360
actacatccg cacccaccgt gaccgcatcc ggtaaccctt tcagcggcta ccagctgtat    420
gccaacccct actactcctc cgaggtccat actctggcca tgccttctct gcccagctcg    480
ctgcagccca aggctagtgc tgttgctgaa gtgccctcat ttgtttggct gtaagtggcc    540
ttatcccaat actgagacca actctctgac agtcgtagcg acgttgccgc caaggtgccc    600
actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cttttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca aagtctacac   1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc ctcttctcaa ggaagccggc ttcgatgccc acttcatcat   1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713
```

<210> SEQ ID NO 10
<211> LENGTH: 454
<212> TYPE: PRT
<213> ORGANISM: Aspergillus fumigatus

<400> SEQUENCE: 10

```
Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30
```

```
Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
```

450

<210> SEQ ID NO 11
<211> LENGTH: 1395
<212> TYPE: DNA
<213> ORGANISM: Aspergillus clavatus

<400> SEQUENCE: 11
atgaagaact tcgccccttc tctcgcgctg tcgctgctgc tgcctaccgt gcaggcccag 60
cagacgatgt ggggacagtg tggtggtgcc ggttggtccg gggcgaccga ctgtgtcgct 120
ggcggtgtct gcagcactca gaatgcttac tacgcccagt gtctccccgg agccacgact 180
gcgacaactc tgtccaccac ctccaagggc accaccacga ccaccacgag ctccaccacg 240
agcaccggcg gaggttcttc cagcaccacc actaagacct cgacttcggc cggccctacc 300
gtcactggca gcccctccgg caatcccttc agcggatacc agcaatatgc caacccctac 360
tactcatccg aggtccacac cctggccatt ccctccatga ctggcgccct tgccgtcaag 420
gccagcgctg tcgctgatgt tccttctttc gtctggcttg atgttgccgc caaggtgccc 480
accatgggaa cctacctcga gaacatccgg gctaagaaca aggccggcgc caaccctccc 540
gttgccggta tcttcgttgt ctatgatctg cctgaccgtg attgcgctgc tctggccagt 600
aacggcgagt atgccatcgc cgacggtggt attgccaagt acaaggcgta catcgatgcc 660
atccgcgctc agctgctgaa gtaccctgat gtgcacacca tcctggttat tgaacccgac 720
agcttggcca acctgatcac caacatcaac gttgccaaat gctctggcgc caaggatgcc 780
tatctcgagt gcatcaacta cgctctgaag cagctcaacc ttcccaacgt cgccatgtac 840
attgatgccg gccacggtgg ctggctcggc tgggacgcca acatcggccc tgccgccgag 900
atgtacgcca aggtctacaa ggacgccgat gcccccgccg ccctccgtgg tcttgccgtc 960
aacgtcgcca actacaacgc ctggaccatc gatacctgcc cctcgtacac ccagggcaac 1020
aagaactgcg atgagaagcg ctacatccac gccctgtatc ccttgctcaa ggccgctggc 1080
tgggacgccc gcttcatcat ggatactggc cgcaatggtg tccagcctac caagcagcag 1140
gctcaggggg actggtgcaa tgtgatcggc actggcttcg gtatccgtcc ttcctctgag 1200
accggcgatg atctcctcga tgccttcgtc tgggtcaagc ccggcgcgga gagcgacggt 1260
acctctgaca ccactgccgc ccgctatgac gctcactgcg gctacaccga tgctctcaag 1320
cctgctcctg aggctggcca gtggttccag gcttactttg agcagctcct gaccaacgca 1380
aaccctgctt tctaa 1395

<210> SEQ ID NO 12
<211> LENGTH: 464
<212> TYPE: PRT
<213> ORGANISM: Aspergillus clavatus

<400> SEQUENCE: 12

Met Lys Asn Phe Ala Pro Ser Leu Ala Leu Ser Leu Leu Leu Pro Thr
1               5                   10                  15

Val Gln Ala Gln Gln Thr Met Trp Gly Gln Cys Gly Gly Ala Gly Trp
            20                  25                  30

Ser Gly Ala Thr Asp Cys Val Ala Gly Gly Val Cys Ser Thr Gln Asn
        35                  40                  45

Ala Tyr Tyr Ala Gln Cys Leu Pro Gly Ala Thr Thr Ala Thr Thr Leu
    50                  55                  60

Ser Thr Thr Ser Lys Gly Thr Thr Thr Thr Thr Thr Ser Ser Thr Thr

```
65                  70                  75                  80

Ser Thr Gly Gly Gly Ser Ser Ser Thr Thr Thr Lys Thr Ser Thr Ser
                85                  90                  95

Ala Gly Pro Thr Val Thr Gly Ser Pro Ser Gly Asn Pro Phe Ser Gly
            100                 105                 110

Tyr Gln Gln Tyr Ala Asn Pro Tyr Tyr Ser Ser Glu Val His Thr Leu
        115                 120                 125

Ala Ile Pro Ser Met Thr Gly Ala Leu Ala Val Lys Ala Ser Ala Val
    130                 135                 140

Ala Asp Val Pro Ser Phe Val Trp Leu Asp Val Ala Ala Lys Val Pro
145                 150                 155                 160

Thr Met Gly Thr Tyr Leu Glu Asn Ile Arg Ala Lys Asn Lys Ala Gly
                165                 170                 175

Ala Asn Pro Pro Val Ala Gly Ile Phe Val Val Tyr Asp Leu Pro Asp
            180                 185                 190

Arg Asp Cys Ala Ala Leu Ala Ser Asn Gly Glu Tyr Ala Ile Ala Asp
        195                 200                 205

Gly Gly Ile Ala Lys Tyr Lys Ala Tyr Ile Asp Ala Ile Arg Ala Gln
    210                 215                 220

Leu Leu Lys Tyr Pro Asp Val His Thr Ile Leu Val Ile Glu Pro Asp
225                 230                 235                 240

Ser Leu Ala Asn Leu Ile Thr Asn Ile Asn Val Ala Lys Cys Ser Gly
                245                 250                 255

Ala Lys Asp Ala Tyr Leu Glu Cys Ile Asn Tyr Ala Leu Lys Gln Leu
            260                 265                 270

Asn Leu Pro Asn Val Ala Met Tyr Ile Asp Ala Gly His Gly Gly Trp
        275                 280                 285

Leu Gly Trp Asp Ala Asn Ile Gly Pro Ala Ala Glu Met Tyr Ala Lys
    290                 295                 300

Val Tyr Lys Asp Ala Asp Ala Pro Ala Ala Leu Arg Gly Leu Ala Val
305                 310                 315                 320

Asn Val Ala Asn Tyr Asn Ala Trp Thr Ile Asp Thr Cys Pro Ser Tyr
                325                 330                 335

Thr Gln Gly Asn Lys Asn Cys Asp Glu Lys Arg Tyr Ile His Ala Leu
            340                 345                 350

Tyr Pro Leu Leu Lys Ala Ala Gly Trp Asp Ala Arg Phe Ile Met Asp
        355                 360                 365

Thr Gly Arg Asn Gly Val Gln Pro Thr Lys Gln Gln Ala Gln Gly Asp
    370                 375                 380

Trp Cys Asn Val Ile Gly Thr Gly Phe Gly Ile Arg Pro Ser Ser Glu
385                 390                 395                 400

Thr Gly Asp Asp Leu Leu Asp Ala Phe Val Trp Val Lys Pro Gly Ala
                405                 410                 415

Glu Ser Asp Gly Thr Ser Asp Thr Thr Ala Ala Arg Tyr Asp Ala His
            420                 425                 430

Cys Gly Tyr Thr Asp Ala Leu Lys Pro Ala Pro Glu Ala Gly Gln Trp
        435                 440                 445

Phe Gln Ala Tyr Phe Glu Gln Leu Leu Thr Asn Ala Asn Pro Ala Phe
    450                 455                 460
```

<210> SEQ ID NO 13
<211> LENGTH: 1200
<212> TYPE: DNA
<213> ORGANISM: Aspergillus clavatus

<400> SEQUENCE: 13

```
atgcggtctc ttctcactct tacccccctg ctgttctctg cagtgagggc tctgcctcaa     60
gcaactggca ctcccacctc gtcaactggc gccacgagct ctcctgcccc taccgcgtct    120
ggtggtaatc ctttcgaggg ttatcagatg tacaccaacc cgtactactc gtccgaggtg    180
gaaaatcttg cgattccttc cctgactggc tctttggtcg cgcaggcaag cgctgcggcg    240
aaggtcccat ccttcctctg gcttgacacg gccgctaagg tcccatcgat gggcgaatac    300
cttgagggca tcaaagcgca gaatgatgcc ggagccagcc ctccaattgc cggtatcttc    360
gttgtttacg atcttcctga tcgcgactgc gccgccctgg ccagtaacgg agagtatctc    420
attgccgacg gcggtgtcga gaagtacaag gcatacattg attctatccg caagcacatt    480
gacaactact cggacactca gatcatcctc atcattgagc ctgacagttt ggccaatctg    540
gtcacgaatc tgaatgtggc caagtgtgcc aatgccgcgg atgcctacaa ggagtgcacc    600
aactatgctc tgaagactct tgatgctccc aacgtttcga tgtatctcga tgctggacac    660
gccggatggc tgggatggcc cgccaacatc ggcccagcgg ccaaactatt cgcaggcgtg    720
tacaaggatg ccggctcgcc caagtctgtg cgtggtctcg cgaccaacgt ggctaactat    780
aacgccttca ttgccaagac atgcccgtca tatacttcgc aaaacgaggt ttgcgacgag    840
aagagctaca tcaacaactt cgctcctgag ctggccagtg ccggatttga cgcgcatttc    900
attgttgaca ccggccgcaa cggaaagcag ccaaccggac agatcgaatg gggtgactgg    960
tgcaacgttg ttgacactgg cttcggagtc cgccctacca ccgagactgg agatgagctg   1020
gtagatgctt ttgtctgggt taagcccggt ggtgagagcg atggcacttc ggtcacctct   1080
gctacccgct acgatgccca ctgtggtctc gaggacgccc tgaaacctgc cccggaggcc   1140
ggaacctggt tccaggccta cttcgagcag cttctcaaga atgctaaccc caccttctaa   1200
```

<210> SEQ ID NO 14
<211> LENGTH: 399
<212> TYPE: PRT
<213> ORGANISM: Aspergillus clavatus

<400> SEQUENCE: 14

```
Met Arg Ser Leu Leu Thr Leu Thr Pro Leu Leu Phe Ser Ala Val Arg
1               5                   10                  15

Ala Leu Pro Gln Ala Thr Gly Thr Pro Thr Ser Ser Thr Gly Ala Thr
            20                  25                  30

Ser Ser Pro Ala Pro Thr Ala Ser Gly Gly Asn Pro Phe Glu Gly Tyr
        35                  40                  45

Gln Met Tyr Thr Asn Pro Tyr Tyr Ser Ser Glu Val Glu Asn Leu Ala
    50                  55                  60

Ile Pro Ser Leu Thr Gly Ser Leu Val Ala Gln Ala Ser Ala Ala Ala
65                  70                  75                  80

Lys Val Pro Ser Phe Leu Trp Leu Asp Thr Ala Ala Lys Val Pro Ser
                85                  90                  95

Met Gly Glu Tyr Leu Glu Gly Ile Lys Ala Gln Asn Asp Ala Gly Ala
            100                 105                 110

Ser Pro Pro Ile Ala Gly Ile Phe Val Val Tyr Asp Leu Pro Asp Arg
        115                 120                 125

Asp Cys Ala Ala Leu Ala Ser Asn Gly Glu Tyr Leu Ile Ala Asp Gly
    130                 135                 140

Gly Val Glu Lys Tyr Lys Ala Tyr Ile Asp Ser Ile Arg Lys His Ile
```

```
145                 150                 155                 160

Asp Asn Tyr Ser Asp Thr Gln Ile Ile Leu Ile Ile Glu Pro Asp Ser
                165                 170                 175

Leu Ala Asn Leu Val Thr Asn Leu Asn Val Ala Lys Cys Ala Asn Ala
            180                 185                 190

Ala Asp Ala Tyr Lys Glu Cys Thr Asn Tyr Ala Leu Lys Thr Leu Asp
        195                 200                 205

Ala Pro Asn Val Ser Met Tyr Leu Asp Ala Gly His Ala Gly Trp Leu
    210                 215                 220

Gly Trp Pro Ala Asn Ile Gly Pro Ala Ala Lys Leu Phe Ala Gly Val
225                 230                 235                 240

Tyr Lys Asp Ala Gly Ser Pro Lys Ser Val Arg Gly Leu Ala Thr Asn
                245                 250                 255

Val Ala Asn Tyr Asn Ala Phe Ile Ala Lys Thr Cys Pro Ser Tyr Thr
            260                 265                 270

Ser Gln Asn Glu Val Cys Asp Glu Lys Ser Tyr Ile Asn Asn Phe Ala
        275                 280                 285

Pro Glu Leu Ala Ser Ala Gly Phe Asp Ala His Phe Ile Val Asp Thr
    290                 295                 300

Gly Arg Asn Gly Lys Gln Pro Thr Gly Gln Ile Glu Trp Gly Asp Trp
305                 310                 315                 320

Cys Asn Val Val Asp Thr Gly Phe Gly Val Arg Pro Thr Thr Glu Thr
                325                 330                 335

Gly Asp Glu Leu Val Asp Ala Phe Val Trp Val Lys Pro Gly Gly Glu
            340                 345                 350

Ser Asp Gly Thr Ser Val Thr Ser Ala Thr Arg Tyr Asp Ala His Cys
        355                 360                 365

Gly Leu Glu Asp Ala Leu Lys Pro Ala Pro Glu Ala Gly Thr Trp Phe
    370                 375                 380

Gln Ala Tyr Phe Glu Gln Leu Leu Lys Asn Ala Asn Pro Thr Phe
385                 390                 395


<210> SEQ ID NO 15
<211> LENGTH: 1203
<212> TYPE: DNA
<213> ORGANISM: Neosartorya fischeri

<400> SEQUENCE: 15

atgcggtctc tttttgctct ttcacccttc ctgctctctg cagtgagagc tttgcctcaa      60

ccaactggca ctcctacctc tcccgctccc actacggagc cccctgcgac cacggcagca     120

gcaggtggta acccctttga gggacatcag ctttatgtga atccttacta tgcgtccgag     180

gttgagaatc ttgccattcc ctcgttgccc ggctctctgg tcgccaaggc aagtgccgtt     240

gcgaaagtgc catctttcgt ttggatggat accaccgcca aagttccgaa aatgggcgaa     300

tacctcaagg acatcaaagc caagaacgat gcagcagcaa gccctccaat tgctgggatt     360

ttcgttgtat acaaccttcc ggatcgtgac tgcgctgcct tggccagcaa tggagaattg     420

gttattgcag atggtggcat tgagaagtac aaggcctaca tcgactccat ccgcgagcac     480

atcgacaatt atcctgatac ccagattatc ctcgtcattg agcctgacag cttggccaac     540

ctcgtgacca acatggcagt gcccaagtgt gcgaacgctc atgatgcata tctggagtgt     600

accaactatg ccctgacgaa actcagtgcc cctaatgttg cgatgtatct tgacgctgga     660

catgctggat ggctgggctg gcctgcgaac attggcccag cagcccaact gtatgcatcc     720
```

```
gtgtacaaga acgcaagttc tcctgcttct gtgcgtggtc ttgtgaccaa cgtggctaat    780

tacaatgcct tcgtcgccac gtcgtgcccc tcttacaccc aaggaaatgc tgtctgcgag    840

gagaagagct atatcaacaa cttcgctcca cagctggcca gcgctggatt taatgctcat    900

ttcatcgtcg acaccggccg caacggaaag cagcccactg gacagcttgc atggggtgac    960

tggtgcaatg tgattggcac tggcttcgga gtccggccta ccactgacac aggagacaag   1020

ttggtggatg ctttcgtctg ggttaagccc ggtggtgaga gtgatggcac ctcggacgcc   1080

tctgctaaac gctacgatgc gaaatgtgga ctcgaggacg ctctcaaacc agcccctgaa   1140

gccggcacct ggttccaggc ctattttgaa cagcttcttc ggtacgccaa cccctcgttc   1200

tag                                                                 1203
```

```
<210> SEQ ID NO 16
<211> LENGTH: 400
<212> TYPE: PRT
<213> ORGANISM: Neosartorya fischeri

<400> SEQUENCE: 16

Met Arg Ser Leu Phe Ala Leu Ser Pro Phe Leu Leu Ser Ala Val Arg
1               5                   10                  15

Ala Leu Pro Gln Pro Thr Gly Thr Pro Thr Ser Pro Ala Pro Thr Thr
            20                  25                  30

Glu Pro Pro Ala Thr Thr Ala Ala Ala Gly Gly Asn Pro Phe Glu Gly
        35                  40                  45

His Gln Leu Tyr Val Asn Pro Tyr Tyr Ala Ser Glu Val Glu Asn Leu
    50                  55                  60

Ala Ile Pro Ser Leu Pro Gly Ser Leu Val Ala Lys Ala Ser Ala Val
65                  70                  75                  80

Ala Lys Val Pro Ser Phe Val Trp Met Asp Thr Thr Ala Lys Val Pro
                85                  90                  95

Lys Met Gly Glu Tyr Leu Lys Asp Ile Lys Ala Lys Asn Asp Ala Ala
            100                 105                 110

Ala Ser Pro Pro Ile Ala Gly Ile Phe Val Val Tyr Asn Leu Pro Asp
        115                 120                 125

Arg Asp Cys Ala Ala Leu Ala Ser Asn Gly Glu Leu Val Ile Ala Asp
    130                 135                 140

Gly Gly Ile Glu Lys Tyr Lys Ala Tyr Ile Asp Ser Ile Arg Glu His
145                 150                 155                 160

Ile Asp Asn Tyr Pro Asp Thr Gln Ile Ile Leu Val Ile Glu Pro Asp
                165                 170                 175

Ser Leu Ala Asn Leu Val Thr Asn Met Ala Val Pro Lys Cys Ala Asn
            180                 185                 190

Ala His Asp Ala Tyr Leu Glu Cys Thr Asn Tyr Ala Leu Thr Lys Leu
        195                 200                 205

Ser Ala Pro Asn Val Ala Met Tyr Leu Asp Ala Gly His Ala Gly Trp
    210                 215                 220

Leu Gly Trp Pro Ala Asn Ile Gly Pro Ala Ala Gln Leu Tyr Ala Ser
225                 230                 235                 240

Val Tyr Lys Asn Ala Ser Ser Pro Ala Ser Val Arg Gly Leu Val Thr
                245                 250                 255

Asn Val Ala Asn Tyr Asn Ala Phe Val Ala Thr Ser Cys Pro Ser Tyr
            260                 265                 270

Thr Gln Gly Asn Ala Val Cys Glu Glu Lys Ser Tyr Ile Asn Asn Phe
        275                 280                 285
```

```
Ala Pro Gln Leu Ala Ser Ala Gly Phe Asn Ala His Phe Ile Val Asp
    290                 295                 300

Thr Gly Arg Asn Gly Lys Gln Pro Thr Gly Gln Leu Ala Trp Gly Asp
305                 310                 315                 320

Trp Cys Asn Val Ile Gly Thr Gly Phe Gly Val Arg Pro Thr Thr Asp
                325                 330                 335

Thr Gly Asp Lys Leu Val Asp Ala Phe Val Trp Val Lys Pro Gly Gly
            340                 345                 350

Glu Ser Asp Gly Thr Ser Asp Ala Ser Ala Lys Arg Tyr Asp Ala Lys
        355                 360                 365

Cys Gly Leu Glu Asp Ala Leu Lys Pro Ala Pro Glu Ala Gly Thr Trp
    370                 375                 380

Phe Gln Ala Tyr Phe Glu Gln Leu Leu Arg Tyr Ala Asn Pro Ser Phe
385                 390                 395                 400


<210> SEQ ID NO 17
<211> LENGTH: 1353
<212> TYPE: DNA
<213> ORGANISM: Neosartorya fischeri

<400> SEQUENCE: 17

atgaagcacc ttgcatcttc catcgcattg actctactgt tgcctgctgt gcaggcccag     60

cagactgtat gggggcaatg tggcggccaa ggctggtctg gcccaacaaa ttgtgttgct    120

ggtgcggcct gtagcacact gaatccctac tacgctcagt gtatcccggg agccaccgcg    180

acgtccacca ccctctcgac aacgacgacg acccagacca ccaccaaacc tacgacgact    240

ggtccaacta catccgcacc caccgtgacc gcatccggta accctttcag cggctaccag    300

ctctatgcca acccctacta ctcctccgag gtccatactc tagccatgcc ttctctgccc    360

agctcgctcc agcccaaggc tagtgccgtc gctgaagtgc cctcatttgt ctggctcgac    420

gttgccgcca aggtgcccac gatgggaacc tacctggccg acattcaggc caagaacaag    480

gccggcgcta gccctcctat cgccggtatc ttcgtggtct acgacttgcc agaccgtgac    540

tgcgccgctc tggccagtaa tggcgagtac tcaattgcta acaacggtgt ggccaactac    600

aaggcgtaca ttgacgccat ccgtgctcag ctggtgaagt actctgacgt tcacaccatc    660

ctcgtcatcg aacccgacag cttggccaac ctggtgacta acctcaacgt cgccaaatgc    720

gccaatgcgc agagcgccta cctggagtgt gtcgactacg ctctgaagca gctcaacctg    780

cccaacgtcg ccatgtacct cgacgcaggc catgctggct ggctcggatg gcccgccaac    840

ttgggccccg ccgcaacact cttcgccaaa gtctacaccg acgcgggttc ccccgcggct    900

cttcgtggtc tggccaccaa cgtcgccaac tacaacgcct ggtcgctcag tacctgcccg    960

tcctacaccc agggagaccc caactgcgac gagaagaagt acatcaacgc catggcgcct   1020

cttctcaaga atgccggctt cgatgcccac ttcatcatgg atacctcccg caatggcgtc   1080

cagcccacga agcaaagcgc ctggggtgac tggtgcaacg tcatcggcac cggctttggt   1140

gttcgcccct cgaccaacac cggcgatccg ctccaggatg cctttgtgtg gatcaagccc   1200

ggtggagaga gtgatggcac gtccaactcg tcttccgccc ggtatgacgc acactgcgga   1260

tacagtgatg ctctgcagcc tgctcctgag gctggtactt ggttccaggc ctactttgag   1320

cagcttctga ccaacgctaa cccgtctttt taa                                 1353


<210> SEQ ID NO 18
<211> LENGTH: 450
```

```
<212> TYPE: PRT
<213> ORGANISM: Neosartorya fischeri

<400> SEQUENCE: 18

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Asn Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Ser Thr Thr Thr Thr Thr Gln Thr Thr Thr Lys Pro Thr Thr Thr
65                  70                  75                  80

Gly Pro Thr Thr Ser Ala Pro Thr Val Thr Ala Ser Gly Asn Pro Phe
                85                  90                  95

Ser Gly Tyr Gln Leu Tyr Ala Asn Pro Tyr Tyr Ser Ser Glu Val His
            100                 105                 110

Thr Leu Ala Met Pro Ser Leu Pro Ser Ser Leu Gln Pro Lys Ala Ser
        115                 120                 125

Ala Val Ala Glu Val Pro Ser Phe Val Trp Leu Asp Val Ala Ala Lys
    130                 135                 140

Val Pro Thr Met Gly Thr Tyr Leu Ala Asp Ile Gln Ala Lys Asn Lys
145                 150                 155                 160

Ala Gly Ala Ser Pro Pro Ile Ala Gly Ile Phe Val Val Tyr Asp Leu
                165                 170                 175

Pro Asp Arg Asp Cys Ala Ala Leu Ala Ser Asn Gly Glu Tyr Ser Ile
            180                 185                 190

Ala Asn Asn Gly Val Ala Asn Tyr Lys Ala Tyr Ile Asp Ala Ile Arg
        195                 200                 205

Ala Gln Leu Val Lys Tyr Ser Asp Val His Thr Ile Leu Val Ile Glu
    210                 215                 220

Pro Asp Ser Leu Ala Asn Leu Val Thr Asn Leu Asn Val Ala Lys Cys
225                 230                 235                 240

Ala Asn Ala Gln Ser Ala Tyr Leu Glu Cys Val Asp Tyr Ala Leu Lys
                245                 250                 255

Gln Leu Asn Leu Pro Asn Val Ala Met Tyr Leu Asp Ala Gly His Ala
            260                 265                 270

Gly Trp Leu Gly Trp Pro Ala Asn Leu Gly Pro Ala Ala Thr Leu Phe
        275                 280                 285

Ala Lys Val Tyr Thr Asp Ala Gly Ser Pro Ala Ala Leu Arg Gly Leu
    290                 295                 300

Ala Thr Asn Val Ala Asn Tyr Asn Ala Trp Ser Leu Ser Thr Cys Pro
305                 310                 315                 320

Ser Tyr Thr Gln Gly Asp Pro Asn Cys Asp Glu Lys Lys Tyr Ile Asn
                325                 330                 335

Ala Met Ala Pro Leu Leu Lys Asn Ala Gly Phe Asp Ala His Phe Ile
            340                 345                 350

Met Asp Thr Ser Arg Asn Gly Val Gln Pro Thr Lys Gln Ser Ala Trp
        355                 360                 365

Gly Asp Trp Cys Asn Val Ile Gly Thr Gly Phe Gly Val Arg Pro Ser
    370                 375                 380

Thr Asn Thr Gly Asp Pro Leu Gln Asp Ala Phe Val Trp Ile Lys Pro
385                 390                 395                 400
```

```
Gly Gly Glu Ser Asp Gly Thr Ser Asn Ser Ser Ser Ala Arg Tyr Asp
                405                 410                 415

Ala His Cys Gly Tyr Ser Asp Ala Leu Gln Pro Ala Pro Glu Ala Gly
            420                 425                 430

Thr Trp Phe Gln Ala Tyr Phe Glu Gln Leu Leu Thr Asn Ala Asn Pro
        435                 440                 445

Ser Phe
    450


<210> SEQ ID NO 19
<211> LENGTH: 1374
<212> TYPE: DNA
<213> ORGANISM: Botryotinia fuckeliana

<400> SEQUENCE: 19

atgggtttta agaatgctct cctcgctgcc gcggctgtag cacctactgt ttatgcacag     60

ggtgcagctt acgcacaatg tggtggtcaa ggttggagtg gcgcaacaac ttgtgtttcg    120

ggatatacct gtgttgtcaa caatgcatac tattctcaat gtttacccgg ctctgcggtc    180

acgactacag caacgacagc ccccaccgca acgactccca caacaatcat cacttctacc    240

accaaagcta ccacgaccac aggtggtagc agtgcaacga caacagcagc agttgctggt    300

aatccattct caggaaaagc actttatgcg aatccatact atgcttcgga aatctctgcc    360

agtgctatcc cttcactcac tggagccatg gccactaaag ctgctgcggt agcaaaggtt    420

ccaactttct attggcttga caccgcagcc aaagttccat tgatgggaac ttaccttgcc    480

aacattcggg ccttgaacaa agcaggagca aatccacctg ttgctggtac tttcgtagtc    540

tatgatttgc cagacagaga ttgtgcagct gcagcttcca acggagaata cagcattgca    600

gacggtggtc tcgtaaaata caaagcttac atcgattcca tcgtcgctct tttgaaaact    660

tactctgatg ttagcgttat tctcgtcatt gaacccgatt cgttggccaa tctagtcacc    720

aacttgtccg tcgcaaaatg ttccaacgcc caagcagcct atctagaagg taccgaatat    780

gccatcgcgc aattgaatct tccaaacgtc gctatgtact tggatgctgg acacgctggt    840

tggttaggat ggcctgcaaa tatcggacca gctgcacagc tcttcggcca aatctacaaa    900

gcagctggaa gcccagctgc agtcagaggt cttgcaacta atgttgcaaa ctacaatgct    960

tggactagca ccacttgccc gtcctacacc tctggcgatt ccaactgtaa cgagaaattg   1020

tacatcaacg ctcttgctcc gcttttgacc gctcaaggtt tcccagctca cttcatcatg   1080

gatactagtc gcaatggtgt tcaaccaacc gcacaacaag cctggggaga ctggtgcaat   1140

ctcatcggca ccggattcgg tgttcgacca accacaaaca caggagatgc attggaagac   1200

gcatttgtct ggatcaagcc cggtggagaa ggcgacggca cttcggacac caccgctgcg   1260

cgatacgatt tccactgcgg actcgcagat gcgctcaagc cagctccaga agcgggtact   1320

tggttccaag cttactttgc ccaattactc accaatgcca atcccagctt ttaa         1374


<210> SEQ ID NO 20
<211> LENGTH: 457
<212> TYPE: PRT
<213> ORGANISM: Botryotinia fuckeliana

<400> SEQUENCE: 20

Met Gly Phe Lys Asn Ala Leu Leu Ala Ala Ala Ala Val Ala Pro Thr
1               5                   10                  15

Val Tyr Ala Gln Gly Ala Ala Tyr Ala Gln Cys Gly Gly Gln Gly Trp
```

```
            20                  25                  30

Ser Gly Ala Thr Thr Cys Val Ser Gly Tyr Thr Cys Val Val Asn Asn
        35                  40                  45

Ala Tyr Tyr Ser Gln Cys Leu Pro Gly Ser Ala Val Thr Thr Thr Ala
    50                  55                  60

Thr Thr Ala Pro Thr Ala Thr Thr Pro Thr Thr Ile Ile Thr Ser Thr
65                  70                  75                  80

Thr Lys Ala Thr Thr Thr Thr Gly Gly Ser Ser Ala Thr Thr Thr Ala
                85                  90                  95

Ala Val Ala Gly Asn Pro Phe Ser Gly Lys Ala Leu Tyr Ala Asn Pro
            100                 105                 110

Tyr Tyr Ala Ser Glu Ile Ser Ala Ser Ala Ile Pro Ser Leu Thr Gly
        115                 120                 125

Ala Met Ala Thr Lys Ala Ala Ala Val Ala Lys Val Pro Thr Phe Tyr
    130                 135                 140

Trp Leu Asp Thr Ala Ala Lys Val Pro Leu Met Gly Thr Tyr Leu Ala
145                 150                 155                 160

Asn Ile Arg Ala Leu Asn Lys Ala Gly Ala Asn Pro Pro Val Ala Gly
                165                 170                 175

Thr Phe Val Val Tyr Asp Leu Pro Asp Arg Asp Cys Ala Ala Ala Ala
            180                 185                 190

Ser Asn Gly Glu Tyr Ser Ile Ala Asp Gly Gly Leu Val Lys Tyr Lys
        195                 200                 205

Ala Tyr Ile Asp Ser Ile Val Ala Leu Leu Lys Thr Tyr Ser Asp Val
    210                 215                 220

Ser Val Ile Leu Val Ile Glu Pro Asp Ser Leu Ala Asn Leu Val Thr
225                 230                 235                 240

Asn Leu Ser Val Ala Lys Cys Ser Asn Ala Gln Ala Ala Tyr Leu Glu
                245                 250                 255

Gly Thr Glu Tyr Ala Ile Ala Gln Leu Asn Leu Pro Asn Val Ala Met
            260                 265                 270

Tyr Leu Asp Ala Gly His Ala Gly Trp Leu Gly Trp Pro Ala Asn Ile
        275                 280                 285

Gly Pro Ala Ala Gln Leu Phe Gly Gln Ile Tyr Lys Ala Ala Gly Ser
    290                 295                 300

Pro Ala Ala Val Arg Gly Leu Ala Thr Asn Val Ala Asn Tyr Asn Ala
305                 310                 315                 320

Trp Thr Ser Thr Thr Cys Pro Ser Tyr Thr Ser Gly Asp Ser Asn Cys
                325                 330                 335

Asn Glu Lys Leu Tyr Ile Asn Ala Leu Ala Pro Leu Leu Thr Ala Gln
            340                 345                 350

Gly Phe Pro Ala His Phe Ile Met Asp Thr Ser Arg Asn Gly Val Gln
        355                 360                 365

Pro Thr Ala Gln Gln Ala Trp Gly Asp Trp Cys Asn Leu Ile Gly Thr
    370                 375                 380

Gly Phe Gly Val Arg Pro Thr Thr Asn Thr Gly Asp Ala Leu Glu Asp
385                 390                 395                 400

Ala Phe Val Trp Ile Lys Pro Gly Gly Glu Gly Asp Gly Thr Ser Asp
                405                 410                 415

Thr Thr Ala Ala Arg Tyr Asp Phe His Cys Gly Leu Ala Asp Ala Leu
            420                 425                 430

Lys Pro Ala Pro Glu Ala Gly Thr Trp Phe Gln Ala Tyr Phe Ala Gln
        435                 440                 445
```

Leu Leu Thr Asn Ala Asn Pro Ser Phe
450 455

<210> SEQ ID NO 21
<211> LENGTH: 1407
<212> TYPE: DNA
<213> ORGANISM: Aspergillus terreus

<400> SEQUENCE: 21
atgggacggg tttcttccct tgcgcttgct cttctactcc ctgctgtgca ggcccagcaa 60 acccttttggg gtcaatgtgg tggcattggg tggacaggcc caacaaattg tgtcgctggc 120
gctgcgtgta gcacgcagaa tccttactat gcgcaatgcc ttcctgggac tgcgaccact 180
tcgactaccc taaccacgac taccagggtt accactacga caacttccac gacatcgaag 240
agctcctcta caggctctac cactacgaca aagtcaaccg gaaccaccac gacctccggc 300
tcctccacca ccatcacctc tgcgccgtct ggcaatccct tcagcggata tcaactctat 360
gccaaccctt actattcctc agaggtgcac accctggcca tgccctccct cgctagctcg 420
ctcttgccag cggccagcgc ggcagccaaa gtcccgtcgt tcacctggct ggacactgcc 480
gccaaagtgc ctaccatggg cacctacctg gcagacatca aggccaagaa tgctgccggt 540
gccaacccac ccatcgctgc ccaattcgtt gtctacgatc tccccgaccg tgactgcgct 600
gctctggcta gcaatggcga gtactcaatt gcgaacggcg gtgttgctaa ctacaagaaa 660
tacattgatg ccatccgggc ccagttgctg aactaccccg atgtccacac cattctcgtc 720
atcgaacccg acagcttggc caatctggtc accaacctga acgtggccaa atgcgccaac 780
gcccagagcg cctatctgga gtgtgtcaat tatgcgctca tccagctgaa cttgcccaat 840
gtcgccatgt atatcgatgc cggtcacgcg ggctggcttg gatggcccgc caacatcggc 900
cctgccgccc aactcttcgc cggagtatac aaggacgccg gcgctcccgc cgcgctgcgc 960
ggcctcgcga ccaacgtcgc caactacaat gccttcagca taagcacctg cccgtcgtac 1020
acgtccggcg atgccaactg cgatgagaac cgctacatca acgcaattgc acccccttctg 1080 aaggatcaag gctgggatgc ccactttatt gttgatactg gtcgcaacgg tgtgcagccc 1140
actaagcaaa acgcttgggg tgactggtgc aatgtcatcg gaactggttt cggtgtccgg 1200
cctaccacca acactggcaa ctcgctggtg gacgcgtttg tctgggttaa gccgggcggc 1260
gagagcgatg gtacctctga ctccagttct gcgcggtatg atgcgcactg cggatatagt 1320
gatgcgctcc aacctgctcc tgaggctgga acttggttcc aggcatactt tgagcagctc 1380
ctgaaaaacg ccaatcctgc cttctaa 1407

<210> SEQ ID NO 22
<211> LENGTH: 468
<212> TYPE: PRT
<213> ORGANISM: Aspergillus terreus

<400> SEQUENCE: 22

Met Gly Arg Val Ser Ser Leu Ala Leu Ala Leu Leu Leu Pro Ala Val
1 5 10 15

Gln Ala Gln Gln Thr Leu Trp Gly Gln Cys Gly Gly Ile Gly Trp Thr
20 25 30

Gly Pro Thr Asn Cys Val Ala Gly Ala Ala Cys Ser Thr Gln Asn Pro
35 40 45

Tyr Tyr Ala Gln Cys Leu Pro Gly Thr Ala Thr Thr Ser Thr Thr Leu
50 55 60

```
Thr Thr Thr Thr Arg Val Thr Thr Thr Thr Thr Ser Thr Thr Ser Lys
65                  70                  75                  80

Ser Ser Ser Thr Gly Ser Thr Thr Thr Thr Lys Ser Thr Gly Thr Thr
                85                  90                  95

Thr Thr Ser Gly Ser Ser Thr Thr Ile Thr Ser Ala Pro Ser Gly Asn
            100                 105                 110

Pro Phe Ser Gly Tyr Gln Leu Tyr Ala Asn Pro Tyr Tyr Ser Ser Glu
        115                 120                 125

Val His Thr Leu Ala Met Pro Ser Leu Ala Ser Ser Leu Leu Pro Ala
    130                 135                 140

Ala Ser Ala Ala Ala Lys Val Pro Ser Phe Thr Trp Leu Asp Thr Ala
145                 150                 155                 160

Ala Lys Val Pro Thr Met Gly Thr Tyr Leu Ala Asp Ile Lys Ala Lys
                165                 170                 175

Asn Ala Ala Gly Ala Asn Pro Pro Ile Ala Ala Gln Phe Val Val Tyr
            180                 185                 190

Asp Leu Pro Asp Arg Asp Cys Ala Ala Leu Ala Ser Asn Gly Glu Tyr
        195                 200                 205

Ser Ile Ala Asn Gly Gly Val Ala Asn Tyr Lys Lys Tyr Ile Asp Ala
    210                 215                 220

Ile Arg Ala Gln Leu Leu Asn Tyr Pro Asp Val His Thr Ile Leu Val
225                 230                 235                 240

Ile Glu Pro Asp Ser Leu Ala Asn Leu Val Thr Asn Leu Asn Val Ala
                245                 250                 255

Lys Cys Ala Asn Ala Gln Ser Ala Tyr Leu Glu Cys Val Asn Tyr Ala
            260                 265                 270

Leu Ile Gln Leu Asn Leu Pro Asn Val Ala Met Tyr Ile Asp Ala Gly
        275                 280                 285

His Ala Gly Trp Leu Gly Trp Pro Ala Asn Ile Gly Pro Ala Ala Gln
    290                 295                 300

Leu Phe Ala Gly Val Tyr Lys Asp Ala Gly Ala Pro Ala Ala Leu Arg
305                 310                 315                 320

Gly Leu Ala Thr Asn Val Ala Asn Tyr Asn Ala Phe Ser Ile Ser Thr
                325                 330                 335

Cys Pro Ser Tyr Thr Ser Gly Asp Ala Asn Cys Asp Glu Asn Arg Tyr
            340                 345                 350

Ile Asn Ala Ile Ala Pro Leu Leu Lys Asp Gln Gly Trp Asp Ala His
        355                 360                 365

Phe Ile Val Asp Thr Gly Arg Asn Gly Val Gln Pro Thr Lys Gln Asn
    370                 375                 380

Ala Trp Gly Asp Trp Cys Asn Val Ile Gly Thr Gly Phe Gly Val Arg
385                 390                 395                 400

Pro Thr Thr Asn Thr Gly Asn Ser Leu Val Asp Ala Phe Val Trp Val
                405                 410                 415

Lys Pro Gly Gly Glu Ser Asp Gly Thr Ser Asp Ser Ser Ser Ala Arg
            420                 425                 430

Tyr Asp Ala His Cys Gly Tyr Ser Asp Ala Leu Gln Pro Ala Pro Glu
        435                 440                 445

Ala Gly Thr Trp Phe Gln Ala Tyr Phe Glu Gln Leu Leu Lys Asn Ala
    450                 455                 460

Asn Pro Ala Phe
465
```

<210> SEQ ID NO 23
<211> LENGTH: 1212
<212> TYPE: DNA
<213> ORGANISM: Aspergillus terreus

<400> SEQUENCE: 23

```
atgcgggccc tgtgggctct tgcacccgtt ctcttccctg ctgtgagcgc tctgcccact      60

gcaagctcta ctccgactcc ctctactccg ggcccatcga ctaccccagc accaactgcg     120

gcccctggtg ggaacccctt cgagggatac cagcaatatg tcaatcctta ctacaagtcc     180

gaggtcctgt cccttgctgt tccttccatg accggcgacc tcgctgcgca ggcgagtgcg     240

gcagctgacg ttccgtcgtt cttctggctc gacacagccg acaaggtccc tcagatgggc     300

accttcctga agaacatcaa ggaggcaaat gacggcggcg ccaatccccc caatgcgggc     360

atcttcgttg tctacgactt gccggaccgc gactgcgccg cgctggccag caacggcgag     420

tattcgattg cggacggcgg tgtcgagaaa tacaaggcgt acatcgactc gatcaagaag     480

cagctggaga cctactctga tgttcagaac atcctcatca tcgagccgga tagtctggcc     540

aacctggtta ccaacatgaa cgtcgagaag tgcgccaacg cccacgatgc ctacctggag     600

tgcaccaact atgccatcac gcagctgaac ctccccaatg tggcgatgta tctcgacgct     660

ggtcatgccg gatggctggg ctggcccgcc aacatcggcc ccgcggccga gctgttcgcc     720

ggagtctaca agaacgcgtc ttcccctgct gccctccgtg gactggcaac taacgtagcc     780

aactacaacg ccttctccat cgacacctgc ccctcgtaca cctcagagaa cgaggtctgc     840

gatgagaaga gctatatcaa caactttgcg cccgaactca agagcaacgg cttcgatgct     900

cacttcattg tcgacactgg tcgcaacggt aaccagccca ctggacagct ggagtggggt     960

gactggtgca atgttgtcga caccggcttc ggtgctcgtc cctccaccga caccggtgat    1020

gaactggttg atgcctttgt ctgggtgaag cctggtggtg agagtgacgg tacctcggac    1080

acctctgctg agcgctatga tgcccactgc ggtctggatg acgccctgaa gccggctcct    1140

gaggctggta cttggttcca ggcgtacttt gagcagctgg tgaagaacgc aaacccacct    1200

ctgtctagct ag                                                        1212
```

<210> SEQ ID NO 24
<211> LENGTH: 403
<212> TYPE: PRT
<213> ORGANISM: Aspergillus terreus

<400> SEQUENCE: 24

```
Met Arg Ala Leu Trp Ala Leu Ala Pro Val Leu Phe Pro Ala Val Ser
1               5                   10                  15

Ala Leu Pro Thr Ala Ser Ser Thr Pro Thr Pro Ser Thr Pro Gly Pro
            20                  25                  30

Ser Thr Thr Pro Ala Pro Thr Ala Ala Pro Gly Gly Asn Pro Phe Glu
        35                  40                  45

Gly Tyr Gln Gln Tyr Val Asn Pro Tyr Tyr Lys Ser Glu Val Leu Ser
    50                  55                  60

Leu Ala Val Pro Ser Met Thr Gly Asp Leu Ala Ala Gln Ala Ser Ala
65                  70                  75                  80

Ala Ala Asp Val Pro Ser Phe Phe Trp Leu Asp Thr Ala Asp Lys Val
                85                  90                  95

Pro Gln Met Gly Thr Phe Leu Lys Asn Ile Lys Glu Ala Asn Asp Gly
            100                 105                 110
```

```
Gly Ala Asn Pro Pro Asn Ala Gly Ile Phe Val Val Tyr Asp Leu Pro
        115                 120                 125

Asp Arg Asp Cys Ala Ala Leu Ala Ser Asn Gly Glu Tyr Ser Ile Ala
    130                 135                 140

Asp Gly Gly Val Glu Lys Tyr Lys Ala Tyr Ile Asp Ser Ile Lys Lys
145                 150                 155                 160

Gln Leu Glu Thr Tyr Ser Asp Val Gln Asn Ile Leu Ile Ile Glu Pro
                165                 170                 175

Asp Ser Leu Ala Asn Leu Val Thr Asn Met Asn Val Glu Lys Cys Ala
            180                 185                 190

Asn Ala His Asp Ala Tyr Leu Glu Cys Thr Asn Tyr Ala Ile Thr Gln
        195                 200                 205

Leu Asn Leu Pro Asn Val Ala Met Tyr Leu Asp Ala Gly His Ala Gly
    210                 215                 220

Trp Leu Gly Trp Pro Ala Asn Ile Gly Pro Ala Ala Glu Leu Phe Ala
225                 230                 235                 240

Gly Val Tyr Lys Asn Ala Ser Ser Pro Ala Ala Leu Arg Gly Leu Ala
                245                 250                 255

Thr Asn Val Ala Asn Tyr Asn Ala Phe Ser Ile Asp Thr Cys Pro Ser
            260                 265                 270

Tyr Thr Ser Glu Asn Glu Val Cys Asp Glu Lys Ser Tyr Ile Asn Asn
        275                 280                 285

Phe Ala Pro Glu Leu Lys Ser Asn Gly Phe Asp Ala His Phe Ile Val
    290                 295                 300

Asp Thr Gly Arg Asn Gly Asn Gln Pro Thr Gly Gln Leu Glu Trp Gly
305                 310                 315                 320

Asp Trp Cys Asn Val Val Asp Thr Gly Phe Gly Ala Arg Pro Ser Thr
                325                 330                 335

Asp Thr Gly Asp Glu Leu Val Asp Ala Phe Val Trp Val Lys Pro Gly
            340                 345                 350

Gly Glu Ser Asp Gly Thr Ser Asp Thr Ser Ala Glu Arg Tyr Asp Ala
        355                 360                 365

His Cys Gly Leu Asp Asp Ala Leu Lys Pro Ala Pro Glu Ala Gly Thr
    370                 375                 380

Trp Phe Gln Ala Tyr Phe Glu Gln Leu Val Lys Asn Ala Asn Pro Pro
385                 390                 395                 400

Leu Ser Ser


<210> SEQ ID NO 25
<211> LENGTH: 1455
<212> TYPE: DNA
<213> ORGANISM: Neurospora crassa

<400> SEQUENCE: 25

atggctgcca agaagctcct tctcgctgcc gccttgacgg cctctgccct cgccgctccc      60

gtcctcgagg atcgccagaa ctgcggctct gcctggagcc agtgcggtgg tattggctgg     120

tctggtgcga cttgctgctc ctccggcaac tcctgcgttg agatcaactc ttactactcc     180

cagtgcttgc ccggcgctca ggttaccacc actgctgggg cttcttccac cagccctacc     240

agcaccagca aggtctctag caccaccagc aaggttacca gcagcagcgc tgcccagccc     300

atcaccacta ctaccgctcc ttcggtgccc accaccacca ttgctggcgg tgcttcctcc     360

actgctagct tcactggcaa ccccttcctt ggtgttcagg gctgggccaa cagctactac     420

tcctccgaga tttacaacca tgccattcct tccatgactg gcagcttggc tgctcaggcg     480
```

```
tctgccgttg ccaaggttcc caccttccag tggcttgacc gcaacgtcac cgttgacacc    540

ctcatgaaga gcacccttga ggagattcgc gcggccaaca aggccggtgc caaccctccc    600

tacgccgctc actttgtcgt ctacgatctc cctgaccgtg actgcgctgc tgccgcctcc    660

aacggcgagt tctccatcgc caacggcggc gttgccaact acaagaccta catcaacgcc    720

atccgcaaac tcctgattga gtactcggac atccgcacca tcctcgtcat cgagcccgac    780

tcgcttgcta acctcgtcac caacaccaac gttgccaagt gtgccaatgc cgcctccgcc    840

tacagggagt gcaccaacta cgccatcacc cagctcgacc ttcctcacgt cgcccagtac    900

cttgatgctg gtcacggtgg ctggctcggc tggcccgcta acatccagcc tgctgccacc    960

ctcttcgccg acatttacaa ggccgccggt aagcccaagt ccgtccgcgg tctcgtcacc   1020

aacgtctcca actacaacgg ctggtcgcta tcctccgctc cctcgtacac cacgcccaac   1080

cccaactacg acgagaagaa gtacatcgag gctttctccc ctcttctcaa cgctgccggc   1140

ttcccggccc agttcatcgt tgacacgggc cgttccggca agcagccgac tggccagatc   1200

gagcagggtg actggtgtaa cgccatcggc actggcttcg gtgtccgccc taccaccaac   1260

actggctcct cgttggctga tgccttcgtc tgggtcaagc ccggtggtga gtccgatggt   1320

accagcgaca cctccgctac ccgctatgac taccactgcg gtctctcgga tgccctcaag   1380

cctgcccctg aggctggcca gtggttccag gcttactttg agcagctgct caagaacgct   1440

aaccccgctt tctga                                                    1455
```

```
<210> SEQ ID NO 26
<211> LENGTH: 484
<212> TYPE: PRT
<213> ORGANISM: Neurospora crassa

<400> SEQUENCE: 26

Met Ala Ala Lys Lys Leu Leu Leu Ala Ala Ala Leu Thr Ala Ser Ala
1               5                   10                  15

Leu Ala Ala Pro Val Leu Glu Asp Arg Gln Asn Cys Gly Ser Ala Trp
            20                  25                  30

Ser Gln Cys Gly Gly Ile Gly Trp Ser Gly Ala Thr Cys Cys Ser Ser
        35                  40                  45

Gly Asn Ser Cys Val Glu Ile Asn Ser Tyr Tyr Ser Gln Cys Leu Pro
    50                  55                  60

Gly Ala Gln Val Thr Thr Thr Ala Gly Ala Ser Ser Thr Ser Pro Thr
65                  70                  75                  80

Ser Thr Ser Lys Val Ser Ser Thr Thr Ser Lys Val Thr Ser Ser Ser
                85                  90                  95

Ala Ala Gln Pro Ile Thr Thr Thr Thr Ala Pro Ser Val Pro Thr Thr
            100                 105                 110

Thr Ile Ala Gly Gly Ala Ser Ser Thr Ala Ser Phe Thr Gly Asn Pro
        115                 120                 125

Phe Leu Gly Val Gln Gly Trp Ala Asn Ser Tyr Tyr Ser Ser Glu Ile
    130                 135                 140

Tyr Asn His Ala Ile Pro Ser Met Thr Gly Ser Leu Ala Ala Gln Ala
145                 150                 155                 160

Ser Ala Val Ala Lys Val Pro Thr Phe Gln Trp Leu Asp Arg Asn Val
                165                 170                 175

Thr Val Asp Thr Leu Met Lys Ser Thr Leu Glu Glu Ile Arg Ala Ala
            180                 185                 190
```

```
Asn Lys Ala Gly Ala Asn Pro Pro Tyr Ala Ala His Phe Val Val Tyr
        195                 200                 205

Asp Leu Pro Asp Arg Asp Cys Ala Ala Ala Ala Ser Asn Gly Glu Phe
    210                 215                 220

Ser Ile Ala Asn Gly Gly Val Ala Asn Tyr Lys Thr Tyr Ile Asn Ala
225                 230                 235                 240

Ile Arg Lys Leu Leu Ile Glu Tyr Ser Asp Ile Arg Thr Ile Leu Val
                245                 250                 255

Ile Glu Pro Asp Ser Leu Ala Asn Leu Val Thr Asn Thr Asn Val Ala
            260                 265                 270

Lys Cys Ala Asn Ala Ala Ser Ala Tyr Arg Glu Cys Thr Asn Tyr Ala
        275                 280                 285

Ile Thr Gln Leu Asp Leu Pro His Val Ala Gln Tyr Leu Asp Ala Gly
    290                 295                 300

His Gly Gly Trp Leu Gly Trp Pro Ala Asn Ile Gln Pro Ala Ala Thr
305                 310                 315                 320

Leu Phe Ala Asp Ile Tyr Lys Ala Ala Gly Lys Pro Lys Ser Val Arg
                325                 330                 335

Gly Leu Val Thr Asn Val Ser Asn Tyr Asn Gly Trp Ser Leu Ser Ser
            340                 345                 350

Ala Pro Ser Tyr Thr Thr Pro Asn Pro Asn Tyr Asp Glu Lys Lys Tyr
        355                 360                 365

Ile Glu Ala Phe Ser Pro Leu Leu Asn Ala Ala Gly Phe Pro Ala Gln
    370                 375                 380

Phe Ile Val Asp Thr Gly Arg Ser Gly Lys Gln Pro Thr Gly Gln Ile
385                 390                 395                 400

Glu Gln Gly Asp Trp Cys Asn Ala Ile Gly Thr Gly Phe Gly Val Arg
                405                 410                 415

Pro Thr Thr Asn Thr Gly Ser Ser Leu Ala Asp Ala Phe Val Trp Val
            420                 425                 430

Lys Pro Gly Gly Glu Ser Asp Gly Thr Ser Asp Thr Ser Ala Thr Arg
        435                 440                 445

Tyr Asp Tyr His Cys Gly Leu Ser Asp Ala Leu Lys Pro Ala Pro Glu
    450                 455                 460

Ala Gly Gln Trp Phe Gln Ala Tyr Phe Glu Gln Leu Leu Lys Asn Ala
465                 470                 475                 480

Asn Pro Ala Phe
```

```
<210> SEQ ID NO 27
<211> LENGTH: 1395
<212> TYPE: DNA
<213> ORGANISM: Penicillium oxalicum

<400> SEQUENCE: 27

atgcagagaa catcagcttg ggcactgctc cttctggcgc agattgccac tgctcagcag      60

accgtctggg gacaatgtgg tggtatcggc tactctggac cgactagctg tgttgcagga     120

tcttcttgta gcacccagaa ctcttactac gcccaatgtc tcccgggcag tggaaacggc     180

ggcggcggtg cggcgaccac gactacggct gctggacaaa ccaccaagac caccatggcc     240

accaccacca cgtcaaccaa gacctcagcc ggtggtagcg gcggtagcac caccactgct     300

cctcctgcca gcaacagtgg caaccccttc aagggatacc agccttacgt gaacccgtac     360

tacgcttctg aggttcagag cctggctatt ccctctctgg cagcctctct ggcgcccaag     420

gccagcgccg tggccaaggt cccatccttc gtttggctgg acactgctgc taaggtccct     480
```

```
actatgggca cttacttggc agacatcaag gccaagaacg cggctggtgc taacccaccc    540

attgccggta tctttgtcgt ttacgatctt cctgaccgtg actgcgctgc tcttgccagt    600

aacggcgagt actccatcgc caacggcggt gttgccaact acaagaagta cattgactcg    660

atccgcgctc agcttctcaa gtaccctgat gtgcacacca ttctggtcat cgaacccgac    720

agtctcgcca acctggtcac caacatgaac gtcgccaaat gctcgggtgc tcacgacgcc    780

tacctggagt gcaccgacta tgcactcaag cagctcaacc tgcccaacgt tgccatgtac    840

cttgatgccg gacacgctgg ctggctcgga tggcccgcca acattggacc cgctgccgac    900

ctcttcgcca gtgtgtacaa gaatgccggc tctcccgccg ccgtccgtgg attggccacc    960

aacgttgcca actacaacgc ctggtccatc tccacctgcc cgtcttacac tcagggtgac   1020

cagaactgtg acgagaagcg ctacatcaac gccctcgctc ctctcctccg cgcgaacggc   1080

ttcgacgccc acttcatcat ggacacctcc cgtaacggtg ttcagcccac taagcaacaa   1140

gcctggggtg actggtgcaa cgtcattggc actggcttcg gtactccctt caccaccgac   1200

accggtgatg ctctccagga cgctttcatc tgggtaaagc ccggtggtga gtgtgacggt   1260

acctccgaca cctcctcccc tcgctacgac gcccactgcg gatacagcga tgccctccag   1320

ccggcccccg aggctggaac ttggttccag gcctacttcg agcagctgct cgtcaacgcc   1380

aacccaagct tctaa                                                    1395
```

```
<210> SEQ ID NO 28
<211> LENGTH: 464
<212> TYPE: PRT
<213> ORGANISM: Penicillium oxalicum

<400> SEQUENCE: 28

Met Gln Arg Thr Ser Ala Trp Ala Leu Leu Leu Leu Ala Gln Ile Ala
1               5                   10                  15

Thr Ala Gln Gln Thr Val Trp Gly Gln Cys Gly Gly Ile Gly Tyr Ser
            20                  25                  30

Gly Pro Thr Ser Cys Val Ala Gly Ser Ser Cys Ser Thr Gln Asn Ser
        35                  40                  45

Tyr Tyr Ala Gln Cys Leu Pro Gly Ser Gly Asn Gly Gly Gly Gly Ala
    50                  55                  60

Ala Thr Thr Thr Thr Ala Ala Gly Gln Thr Thr Lys Thr Thr Met Ala
65                  70                  75                  80

Thr Thr Thr Thr Ser Thr Lys Thr Ser Ala Gly Gly Ser Gly Gly Ser
                85                  90                  95

Thr Thr Thr Ala Pro Pro Ala Ser Asn Ser Gly Asn Pro Phe Lys Gly
            100                 105                 110

Tyr Gln Pro Tyr Val Asn Pro Tyr Tyr Ala Ser Glu Val Gln Ser Leu
        115                 120                 125

Ala Ile Pro Ser Leu Ala Ala Ser Leu Ala Pro Lys Ala Ser Ala Val
    130                 135                 140

Ala Lys Val Pro Ser Phe Val Trp Leu Asp Thr Ala Ala Lys Val Pro
145                 150                 155                 160

Thr Met Gly Thr Tyr Leu Ala Asp Ile Lys Ala Lys Asn Ala Ala Gly
                165                 170                 175

Ala Asn Pro Pro Ile Ala Gly Ile Phe Val Val Tyr Asp Leu Pro Asp
            180                 185                 190

Arg Asp Cys Ala Ala Leu Ala Ser Asn Gly Glu Tyr Ser Ile Ala Asn
        195                 200                 205
```

```
Gly Gly Val Ala Asn Tyr Lys Lys Tyr Ile Asp Ser Ile Arg Ala Gln
    210                 215                 220

Leu Leu Lys Tyr Pro Asp Val His Thr Ile Leu Val Ile Glu Pro Asp
225                 230                 235                 240

Ser Leu Ala Asn Leu Val Thr Asn Met Asn Val Ala Lys Cys Ser Gly
                245                 250                 255

Ala His Asp Ala Tyr Leu Glu Cys Thr Asp Tyr Ala Leu Lys Gln Leu
            260                 265                 270

Asn Leu Pro Asn Val Ala Met Tyr Leu Asp Ala Gly His Ala Gly Trp
        275                 280                 285

Leu Gly Trp Pro Ala Asn Ile Gly Pro Ala Ala Asp Leu Phe Ala Ser
    290                 295                 300

Val Tyr Lys Asn Ala Gly Ser Pro Ala Ala Val Arg Gly Leu Ala Thr
305                 310                 315                 320

Asn Val Ala Asn Tyr Asn Ala Trp Ser Ile Ser Thr Cys Pro Ser Tyr
                325                 330                 335

Thr Gln Gly Asp Gln Asn Cys Asp Glu Lys Arg Tyr Ile Asn Ala Leu
            340                 345                 350

Ala Pro Leu Leu Arg Ala Asn Gly Phe Asp Ala His Phe Ile Met Asp
        355                 360                 365

Thr Ser Arg Asn Gly Val Gln Pro Thr Lys Gln Gln Ala Trp Gly Asp
    370                 375                 380

Trp Cys Asn Val Ile Gly Thr Gly Phe Gly Thr Pro Phe Thr Thr Asp
385                 390                 395                 400

Thr Gly Asp Ala Leu Gln Asp Ala Phe Ile Trp Val Lys Pro Gly Gly
                405                 410                 415

Glu Cys Asp Gly Thr Ser Asp Thr Ser Ser Pro Arg Tyr Asp Ala His
            420                 425                 430

Cys Gly Tyr Ser Asp Ala Leu Gln Pro Ala Pro Glu Ala Gly Thr Trp
        435                 440                 445

Phe Gln Ala Tyr Phe Glu Gln Leu Leu Val Asn Ala Asn Pro Ser Phe
    450                 455                 460
```

<210> SEQ ID NO 29
<211> LENGTH: 1458
<212> TYPE: DNA
<213> ORGANISM: Lecythophora hoffmannii

<400> SEQUENCE: 29

```
atggctgcca gacgcatctt tcttgccgcg gctcttacgg caactgtgct cgctgcacca      60

gtcgtcgaag agcgtcagaa ctgtggtgga acatggagcc agtgcggagg tattgggttc     120

agcggtccaa cctgctgtgc gtcggggagt agctgtgtaa aacagaatga ctattattcg     180

caatgcttgc cggggaatca agtaacgaca actacgactg cgaagaccag ttcgacaact     240

tccaagacca gcagcagcac ttcgccgccg accactgtga agtctacgac gacttcgagc     300

aagcccacga ccacgggttc cactaccact acgaccaagc cgcctactgg aactgcctcg     360

ggcactgcct catacagcgg aaacccattt tccggcgttc agatgtgggc aaacaattat     420

tatgcttcgg aggtactcaa cctcgcagtg cccagcctga gcggtgctct cgctgcaaag     480

gcttctgctg tggccaaggt tcctagcttc cagtggctcg acaccgcctc caaggtccca     540

actgtcatgg ccgacactct tgcagatatc cgggctgcca acaaagccgg cgccaaccct     600

ccctacgctg gtctctttgt tgtctatgac ctgcccgacc gcgactgtgc cgccgctgcg     660
```

```
tccaacggag agtatagcat cgccaatgga ggcgttgcca actacaaggc ttatatcgac     720

gcgatccgag ctcagctcgt cacttattcg gatctccgta tccttttgat cgttgagcct     780

gactctctgg caaacctagt gactaacatg aacgtcgcca aatgctccgg cgcccatgac     840

gcctaccttg agtgcgtaaa ttacgccgtc aagcagctca accttccgaa tgtggccatg     900

tatctcgacg ccggccatgc tggctggctc ggctggagtg ccaatctcca gccggccgct     960

accctctttg ccaatgtcta caccaacgcc gggaagccgg ctgctctccg tggtctggcg    1020

accaacgtcg cgaactacaa tggttggaat ctcacctccc cgccttcgta cacccaagga    1080

aatagcaact acgatgagat tcattacgtc caggccattg cccctcttct cagctccgcc    1140

ggctggaacg ctcactttgt taccgatacg ggccgctcgg gcaagcagcc cacggggcag    1200

caagcctggg gtgattggtg taatcaaaag ggtactggat tcggtatgcg tccaactgcc    1260

aacactgggc ttgagcttga ggatgcgttc gtctggatca agccgggtgg cgaatgcgac    1320

ggcaccagcg acactagtgc agctcgatac gacttccact gcggcctatc agacgctctg    1380

cagcctgcgc ctgaagctgg tacatggttc caggcatact tcgagcagct gctcacgaac    1440

gccaaccctt ctttctaa                                                  1458
```

<210> SEQ ID NO 30
<211> LENGTH: 485
<212> TYPE: PRT
<213> ORGANISM: Lecythophora hoffmannii

<400> SEQUENCE: 30

```
Met Ala Ala Arg Arg Ile Phe Leu Ala Ala Ala Leu Thr Ala Thr Val
1               5                   10                  15

Leu Ala Ala Pro Val Val Glu Glu Arg Gln Asn Cys Gly Gly Thr Trp
            20                  25                  30

Ser Gln Cys Gly Gly Ile Gly Phe Ser Gly Pro Thr Cys Cys Ala Ser
        35                  40                  45

Gly Ser Ser Cys Val Lys Gln Asn Asp Tyr Tyr Ser Gln Cys Leu Pro
    50                  55                  60

Gly Asn Gln Val Thr Thr Thr Thr Thr Ala Lys Thr Ser Ser Thr Thr
65                  70                  75                  80

Ser Lys Thr Ser Ser Ser Thr Ser Pro Pro Thr Thr Val Lys Ser Thr
                85                  90                  95

Thr Thr Ser Ser Lys Pro Thr Thr Thr Gly Ser Thr Thr Thr Thr Thr
            100                 105                 110

Lys Pro Pro Thr Gly Thr Ala Ser Gly Thr Ala Ser Tyr Ser Gly Asn
        115                 120                 125

Pro Phe Ser Gly Val Gln Met Trp Ala Asn Asn Tyr Tyr Ala Ser Glu
    130                 135                 140

Val Leu Asn Leu Ala Val Pro Ser Leu Ser Gly Ala Leu Ala Ala Lys
145                 150                 155                 160

Ala Ser Ala Val Ala Lys Val Pro Ser Phe Gln Trp Leu Asp Thr Ala
                165                 170                 175

Ser Lys Val Pro Thr Val Met Ala Asp Thr Leu Ala Asp Ile Arg Ala
            180                 185                 190

Ala Asn Lys Ala Gly Ala Asn Pro Pro Tyr Ala Gly Leu Phe Val Val
        195                 200                 205

Tyr Asp Leu Pro Asp Arg Asp Cys Ala Ala Ala Ala Ser Asn Gly Glu
    210                 215                 220

Tyr Ser Ile Ala Asn Gly Gly Val Ala Asn Tyr Lys Ala Tyr Ile Asp
```

```
225                 230                 235                 240

Ala Ile Arg Ala Gln Leu Val Thr Tyr Ser Asp Leu Arg Ile Leu Leu
                245                 250                 255

Ile Val Glu Pro Asp Ser Leu Ala Asn Leu Val Thr Asn Met Asn Val
            260                 265                 270

Ala Lys Cys Ser Gly Ala His Asp Ala Tyr Leu Glu Cys Val Asn Tyr
        275                 280                 285

Ala Val Lys Gln Leu Asn Leu Pro Asn Val Ala Met Tyr Leu Asp Ala
    290                 295                 300

Gly His Ala Gly Trp Leu Gly Trp Ser Ala Asn Leu Gln Pro Ala Ala
305                 310                 315                 320

Thr Leu Phe Ala Asn Val Tyr Thr Asn Ala Gly Lys Pro Ala Ala Leu
                325                 330                 335

Arg Gly Leu Ala Thr Asn Val Ala Asn Tyr Asn Gly Trp Asn Leu Thr
            340                 345                 350

Ser Pro Pro Ser Tyr Thr Gln Gly Asn Ser Asn Tyr Asp Glu Ile His
        355                 360                 365

Tyr Val Gln Ala Ile Ala Pro Leu Leu Ser Ser Ala Gly Trp Asn Ala
    370                 375                 380

His Phe Val Thr Asp Thr Gly Arg Ser Gly Lys Gln Pro Thr Gly Gln
385                 390                 395                 400

Gln Ala Trp Gly Asp Trp Cys Asn Gln Lys Gly Thr Gly Phe Gly Met
                405                 410                 415

Arg Pro Thr Ala Asn Thr Gly Leu Glu Leu Glu Asp Ala Phe Val Trp
            420                 425                 430

Ile Lys Pro Gly Gly Glu Cys Asp Gly Thr Ser Asp Thr Ser Ala Ala
        435                 440                 445

Arg Tyr Asp Phe His Cys Gly Leu Ser Asp Ala Leu Gln Pro Ala Pro
    450                 455                 460

Glu Ala Gly Thr Trp Phe Gln Ala Tyr Phe Glu Gln Leu Leu Thr Asn
465                 470                 475                 480

Ala Asn Pro Ser Phe
                485
```

<210> SEQ ID NO 31
<211> LENGTH: 1158
<212> TYPE: DNA
<213> ORGANISM: Penicillium capsulatum

<400> SEQUENCE: 31

```
atgcacttta tagtctcaat tgcaaccttt gcagcctgtg tttcggcggc tgccattgcc     60

cgtgcgaacc aggccaccgt tggcaatccc ttctcgggat accaactcta tgccaacacg    120

tactatgcat cagaagtttc agcttcggct ttgccgtcca tgactggcac tgcgaaagct    180

gcggcaagtt cagctgctaa agtgccttca ttctattggc tagataccgc tgacaaggta    240

tctgtaatgg gagagtttct atccgacatt caatcgaaga attccgctgg cgcaagtcct    300

cctattgctg gcatctttgt cgtgtatgac ttgccggaca gggactgcgc tgcgctggcc    360

agcaacggcg agtacacaat cgctaacggg ggagtggaaa agtacaaggc gtacattgac    420

tccatcaaaa ctacccttga gaaatactcc gacgtccaca ctattctgat tatcgaaccc    480

gatagtctgg cgaatctggt caccaacatg gcggtatcaa agtgtgccaa tgcatataat    540

gcatacctgg aatgtacaaa ctacgcaatt acccagctga accttgataa tgtcgccatg    600

tatctcgatg ccggacatgc tgggtggcta ggctggccag caaatctgag ccctgcagcc    660
```

```
gtattattcg gccaggtgta taaaaatgcc tcgcagccct catcacttcg tggcctggca    720

accaatgttg ccaactacaa cggctggtct cttaacacct gtccttcgta tacctcaggc    780

gattccaact gtgatgaaaa gagatacgtg aatgcacttg ctcctctgct actcaacgag    840

ggttgggacg cacattttat cactgatact ggcaggaatg gtgtacagcc taccaagcaa    900

aatgcatggg gagattggtg taatgtgaag ggtactggct ttggcgttcg ccctaccaca    960

gacaccgggg acaatctgga ggatgcattt gtctgggtca agcctggtgg tgagagcgat   1020

gggacttcga ataccacatc ttcacggtat gatgcccatt gtgggtatag tgatgctctc   1080

caacccgcac ccgaggctgg cacttggttc caagcttact ttgcgcagtt ggttgcgaat   1140

gcgaacccat cactctga                                                 1158
```

<210> SEQ ID NO 32
<211> LENGTH: 385
<212> TYPE: PRT
<213> ORGANISM: Penicillium capsulatum

<400> SEQUENCE: 32

```
Met His Phe Ile Val Ser Ile Ala Thr Phe Ala Ala Cys Val Ser Ala
1               5                   10                  15

Ala Ala Ile Ala Arg Ala Asn Gln Ala Thr Val Gly Asn Pro Phe Ser
            20                  25                  30

Gly Tyr Gln Leu Tyr Ala Asn Thr Tyr Tyr Ala Ser Glu Val Ser Ala
        35                  40                  45

Ser Ala Leu Pro Ser Met Thr Gly Thr Ala Lys Ala Ala Ala Ser Ser
    50                  55                  60

Ala Ala Lys Val Pro Ser Phe Tyr Trp Leu Asp Thr Ala Asp Lys Val
65                  70                  75                  80

Ser Val Met Gly Glu Phe Leu Ser Asp Ile Gln Ser Lys Asn Ser Ala
                85                  90                  95

Gly Ala Ser Pro Pro Ile Ala Gly Ile Phe Val Val Tyr Asp Leu Pro
            100                 105                 110

Asp Arg Asp Cys Ala Ala Leu Ala Ser Asn Gly Glu Tyr Thr Ile Ala
        115                 120                 125

Asn Gly Gly Val Glu Lys Tyr Lys Ala Tyr Ile Asp Ser Ile Lys Thr
    130                 135                 140

Thr Leu Glu Lys Tyr Ser Asp Val His Thr Ile Leu Ile Ile Glu Pro
145                 150                 155                 160

Asp Ser Leu Ala Asn Leu Val Thr Asn Met Ala Val Ser Lys Cys Ala
                165                 170                 175

Asn Ala Tyr Asn Ala Tyr Leu Glu Cys Thr Asn Tyr Ala Ile Thr Gln
            180                 185                 190

Leu Asn Leu Asp Asn Val Ala Met Tyr Leu Asp Ala Gly His Ala Gly
        195                 200                 205

Trp Leu Gly Trp Pro Ala Asn Leu Ser Pro Ala Ala Val Leu Phe Gly
    210                 215                 220

Gln Val Tyr Lys Asn Ala Ser Gln Pro Ser Ser Leu Arg Gly Leu Ala
225                 230                 235                 240

Thr Asn Val Ala Asn Tyr Asn Gly Trp Ser Leu Asn Thr Cys Pro Ser
                245                 250                 255

Tyr Thr Ser Gly Asp Ser Asn Cys Asp Glu Lys Arg Tyr Val Asn Ala
            260                 265                 270

Leu Ala Pro Leu Leu Leu Asn Glu Gly Trp Asp Ala His Phe Ile Thr
```

```
        275                 280                 285

Asp Thr Gly Arg Asn Gly Val Gln Pro Thr Lys Gln Asn Ala Trp Gly
    290                 295                 300

Asp Trp Cys Asn Val Lys Gly Thr Gly Phe Gly Val Arg Pro Thr Thr
305                 310                 315                 320

Asp Thr Gly Asp Asn Leu Glu Asp Ala Phe Val Trp Val Lys Pro Gly
                325                 330                 335

Gly Glu Ser Asp Gly Thr Ser Asn Thr Thr Ser Ser Arg Tyr Asp Ala
            340                 345                 350

His Cys Gly Tyr Ser Asp Ala Leu Gln Pro Ala Pro Glu Ala Gly Thr
        355                 360                 365

Trp Phe Gln Ala Tyr Phe Ala Gln Leu Val Ala Asn Ala Asn Pro Ser
    370                 375                 380

Leu
385


<210> SEQ ID NO 33
<211> LENGTH: 1374
<212> TYPE: DNA
<213> ORGANISM: Penicillium pinophilum

<400> SEQUENCE: 33

atgttgcgat atctttccac cgttgccgcc acggcaattc tgaccggagt tgaagctcag      60

caatcagtct ggggacaatg tggcggccaa ggctggtctg gcgcgacttc atgcgccgcc     120

ggttctacgt gcagcactct aaacccttac tacgcacaat gtatccctgg taccgctact     180

tcaactacat tggtgaaaac aacgtcttct accagcgtcg gaacgacatc gccgccgaca     240

acaaccacga cgaaagctag taccactgct actaccactg ccgctgcatc cggaaaccct     300

ttctctggtt accagcttta tgccaatccg tactattctt cagaagtaca cactcttgcc     360

atcccatctt tgactggctc gctcgctgct gctgctacca aagctgccga gatcccctca     420

tttgtctggc ttgacacggc agccaaagtg cctacaatgg gcacctactt ggccaacatt     480

gaggctgcaa acaaggctgg cgccagccca cctattgccg gtatcttcgt tgtctatgac     540

ctgcctgacc gtgactgtgc agctgctgca agtaatggcg aatacactgt agcaaacaac     600

ggtgttgcaa actacaaggc ttacatcgac agcattgtgg cacagttgaa agcttatccc     660

gatgtgcaca caatccttat cattgagcct gatagtctcg ccaacatggt caccaatctg     720

tctacagcca agtgtgctga ggctcaatct gcatactatg agtgcgtcaa ctacgcattg     780

atcaacctca acttggccaa cgtggccatg tacattgatg ctggtcatgc tggttggctc     840

ggatggtctg cgaatctttc accagcggct caactcttcg caacagtcta taagaatgca     900

agtgcccctg catctcttcg tggattggcc accaacgttg ccaactacaa cgcttggtcg     960

atcagcagcc caccctcata cacatctggc gactccaact acgacgaaaa gctctacatc    1020

aacgctttgt ctcctctcct gacatctaac ggctggccta acgctcactt catcatggat    1080

acttcccgaa acggtgttca accgactaag cagcaggcat ggggtgactg gtgcaatgtg    1140

atcggaaccg gcttcggtgt tcaaccgaca acaaatactg gtgacccact tgaggatgcc    1200

tttgtctggg tcaagccagg tggtgaaagt gatggtacat caaacagttc cgctactcgt    1260

tacgatttcc attgcggcta cagtgatgca cttcaacccg cccccgaggc tgggacttgg    1320

ttccaagcat actttgtcca gcttttgaca aatgccaacc cagctttggt ctag          1374


<210> SEQ ID NO 34
```

<211> LENGTH: 457
<212> TYPE: PRT
<213> ORGANISM: Penicillium pinophilum

<400> SEQUENCE: 34

```
Met Leu Arg Tyr Leu Ser Thr Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Thr Ala Ala Ala
                85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
            180                 185                 190

Gly Glu Tyr Thr Val Ala Asn Asn Gly Val Ala Asn Tyr Lys Ala Tyr
        195                 200                 205

Ile Asp Ser Ile Val Ala Gln Leu Lys Ala Tyr Pro Asp Val His Thr
    210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
            260                 265                 270

Asp Ala Gly His Ala Gly Trp Leu Gly Trp Ser Ala Asn Leu Ser Pro
        275                 280                 285

Ala Ala Gln Leu Phe Ala Thr Val Tyr Lys Asn Ala Ser Ala Pro Ala
    290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asn Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
    370                 375                 380

Phe Gly Val Gln Pro Thr Thr Asn Thr Gly Asp Pro Leu Glu Asp Ala
```

```
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Asp Ala Leu Gln
            420                 425                 430

Pro Ala Pro Glu Ala Gly Thr Trp Phe Gln Ala Tyr Phe Val Gln Leu
        435                 440                 445

Leu Thr Asn Ala Asn Pro Ala Leu Val
    450                 455


<210> SEQ ID NO 35
<211> LENGTH: 1374
<212> TYPE: DNA
<213> ORGANISM: Penicillium funiculosum

<400> SEQUENCE: 35

atgttgcgat atctttccat cgttgccgcc acggcaattc tgaccggagt tgaagctcag      60

caatcagtct ggggacaatg tggcggccaa ggctggtctg gcgcgacttc atgcgccgcc     120

ggttctacgt gcagcactct aaacccttac tacgcacaat gtatccctgg taccgctact     180

tcaactacat tggtgaaaac aacgtcttct accagcgtcg gaacgacatc gccgccgaca     240

acaaccacga cgaaagctag taccactgct actaccactg ccgctgcatc cggaaaccct     300

ttctctggtt accagcttta tgccaatccg tactattctt cagaagtaca cactcttgcc     360

atcccatctt tgactggctc gctcgctgct gctgctacca aagctgccga gatcccctca     420

tttgtctggc ttgacacggc agccaaagtg cctacaatgg gcacctactt ggccaacatt     480

gaggctgcaa acaaggctgg cgccagccca cctattgccg gtatcttcgt tgtctatgac     540

ctgcctgacc gtgactgtgc agctgctgca agtaatggcg aatacactgt agcaaacaac     600

ggtgttgcaa actacaaggc ttacatcgac agcattgtgg cacagttgaa agcttatccc     660

gatgtgcaca caatccttat cattgagcct gatagtctcg ccaacatggt caccaatctg     720

tctacagcca agtgtgctga agctcaatct gcatactatg agtgcgtcaa ctacgcattg     780

atcaaacctc acttggccca cgtggccatg tacattgatg ctggtcatgc tggttggctc     840

ggatggtctg cgaatctttc accagcggct caactcttcg caacagtcta taagaatgca     900

agtgcccctg catctcttcg tggattggcc accaacgttg ccaactacaa cgcttggtcg     960

atcagcagcc caccctcata cacatctggc gactccaact acgacgaaaa gctctacatc    1020

aacgctttgt ctcctctcct gacatctaac ggctggcctg acgctcactt catcatggat    1080

acttcccgaa acggtgttca accgactaag cagcaggcat ggggtgactg gtgcaatgtg    1140

atcggaaccg gcttcggtgt tcaaccgaca acaaatactg gtgacccact tgaggatgcc    1200

tttgtctggg tcaagccagg tggtgaaagt gatggtacat caaacagttc cgctactcgt    1260

tacgatttcc attgcggcta cagtggtgca cttcaacccg cccccgaggc tgggacttgg    1320

ttccaagcat actttgtcca gcttttgaca aatgccaacc cagctttggt ctag          1374


<210> SEQ ID NO 36
<211> LENGTH: 457
<212> TYPE: PRT
<213> ORGANISM: Penicillium funiculosum

<400> SEQUENCE: 36

Met Leu Arg Tyr Leu Ser Ile Val Ala Ala Thr Ala Ile Leu Thr Gly
1               5                   10                  15
```

```
Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Ala Thr Thr Thr Ala Ala Ala
                85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
            180                 185                 190

Gly Glu Tyr Thr Val Ala Asn Asn Gly Val Ala Asn Tyr Lys Ala Tyr
        195                 200                 205

Ile Asp Ser Ile Val Ala Gln Leu Lys Ala Tyr Pro Asp Val His Thr
    210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Lys Pro His Leu Ala His Val Ala Met Tyr Ile
            260                 265                 270

Asp Ala Gly His Ala Gly Trp Leu Gly Trp Ser Ala Asn Leu Ser Pro
        275                 280                 285

Ala Ala Gln Leu Phe Ala Thr Val Tyr Lys Asn Ala Ser Ala Pro Ala
    290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asp Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
    370                 375                 380

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Gly Ala Leu Gln
            420                 425                 430

Pro Ala Pro Glu Ala Gly Thr Trp Phe Gln Ala Tyr Phe Val Gln Leu
```

```
        435                 440                 445

Leu Thr Asn Ala Asn Pro Ala Leu Val
    450                 455


<210> SEQ ID NO 37
<211> LENGTH: 1368
<212> TYPE: DNA
<213> ORGANISM: Sclerotinia sclerotiorum

<400> SEQUENCE: 37

atgggtctca agaatgttct tctcgctgct gctgcagtag cacctactgt gtatgctcag      60

ggcgctggtt attcacaatg tggcggtcaa ggctggagtg gcgcaacaac ttgtgtttct     120

ggattcacct gtacttatac caacgagtac tattctcaat gtctacctgg ttcgggtggt     180

ggtgcatcta gttcccgccc aacaactacc gctcctacaa caatcgtcac atccacgaaa     240

gcttccacta ctacaggcag cagtgcaacg acgacagcag caccagccgc aggcaaccca     300

tttgtaggca aagcacttta cgtaaaccca tactatgctt ctgagatttc cgcaagtgcc     360

attccttcac tcactggagc catggccact aaagccgccg cggtagcaaa agttccaacc     420

tttttctggc tggataccgc tgataaagtt ccaacaatgg gaacctacct ttccaatatt     480

cgagccttaa ataaggcagg agcaaaccca ccagttgctg gtactttcgt ggtctacgat     540

ttacctgaca gagattgtgc agcagctgct tccaatggag aatatagcat tgcaaacaat     600

ggtgtagcga actacaaagc ttatatcgat tcgattgtta ctatcctcaa gaactattct     660

gacactagcg ttattctaat catcgagccg gagtcgttgg caaatctcgt taccaaccta     720

aatgttcaaa aatgttccaa tgcacaagca gcttacctag aatgtaccga atatgccatc     780

tcaaagttga atctaccaaa cgtctccatg tacttggatg ctggacatgc tggttggtta     840

ggatggtccg caaacattgg tccagctgca caactctttg gtcaagtcta caaagcagca     900

ggaagcccat ctcaagtcag aggtctcgca accaatgtcg caaactacaa tgcttggact     960

agcagcagtt gcccatctta tacctccggt gactctaact gtaacgagaa attgtacatc    1020

aatgctctcg ctccactctt gaccgcacaa ggtttcccag ctcatttcat catggatact    1080

ggtcgcaatg gagttcaacc aaccgctcaa caagcatggg gagactggtg taatgtcatc    1140

ggaaccggat tcggtgttcg acctaccacc aacaccggag atgctttgga agatgccttt    1200

gtctgggtca aacctggtgg agaagccgat ggtacttcaa atacaacagc agctcgatac    1260

gatttccact gcggtctctc agatgccctt caaccggctc cggaagctgg tacctggttc    1320

caagcttact ttgcccaatt acttacaaat gctaatccta gcttttaa                 1368


<210> SEQ ID NO 38
<211> LENGTH: 455
<212> TYPE: PRT
<213> ORGANISM: Sclerotinia sclerotiorum

<400> SEQUENCE: 38

Met Gly Leu Lys Asn Val Leu Leu Ala Ala Ala Ala Val Ala Pro Thr
1               5                   10                  15

Val Tyr Ala Gln Gly Ala Gly Tyr Ser Gln Cys Gly Gly Gln Gly Trp
            20                  25                  30

Ser Gly Ala Thr Thr Cys Val Ser Gly Phe Thr Cys Thr Tyr Thr Asn
        35                  40                  45

Glu Tyr Tyr Ser Gln Cys Leu Pro Gly Ser Gly Gly Gly Ala Ser Ser
    50                  55                  60
```

```
Ser Arg Pro Thr Thr Thr Ala Pro Thr Thr Ile Val Thr Ser Thr Lys
65                  70                  75                  80

Ala Ser Thr Thr Thr Gly Ser Ser Ala Thr Thr Thr Ala Ala Pro Ala
                85                  90                  95

Ala Gly Asn Pro Phe Val Gly Lys Ala Leu Tyr Val Asn Pro Tyr Tyr
            100                 105                 110

Ala Ser Glu Ile Ser Ala Ser Ala Ile Pro Ser Leu Thr Gly Ala Met
        115                 120                 125

Ala Thr Lys Ala Ala Ala Val Ala Lys Val Pro Thr Phe Phe Trp Leu
    130                 135                 140

Asp Thr Ala Asp Lys Val Pro Thr Met Gly Thr Tyr Leu Ser Asn Ile
145                 150                 155                 160

Arg Ala Leu Asn Lys Ala Gly Ala Asn Pro Pro Val Ala Gly Thr Phe
                165                 170                 175

Val Val Tyr Asp Leu Pro Asp Arg Asp Cys Ala Ala Ala Ala Ser Asn
            180                 185                 190

Gly Glu Tyr Ser Ile Ala Asn Asn Gly Val Ala Asn Tyr Lys Ala Tyr
        195                 200                 205

Ile Asp Ser Ile Val Thr Ile Leu Lys Asn Tyr Ser Asp Thr Ser Val
    210                 215                 220

Ile Leu Ile Ile Glu Pro Glu Ser Leu Ala Asn Leu Val Thr Asn Leu
225                 230                 235                 240

Asn Val Gln Lys Cys Ser Asn Ala Gln Ala Ala Tyr Leu Glu Cys Thr
                245                 250                 255

Glu Tyr Ala Ile Ser Lys Leu Asn Leu Pro Asn Val Ser Met Tyr Leu
            260                 265                 270

Asp Ala Gly His Ala Gly Trp Leu Gly Trp Ser Ala Asn Ile Gly Pro
        275                 280                 285

Ala Ala Gln Leu Phe Gly Gln Val Tyr Lys Ala Ala Gly Ser Pro Ser
    290                 295                 300

Gln Val Arg Gly Leu Ala Thr Asn Val Ala Asn Tyr Asn Ala Trp Thr
305                 310                 315                 320

Ser Ser Ser Cys Pro Ser Tyr Thr Ser Gly Asp Ser Asn Cys Asn Glu
                325                 330                 335

Lys Leu Tyr Ile Asn Ala Leu Ala Pro Leu Leu Thr Ala Gln Gly Phe
            340                 345                 350

Pro Ala His Phe Ile Met Asp Thr Gly Arg Asn Gly Val Gln Pro Thr
        355                 360                 365

Ala Gln Gln Ala Trp Gly Asp Trp Cys Asn Val Ile Gly Thr Gly Phe
    370                 375                 380

Gly Val Arg Pro Thr Thr Asn Thr Gly Asp Ala Leu Glu Asp Ala Phe
385                 390                 395                 400

Val Trp Val Lys Pro Gly Gly Glu Ala Asp Gly Thr Ser Asn Thr Thr
                405                 410                 415

Ala Ala Arg Tyr Asp Phe His Cys Gly Leu Ser Asp Ala Leu Gln Pro
            420                 425                 430

Ala Pro Glu Ala Gly Thr Trp Phe Gln Ala Tyr Phe Ala Gln Leu Leu
        435                 440                 445

Thr Asn Ala Asn Pro Ser Phe
    450                 455
```

<210> SEQ ID NO 39
<211> LENGTH: 1410
<212> TYPE: DNA

<213> ORGANISM: Aspergillus aculeatus

<400> SEQUENCE: 39

```
atgcgttata cattgtctct cgcagcggcg ctgctgccat gcgcaatcca ggcccagcaa      60
accctgtacg gacaatgtgg tggtcaaggc tattccggac tcaccagctg cgtggcagga     120
gcaacatgct ctaccgtgaa tgaatactac gctcagtgta cgccagcagc gggcgccacc     180
tctaccacct tgaagacaac tactaccact gccggggcga ccacgacgac tactaccaag     240
agctctgctt ctcagacatc tactactaag acctctaccg gcaccgtctc gacgaccacg     300
gcgactacca cggccagcgc gagcggcaac ccgttcagtg ggtaccagct ctacgtgaac     360
ccatactact cctccgaagt ggcgtcgctg gccattccat ctctcactgg gacgctttcc     420
tcgctccagg cagcggccac ggccgcggcc aaggtgcctt cttttgtctg gctggatgtg     480
gccgccaagg tgccgacgat ggccacctac ctggccgaca tcaaagccca gaatgccgct     540
ggagccaatc cccgatcgc aggccaattt gtggtgtacg acctccctga ccgtgactgc      600
gccgctctag ccagtaacgg cgagtactcc attgccaaca acggtgtggc caactacaag     660
gcctacatcg actccatccg caaggtcctc gtgcagtatt ccgatgtgca caccattctg     720
gtgattgagc ccgacagtct cgccaacctg gtgaccaacc tcaacgtggc caaatgcgcc     780
aacgcccaga gcgcctatct cgaatgcacc aactatgcct tggagcagct gaacctcccc     840
aacgtggcca tgtatctcga tgccggacac gccggctggc tcggctggcc cgcaaaccag     900
caaccggccg ccaacttgta cgcgagcgtt tacaagaacg ctagttcccc cgccgcagtg     960
cgcggcctgg ccacgaatgt cgccaactac aacgccttca ccatctcctc ctgcccctcc    1020
tacacccagg gcaacagcgt ttgcgacgag cagcagtaca tcaacgcgat cgccccgctc    1080
ctctcagccc agggcttcga cgcccacttc atcgtcgaca ccggccgcaa cggcaaacag    1140
ccaaccggtc agcaagcctg ggcgattgg tgcaacgtca tcaacaccgg gttcggcgtg     1200
cgcccgacca ccagcacggg cgatgcgctc gtcgacgcct tcgtctgggt gaagcccggc    1260
ggcgagagcg acggcacctc cgatagctcg gccacccgct acgacgccca ctgcgggtac    1320
agcgatgcct tgcagccggc ccctgaggcg ggaacctggt tccaggccta tttcgtgcag    1380
ttgctcacga acgccaaccc ggccttttag                                     1410
```

<210> SEQ ID NO 40
<211> LENGTH: 469
<212> TYPE: PRT
<213> ORGANISM: Aspergillus aculeatus

<400> SEQUENCE: 40

```
Met Arg Tyr Thr Leu Ser Leu Ala Ala Ala Leu Leu Pro Cys Ala Ile
1               5                   10                  15

Gln Ala Gln Gln Thr Leu Tyr Gly Gln Cys Gly Gly Gln Gly Tyr Ser
            20                  25                  30

Gly Leu Thr Ser Cys Val Ala Gly Ala Thr Cys Ser Thr Val Asn Glu
        35                  40                  45

Tyr Tyr Ala Gln Cys Thr Pro Ala Ala Gly Ala Thr Ser Thr Thr Leu
    50                  55                  60

Lys Thr Thr Thr Thr Thr Ala Gly Ala Thr Thr Thr Thr Thr Thr Lys
65                  70                  75                  80

Ser Ser Ala Ser Gln Thr Ser Thr Thr Lys Thr Ser Thr Gly Thr Val
                85                  90                  95

Ser Thr Thr Thr Ala Thr Thr Thr Ala Ser Ala Ser Gly Asn Pro Phe
```

```
            100                 105                 110

Ser Gly Tyr Gln Leu Tyr Val Asn Pro Tyr Tyr Ser Ser Glu Val Ala
        115                 120                 125

Ser Leu Ala Ile Pro Ser Leu Thr Gly Thr Leu Ser Ser Leu Gln Ala
    130                 135                 140

Ala Ala Thr Ala Ala Ala Lys Val Pro Ser Phe Val Trp Leu Asp Val
145                 150                 155                 160

Ala Ala Lys Val Pro Thr Met Ala Thr Tyr Leu Ala Asp Ile Lys Ala
                165                 170                 175

Gln Asn Ala Ala Gly Ala Asn Pro Pro Ile Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asn Asn Gly Val Ala Asn Tyr Lys Ala Tyr Ile Asp
    210                 215                 220

Ser Ile Arg Lys Val Leu Val Gln Tyr Ser Asp Val His Thr Ile Leu
225                 230                 235                 240

Val Ile Glu Pro Asp Ser Leu Ala Asn Leu Val Thr Asn Leu Asn Val
                245                 250                 255

Ala Lys Cys Ala Asn Ala Gln Ser Ala Tyr Leu Glu Cys Thr Asn Tyr
            260                 265                 270

Ala Leu Glu Gln Leu Asn Leu Pro Asn Val Ala Met Tyr Leu Asp Ala
        275                 280                 285

Gly His Ala Gly Trp Leu Gly Trp Pro Ala Asn Gln Gln Pro Ala Ala
    290                 295                 300

Asn Leu Tyr Ala Ser Val Tyr Lys Asn Ala Ser Ser Pro Ala Ala Val
305                 310                 315                 320

Arg Gly Leu Ala Thr Asn Val Ala Asn Tyr Asn Ala Phe Thr Ile Ser
                325                 330                 335

Ser Cys Pro Ser Tyr Thr Gln Gly Asn Ser Val Cys Asp Glu Gln Gln
            340                 345                 350

Tyr Ile Asn Ala Ile Ala Pro Leu Leu Ser Ala Gln Gly Phe Asp Ala
        355                 360                 365

His Phe Ile Val Asp Thr Gly Arg Asn Gly Lys Gln Pro Thr Gly Gln
    370                 375                 380

Gln Ala Trp Gly Asp Trp Cys Asn Val Ile Asn Thr Gly Phe Gly Val
385                 390                 395                 400

Arg Pro Thr Thr Ser Thr Gly Asp Ala Leu Val Asp Ala Phe Val Trp
                405                 410                 415

Val Lys Pro Gly Gly Glu Ser Asp Gly Thr Ser Asp Ser Ser Ala Thr
            420                 425                 430

Arg Tyr Asp Ala His Cys Gly Tyr Ser Asp Ala Leu Gln Pro Ala Pro
        435                 440                 445

Glu Ala Gly Thr Trp Phe Gln Ala Tyr Phe Val Gln Leu Leu Thr Asn
    450                 455                 460

Ala Asn Pro Ala Phe
465


<210> SEQ ID NO 41
<211> LENGTH: 1464
<212> TYPE: DNA
<213> ORGANISM: Thielavia hyrcaniae

<400> SEQUENCE: 41
```

```
atggccaaga agctccttct caccgccgcc ctcgcggcct ctgccctggc tgctcccatt      60

gtcgaggagc gccagaactg cggctccgtc tggagtcaat gtggtggcaa cgggtggtcg     120

ggcgccacct gctgcgcgtc tggaagcacc tgcgtagccc agaacccctg gtactcgcag     180

tgcctgccca gcagccaggt gaccaccacc acgactagcg ctcgcgcctc gtcgtcgtct     240

tcgtcgtcca cccgggcgag caccagcagc accagccgca ccacctcggt gggcaccacc     300

acccgtgcta gctccacgac cacctcggcc cctggcgtca cgtccagcgt tcctggcggt     360

gctacggcca cggccagcta ctcgggcaac cccttctccg ggtgcgcct gtgggccaac      420

gactactacg cctccgaggt gtcgaccctc gccatgcctt ccctgacggg cgccatggcc     480

accaaggcgg ccgccgtcgc caaggtcccc agcttccagt ggctggaccg caacgtcacc     540

atcgacaccc tgatggtcaa gactctgtcc cagatccggg ccgccaacca ggccggtgcc     600

aaccccccgt atgccgccca gctggtggtc tacgacctcc ccgaccgtga ctgcgctgcc     660

gccgcctcca acggcgagtt ctcgattgcc aacaacggcg cggccaacta caagtcgtac     720

atcgactcga tccgcaagca cctcatcgag tactcggaca tccgcaccat cctggttatt     780

gagcccgatt cgatggccaa catggtcacc aacatgaacg tcgccaagtg cagcaacgcc     840

gccacgacct accgcgagct gaccatctac gctctcaagc agctgaacct gccccacgtc     900

gccatgtacc tcgacgccgg ccacgccggc tggctcggct ggcccgccaa catccagccc     960

gctgctaccc tgttcgccgg catctacaac gacgctggca agcccgcctc ggtccgtggt    1020

ctggccacca acgtcgccaa ctacaacgcc tggagcctgt cctcggcccc gtcgtacacg    1080

acccccaacg ccaactacga cgagaagcac tacgtcgagg cctttgcccc gcttctctcg    1140

gccgctggct tccccgccaa gttcatcacc gacactggcc gcaacggcaa gcagcccacc    1200

ggccagagcc agtggggcga ttggtgcaac gtcaagggca ccggcttcgg tgtccgcccg    1260

acctccgaga cgggccacga gctcctggat gcctttgtct gggtcaagcc cggtggcgag    1320

tccgacggta ccagcgacac cagcgctgcc cgctacgact accactgcgg tctgtcggat    1380

gccctccagc ccgctcccga ggccggcacg tggttccagg cctactttga acagctcctc    1440

accaacgcca accctccttt ttag                                           1464
```

```
<210> SEQ ID NO 42
<211> LENGTH: 487
<212> TYPE: PRT
<213> ORGANISM: Thielavia hyrcaniae

<400> SEQUENCE: 42

Met Ala Lys Lys Leu Leu Leu Thr Ala Ala Leu Ala Ala Ser Ala Leu
1               5                   10                  15

Ala Ala Pro Ile Val Glu Glu Arg Gln Asn Cys Gly Ser Val Trp Ser
            20                  25                  30

Gln Cys Gly Gly Asn Gly Trp Ser Gly Ala Thr Cys Cys Ala Ser Gly
        35                  40                  45

Ser Thr Cys Val Ala Gln Asn Pro Trp Tyr Ser Gln Cys Leu Pro Ser
    50                  55                  60

Ser Gln Val Thr Thr Thr Thr Thr Ser Ala Arg Ala Ser Ser Ser Ser
65                  70                  75                  80

Ser Ser Ser Thr Arg Ala Ser Thr Ser Ser Thr Ser Arg Thr Thr Ser
                85                  90                  95

Val Gly Thr Thr Thr Arg Ala Ser Ser Thr Thr Thr Ser Ala Pro Gly
            100                 105                 110
```

```
Val Thr Ser Ser Val Pro Gly Gly Ala Thr Ala Thr Ala Ser Tyr Ser
        115                 120                 125

Gly Asn Pro Phe Ser Gly Val Arg Leu Trp Ala Asn Asp Tyr Tyr Ala
    130                 135                 140

Ser Glu Val Ser Thr Leu Ala Met Pro Ser Leu Thr Gly Ala Met Ala
145                 150                 155                 160

Thr Lys Ala Ala Ala Val Ala Lys Val Pro Ser Phe Gln Trp Leu Asp
                165                 170                 175

Arg Asn Val Thr Ile Asp Thr Leu Met Val Lys Thr Leu Ser Gln Ile
            180                 185                 190

Arg Ala Ala Asn Gln Ala Gly Ala Asn Pro Pro Tyr Ala Ala Gln Leu
        195                 200                 205

Val Val Tyr Asp Leu Pro Asp Arg Asp Cys Ala Ala Ala Ala Ser Asn
    210                 215                 220

Gly Glu Phe Ser Ile Ala Asn Asn Gly Ala Ala Asn Tyr Lys Ser Tyr
225                 230                 235                 240

Ile Asp Ser Ile Arg Lys His Leu Ile Glu Tyr Ser Asp Ile Arg Thr
                245                 250                 255

Ile Leu Val Ile Glu Pro Asp Ser Met Ala Asn Met Val Thr Asn Met
            260                 265                 270

Asn Val Ala Lys Cys Ser Asn Ala Ala Thr Thr Tyr Arg Glu Leu Thr
        275                 280                 285

Ile Tyr Ala Leu Lys Gln Leu Asn Leu Pro His Val Ala Met Tyr Leu
    290                 295                 300

Asp Ala Gly His Ala Gly Trp Leu Gly Trp Pro Ala Asn Ile Gln Pro
305                 310                 315                 320

Ala Ala Thr Leu Phe Ala Gly Ile Tyr Asn Asp Ala Gly Lys Pro Ala
                325                 330                 335

Ser Val Arg Gly Leu Ala Thr Asn Val Ala Asn Tyr Asn Ala Trp Ser
            340                 345                 350

Leu Ser Ser Ala Pro Ser Tyr Thr Thr Pro Asn Ala Asn Tyr Asp Glu
        355                 360                 365

Lys His Tyr Val Glu Ala Phe Ala Pro Leu Leu Ser Ala Ala Gly Phe
    370                 375                 380

Pro Ala Lys Phe Ile Thr Asp Thr Gly Arg Asn Gly Lys Gln Pro Thr
385                 390                 395                 400

Gly Gln Ser Gln Trp Gly Asp Trp Cys Asn Val Lys Gly Thr Gly Phe
                405                 410                 415

Gly Val Arg Pro Thr Ser Glu Thr Gly His Glu Leu Leu Asp Ala Phe
            420                 425                 430

Val Trp Val Lys Pro Gly Gly Glu Ser Asp Gly Thr Ser Asp Thr Ser
        435                 440                 445

Ala Ala Arg Tyr Asp Tyr His Cys Gly Leu Ser Asp Ala Leu Gln Pro
    450                 455                 460

Ala Pro Glu Ala Gly Thr Trp Phe Gln Ala Tyr Phe Glu Gln Leu Leu
465                 470                 475                 480

Thr Asn Ala Asn Pro Pro Phe
                485
```

<210> SEQ ID NO 43
<211> LENGTH: 1416
<212> TYPE: DNA
<213> ORGANISM: Trichoderma gamsii

<400> SEQUENCE: 43

```
atggcgggac gtgtatttgc tactttggct actttggccg cattggcagc ctctgcccct      60
gtcgtagaag aacgacaggc ttgcgctacc gtttggggac aatgcggagg ccaaggttgg     120
tctggagcaa cgtgctgtgc ttctggtagc tcgtgtgtcg tctcaaacca atactactcg     180
caatgtcttc ctggctccgg aggaggttcg agttcctcta cagtcgcttc ctccacccgt     240
gtgtcaagca cgacagttag gtcaagctcg acgactcctc caccaacctc gtctacaggg     300
tcaccacctc cagttggatc aggaaccgcc acttaccagg gcaatccatt ttctggagtc     360
aacctctggg ccaacaaatt ctatcaagat gaagttacca gctctgcaat tcccagtttg     420
tccggagcca tggccaccgc tgcagcggct gctgctaaag tacctgcgtt tatgtggttg     480
gataccctta gcaagaccac cctgttgagc tcgacattgg cagatatccg tgccgcaaac     540
aaggctggag gcaactacgc tggtcaattc gttgtatacg acttgcctga ccgtgactgc     600
gccgctgctg cctccaacgg agagtactct atcgcgaata acggagttgc caactacaag     660
aactacattg ataccattgt cggcattctg aagacatatt ccgacattcg gaccattcta     720
gtcgttgagc ctgactctct cgccaatctt gttaccaacc tcaacgttac gaaatgtgca     780
aacgctcagt ctgcttacct ggaatccatc aactatgcta ttacaaagct gaaccttcca     840
aacgttgcca tgtacctcga tgccggccac gcagggtggc ttggctggcc cgccaatcag     900
cagccagcgg ctcagctgtt cgccagcgtg tacaagaatg cctcatcacc ccgagcggtt     960
cgtggattgg caaccaacgt tgccaactac aatggatgga acatcacttc tgccccgtca    1020
tacactcaag gaaacgccgt ttacaacgag cagctgtaca ttcacgcttt atcacccctt    1080
cttgctcagc agggctggag cggcgctcaa ttcattaccg atcagggtcg ctccggcagg    1140
caacccaccg gacagcaggc gtggggtgac tggtgcaacg tgattggcac tggattcggc    1200
attcgccctt ctgccaacac tggagactcc ttgcttgatg cattcacttg gatcaagccc    1260
ggtggtgaat gtgacggaac cagcaacaca tctgcgacac gatacgatta ccactgcggc    1320
ttgtcagatg ctttgcagcc ggctcctgag gctggttctt ggttccaggc ttactttgtg    1380
cagcttctta ccaatgccaa cccttcattt ttgtag                              1416
```

```
<210> SEQ ID NO 44
<211> LENGTH: 471
<212> TYPE: PRT
<213> ORGANISM: Trichoderma gamsii

<400> SEQUENCE: 44

Met Ala Gly Arg Val Phe Ala Thr Leu Ala Thr Leu Ala Ala Leu Ala
1               5                   10                  15

Ala Ser Ala Pro Val Val Glu Glu Arg Gln Ala Cys Ala Thr Val Trp
            20                  25                  30

Gly Gln Cys Gly Gly Gln Gly Trp Ser Gly Ala Thr Cys Cys Ala Ser
        35                  40                  45

Gly Ser Ser Cys Val Val Ser Asn Gln Tyr Tyr Ser Gln Cys Leu Pro
    50                  55                  60

Gly Ser Gly Gly Gly Ser Ser Ser Ser Thr Val Ala Ser Ser Thr Arg
65                  70                  75                  80

Val Ser Ser Thr Thr Val Arg Ser Ser Ser Thr Thr Pro Pro Pro Thr
                85                  90                  95

Ser Ser Thr Gly Ser Pro Pro Pro Val Gly Ser Gly Thr Ala Thr Tyr
            100                 105                 110

Gln Gly Asn Pro Phe Ser Gly Val Asn Leu Trp Ala Asn Lys Phe Tyr
```

```
        115                 120                 125

Gln Asp Glu Val Thr Ser Ser Ala Ile Pro Ser Leu Ser Gly Ala Met
    130                 135                 140

Ala Thr Ala Ala Ala Ala Ala Ala Lys Val Pro Ala Phe Met Trp Leu
145                 150                 155                 160

Asp Thr Leu Ser Lys Thr Thr Leu Leu Ser Ser Thr Leu Ala Asp Ile
                165                 170                 175

Arg Ala Ala Asn Lys Ala Gly Gly Asn Tyr Ala Gly Gln Phe Val Val
            180                 185                 190

Tyr Asp Leu Pro Asp Arg Asp Cys Ala Ala Ala Ala Ser Asn Gly Glu
        195                 200                 205

Tyr Ser Ile Ala Asn Asn Gly Val Ala Asn Tyr Lys Asn Tyr Ile Asp
    210                 215                 220

Thr Ile Val Gly Ile Leu Lys Thr Tyr Ser Asp Ile Arg Thr Ile Leu
225                 230                 235                 240

Val Val Glu Pro Asp Ser Leu Ala Asn Leu Val Thr Asn Leu Asn Val
                245                 250                 255

Thr Lys Cys Ala Asn Ala Gln Ser Ala Tyr Leu Glu Ser Ile Asn Tyr
            260                 265                 270

Ala Ile Thr Lys Leu Asn Leu Pro Asn Val Ala Met Tyr Leu Asp Ala
        275                 280                 285

Gly His Ala Gly Trp Leu Gly Trp Pro Ala Asn Gln Gln Pro Ala Ala
    290                 295                 300

Gln Leu Phe Ala Ser Val Tyr Lys Asn Ala Ser Ser Pro Arg Ala Val
305                 310                 315                 320

Arg Gly Leu Ala Thr Asn Val Ala Asn Tyr Asn Gly Trp Asn Ile Thr
                325                 330                 335

Ser Ala Pro Ser Tyr Thr Gln Gly Asn Ala Val Tyr Asn Glu Gln Leu
            340                 345                 350

Tyr Ile His Ala Leu Ser Pro Leu Leu Ala Gln Gln Gly Trp Ser Gly
        355                 360                 365

Ala Gln Phe Ile Thr Asp Gln Gly Arg Ser Gly Arg Gln Pro Thr Gly
    370                 375                 380

Gln Gln Ala Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ala Phe Thr
                405                 410                 415

Trp Ile Lys Pro Gly Gly Glu Cys Asp Gly Thr Ser Asn Thr Ser Ala
            420                 425                 430

Thr Arg Tyr Asp Tyr His Cys Gly Leu Ser Asp Ala Leu Gln Pro Ala
        435                 440                 445

Pro Glu Ala Gly Ser Trp Phe Gln Ala Tyr Phe Val Gln Leu Leu Thr
    450                 455                 460

Asn Ala Asn Pro Ser Phe Leu
465                 470


<210> SEQ ID NO 45
<211> LENGTH: 1206
<212> TYPE: DNA
<213> ORGANISM: Penicillium piceum

<400> SEQUENCE: 45

atgcagactc tcctgtccct tctgcccgtg gcggccctcg ccggagccgc tgccattcac      60

cctgctccaa ccaaggtgaa cgcagcagca ccgcagccag ctgcaacgac tgctgccgca     120
```

```
ggaagcaacc cgttctctgg ctatcagcag taccccaatc ccttctattc gtctgaggtc    180

atcagcctgg ctatcccgtc tctttcggct tcctcgctgg ctgccgcggc cagcaaggtt    240

gctgaagttc cttcgttctt ctggattgac acggctgaca aggtccccgt tgttggcgag    300

catctggcgg atatccagag caagaacgag gccggtgcca gccctccgta tgccggtctc    360

ttcgtcgtct acgatctgcc ggatcgtgac tgcgctgccc tggccagtaa cggcgagtac    420

tcgattgccg acggcggtgt tgagaagtac aagacataca ttgacaacat tgcggctcaa    480

atctccaact actcggatgt caacaccatc ctggtcatcg aacctgatag cttggcgaac    540

atggtcacca acctgaatgt ctcgaaatgt gccaatgccc agtctgcgta ctacgagtgc    600

gtcaactacg ccgttaccaa gctgaacctg gacaatgtct ccatgtacat cgatgccggt    660

cacgctggtt ggcttggatg ggaggccaac ctcaccccag cagcccagct gttcggtcaa    720

gtctatgcca acgcgagctc accggccgct ctccgcggtc tggccaccaa tgtcgctaac    780

tacaatgcct ggactatcag cagctgcccg tcctatactc agggcgacag caactgcgac    840

gaggagaaat atatcaatgc ccttggtcct cttctttcca acgaaggctg ggacgctcac    900

tttatcgtcg acacatctcg caacggagtc cagcccacca agcaacaggc atggggtgac    960

tggtgcaacg tggttggcac cggcttcggt gtgcgcccaa catccgagac gggcagtgac   1020

ctggtggatg cctttgtctg ggtgaagccc ggtggcgaga gtgacggcac ctcggactcg   1080

agctcgtctc gctatgatgc tcactgcggt tacagtgatg ccttgcagcc cgccccggag   1140

gctggtacct ggttccaggc ttactttgag cagctgctca ccaacgccaa cccgtccttc   1200

tcatag                                                              1206
```

<210> SEQ ID NO 46
<211> LENGTH: 401
<212> TYPE: PRT
<213> ORGANISM: Penicillium piceum

<400> SEQUENCE: 46

```
Met Gln Thr Leu Leu Ser Leu Leu Pro Val Ala Ala Leu Ala Gly Ala
1               5                   10                  15

Ala Ala Ile His Pro Ala Pro Thr Lys Val Asn Ala Ala Ala Pro Gln
            20                  25                  30

Pro Ala Ala Thr Thr Ala Ala Ala Gly Ser Asn Pro Phe Ser Gly Tyr
        35                  40                  45

Gln Gln Tyr Pro Asn Pro Phe Tyr Ser Ser Glu Val Ile Ser Leu Ala
    50                  55                  60

Ile Pro Ser Leu Ser Ala Ser Ser Leu Ala Ala Ala Ala Ser Lys Val
65                  70                  75                  80

Ala Glu Val Pro Ser Phe Phe Trp Ile Asp Thr Ala Asp Lys Val Pro
                85                  90                  95

Val Val Gly Glu His Leu Ala Asp Ile Gln Ser Lys Asn Glu Ala Gly
            100                 105                 110

Ala Ser Pro Pro Tyr Ala Gly Leu Phe Val Val Tyr Asp Leu Pro Asp
        115                 120                 125

Arg Asp Cys Ala Ala Leu Ala Ser Asn Gly Glu Tyr Ser Ile Ala Asp
    130                 135                 140

Gly Gly Val Glu Lys Tyr Lys Thr Tyr Ile Asp Asn Ile Ala Ala Gln
145                 150                 155                 160

Ile Ser Asn Tyr Ser Asp Val Asn Thr Ile Leu Val Ile Glu Pro Asp
                165                 170                 175
```

```
Ser Leu Ala Asn Met Val Thr Asn Leu Asn Val Ser Lys Cys Ala Asn
            180                 185                 190

Ala Gln Ser Ala Tyr Tyr Glu Cys Val Asn Tyr Ala Val Thr Lys Leu
        195                 200                 205

Asn Leu Asp Asn Val Ser Met Tyr Ile Asp Ala Gly His Ala Gly Trp
    210                 215                 220

Leu Gly Trp Glu Ala Asn Leu Thr Pro Ala Ala Gln Leu Phe Gly Gln
225                 230                 235                 240

Val Tyr Ala Asn Ala Ser Ser Pro Ala Ala Leu Arg Gly Leu Ala Thr
                245                 250                 255

Asn Val Ala Asn Tyr Asn Ala Trp Thr Ile Ser Ser Cys Pro Ser Tyr
            260                 265                 270

Thr Gln Gly Asp Ser Asn Cys Asp Glu Glu Lys Tyr Ile Asn Ala Leu
        275                 280                 285

Gly Pro Leu Leu Ser Asn Glu Gly Trp Asp Ala His Phe Ile Val Asp
    290                 295                 300

Thr Ser Arg Asn Gly Val Gln Pro Thr Lys Gln Gln Ala Trp Gly Asp
305                 310                 315                 320

Trp Cys Asn Val Val Gly Thr Gly Phe Gly Val Arg Pro Thr Ser Glu
                325                 330                 335

Thr Gly Ser Asp Leu Val Asp Ala Phe Val Trp Val Lys Pro Gly Gly
            340                 345                 350

Glu Ser Asp Gly Thr Ser Asp Ser Ser Ser Ser Arg Tyr Asp Ala His
        355                 360                 365

Cys Gly Tyr Ser Asp Ala Leu Gln Pro Ala Pro Glu Ala Gly Thr Trp
    370                 375                 380

Phe Gln Ala Tyr Phe Glu Gln Leu Leu Thr Asn Ala Asn Pro Ser Phe
385                 390                 395                 400

Ser


<210> SEQ ID NO 47
<211> LENGTH: 1227
<212> TYPE: DNA
<213> ORGANISM: Fennellia nivea

<400> SEQUENCE: 47

atgcagactg tcaacatgcg gaccctgtgg gctcttgcac ccgttctctt ccctgcggtg      60

agcgctctgc ccaccgcaag ctctacccca actccctcca ctccgggctc gtcgagcacc     120

cccgctccaa ctgcggcccc tagtgggaac cctttcgagg gataccagca atatgtcaat     180

ccttactaca agtccgaggt cctgtccctc gctgttcctt cgatgaccgg ctcgctcgct     240

gcgcaggcaa gcgcggcagc tgacgtgccg tcgttcttct ggcttgacac ggccgacaag     300

gtccctcaga tgggtacctt cctgaagaac atcaaggaag cgaacgatgg cggcgccagc     360

ccccccaatg ccggcatctt cgttgtgtac gacctgcctg accgtgactg tgccgcgctg     420

gccagtaacg gcgagtatgc tatcgccgat ggcggtgtcg agaagtacaa ggcgtacatc     480

gactcgatca aggagcagct ggagacctac tctgatgttc agaacatcct tgtcattgag     540

ccggatagtc tggccaacct ggtcaccaac ctgaacgtcg agaagtgtgc caacgcccac     600

gatgcctacc tggagtgcac caactacgcc atcacgcagc tgaacctccc caatgtggcg     660

atgtatctcg atgctggtca cgccggatgg ctgggctggc ctgccaacat tggccccgca     720

gctgagctgt acgcttcagt ctacaagaac gcgtcttccc ccgctgccgt ccgtggactg     780
```

```
gcaaccaacg tggccaacta caacgccttc tccatcgaca cctgcccctc gtacacgtcg    840

gagaacgagg tttgcgatga gaagagctac attaacaact ttgcgcccga gctccggagc    900

gccggttttg atgcccactt cattgtcgac actggccgca acggcaacca gcccacggga    960

cagctcgagt ggggtgactg gtgcaatgtt gtcgacactg gcttcggtgc tcgccccact   1020

actgataccg gtgatgagct ggtcgatgcc tttgtctggg tcaagccggg tggtgagagc   1080

gacggtacct cggacacctc cgccgagcgc tacgatgccc actgcggttt ggatgattcc   1140

ctgaagccgg ctcctgaggc tggtacttgg ttccaggcgt actttgagca gctggtgaag   1200

aacgccaacc cccctttgtc tagctag                                       1227


<210> SEQ ID NO 48
<211> LENGTH: 408
<212> TYPE: PRT
<213> ORGANISM: Fennellia nivea

<400> SEQUENCE: 48

Met Gln Thr Val Asn Met Arg Thr Leu Trp Ala Leu Ala Pro Val Leu
1               5                   10                  15

Phe Pro Ala Val Ser Ala Leu Pro Thr Ala Ser Ser Thr Pro Thr Pro
            20                  25                  30

Ser Thr Pro Gly Ser Ser Ser Thr Pro Ala Pro Thr Ala Ala Pro Ser
        35                  40                  45

Gly Asn Pro Phe Glu Gly Tyr Gln Gln Tyr Val Asn Pro Tyr Tyr Lys
    50                  55                  60

Ser Glu Val Leu Ser Leu Ala Val Pro Ser Met Thr Gly Ser Leu Ala
65                  70                  75                  80

Ala Gln Ala Ser Ala Ala Ala Asp Val Pro Ser Phe Phe Trp Leu Asp
                85                  90                  95

Thr Ala Asp Lys Val Pro Gln Met Gly Thr Phe Leu Lys Asn Ile Lys
            100                 105                 110

Glu Ala Asn Asp Gly Gly Ala Ser Pro Pro Asn Ala Gly Ile Phe Val
        115                 120                 125

Val Tyr Asp Leu Pro Asp Arg Asp Cys Ala Ala Leu Ala Ser Asn Gly
    130                 135                 140

Glu Tyr Ala Ile Ala Asp Gly Gly Val Glu Lys Tyr Lys Ala Tyr Ile
145                 150                 155                 160

Asp Ser Ile Lys Glu Gln Leu Glu Thr Tyr Ser Asp Val Gln Asn Ile
                165                 170                 175

Leu Val Ile Glu Pro Asp Ser Leu Ala Asn Leu Val Thr Asn Leu Asn
            180                 185                 190

Val Glu Lys Cys Ala Asn Ala His Asp Ala Tyr Leu Glu Cys Thr Asn
        195                 200                 205

Tyr Ala Ile Thr Gln Leu Asn Leu Pro Asn Val Ala Met Tyr Leu Asp
    210                 215                 220

Ala Gly His Ala Gly Trp Leu Gly Trp Pro Ala Asn Ile Gly Pro Ala
225                 230                 235                 240

Ala Glu Leu Tyr Ala Ser Val Tyr Lys Asn Ala Ser Ser Pro Ala Ala
                245                 250                 255

Val Arg Gly Leu Ala Thr Asn Val Ala Asn Tyr Asn Ala Phe Ser Ile
            260                 265                 270

Asp Thr Cys Pro Ser Tyr Thr Ser Glu Asn Glu Val Cys Asp Glu Lys
        275                 280                 285

Ser Tyr Ile Asn Asn Phe Ala Pro Glu Leu Arg Ser Ala Gly Phe Asp
```

```
    290                 295                 300

Ala His Phe Ile Val Asp Thr Gly Arg Asn Gly Asn Gln Pro Thr Gly
305                 310                 315                 320

Gln Leu Glu Trp Gly Asp Trp Cys Asn Val Val Asp Thr Gly Phe Gly
                325                 330                 335

Ala Arg Pro Thr Thr Asp Thr Gly Asp Glu Leu Val Asp Ala Phe Val
            340                 345                 350

Trp Val Lys Pro Gly Gly Glu Ser Asp Gly Thr Ser Asp Thr Ser Ala
        355                 360                 365

Glu Arg Tyr Asp Ala His Cys Gly Leu Asp Asp Ser Leu Lys Pro Ala
    370                 375                 380

Pro Glu Ala Gly Thr Trp Phe Gln Ala Tyr Phe Glu Gln Leu Val Lys
385                 390                 395                 400

Asn Ala Asn Pro Pro Leu Ser Ser
                405


<210> SEQ ID NO 49
<211> LENGTH: 1161
<212> TYPE: DNA
<213> ORGANISM: Penicillium raistrickii

<400> SEQUENCE: 49

atgagatctt tcatcccact tgtcctgctg gtgtccagcg cagttggggc tgcaatctcg      60

aatgaagtta aagcaactgt taccacaaac ccattctctg ggtatcagct gtatgttaat     120

ccattctatg catccgaggt ttcagcctcg gcgctgccct cgatgacggg agctgccaaa     180

gccgctgcaa gtgaggccgc taaagttcca tccttctttt ggatggatac tgcttccaag     240

gtcccaacaa tggctacttt cctggctgat atcaagacca agaatgcagc tggtgctagc     300

ccacccattg ctggtacctt tgtggtgtac gatctccctg atcgtgactg tgccgcattg     360

gcaagcaatg gagagtattc tattgccaat ggtggtcttg ccaaatacaa ggcgtacatt     420

gactccattc gcaaggtgct ggtccaatac tctgatgtcc ataccatcct ggttatcgag     480

cccgatagct tgggtaacct cgttacaaat atgaatgttg ccaagtgtgc taatgcgcat     540

gacgcttatc tggagggcat taactatgca gtgacccaat tgaatctggc taacgttgcc     600

atgtatatcg acgccggaca tgcgggttgg ctcggatggc cggcaaacct aagcccagca     660

gccgagctct tcgccggcgt ctacaacaat gctgggaagc ccgccgccct tcgaggcctt     720

gtaaccaacg tttccaacta caacggctgg tctctgtcga catgcccatc ctacacctcg     780

ggtgacccca attgcgacga gaagagatat atcaatgctc tttatccctt gttgaagagc     840

gcaggctggg atgcgcgttt catcaccgac actggccgca atggagtcca acctacacag     900

cagaacgcgt ggggtgattg gtgcaatgtc aagggaactg gcttcggagt gcgaccgacc     960

acgaataccg gtgatgcact ggctgatgca ttcgtctggg taaagcctgg tggcgagagt    1020

gatggtactt cagatagtag ctcggctcgg tatgatgctc actgcggata ctccgatgcg    1080

cttcaacccg cacccgaggc tggcacttgg ttccaggcat actttgcgca gcttatccag    1140

aatgccaacc cctcgttcta g                                               1161


<210> SEQ ID NO 50
<211> LENGTH: 386
<212> TYPE: PRT
<213> ORGANISM: Penicillium raistrickii

<400> SEQUENCE: 50
```

```
Met Arg Ser Phe Ile Pro Leu Val Leu Leu Val Ser Ser Ala Val Gly
1               5                   10                  15

Ala Ala Ile Ser Asn Glu Val Lys Ala Thr Val Thr Thr Asn Pro Phe
            20                  25                  30

Ser Gly Tyr Gln Leu Tyr Val Asn Pro Phe Tyr Ala Ser Glu Val Ser
        35                  40                  45

Ala Ser Ala Leu Pro Ser Met Thr Gly Ala Ala Lys Ala Ala Ala Ser
    50                  55                  60

Glu Ala Ala Lys Val Pro Ser Phe Phe Trp Met Asp Thr Ala Ser Lys
65                  70                  75                  80

Val Pro Thr Met Ala Thr Phe Leu Ala Asp Ile Lys Thr Lys Asn Ala
                85                  90                  95

Ala Gly Ala Ser Pro Pro Ile Ala Gly Thr Phe Val Val Tyr Asp Leu
            100                 105                 110

Pro Asp Arg Asp Cys Ala Ala Leu Ala Ser Asn Gly Glu Tyr Ser Ile
        115                 120                 125

Ala Asn Gly Gly Leu Ala Lys Tyr Lys Ala Tyr Ile Asp Ser Ile Arg
    130                 135                 140

Lys Val Leu Val Gln Tyr Ser Asp Val His Thr Ile Leu Val Ile Glu
145                 150                 155                 160

Pro Asp Ser Leu Gly Asn Leu Val Thr Asn Met Asn Val Ala Lys Cys
                165                 170                 175

Ala Asn Ala His Asp Ala Tyr Leu Glu Gly Ile Asn Tyr Ala Val Thr
            180                 185                 190

Gln Leu Asn Leu Ala Asn Val Ala Met Tyr Ile Asp Ala Gly His Ala
        195                 200                 205

Gly Trp Leu Gly Trp Pro Ala Asn Leu Ser Pro Ala Ala Glu Leu Phe
    210                 215                 220

Ala Gly Val Tyr Asn Asn Ala Gly Lys Pro Ala Ala Leu Arg Gly Leu
225                 230                 235                 240

Val Thr Asn Val Ser Asn Tyr Asn Gly Trp Ser Leu Ser Thr Cys Pro
                245                 250                 255

Ser Tyr Thr Ser Gly Asp Pro Asn Cys Asp Glu Lys Arg Tyr Ile Asn
            260                 265                 270

Ala Leu Tyr Pro Leu Leu Lys Ser Ala Gly Trp Asp Ala Arg Phe Ile
        275                 280                 285

Thr Asp Thr Gly Arg Asn Gly Val Gln Pro Thr Gln Gln Asn Ala Trp
    290                 295                 300

Gly Asp Trp Cys Asn Val Lys Gly Thr Gly Phe Gly Val Arg Pro Thr
305                 310                 315                 320

Thr Asn Thr Gly Asp Ala Leu Ala Asp Ala Phe Val Trp Val Lys Pro
                325                 330                 335

Gly Gly Glu Ser Asp Gly Thr Ser Asp Ser Ser Ser Ala Arg Tyr Asp
            340                 345                 350

Ala His Cys Gly Tyr Ser Asp Ala Leu Gln Pro Ala Pro Glu Ala Gly
        355                 360                 365

Thr Trp Phe Gln Ala Tyr Phe Ala Gln Leu Ile Gln Asn Ala Asn Pro
    370                 375                 380

Ser Phe
385
```

<210> SEQ ID NO 51
<211> LENGTH: 1200
<212> TYPE: DNA

<213> ORGANISM: Penicillium brefeldianum

<400> SEQUENCE: 51

```
atgcgatcct tcatccctct tgttcccctg ctggtccatt cagcggcagc tggagtcatc     60
catgcacggg caagtacatc ttcagccgcg agtgcggcgt ccgtcacccc tgccgcgacg    120
actggcaatc cgttctcggg ataccagctc tacgccaacc cctactattc ctccgaggtc    180
tatgcctccg ccataccctc catgaccggt gcggcacagg cagctgccag ttcggcggca    240
gtcgtcccgt ccttcttctg gctcgatacg gccgacaaag taccaaccat ggacaaattc    300
ctcgccgaca tccagtcgaa aaatgccgcc ggcgcgagcc caccgtacgc gggtcaattc    360
gtggtctacg atctccccga tcgtgactgc gccgcgctcg cgagtaacgg cgaatactcg    420
attgctgatg gcggtctggc aaagtacaag acgtacattg ataatatcaa ggcgacgctg    480
acaaagtact cggatgttca cactattctc gtcatcgagc ctgacagtct agccaaccta    540
gtcacaaaca tgaacgtcgc taagtgcgca ggcgcacacg acgcatacct cgaaggcgtc    600
aactacgccg tgacacaact gaacctcgcc aatgtggcca tgtacatcga tgccggacac    660
gccggctggc taggctggcc cgccaatcta agtcctgcgg ctacactctt cgcgcaggtt    720
tacaccaatg cttcccagcc agcttcgctg cgaggtctgg ctaccaatgt cgctaactat    780
aacggctggg cgctgtctac ctgcccctcg tatacgtcgg gtgattcaaa ctgcgatgag    840
aagaaatacg ttaatgcgct tgctccgttg cttaagagtg cgggctggga tgcgcatttc    900
atcactgata ctggccgcaa cggcgtccag cccacccaac aacaagcctg ggtgactgg     960
tgcaacgtga aaggcactgg tttcggcgtc cgacctacaa ccgacaccgg cgatgccctg   1020
gaagacgctt ttgtctgggt taagcctggt ggtgagagtg atggcacttc ggactcgtct   1080
gctacgcgct acgatgcgca ttgtgggtat agtgatgcgc tgcagcctgc gcctgaggct   1140
gggacttggt tccaggctta ctttgcgcaa cttgttgaga atgcgaatcc ttcgttctga   1200
```

<210> SEQ ID NO 52
<211> LENGTH: 399
<212> TYPE: PRT
<213> ORGANISM: Penicillium brefeldianum

<400> SEQUENCE: 52

```
Met Arg Ser Phe Ile Pro Leu Val Pro Leu Leu Val His Ser Ala Ala
1               5                   10                  15

Ala Gly Val Ile His Ala Arg Ala Ser Thr Ser Ser Ala Ala Ser Ala
            20                  25                  30

Ala Ser Val Thr Pro Ala Ala Thr Thr Gly Asn Pro Phe Ser Gly Tyr
        35                  40                  45

Gln Leu Tyr Ala Asn Pro Tyr Tyr Ser Ser Glu Val Tyr Ala Ser Ala
    50                  55                  60

Ile Pro Ser Met Thr Gly Ala Ala Gln Ala Ala Ala Ser Ser Ala Ala
65                  70                  75                  80

Val Val Pro Ser Phe Phe Trp Leu Asp Thr Ala Asp Lys Val Pro Thr
                85                  90                  95

Met Asp Lys Phe Leu Ala Asp Ile Gln Ser Lys Asn Ala Ala Gly Ala
            100                 105                 110

Ser Pro Pro Tyr Ala Gly Gln Phe Val Val Tyr Asp Leu Pro Asp Arg
        115                 120                 125

Asp Cys Ala Ala Leu Ala Ser Asn Gly Glu Tyr Ser Ile Ala Asp Gly
    130                 135                 140
```

```
Gly Leu Ala Lys Tyr Lys Thr Tyr Ile Asp Asn Ile Lys Ala Thr Leu
145                 150                 155                 160

Thr Lys Tyr Ser Asp Val His Thr Ile Leu Val Ile Glu Pro Asp Ser
                165                 170                 175

Leu Ala Asn Leu Val Thr Asn Met Asn Val Ala Lys Cys Ala Gly Ala
            180                 185                 190

His Asp Ala Tyr Leu Glu Gly Val Asn Tyr Ala Val Thr Gln Leu Asn
        195                 200                 205

Leu Ala Asn Val Ala Met Tyr Ile Asp Ala Gly His Ala Gly Trp Leu
    210                 215                 220

Gly Trp Pro Ala Asn Leu Ser Pro Ala Ala Thr Leu Phe Ala Gln Val
225                 230                 235                 240

Tyr Thr Asn Ala Ser Gln Pro Ala Ser Leu Arg Gly Leu Ala Thr Asn
                245                 250                 255

Val Ala Asn Tyr Asn Gly Trp Ala Leu Ser Thr Cys Pro Ser Tyr Thr
            260                 265                 270

Ser Gly Asp Ser Asn Cys Asp Glu Lys Lys Tyr Val Asn Ala Leu Ala
        275                 280                 285

Pro Leu Leu Lys Ser Ala Gly Trp Asp Ala His Phe Ile Thr Asp Thr
    290                 295                 300

Gly Arg Asn Gly Val Gln Pro Thr Gln Gln Gln Ala Trp Gly Asp Trp
305                 310                 315                 320

Cys Asn Val Lys Gly Thr Gly Phe Gly Val Arg Pro Thr Thr Asp Thr
                325                 330                 335

Gly Asp Ala Leu Glu Asp Ala Phe Val Trp Val Lys Pro Gly Gly Glu
            340                 345                 350

Ser Asp Gly Thr Ser Asp Ser Ser Ala Thr Arg Tyr Asp Ala His Cys
        355                 360                 365

Gly Tyr Ser Asp Ala Leu Gln Pro Ala Pro Glu Ala Gly Thr Trp Phe
    370                 375                 380

Gln Ala Tyr Phe Ala Gln Leu Val Glu Asn Ala Asn Pro Ser Phe
385                 390                 395
```

<210> SEQ ID NO 53
<211> LENGTH: 1410
<212> TYPE: DNA
<213> ORGANISM: Fennellia nivea

<400> SEQUENCE: 53

```
atgggacggg tttcttctct tgcgcttgcc cttctgcttc ctgctgtgca ggcccagcag     60

accctctggg gtcaatgcgg tggcattgga tggacaggag caaccaactg tgtcgctggt    120

gctgcttgta gcacgcagaa tccttactat gcgcagtgcc tccctgcgac ggcgaccacc    180

tccaccaccc tgaccaccac gaccaggtct accactacca cgacggcaac gtccaccacg    240

tctcagggct catcttcaag ctcctctacg actacgacaa agtcgacgag caccaccacc    300

ggctcttcta ccaccatcac ctctgcgccg tccggcaacc cgttcagtgg atatcaactc    360

tatgccaacc cttactattc ttccgaggtc cacaccctcg ccatgccctc ccttgctagc    420

tcccttctgc cggctgccag tgctgccgcc aaggttccct cgttcacctg gctggacacc    480

gctgccaaag tgccgaccat gggcacctac ctggcggaca tcaaggccaa gaacgccgct    540

ggtgccaacc cgcccattgc tgcccagttc gtcgtctacg atcttcccga tcgtgactgt    600

gctgccctgg ctagcaatgg cgagtactcg attgcgaaca acggtgttgc caactacaag    660

gcgtacattg actccatccg ggcccagttg gtgaaatacc cggacgtcca caccatcctt    720
```

```
gttatcgagc ccgatagctt ggccaacctg gtcaccaacc tgaacgtggc caaatgcgcc    780

aacgcccaga gcgcgtatct ggagtgcgtc aactacgccc tgatcaacct gaacctgccc    840

aacgttgcca tgtacatcga cgctggacac gccggctggc tcggatggcc cgccaacatc    900

ggccccgcgg ccaccctctt cgccggggtg tacaatgacg ccggctctcc cgctgcactg    960

cgcggcctcg cgaccaacgt cgccaactac aacgccttca gcatcagcac ctgcccgtcc   1020

tacacgtcgg gcgacgccaa ctgcgacgaa aaccgctaca tcaacgcctt ggcccctctc   1080

ttgaaatcgg ctggcttcga tgcgcatttt atcgttgata ctggtcgcaa cggtgtccag   1140

cctactaagc agcaggcttg gggcgattgg tgcaacgtca tcggcactgg attcggtgtc   1200

cggccgacca ctaacactgg caattcgctg gttgatgcgt ttgtctgggt taagcctggc   1260

ggcgagagcg atggcacctc caactctagc tctccgcggt acgatgcgca ctgtggatac   1320

agtgatgcgc tccagcctgc tcctgaggcc ggaacctggt tccaggcgta ctttgagcag   1380

cttctgacca acgctaaccc tgcgttctga                                    1410
```

```
<210> SEQ ID NO 54
<211> LENGTH: 469
<212> TYPE: PRT
<213> ORGANISM: Fennellia nivea

<400> SEQUENCE: 54

Met Gly Arg Val Ser Ser Leu Ala Leu Ala Leu Leu Leu Pro Ala Val
1               5                   10                  15

Gln Ala Gln Gln Thr Leu Trp Gly Gln Cys Gly Gly Ile Gly Trp Thr
            20                  25                  30

Gly Ala Thr Asn Cys Val Ala Gly Ala Ala Cys Ser Thr Gln Asn Pro
        35                  40                  45

Tyr Tyr Ala Gln Cys Leu Pro Ala Thr Ala Thr Thr Ser Thr Thr Leu
    50                  55                  60

Thr Thr Thr Thr Arg Ser Thr Thr Thr Thr Thr Ala Thr Ser Thr Thr
65                  70                  75                  80

Ser Gln Gly Ser Ser Ser Ser Ser Ser Thr Thr Thr Thr Lys Ser Thr
                85                  90                  95

Ser Thr Thr Thr Gly Ser Ser Thr Thr Ile Thr Ser Ala Pro Ser Gly
            100                 105                 110

Asn Pro Phe Ser Gly Tyr Gln Leu Tyr Ala Asn Pro Tyr Tyr Ser Ser
        115                 120                 125

Glu Val His Thr Leu Ala Met Pro Ser Leu Ala Ser Ser Leu Leu Pro
    130                 135                 140

Ala Ala Ser Ala Ala Ala Lys Val Pro Ser Phe Thr Trp Leu Asp Thr
145                 150                 155                 160

Ala Ala Lys Val Pro Thr Met Gly Thr Tyr Leu Ala Asp Ile Lys Ala
                165                 170                 175

Lys Asn Ala Ala Gly Ala Asn Pro Pro Ile Ala Ala Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asn Asn Gly Val Ala Asn Tyr Lys Ala Tyr Ile Asp
    210                 215                 220

Ser Ile Arg Ala Gln Leu Val Lys Tyr Pro Asp Val His Thr Ile Leu
225                 230                 235                 240

Val Ile Glu Pro Asp Ser Leu Ala Asn Leu Val Thr Asn Leu Asn Val
```

```
                245                 250                 255

Ala Lys Cys Ala Asn Ala Gln Ser Ala Tyr Leu Glu Cys Val Asn Tyr
            260                 265                 270

Ala Leu Ile Asn Leu Asn Leu Pro Asn Val Ala Met Tyr Ile Asp Ala
        275                 280                 285

Gly His Ala Gly Trp Leu Gly Trp Pro Ala Asn Ile Gly Pro Ala Ala
    290                 295                 300

Thr Leu Phe Ala Gly Val Tyr Asn Asp Ala Gly Ser Pro Ala Ala Leu
305                 310                 315                 320

Arg Gly Leu Ala Thr Asn Val Ala Asn Tyr Asn Ala Phe Ser Ile Ser
                325                 330                 335

Thr Cys Pro Ser Tyr Thr Ser Gly Asp Ala Asn Cys Asp Glu Asn Arg
            340                 345                 350

Tyr Ile Asn Ala Leu Ala Pro Leu Leu Lys Ser Ala Gly Phe Asp Ala
        355                 360                 365

His Phe Ile Val Asp Thr Gly Arg Asn Gly Val Gln Pro Thr Lys Gln
    370                 375                 380

Gln Ala Trp Gly Asp Trp Cys Asn Val Ile Gly Thr Gly Phe Gly Val
385                 390                 395                 400

Arg Pro Thr Thr Asn Thr Gly Asn Ser Leu Val Asp Ala Phe Val Trp
                405                 410                 415

Val Lys Pro Gly Gly Glu Ser Asp Gly Thr Ser Asn Ser Ser Ser Pro
            420                 425                 430

Arg Tyr Asp Ala His Cys Gly Tyr Ser Asp Ala Leu Gln Pro Ala Pro
        435                 440                 445

Glu Ala Gly Thr Trp Phe Gln Ala Tyr Phe Glu Gln Leu Leu Thr Asn
    450                 455                 460

Ala Asn Pro Ala Phe
465
```

<210> SEQ ID NO 55
<211> LENGTH: 1203
<212> TYPE: DNA
<213> ORGANISM: Aspergillus niger

<400> SEQUENCE: 55

```
atgcgagcca tctggcccct cgtttctctt ttctctgccg tcaaggccct ccccgccgca     60

agcgcaactg cttcagcgtc cgttgctgca tcgagctctc cggcgccgac ggcctctgct    120

actggcaatc cctttgaggg ataccagctc tatgcgaacc cctactataa gtcacaagtg    180

gagagttcgg ccattccatc attgtctgct acttcgctgg tcgcgcaggc gagtgctgct    240

gcagatgtgc cttcgttcta ctggctggac acggccgaca aggtacctac aatgggtgaa    300

tatctggaag acatccagac acaaaatgct gctggagcga gccccccaat tgctggtatc    360

ttcgttgtct atgacctacc agatcgggat tgttctgcct tggctagtaa tggggaatac    420

tcgatcagtg atggcggtgt ggagaagtac aaggcgtaca ttgattctat tcgggagcag    480

gtcgagacgt actcggatgt tcagactatt ctgattattg aacccgatag cttggctaac    540

ctggtgacga atctcgatgt ggctaaatgc gccaatgctg aatccgctta cctggaatgc    600

accaactatg cccttgagca actgaatctg ccgaacgtgg ctatgtatct tgatgctggc    660

catgcgggat ggctgggatg gcctgccaac atcggtcccg cggcgcaact ctacgcatca    720

gtgtataaga atgcgtcgtc cccagctgct gttcgcggcc tcgccaccaa tgtagctaac    780

ttcaacgcct ggagcatcga cacttgcccc tcttatacat cgggcaacga tgtctgtgat    840
```

```
gagaaaagct acatcaatgc cattgcgccg gagctgtcta gtgccgggtt tgatgcccac    900

ttcattaccg atacgggtcg caatggaaag caacccactg gtcagagcgc gtggggtgac    960

tggtgcaatg tcaaggatac cggcttcggt gctcagccga cgaccgatac tggagacgag   1020

ctggctgatg cctttgtctg ggtcaagccg ggcggagaga gcgacgggac atcggatacc   1080

agctcttctc gctacgatgc gcattgcgga tatagcgatg ccttgcagcc tgctccggag   1140

gccggaacct ggttccaggc atactttgag caacttttga ccaacgccaa tccttccctt   1200

tag                                                                 1203
```

<210> SEQ ID NO 56
<211> LENGTH: 400
<212> TYPE: PRT
<213> ORGANISM: Aspergillus niger

<400> SEQUENCE: 56

```
Met Arg Ala Ile Trp Pro Leu Val Ser Leu Phe Ser Ala Val Lys Ala
1               5                   10                  15

Leu Pro Ala Ala Ser Ala Thr Ala Ser Ala Ser Val Ala Ala Ser Ser
            20                  25                  30

Ser Pro Ala Pro Thr Ala Ser Ala Thr Gly Asn Pro Phe Glu Gly Tyr
        35                  40                  45

Gln Leu Tyr Ala Asn Pro Tyr Tyr Lys Ser Gln Val Glu Ser Ser Ala
    50                  55                  60

Ile Pro Ser Leu Ser Ala Thr Ser Leu Val Ala Gln Ala Ser Ala Ala
65                  70                  75                  80

Ala Asp Val Pro Ser Phe Tyr Trp Leu Asp Thr Ala Asp Lys Val Pro
                85                  90                  95

Thr Met Gly Glu Tyr Leu Glu Asp Ile Gln Thr Gln Asn Ala Ala Gly
            100                 105                 110

Ala Ser Pro Pro Ile Ala Gly Ile Phe Val Val Tyr Asp Leu Pro Asp
        115                 120                 125

Arg Asp Cys Ser Ala Leu Ala Ser Asn Gly Glu Tyr Ser Ile Ser Asp
    130                 135                 140

Gly Gly Val Glu Lys Tyr Lys Ala Tyr Ile Asp Ser Ile Arg Glu Gln
145                 150                 155                 160

Val Glu Thr Tyr Ser Asp Val Gln Thr Ile Leu Ile Ile Glu Pro Asp
                165                 170                 175

Ser Leu Ala Asn Leu Val Thr Asn Leu Asp Val Ala Lys Cys Ala Asn
            180                 185                 190

Ala Glu Ser Ala Tyr Leu Glu Cys Thr Asn Tyr Ala Leu Glu Gln Leu
        195                 200                 205

Asn Leu Pro Asn Val Ala Met Tyr Leu Asp Ala Gly His Ala Gly Trp
    210                 215                 220

Leu Gly Trp Pro Ala Asn Ile Gly Pro Ala Ala Gln Leu Tyr Ala Ser
225                 230                 235                 240

Val Tyr Lys Asn Ala Ser Ser Pro Ala Ala Val Arg Gly Leu Ala Thr
                245                 250                 255

Asn Val Ala Asn Phe Asn Ala Trp Ser Ile Asp Thr Cys Pro Ser Tyr
            260                 265                 270

Thr Ser Gly Asn Asp Val Cys Asp Glu Lys Ser Tyr Ile Asn Ala Ile
        275                 280                 285

Ala Pro Glu Leu Ser Ser Ala Gly Phe Asp Ala His Phe Ile Thr Asp
    290                 295                 300
```

```
Thr Gly Arg Asn Gly Lys Gln Pro Thr Gly Gln Ser Ala Trp Gly Asp
305                 310                 315                 320

Trp Cys Asn Val Lys Asp Thr Gly Phe Gly Ala Gln Pro Thr Thr Asp
                325                 330                 335

Thr Gly Asp Glu Leu Ala Asp Ala Phe Val Trp Val Lys Pro Gly Gly
            340                 345                 350

Glu Ser Asp Gly Thr Ser Asp Thr Ser Ser Ser Arg Tyr Asp Ala His
        355                 360                 365

Cys Gly Tyr Ser Asp Ala Leu Gln Pro Ala Pro Glu Ala Gly Thr Trp
    370                 375                 380

Phe Gln Ala Tyr Phe Glu Gln Leu Leu Thr Asn Ala Asn Pro Ser Leu
385                 390                 395                 400
```

<210> SEQ ID NO 57
<211> LENGTH: 1380
<212> TYPE: DNA
<213> ORGANISM: Aspergillus niger

<400> SEQUENCE: 57

```
atgcactatc cattgtctct cgcattggca tttctgccat tcggaatcca ggctcagcaa     60

accctttggg gacaatgtgg aggtcaggga tattcaggag ccaccagttg tgtggctggc    120

gcaacatgcg caactgtgaa tgaatactat gctcagtgta cgccagcggc aggcacgagc    180

tcagccacta ccttgaagac aactactagt agtaccactg ctgcagtgac gacgactacc    240

actactcaaa gccctaccgg ctctgcctcg ccgactacca cggccagcgc tagcggcaac    300

ccgttcagtg ggtaccagct ctacgtgaac ccatactact catcggaagt cgcgtctctg    360

gccattccat ctctcactgg ttctctctcc tcgctccagg cggcggcaac cgccgcagcc    420

aaggtgcctt cttttgtgtg gctggatact gccgctaaag ttcctaccat gggcgactac    480

ctggccgaca tccaatccca gaatgctgct ggagcgaacc ccccaatcgc cggtcaattt    540

gtggtatacg acctccccga ccgcgactgc gccgcgctcg ccagcaacgg cgagtattcg    600

atcgcggaca atggggttga acactacaag tcctacattg attccatccg cgagattctt    660

gtgcagtatt cagatgttca taccctcctg gtgattgagc ctgacagtct cgccaacctg    720

gtgacaaacc tcaatgtggc caaatgtgcc aatgctgaaa gtgcatacct tgaatgtacg    780

aattatgcgt tgactcagct caatcttccc aacgtggcca tgtatcttga cgccggacac    840

gccggctggc tcggctggcc cgcaaatcag caacccgccg ccgacctgtt tgcgagcgtc    900

tacaaaaatg ccagttcccc cgctgcggtg cgcggcctgg ccaccaacgt tgctaactac    960

aacgcctgga ccatttcttc ctgtccctcc tacacccagg gaaacagcgt ctgcgacgag   1020

caacagtaca tcaatgctat tgccccacta ctacaggcac agggcttcga tgcccacttt   1080

gtcgtcgata ccggccgcaa cggcaaacag cccacgggcc aacaggcctg gggtgactgg   1140

tgcaatgtca ttaacacagg ctttggcgag cgcccgacca ccgacaccgg cgatgcgctc   1200

gtcgacgcct tcgtctgggt gaagccgggg ggcgagagcg atggcacctc cgatagctcg   1260

gccactcgat acgatgccca ctgcgggtat agcgatgcct tgcagccggc gcctgaggcg   1320

ggaacttggt tccaggccta cttcgtgcag ctgctcacca acgccaatcc agctttctag   1380
```

<210> SEQ ID NO 58
<211> LENGTH: 459
<212> TYPE: PRT
<213> ORGANISM: Aspergillus niger

<400> SEQUENCE: 58

```
Met His Tyr Pro Leu Ser Leu Ala Leu Ala Phe Leu Pro Phe Gly Ile
1               5                   10                  15

Gln Ala Gln Gln Thr Leu Trp Gly Gln Cys Gly Gly Gln Gly Tyr Ser
            20                  25                  30

Gly Ala Thr Ser Cys Val Ala Gly Ala Thr Cys Ala Thr Val Asn Glu
        35                  40                  45

Tyr Tyr Ala Gln Cys Thr Pro Ala Ala Gly Thr Ser Ser Ala Thr Thr
    50                  55                  60

Leu Lys Thr Thr Thr Ser Ser Thr Thr Ala Ala Val Thr Thr Thr Thr
65                  70                  75                  80

Thr Thr Gln Ser Pro Thr Gly Ser Ala Ser Pro Thr Thr Thr Ala Ser
                85                  90                  95

Ala Ser Gly Asn Pro Phe Ser Gly Tyr Gln Leu Tyr Val Asn Pro Tyr
            100                 105                 110

Tyr Ser Ser Glu Val Ala Ser Leu Ala Ile Pro Ser Leu Thr Gly Ser
        115                 120                 125

Leu Ser Ser Leu Gln Ala Ala Ala Thr Ala Ala Ala Lys Val Pro Ser
    130                 135                 140

Phe Val Trp Leu Asp Thr Ala Ala Lys Val Pro Thr Met Gly Asp Tyr
145                 150                 155                 160

Leu Ala Asp Ile Gln Ser Gln Asn Ala Ala Gly Ala Asn Pro Pro Ile
                165                 170                 175

Ala Gly Gln Phe Val Val Tyr Asp Leu Pro Asp Arg Asp Cys Ala Ala
            180                 185                 190

Leu Ala Ser Asn Gly Glu Tyr Ser Ile Ala Asp Asn Gly Val Glu His
        195                 200                 205

Tyr Lys Ser Tyr Ile Asp Ser Ile Arg Glu Ile Leu Val Gln Tyr Ser
    210                 215                 220

Asp Val His Thr Leu Leu Val Ile Glu Pro Asp Ser Leu Ala Asn Leu
225                 230                 235                 240

Val Thr Asn Leu Asn Val Ala Lys Cys Ala Asn Ala Glu Ser Ala Tyr
                245                 250                 255

Leu Glu Cys Thr Asn Tyr Ala Leu Thr Gln Leu Asn Leu Pro Asn Val
            260                 265                 270

Ala Met Tyr Leu Asp Ala Gly His Ala Gly Trp Leu Gly Trp Pro Ala
        275                 280                 285

Asn Gln Gln Pro Ala Ala Asp Leu Phe Ala Ser Val Tyr Lys Asn Ala
    290                 295                 300

Ser Ser Pro Ala Ala Val Arg Gly Leu Ala Thr Asn Val Ala Asn Tyr
305                 310                 315                 320

Asn Ala Trp Thr Ile Ser Ser Cys Pro Ser Tyr Thr Gln Gly Asn Ser
                325                 330                 335

Val Cys Asp Glu Gln Gln Tyr Ile Asn Ala Ile Ala Pro Leu Leu Gln
            340                 345                 350

Ala Gln Gly Phe Asp Ala His Phe Val Val Asp Thr Gly Arg Asn Gly
        355                 360                 365

Lys Gln Pro Thr Gly Gln Gln Ala Trp Gly Asp Trp Cys Asn Val Ile
    370                 375                 380

Asn Thr Gly Phe Gly Glu Arg Pro Thr Thr Asp Thr Gly Asp Ala Leu
385                 390                 395                 400

Val Asp Ala Phe Val Trp Val Lys Pro Gly Gly Glu Ser Asp Gly Thr
                405                 410                 415
```

```
Ser Asp Ser Ser Ala Thr Arg Tyr Asp Ala His Cys Gly Tyr Ser Asp
            420                 425                 430

Ala Leu Gln Pro Ala Pro Glu Ala Gly Thr Trp Phe Gln Ala Tyr Phe
        435                 440                 445

Val Gln Leu Leu Thr Asn Ala Asn Pro Ala Phe
    450                 455


<210> SEQ ID NO 59
<211> LENGTH: 1182
<212> TYPE: DNA
<213> ORGANISM: Penicillium griseofulvum

<400> SEQUENCE: 59

atgcggtctt tcattccatt cgtgcctttg ctggcttcgt ccgcagcggc tgctgcaatt      60

gacgttgcgg ctcgcgcaac tgtcaccact gcaccttcgg cagctggaaa tcccttcgag     120

ggataccagc tctacgtgaa ccccttttac gcatccgaag tctctgcatc agccttgcca     180

tccatgacgg gagctgctaa ggccgctgcg agcaaggccg ctgaagttcc atccttctac     240

tggctggaca ctgccgacaa ggtgccaact atgggtgact tcttggctga catcaaggct     300

aagaacgcag acggtgctag cccgccgatt gctggccagt tcgttgttta cgatctgcct     360

gatcgtgact gcgctgcttt ggccagtaat ggagagtact ccattgctga tggtggtgtc     420

gccaagtaca aggcatacat tgactccatc cgcgagatcc tcgtcgagta ctctgatgtc     480

cagactattc ttgtcattga acctgactca ttggccaact tggttaccaa catgaacgta     540

gccaagtgct ctggtgcaca tgacgcatac cttgagtgca ctaattacgc tgtctccaag     600

ttgaacttgc ccaatgttgc catgtacctt gatgccggac acgctggatg gttgggctgg     660

cccgccaatc tgggccccgc cgctacgctc tacgctggtg tctacactga cgcagggaag     720

ccctcttctc tgcgcggact tgccaccaac gttgccaact acaacgcctg gtctctctct     780

acctgcccct catacaccca gggagatgaa aactgcgatg agaagaaata cattaacgcc     840

cttgctcccc tcctcaaggc tgctggctgg gacgcccact tcatcactga cactggccgc     900

aacggtgttc agcccactaa gcaaagcgcc tggggcgatt ggtgcaacgt cgaaggaacc     960

ggcttcggtg tccgccccac taccgatact ggtgattctc tggccgatgc ttttgtctgg    1020

gtcaagcccg gcggtgagag tgatggtacc tcggatacca gcgcgacccg ctacgatgcc    1080

cactgtggac ttggcgatgc tcttaagcct gctcctgaag ctggtacttg gttccaggca    1140

tactttgctc agcttgtgga gaatgctaac ccctcgctct aa                       1182


<210> SEQ ID NO 60
<211> LENGTH: 393
<212> TYPE: PRT
<213> ORGANISM: Penicillium griseofulvum

<400> SEQUENCE: 60

Met Arg Ser Phe Ile Pro Phe Val Pro Leu Leu Ala Ser Ser Ala Ala
1               5                   10                  15

Ala Ala Ala Ile Asp Val Ala Ala Arg Ala Thr Val Thr Thr Ala Pro
            20                  25                  30

Ser Ala Ala Gly Asn Pro Phe Glu Gly Tyr Gln Leu Tyr Val Asn Pro
        35                  40                  45

Phe Tyr Ala Ser Glu Val Ser Ala Ser Ala Leu Pro Ser Met Thr Gly
    50                  55                  60

Ala Ala Lys Ala Ala Ala Ser Lys Ala Ala Glu Val Pro Ser Phe Tyr
```

```
65                  70                  75                  80

Trp Leu Asp Thr Ala Asp Lys Val Pro Thr Met Gly Asp Phe Leu Ala
                85                  90                  95

Asp Ile Lys Ala Lys Asn Ala Asp Gly Ala Ser Pro Pro Ile Ala Gly
            100                 105                 110

Gln Phe Val Val Tyr Asp Leu Pro Asp Arg Asp Cys Ala Ala Leu Ala
        115                 120                 125

Ser Asn Gly Glu Tyr Ser Ile Ala Asp Gly Gly Val Ala Lys Tyr Lys
    130                 135                 140

Ala Tyr Ile Asp Ser Ile Arg Glu Ile Leu Val Glu Tyr Ser Asp Val
145                 150                 155                 160

Gln Thr Ile Leu Val Ile Glu Pro Asp Ser Leu Ala Asn Leu Val Thr
                165                 170                 175

Asn Met Asn Val Ala Lys Cys Ser Gly Ala His Asp Ala Tyr Leu Glu
            180                 185                 190

Cys Thr Asn Tyr Ala Val Ser Lys Leu Asn Leu Pro Asn Val Ala Met
        195                 200                 205

Tyr Leu Asp Ala Gly His Ala Gly Trp Leu Gly Trp Pro Ala Asn Leu
    210                 215                 220

Gly Pro Ala Ala Thr Leu Tyr Ala Gly Val Tyr Thr Asp Ala Gly Lys
225                 230                 235                 240

Pro Ser Ser Leu Arg Gly Leu Ala Thr Asn Val Ala Asn Tyr Asn Ala
                245                 250                 255

Trp Ser Leu Ser Thr Cys Pro Ser Tyr Thr Gln Gly Asp Glu Asn Cys
            260                 265                 270

Asp Glu Lys Lys Tyr Ile Asn Ala Leu Ala Pro Leu Leu Lys Ala Ala
        275                 280                 285

Gly Trp Asp Ala His Phe Ile Thr Asp Thr Gly Arg Asn Gly Val Gln
    290                 295                 300

Pro Thr Lys Gln Ser Ala Trp Gly Asp Trp Cys Asn Val Glu Gly Thr
305                 310                 315                 320

Gly Phe Gly Val Arg Pro Thr Thr Asp Thr Gly Asp Ser Leu Ala Asp
                325                 330                 335

Ala Phe Val Trp Val Lys Pro Gly Gly Glu Ser Asp Gly Thr Ser Asp
            340                 345                 350

Thr Ser Ala Thr Arg Tyr Asp Ala His Cys Gly Leu Gly Asp Ala Leu
        355                 360                 365

Lys Pro Ala Pro Glu Ala Gly Thr Trp Phe Gln Ala Tyr Phe Ala Gln
    370                 375                 380

Leu Val Glu Asn Ala Asn Pro Ser Leu
385                 390
```

<210> SEQ ID NO 61
<211> LENGTH: 1212
<212> TYPE: DNA
<213> ORGANISM: Aspergillus lentulus

<400> SEQUENCE: 61

```
atgcggtctc tttttgctct ttcacccttc ctgctctctg cagtgagagc tttgcctcaa      60

ccaactggca ctcctacctc tcctgctccc actaccgtcc cccctgcgac cacggcagca     120

gcaggtggta atccctttga gggacatcag ctctatgtga atccttacta tgcgtccgag     180

gttgagaatc ttgccattcc atcgttgacc ggctctctgg tcgcgaaggc aagtgccgtt     240

gcgaaagtac cttctttcgt ttggatattg ttcagggaca ccagcgccaa agtctcgaaa     300
```

```
atgggcgaat acctcaagga catcaaagcc atgaacgatg caggagcaag ccctccaatt    360
gccgggattt tcgttgtata caaccttccg gaccgtgact gcgctgcctt ggccagcaat    420
ggagaattag ttattgcaga tggtggtgtt gagaagtaca aggcctacat cgattccatc    480
cgcgatcaca tcgacaatta tcctgatacc cagattatcc tcgtcattga gcctgacagc    540
ttggccaatc tcgtgacaaa cacggcagtg cccaagtgtg ctaacgctca tgatgcgtat    600
ttggagtgta ccaactatgc tctgacgaag ctcagtgccc ctaatgttgc gatgtatctc    660
gacgctggac atgctggatg gctgggctgg cctgcgaaca ttggtccagc agcccaactg    720
tatgcatccg tgtacaagaa cgcgagttcc cctgcttctg tgcgtggtct tgtgaccaac    780
gtggctaatt acaacgcctt cgtggccacg acatgcccct cttacaccca aggaaatgct    840
gtctgcgacg agaagagcta tatcaacagc ttcgccccac agctggccag cgctggattc    900
gatgctcatt tcattgtcga caccggccgc aacggaaagc agcccacggg acagcttgca    960
tggggtgact ggtgcaatgt gattggcact ggcttcggag tccggcctac cactgacaca   1020
ggagacaagt tggtggatgc tttcgtctgg gttaagcccg gtggtgagag tgatggcacc   1080
tcggacacct ctgctaaacg ctacgatgcg aagtgtggac tcgaggacgc tctcaaacca   1140
gcgcccgaag ccggcagctg gttccacgcc tatttcgaac agcttctgcg gaacgccaac   1200
cccccgttct ag                                                       1212

<210> SEQ ID NO 62
<211> LENGTH: 403
<212> TYPE: PRT
<213> ORGANISM: Aspergillus lentulus

<400> SEQUENCE: 62

Met Arg Ser Leu Phe Ala Leu Ser Pro Phe Leu Leu Ser Ala Val Arg
1               5                   10                  15

Ala Leu Pro Gln Pro Thr Gly Thr Pro Thr Ser Pro Ala Pro Thr Thr
            20                  25                  30

Val Pro Pro Ala Thr Thr Ala Ala Ala Gly Gly Asn Pro Phe Glu Gly
        35                  40                  45

His Gln Leu Tyr Val Asn Pro Tyr Tyr Ala Ser Glu Val Glu Asn Leu
    50                  55                  60

Ala Ile Pro Ser Leu Thr Gly Ser Leu Val Ala Lys Ala Ser Ala Val
65                  70                  75                  80

Ala Lys Val Pro Ser Phe Val Trp Ile Leu Phe Arg Asp Thr Ser Ala
                85                  90                  95

Lys Val Ser Lys Met Gly Glu Tyr Leu Lys Asp Ile Lys Ala Met Asn
            100                 105                 110

Asp Ala Gly Ala Ser Pro Pro Ile Ala Gly Ile Phe Val Val Tyr Asn
        115                 120                 125

Leu Pro Asp Arg Asp Cys Ala Ala Leu Ala Ser Asn Gly Glu Leu Val
    130                 135                 140

Ile Ala Asp Gly Gly Val Glu Lys Tyr Lys Ala Tyr Ile Asp Ser Ile
145                 150                 155                 160

Arg Asp His Ile Asp Asn Tyr Pro Asp Thr Gln Ile Ile Leu Val Ile
                165                 170                 175

Glu Pro Asp Ser Leu Ala Asn Leu Val Thr Asn Thr Ala Val Pro Lys
            180                 185                 190

Cys Ala Asn Ala His Asp Ala Tyr Leu Glu Cys Thr Asn Tyr Ala Leu
        195                 200                 205
```

```
Thr Lys Leu Ser Ala Pro Asn Val Ala Met Tyr Leu Asp Ala Gly His
    210                 215                 220

Ala Gly Trp Leu Gly Trp Pro Ala Asn Ile Gly Pro Ala Ala Gln Leu
225                 230                 235                 240

Tyr Ala Ser Val Tyr Lys Asn Ala Ser Ser Pro Ala Ser Val Arg Gly
                245                 250                 255

Leu Val Thr Asn Val Ala Asn Tyr Asn Ala Phe Val Ala Thr Thr Cys
            260                 265                 270

Pro Ser Tyr Thr Gln Gly Asn Ala Val Cys Asp Glu Lys Ser Tyr Ile
        275                 280                 285

Asn Ser Phe Ala Pro Gln Leu Ala Ser Ala Gly Phe Asp Ala His Phe
    290                 295                 300

Ile Val Asp Thr Gly Arg Asn Gly Lys Gln Pro Thr Gly Gln Leu Ala
305                 310                 315                 320

Trp Gly Asp Trp Cys Asn Val Ile Gly Thr Gly Phe Gly Val Arg Pro
                325                 330                 335

Thr Thr Asp Thr Gly Asp Lys Leu Val Asp Ala Phe Val Trp Val Lys
            340                 345                 350

Pro Gly Gly Glu Ser Asp Gly Thr Ser Asp Thr Ser Ala Lys Arg Tyr
        355                 360                 365

Asp Ala Lys Cys Gly Leu Glu Asp Ala Leu Lys Pro Ala Pro Glu Ala
    370                 375                 380

Gly Ser Trp Phe His Ala Tyr Phe Glu Gln Leu Leu Arg Asn Ala Asn
385                 390                 395                 400

Pro Pro Phe
```

<210> SEQ ID NO 63
<211> LENGTH: 1479
<212> TYPE: DNA
<213> ORGANISM: Thielavia ovispora

<400> SEQUENCE: 63

```
atggctgcga agcttcttct caccgccgcc ctggcggcta ctgccctcgc cgctcccgtc     60

gtcgaggagc gccagaactg cggcggcacc tggactcagt gcggcggcaa cggctggacc    120

ggcgccacct gctgcacttc gggcaacacc tgtgtgaagc agaacgactg gtactcccag    180

tgcctgccca acagccaggt caccaccact acgtccgcca gtccttcgac ttctacctcc    240

aagaccagca gcagcaccag cactcccacc tcgaccacca cgtcgatccg cacctcgtcc    300

agcagctcgt ccagcagctc gtccagcagc acccgggtga ctaccagcac ccccgtcgtc    360

accatccccg gtggtgctac cgtcacggcc agctacagcg gcaacccctt ctcgggcatc    420

cagcagtacg ccaacgatta ctatgcctcc gaggtctcgt cgctggctat ccccagcatg    480

acgggcgcca tggccaccaa ggccgcggcc gtcgccaagg tccccagctt ccagtggctc    540

gaccgcaacg tcaccatcga caccctgctc gccggcagtc tgtccaagat ccgctccctg    600

aacaacgcgg gcgccaaccc gccctacgcc ggcatcttcg tcgtctacga cctgcctgac    660

cgtgactgcg ccgctgctgc ctctaacggc gagttctcca ttgccaacaa cggtgctgcc    720

aactacaagt cgtacatcga tgccatccgc cgctacctcg tcgcctactc cgatgtccgc    780

accatcctcg tcatcgagcc cgattcgctc gccaacctgg tcaccaacct gaacgtcgcc    840

aagtgcgcca atgccgagca gacctacaag gacctggtca cctacgccat ccagcagctg    900

aacctgcccc acgtcgccat gtacctcgat gctggccatg ccggctggct cggctggtcc    960
```

```
gccaacatcc agcccgccgc caccctgttt gcctctatct actcgggcgc tggcaagccg   1020

gcttccgtcc gcggcctggc caccaacgtc gccaactaca acggctggaa cctgaccacc   1080

gccccctcct acactcaggg cgactccaac tacgacgagt cccactacgt ccaggccctc   1140

gccccgctcc tgacctcggc cggcttcccg gctcacttca tcaccgatac cggccgctcc   1200

ggcaagcagc ccactggcca ggctcagtgg ggtgactggt gcaatgccat cggtaccggc   1260

ttcggtaccc gcccgacctc caacaccggc cttgccatcc aggacgcctt cgtctgggtc   1320

aagcccggtg gcgagtgcga cggcaccagc gacaccagcg ccgcccgcta cgactaccac   1380

tgcggcctgt cggacgccct ccagcccgct cccgaggccg gcacctggtt ccaggcctac   1440

ttcgagcagc tgctcaccaa cgccaacccg cccttctaa                          1479
```

```
<210> SEQ ID NO 64
<211> LENGTH: 492
<212> TYPE: PRT
<213> ORGANISM: Thielavia ovispora

<400> SEQUENCE: 64

Met Ala Ala Lys Leu Leu Leu Thr Ala Ala Leu Ala Ala Thr Ala Leu
1               5                   10                  15

Ala Ala Pro Val Val Glu Glu Arg Gln Asn Cys Gly Gly Thr Trp Thr
            20                  25                  30

Gln Cys Gly Gly Asn Gly Trp Thr Gly Ala Thr Cys Cys Thr Ser Gly
        35                  40                  45

Asn Thr Cys Val Lys Gln Asn Asp Trp Tyr Ser Gln Cys Leu Pro Asn
    50                  55                  60

Ser Gln Val Thr Thr Thr Thr Ser Ala Ser Pro Ser Thr Ser Thr Ser
65                  70                  75                  80

Lys Thr Ser Ser Ser Thr Ser Thr Pro Thr Ser Thr Thr Thr Ser Ile
                85                  90                  95

Arg Thr Ser Ser Ser Ser Ser Ser Ser Ser Ser Ser Ser Ser Thr Arg
            100                 105                 110

Val Thr Thr Ser Thr Pro Val Val Thr Ile Pro Gly Gly Ala Thr Val
        115                 120                 125

Thr Ala Ser Tyr Ser Gly Asn Pro Phe Ser Gly Ile Gln Gln Tyr Ala
    130                 135                 140

Asn Asp Tyr Tyr Ala Ser Glu Val Ser Ser Leu Ala Ile Pro Ser Met
145                 150                 155                 160

Thr Gly Ala Met Ala Thr Lys Ala Ala Ala Val Ala Lys Val Pro Ser
                165                 170                 175

Phe Gln Trp Leu Asp Arg Asn Val Thr Ile Asp Thr Leu Leu Ala Gly
            180                 185                 190

Ser Leu Ser Lys Ile Arg Ser Leu Asn Asn Ala Gly Ala Asn Pro Pro
        195                 200                 205

Tyr Ala Gly Ile Phe Val Val Tyr Asp Leu Pro Asp Arg Asp Cys Ala
    210                 215                 220

Ala Ala Ala Ser Asn Gly Glu Phe Ser Ile Ala Asn Asn Gly Ala Ala
225                 230                 235                 240

Asn Tyr Lys Ser Tyr Ile Asp Ala Ile Arg Arg Tyr Leu Val Ala Tyr
                245                 250                 255

Ser Asp Val Arg Thr Ile Leu Val Ile Glu Pro Asp Ser Leu Ala Asn
            260                 265                 270

Leu Val Thr Asn Leu Asn Val Ala Lys Cys Ala Asn Ala Glu Gln Thr
        275                 280                 285
```

```
Tyr Lys Asp Leu Val Thr Tyr Ala Ile Gln Gln Leu Asn Leu Pro His
    290                 295                 300

Val Ala Met Tyr Leu Asp Ala Gly His Ala Gly Trp Leu Gly Trp Ser
305                 310                 315                 320

Ala Asn Ile Gln Pro Ala Ala Thr Leu Phe Ala Ser Ile Tyr Ser Gly
                325                 330                 335

Ala Gly Lys Pro Ala Ser Val Arg Gly Leu Ala Thr Asn Val Ala Asn
            340                 345                 350

Tyr Asn Gly Trp Asn Leu Thr Thr Ala Pro Ser Tyr Thr Gln Gly Asp
        355                 360                 365

Ser Asn Tyr Asp Glu Ser His Tyr Val Gln Ala Leu Ala Pro Leu Leu
    370                 375                 380

Thr Ser Ala Gly Phe Pro Ala His Phe Ile Thr Asp Thr Gly Arg Ser
385                 390                 395                 400

Gly Lys Gln Pro Thr Gly Gln Ala Gln Trp Gly Asp Trp Cys Asn Ala
                405                 410                 415

Ile Gly Thr Gly Phe Gly Thr Arg Pro Thr Ser Asn Thr Gly Leu Ala
            420                 425                 430

Ile Gln Asp Ala Phe Val Trp Val Lys Pro Gly Gly Glu Cys Asp Gly
        435                 440                 445

Thr Ser Asp Thr Ser Ala Ala Arg Tyr Asp Tyr His Cys Gly Leu Ser
    450                 455                 460

Asp Ala Leu Gln Pro Ala Pro Glu Ala Gly Thr Trp Phe Gln Ala Tyr
465                 470                 475                 480

Phe Glu Gln Leu Leu Thr Asn Ala Asn Pro Pro Phe
                485                 490
```

<210> SEQ ID NO 65
<211> LENGTH: 1380
<212> TYPE: DNA
<213> ORGANISM: Penicillium emersonii

<400> SEQUENCE: 65

```
atgcggaatc ttcttgctct tgcaccggcc gcgctgcttg tcggcgcagc ggaagcgcag     60

caatccctct ggggacaatg cggcgggagt tcgtggactg gcgcaacgag ctgtgctgct    120

ggagcgacgt gcagcacgat caatccttac tacgcacaat gcgtccctgc aacggccact    180

ccgaccacgc tgacgacaac gacaaaacca acgtccaccg gcggcgctgc tccaacgact    240

cctcctccga caacgactgg aacaacgaca tcgcccgtcg tcaccaggcc cgcgtctgcc    300

tccggcaacc cgttcgaagg ctaccagctc tacgccaatc cgtactatgc gtcggaggtg    360

attagtttgg caattccctc gctgagcagc gagctggttc ccaaggcgag cgaggtggcc    420

aaggtgccgt ctttcgtctg gctcgaccaa gccgccaagg tgcccagcat gggtgactat    480

ctgaaagaca tccagtcgca gaacgcagcc ggcgcagacc ccccgattgc aggcatcttt    540

gtcgtctacg acctgcctga ccgtgactgc gcggctgcag ccagcaatgg cgagttctcc    600

atcgccaaca acggcgtcgc cctgtacaag cagtacatcg actcgatccg cgagcagctg    660

acgacctatt cagatgtgca caccatcctg gtcatcgaac ccgacagcct ggccaacctg    720

gtcaccaacc tgaacgtgcc gaaatgcgca aatgcccagg acgcctatct cgaatgcatc    780

aactacgcca tcacccagct cgatctgccc aacgtggcca tgtatcttga tgctggacac    840

gccggatggc taggctggca agccaacctc gcccccgccg cccagctgtt tgcctcggtg    900

tacaagaacg cctcctcgcc ggcatccgtc cgcggtctcg ccaccaacgt cgccaactac    960
```

```
aacgcctggt cgatcagccc gtgcccgtcg tacacgcagg gcgactccaa ctgcgacgag   1020

gaggactacg tgaatgccct ggggccgctg ctccaggaac agggattccc ggcgtacttt   1080

atcactgata catcccgcaa tggcgtccaa cccaccaagc aaagccaatg ggcgactgg    1140

tgcaacgtca tcggcacggg cttcggcgtc cggcccacga ccgacaccgg caatcctctc   1200

gaggacgcct tcgtctgggt caagcccggt ggcgagagcg atggcacgtc caacacgacc   1260

tctccgcggt acgactacca ctgcgggctg agcgatgcgc tgcagccggc gccggaggcg   1320

gggacttggt tccaggcgta ctttgagcag ttgctcacga atgctaaccc gctgttctga   1380
```

<210> SEQ ID NO 66
<211> LENGTH: 459
<212> TYPE: PRT
<213> ORGANISM: Penicillium emersonii

<400> SEQUENCE: 66

```
Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
        35                  40                  45

Pro Tyr Tyr Ala Gln Cys Val Pro Ala Thr Ala Thr Pro Thr Thr Leu
    50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Leu
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala
    290                 295                 300
```

```
Ser Ser Pro Ala Ser Val Arg Gly Leu Ala Thr Asn Val Ala Asn Tyr
305                 310                 315                 320

Asn Ala Trp Ser Ile Ser Pro Cys Pro Ser Tyr Thr Gln Gly Asp Ser
                325                 330                 335

Asn Cys Asp Glu Glu Asp Tyr Val Asn Ala Leu Gly Pro Leu Leu Gln
            340                 345                 350

Glu Gln Gly Phe Pro Ala Tyr Phe Ile Thr Asp Thr Ser Arg Asn Gly
        355                 360                 365

Val Gln Pro Thr Lys Gln Ser Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Leu Phe
    450                 455
```

<210> SEQ ID NO 67
<211> LENGTH: 1413
<212> TYPE: DNA
<213> ORGANISM: Trichoderma atraviride

<400> SEQUENCE: 67

```
atggcgggac gtgtatttgc tactttggct actttggccg cattggcagt ctctgcccct      60

gtcgtggaag aacgacaggc ttgcgctagc gtttggggac aatgcggagg ccaaggttgg     120

tctggagcaa catgctgtgc ttctggtagc tcatgtgtcg tctccaaccc ctactactca     180

caatgtcttc ctggctccgg aggaggttcg agctcctcta cactcgcttc ctctacccgt     240

gcgtcatcca cgacagtgag atcaagcgcc acgactcctc caccaagctc ttctacacca     300

ccacctcccg ttggatcagg aaccgctact taccagggca atccattttc tggaatccaa     360

ccctgggcga atagcttcta cgcccaggaa gtaagcagct cggcgattcc cagtttgtcc     420

ggagccatgg ctactgctgc agcggccgct gccaaagtac cttcgttcat gtggctggat     480

actcttagca agaccagcct gttgagctcg acactgtcag atatccgtgc cgcaaacaag     540

gccggaggca actacgctgg tcagttcgtt gtgtacgact tgcctgaccg tgactgcgcc     600

gccgctgcct ccaacggaga gtactctatc gcggacaacg gagtagccaa ctacaagaac     660

tacattgaca ccattgtcgg cattctgaag acgtactccg atattcggac catcttggtc     720

attgagcctg actctctcgc caatcttgtt actaacctca gcgttgcgaa gtgctcaaac     780

gctcaggctg cttacttgga atgtatcaac tatgctatta cgcagctgaa ccttcccaac     840

gttgccatgt acctcgatgc cggccacgca ggatggcttg gctggcccgc caatcagcag     900

ccagcggctc aactgttcgc cagcgtgtac aagaatgcat cgtcaccccg agcggttcgt     960

ggactggcaa ccaacgttgc caactacaat ggatggaaca tcacttctgc tccgtcatac    1020

actcaaggaa actccgttta taacgagcag ttgtacattc acgccatttc accccttctc    1080

actcagcaag gctggagcaa cacctacttc attaccgacc agggtcgttc cggcaagcag    1140

cccaccggcc agcaggcgtg ggtgactggt tgcaacgtta ttggcactgg attcggcatc    1200
```

```
cgcccttctt ccaacactgg agactctctg cttgatgcat tcacttggat taagccaggt   1260

ggtgaatgtg acggaaccag caacacatct gcgacacgat acgattacca ctgtggcttg   1320

tcagatgctc tgcagcccgc tcccgaggct ggttcttggt tccaggctta ctttgtgcag   1380

cttcttacca atgccaaccc ttcatttttg tag                                1413


<210> SEQ ID NO 68
<211> LENGTH: 470
<212> TYPE: PRT
<213> ORGANISM: Trichoderma atraviride

<400> SEQUENCE: 68

Met Ala Gly Arg Val Phe Ala Thr Leu Ala Thr Leu Ala Ala Leu Ala
1               5                   10                  15

Val Ser Ala Pro Val Val Glu Glu Arg Gln Ala Cys Ala Ser Val Trp
            20                  25                  30

Gly Gln Cys Gly Gly Gln Gly Trp Ser Gly Ala Thr Cys Cys Ala Ser
        35                  40                  45

Gly Ser Ser Cys Val Val Ser Asn Pro Tyr Tyr Ser Gln Cys Leu Pro
    50                  55                  60

Gly Ser Gly Gly Gly Ser Ser Ser Ser Thr Leu Ala Ser Ser Thr Arg
65                  70                  75                  80

Ala Ser Ser Thr Thr Val Arg Ser Ser Ala Thr Thr Pro Pro Pro Ser
                85                  90                  95

Ser Ser Thr Pro Pro Pro Pro Val Gly Ser Gly Thr Ala Thr Tyr Gln
            100                 105                 110

Gly Asn Pro Phe Ser Gly Ile Gln Pro Trp Ala Asn Ser Phe Tyr Ala
        115                 120                 125

Gln Glu Val Ser Ser Ser Ala Ile Pro Ser Leu Ser Gly Ala Met Ala
    130                 135                 140

Thr Ala Ala Ala Ala Ala Ala Lys Val Pro Ser Phe Met Trp Leu Asp
145                 150                 155                 160

Thr Leu Ser Lys Thr Ser Leu Leu Ser Ser Thr Leu Ser Asp Ile Arg
                165                 170                 175

Ala Ala Asn Lys Ala Gly Gly Asn Tyr Ala Gly Gln Phe Val Val Tyr
            180                 185                 190

Asp Leu Pro Asp Arg Asp Cys Ala Ala Ala Ala Ser Asn Gly Glu Tyr
        195                 200                 205

Ser Ile Ala Asp Asn Gly Val Ala Asn Tyr Lys Asn Tyr Ile Asp Thr
    210                 215                 220

Ile Val Gly Ile Leu Lys Thr Tyr Ser Asp Ile Arg Thr Ile Leu Val
225                 230                 235                 240

Ile Glu Pro Asp Ser Leu Ala Asn Leu Val Thr Asn Leu Ser Val Ala
                245                 250                 255

Lys Cys Ser Asn Ala Gln Ala Ala Tyr Leu Glu Cys Ile Asn Tyr Ala
            260                 265                 270

Ile Thr Gln Leu Asn Leu Pro Asn Val Ala Met Tyr Leu Asp Ala Gly
        275                 280                 285

His Ala Gly Trp Leu Gly Trp Pro Ala Asn Gln Gln Pro Ala Ala Gln
    290                 295                 300

Leu Phe Ala Ser Val Tyr Lys Asn Ala Ser Ser Pro Arg Ala Val Arg
305                 310                 315                 320

Gly Leu Ala Thr Asn Val Ala Asn Tyr Asn Gly Trp Asn Ile Thr Ser
                325                 330                 335
```

```
Ala Pro Ser Tyr Thr Gln Gly Asn Ser Val Tyr Asn Glu Gln Leu Tyr
            340                 345                 350

Ile His Ala Ile Ser Pro Leu Leu Thr Gln Gln Gly Trp Ser Asn Thr
        355                 360                 365

Tyr Phe Ile Thr Asp Gln Gly Arg Ser Gly Lys Gln Pro Thr Gly Gln
    370                 375                 380

Gln Ala Trp Gly Asp Trp Cys Asn Val Ile Gly Thr Gly Phe Gly Ile
385                 390                 395                 400

Arg Pro Ser Ser Asn Thr Gly Asp Ser Leu Leu Asp Ala Phe Thr Trp
                405                 410                 415

Ile Lys Pro Gly Gly Glu Cys Asp Gly Thr Ser Asn Thr Ser Ala Thr
            420                 425                 430

Arg Tyr Asp Tyr His Cys Gly Leu Ser Asp Ala Leu Gln Pro Ala Pro
        435                 440                 445

Glu Ala Gly Ser Trp Phe Gln Ala Tyr Phe Val Gln Leu Leu Thr Asn
    450                 455                 460

Ala Asn Pro Ser Phe Leu
465                 470
```

<210> SEQ ID NO 69
<211> LENGTH: 1443
<212> TYPE: DNA
<213> ORGANISM: Penicillium sclerotiorum

<400> SEQUENCE: 69

```
atgcagcgta catcagggtt ggcgctgctc ctccttgcca atatcgcata tgcgcagcag     60

tctctgtacg ggcagtgcgg cggtagcgga tggactggat caactgtctg cacagcgcag    120

gcaacttgta gcagtttgaa tgcttggaaa cataacgctg atcccttcac aaaatctgaa    180

gattatttcc aatgtgtttc tgctacagct acagcaagca caaccagcaa aactagcaca    240

agcaccgcga ccaagactac catggtgacc accactacag gaaccactac taaagcgtca    300

acaaccacca cgggaacaac cactaaagca tcaaccacca ctacggcggc cgcctctacc    360

aacagtggca accccttag cggttaccag ctttatgcaa acccttacta cgcctcagag    420

gtttcagcat cggctattcc gtccctgagc agctccctcg cagcgaaggc tagcgcggtt    480

gctaaagttc catcattcgc ctggattgac acagctgcca aggtcccgac tatgggaacc    540

tatcttgcgg acatccagtc acagaatgcc gccggcgcca gcccacccat cgcaggtatt    600

tttgtggttt atgacctacc agaccgtgac tgcgctgctc ttgccagcaa tggcgagtac    660

tccattgcga acaacggagt tgcgaactac aaagcgtaca ttgacgcgat cagagcccag    720

attgtgaaat attccgatgt gcagactatt ttggtcattg agcccgacag tctcgcgaat    780

ctggtcacaa atttgaatgt ggctaaatgt gctaatgctc aaagtgctta tctggagtgc    840

atcaactatg ctttggtcca gctcaacctg gcaaacgtag ccatgtacat cgatgccgga    900

catgctggtt ggctgggctg gtcggctaat ctccagccag ccgctacgct ctttgccaat    960

gtatacaaga acgcgtcctc gcctgctgct gtgcgcggat tggccactaa cgttgctaac   1020

tacaacgcct ggacaattga cacctgtccg tcatacacgc agggcgactc aaactgcgac   1080

gaaaagcgat acgtcaatgc tatcgccccc ttgcttgcgt ctgcgggctt taatgctcat   1140

ttcatcaccg acacttcccg caatggtgtc cagccaacca agcaaaatgc ctggggtgac   1200

tggtgcaacc ttatcggtac tggcttcggt gttcgcccca caactgatac cggggatgct   1260

cttgaggacg cgtttgtttg ggtcaagccc ggtggagaat gcgatggtac atcggacacc   1320
```

```
acatcagcac gatatgatgc gcactgcgga tacagcgatg ccctgcagcc tgccccagaa   1380

gctggaacct ggttcgaagc ctatttcgag caattgcttg agaatgctaa ctcatctttc   1440

taa                                                                 1443


<210> SEQ ID NO 70
<211> LENGTH: 480
<212> TYPE: PRT
<213> ORGANISM: Penicillium sclerotiorum

<400> SEQUENCE: 70

Met Gln Arg Thr Ser Gly Leu Ala Leu Leu Leu Leu Ala Asn Ile Ala
1               5                   10                  15

Tyr Ala Gln Gln Ser Leu Tyr Gly Gln Cys Gly Gly Ser Gly Trp Thr
            20                  25                  30

Gly Ser Thr Val Cys Thr Ala Gln Ala Thr Cys Ser Ser Leu Asn Ala
        35                  40                  45

Trp Lys His Asn Ala Asp Pro Phe Thr Lys Ser Glu Asp Tyr Phe Gln
    50                  55                  60

Cys Val Ser Ala Thr Ala Thr Ala Ser Thr Thr Ser Lys Thr Ser Thr
65                  70                  75                  80

Ser Thr Ala Thr Lys Thr Thr Met Val Thr Thr Thr Thr Gly Thr Thr
                85                  90                  95

Thr Lys Ala Ser Thr Thr Thr Thr Gly Thr Thr Thr Lys Ala Ser Thr
            100                 105                 110

Thr Thr Thr Ala Ala Ala Ser Thr Asn Ser Gly Asn Pro Phe Ser Gly
        115                 120                 125

Tyr Gln Leu Tyr Ala Asn Pro Tyr Tyr Ala Ser Glu Val Ser Ala Ser
    130                 135                 140

Ala Ile Pro Ser Leu Ser Ser Ser Leu Ala Ala Lys Ala Ser Ala Val
145                 150                 155                 160

Ala Lys Val Pro Ser Phe Ala Trp Ile Asp Thr Ala Ala Lys Val Pro
                165                 170                 175

Thr Met Gly Thr Tyr Leu Ala Asp Ile Gln Ser Gln Asn Ala Ala Gly
            180                 185                 190

Ala Ser Pro Pro Ile Ala Gly Ile Phe Val Val Tyr Asp Leu Pro Asp
        195                 200                 205

Arg Asp Cys Ala Ala Leu Ala Ser Asn Gly Glu Tyr Ser Ile Ala Asn
    210                 215                 220

Asn Gly Val Ala Asn Tyr Lys Ala Tyr Ile Asp Ala Ile Arg Ala Gln
225                 230                 235                 240

Ile Val Lys Tyr Ser Asp Val Gln Thr Ile Leu Val Ile Glu Pro Asp
                245                 250                 255

Ser Leu Ala Asn Leu Val Thr Asn Leu Asn Val Ala Lys Cys Ala Asn
            260                 265                 270

Ala Gln Ser Ala Tyr Leu Glu Cys Ile Asn Tyr Ala Leu Val Gln Leu
        275                 280                 285

Asn Leu Ala Asn Val Ala Met Tyr Ile Asp Ala Gly His Ala Gly Trp
    290                 295                 300

Leu Gly Trp Ser Ala Asn Leu Gln Pro Ala Ala Thr Leu Phe Ala Asn
305                 310                 315                 320

Val Tyr Lys Asn Ala Ser Ser Pro Ala Ala Val Arg Gly Leu Ala Thr
                325                 330                 335

Asn Val Ala Asn Tyr Asn Ala Trp Thr Ile Asp Thr Cys Pro Ser Tyr
            340                 345                 350
```

Thr Gln Gly Asp Ser Asn Cys Asp Glu Lys Arg Tyr Val Asn Ala Ile
355 360 365

Ala Pro Leu Leu Ala Ser Ala Gly Phe Asn Ala His Phe Ile Thr Asp
370 375 380

Thr Ser Arg Asn Gly Val Gln Pro Thr Lys Gln Asn Ala Trp Gly Asp
385 390 395 400

Trp Cys Asn Leu Ile Gly Thr Gly Phe Gly Val Arg Pro Thr Thr Asp
405 410 415

Thr Gly Asp Ala Leu Glu Asp Ala Phe Val Trp Val Lys Pro Gly Gly
420 425 430

Glu Cys Asp Gly Thr Ser Asp Thr Thr Ser Ala Arg Tyr Asp Ala His
435 440 445

Cys Gly Tyr Ser Asp Ala Leu Gln Pro Ala Pro Glu Ala Gly Thr Trp
450 455 460

Phe Glu Ala Tyr Phe Glu Gln Leu Leu Glu Asn Ala Asn Ser Ser Phe
465 470 475 480

<210> SEQ ID NO 71
<211> LENGTH: 19
<212> TYPE: DNA
<213> ORGANISM: Artificial Sequence
<220> FEATURE:
<223> OTHER INFORMATION: ARTIFICIAL DNA PRIMER

<400> SEQUENCE: 71
tkccygaycg ygaytgygc 19

<210> SEQ ID NO 72
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 72
tcrccacckg gcttkaycca 20

<210> SEQ ID NO 73
<211> LENGTH: 18
<212> TYPE: DNA
<213> ORGANISM: Artificial Sequence
<220> FEATURE:
<223> OTHER INFORMATION: ARTIFICIAL DNA PRIMER

<400> SEQUENCE: 73
tgtaaaacga cggccagt 18

<210> SEQ ID NO 74
<211> LENGTH: 23
<212> TYPE: DNA
<213> ORGANISM: Artificial Sequence
<220> FEATURE:
<223> OTHER INFORMATION: ARTIFICIAL DNA PRIMER

<400> SEQUENCE: 74
agcggataac aatttcacac agg 23

<210> SEQ ID NO 75
<211> LENGTH: 21
<212> TYPE: DNA
<213> ORGANISM: Artificial Sequence
<220> FEATURE:

<223> OTHER INFORMATION: ARTIFICIAL DNA PRIMER

<400> SEQUENCE: 75
agagtctcgt ctcagtacat g 21

<210> SEQ ID NO 76
<211> LENGTH: 19
<212> TYPE: DNA
<213> ORGANISM: Artificial Sequence
<220> FEATURE:
<223> OTHER INFORMATION: ARTIFICIAL DNA PRIMER

<400> SEQUENCE: 76
cgaatacgtc accagccac 19

<210> SEQ ID NO 77
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 77
aattgctgag ctgtttcagc 20

<210> SEQ ID NO 78
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 78
tgactggtgc aacgtgatcg 20

<210> SEQ ID NO 79
<211> LENGTH: 37
<212> TYPE: DNA
<213> ORGANISM: Artificial Sequence
<220> FEATURE:
<223> OTHER INFORMATION: ARTIFICIAL DNA PRIMER

<400> SEQUENCE: 79
acacaactgg ggatcctcac catgcgaaat attcttg 37

<210> SEQ ID NO 80
<211> LENGTH: 37
<212> TYPE: DNA
<213> ORGANISM: Artificial Sequence
<220> FEATURE:
<223> OTHER INFORMATION: ARTIFICIAL DNA PRIMER

<400> SEQUENCE: 80
ccctctagat ctcgagctag aatgacggat tggcgtt 37

<210> SEQ ID NO 81
<211> LENGTH: 41
<212> TYPE: DNA
<213> ORGANISM: Artificial Sequence
<220> FEATURE:
<223> OTHER INFORMATION: ARTIFICIAL DNA PRIMER

<400> SEQUENCE: 81
caaccgcgga ctgcgcacca tgcgaaatat tcttgctctt g 41

<210> SEQ ID NO 82
<211> LENGTH: 41
<212> TYPE: DNA
<213> ORGANISM: Artificial Sequence
<220> FEATURE:
<223> OTHER INFORMATION: ARTIFICIAL DNA PRIMER

<400> SEQUENCE: 82
caggctttcg ccacggagct tactagaatg acggattggc g 41

<210> SEQ ID NO 83
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 83
cgtcgtacac gcagggcaac tccaactgcg atg 33

<210> SEQ ID NO 84
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 84
catcgcagtt ggagttgccc tgcgtgtacg acg 33

<210> SEQ ID NO 85
<211> LENGTH: 47
<212> TYPE: DNA
<213> ORGANISM: Artificial Sequence
<220> FEATURE:
<223> OTHER INFORMATION: ARTIFICIAL DNA PRIMER

<400> SEQUENCE: 85
cgcagagagc gcgtatttgg agctcatcaa ctatgcgata acgaagc 47

<210> SEQ ID NO 86
<211> LENGTH: 47
<212> TYPE: DNA
<213> ORGANISM: Artificial Sequence
<220> FEATURE:
<223> OTHER INFORMATION: ARTIFICIAL DNA PRIMER

<400> SEQUENCE: 86
gcttcgttat cgcatagttg atgagctcca aatacgcgct ctctgcg 47

<210> SEQ ID NO 87
<211> LENGTH: 31
<212> TYPE: DNA
<213> ORGANISM: Artificial Sequence
<220> FEATURE:
<223> OTHER INFORMATION: ARTIFICIAL DNA PRIMER

<400> SEQUENCE: 87
gccaaggtgc ctaccatggg cgagtatctg g 31

<210> SEQ ID NO 88
<211> LENGTH: 31
<212> TYPE: DNA
<213> ORGANISM: Artificial Sequence
<220> FEATURE:
<223> OTHER INFORMATION: ARTIFICIAL DNA PRIMER

<400> SEQUENCE: 88
ccagatactc gcccatggta ggcaccttgg c 31

<210> SEQ ID NO 89
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 89
gtccacacca tcctggtcat tggtacgtcg gc 32

<210> SEQ ID NO 90
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 90
gccgacgtac caatgaccag gatggtgtgg ac 32

<210> SEQ ID NO 91
<211> LENGTH: 29
<212> TYPE: DNA
<213> ORGANISM: Artificial Sequence
<220> FEATURE:
<223> OTHER INFORMATION: ARTIFICIAL DNA PRIMER

<400> SEQUENCE: 91
ctcatcgccg gctgccgtgc gcggtctgg 29

<210> SEQ ID NO 92
<211> LENGTH: 29
<212> TYPE: DNA
<213> ORGANISM: Artificial Sequence
<220> FEATURE:
<223> OTHER INFORMATION: ARTIFICIAL DNA PRIMER

<400> SEQUENCE: 92
ccagaccgcg cacggcagcc ggcgatgag 29

<210> SEQ ID NO 93
<211> LENGTH: 38
<212> TYPE: DNA
<213> ORGANISM: Artificial Sequence
<220> FEATURE:
<223> OTHER INFORMATION: ARTIFICIAL DNA PRIMER

<400> SEQUENCE: 93
ggactatgtg aatgccttcg gaccactggt cgcggcgc 38

<210> SEQ ID NO 94
<211> LENGTH: 38
<212> TYPE: DNA
<213> ORGANISM: Artificial Sequence
<220> FEATURE:
<223> OTHER INFORMATION: ARTIFICIAL DNA PRIMER

<400> SEQUENCE: 94
gcgccgcgac cagtggtccg aaggcattca catagtcc 38

<210> SEQ ID NO 95
<211> LENGTH: 39

<212> TYPE: DNA
<213> ORGANISM: Artificial Sequence
<220> FEATURE:
<223> OTHER INFORMATION: ARTIFICIAL DNA PRIMER

<400> SEQUENCE: 95
ggagtgcatc aactatgcgc taacgaagct caacctgcc 39

<210> SEQ ID NO 96
<211> LENGTH: 39
<212> TYPE: DNA
<213> ORGANISM: Artificial Sequence
<220> FEATURE:
<223> OTHER INFORMATION: ARTIFICIAL DNA PRIMER

<400> SEQUENCE: 96
ggcaggttga gcttcgttag cgcatagttg atgcactcc 39

<210> SEQ ID NO 97
<211> LENGTH: 43
<212> TYPE: DNA
<213> ORGANISM: Artificial Sequence
<220> FEATURE:
<223> OTHER INFORMATION: ARTIFICIAL DNA PRIMER

<400> SEQUENCE: 97
gtgcatcaac tatgcgataa agaagctcaa cctgcccaat gtg 43

<210> SEQ ID NO 98
<211> LENGTH: 43
<212> TYPE: DNA
<213> ORGANISM: Artificial Sequence
<220> FEATURE:
<223> OTHER INFORMATION: ARTIFICIAL DNA PRIMER

<400> SEQUENCE: 98
cacattgggc aggttgagct tctttatcgc atagttgatg cac 43

<210> SEQ ID NO 99
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 99
ctacaacgcc tggaccatca gtccgtgccc gtc 33

<210> SEQ ID NO 100
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 100
gacgggcacg gactgatggt ccaggcgttg tag 33

<210> SEQ ID NO 101
<211> LENGTH: 49
<212> TYPE: DNA
<213> ORGANISM: Artificial Sequence
<220> FEATURE:
<223> OTHER INFORMATION: ARTIFICIAL DNA PRIMER

<400> SEQUENCE: 101
ctaccagctc tatgccaatc cgcactattc gtctgaagtg tacactttg 49

<210> SEQ ID NO 102
<211> LENGTH: 49
<212> TYPE: DNA
<213> ORGANISM: Artificial Sequence
<220> FEATURE:
<223> OTHER INFORMATION: ARTIFICIAL DNA PRIMER

<400> SEQUENCE: 102
caaagtgtac acttcagacg aatagtgcgg attggcatag agctggtag 49

<210> SEQ ID NO 103
<211> LENGTH: 45
<212> TYPE: DNA
<213> ORGANISM: Artificial Sequence
<220> FEATURE:
<223> OTHER INFORMATION: ARTIFICIAL DNA PRIMER

<400> SEQUENCE: 103
cccacccagc aacaacaatg ggaggactgg tgcaacgtga tcggc 45

<210> SEQ ID NO 104
<211> LENGTH: 45
<212> TYPE: DNA
<213> ORGANISM: Artificial Sequence
<220> FEATURE:
<223> OTHER INFORMATION: ARTIFICIAL DNA PRIMER

<400> SEQUENCE: 104
gccgatcacg ttgcaccagt cctcccattg ttgttgctgg gtggg 45

<210> SEQ ID NO 105
<211> LENGTH: 46
<212> TYPE: DNA
<213> ORGANISM: Artificial Sequence
<220> FEATURE:
<223> OTHER INFORMATION: ARTIFICIAL DNA PRIMER

<400> SEQUENCE: 105
agcagccagc aatggagaat tctacattgc cgacaatgga gtcgcc 46

<210> SEQ ID NO 106
<211> LENGTH: 46
<212> TYPE: DNA
<213> ORGANISM: Artificial Sequence
<220> FEATURE:
<223> OTHER INFORMATION: ARTIFICIAL DNA PRIMER

<400> SEQUENCE: 106
ggcgactcca ttgtcggcaa tgtagaattc tccattgctg gctgct 46

<210> SEQ ID NO 107
<211> LENGTH: 31
<212> TYPE: DNA
<213> ORGANISM: Artificial Sequence
<220> FEATURE:
<223> OTHER INFORMATION: ARTIFICIAL DNA PRIMER

<400> SEQUENCE: 107
actggattta ccatgcgaaa tattcttgct c 31

<210> SEQ ID NO 108
<211> LENGTH: 33
<212> TYPE: DNA
<213> ORGANISM: Artificial Sequence

<220> FEATURE:
<223> OTHER INFORMATION: ARTIFICIAL DNA PRIMER

<400> SEQUENCE: 108
agtcacctct agttactaga atgacggatt ggc 33

<210> SEQ ID NO 109
<211> LENGTH: 1578
<212> TYPE: DNA
<213> ORGANISM: Trichoderma atroviride

<400> SEQUENCE: 109
atggcgggac gtgtatttgc tactttggct actttggccg cattggcagt ctctgcccct 60
gtcgtggaag aacgacaggc ttgcgctagc gtttggtgag atttgatgtc acgtttcaag 120
aggtatatat atactaatgc cggtgcaata ggggacaatg cggaggccaa ggttggtctg 180
gagcaacatg ctgtgcttct ggtagctcat gtgtcgtctc caacccctac tactcacaat 240
gtcttcctgg ctccggagga ggttcgagct cctctacact cgcttcctct acccgtgcgt 300
catccacgac agtgagatca agcgccacga ctcctccacc aagctcttct acaccaccac 360
ctcccgttgg atcaggaacc gctacttacc agggcaatcc attttctgga atccaaccct 420
gggcgaatag cttctacgcc caggaagtaa gcagctcggc gattcccagt ttgtccggag 480
ccatggctac tgctgcagcg gccgctgcca aagtaccttc gttcatgtgg ctgtaagtgc 540
ttcagagatg ttaatagtct tacaattgct gactagcgat gcagggatac tcttagcaag 600
accagcctgt tgagctcgac actgtcagat atccgtgccg caaacaaggc cggaggcaac 660
tacgctggtc agttcgttgt gtacgacttg cctgaccgtg actgcgccgc cgctgcctcc 720
aacggagagt actctatcgc ggacaacgga gtagccaact acaagaacta cattgacacc 780
attgtcggca ttctgaagac gtactccgat attcggacca tcttggtcat tggtaaagct 840
tttcttcctt gacgagagat tgaaattgag ctaacctgtc attgtataga gcctgactct 900
ctcgccaatc ttgttactaa cctcagcgtt gcgaagtgct caaacgctca ggctgcttac 960
ttggaatgta tcaactatgc tattacgcag ctgaaccttc ccaacgttgc catgtacctc 1020
gatgccggcc acgcaggatg gcttggctgg cccgccaatc agcagccagc ggctcaactg 1080
ttcgccagcg tgtacaagaa tgcatcgtca ccccgagcgg ttcgtggact ggcaaccaac 1140
gttgccaact acaatggatg gaacatcact tctgctccgt catacactca aggaaactcc 1200
gtttataacg agcagttgta cattcacgcc atttcacccc ttctcactca gcaaggctgg 1260
agcaacacct acttcattac cgaccagggt cgttccggca agcagcccac cggccagcag 1320
gcgtggggtg actggtgcaa cgttattggc actggattcg gcatccgccc ttcttccaac 1380
actggagact ctctgcttga tgcattcact tggattaagc caggtggtga atgtgacgga 1440
accagcaaca catctgcgac acgatacgat taccactgtg gcttgtcaga tgctctgcag 1500
cccgctcccg aggctggttc ttggttccag gcttactttg tgcagcttct taccaatgcc 1560
aacccttcat tttgtag 1578

<210> SEQ ID NO 110
<211> LENGTH: 470
<212> TYPE: PRT
<213> ORGANISM: Trichoderma atroviride

<400> SEQUENCE: 110

Met Ala Gly Arg Val Phe Ala Thr Leu Ala Thr Leu Ala Ala Leu Ala
1 5 10 15

```
Val Ser Ala Pro Val Val Glu Glu Arg Gln Ala Cys Ala Ser Val Trp
            20                  25                  30

Gly Gln Cys Gly Gly Gln Gly Trp Ser Gly Ala Thr Cys Cys Ala Ser
        35                  40                  45

Gly Ser Ser Cys Val Val Ser Asn Pro Tyr Tyr Ser Gln Cys Leu Pro
    50                  55                  60

Gly Ser Gly Gly Gly Ser Ser Ser Ser Thr Leu Ala Ser Ser Thr Arg
65                  70                  75                  80

Ala Ser Ser Thr Thr Val Arg Ser Ser Ala Thr Thr Pro Pro Pro Ser
                85                  90                  95

Ser Ser Thr Pro Pro Pro Pro Val Gly Ser Gly Thr Ala Thr Tyr Gln
            100                 105                 110

Gly Asn Pro Phe Ser Gly Ile Gln Pro Trp Ala Asn Ser Phe Tyr Ala
        115                 120                 125

Gln Glu Val Ser Ser Ser Ala Ile Pro Ser Leu Ser Gly Ala Met Ala
    130                 135                 140

Thr Ala Ala Ala Ala Ala Ala Lys Val Pro Ser Phe Met Trp Leu Asp
145                 150                 155                 160

Thr Leu Ser Lys Thr Ser Leu Leu Ser Ser Thr Leu Ser Asp Ile Arg
                165                 170                 175

Ala Ala Asn Lys Ala Gly Gly Asn Tyr Ala Gly Gln Phe Val Val Tyr
            180                 185                 190

Asp Leu Pro Asp Arg Asp Cys Ala Ala Ala Ala Ser Asn Gly Glu Tyr
        195                 200                 205

Ser Ile Ala Asp Asn Gly Val Ala Asn Tyr Lys Asn Tyr Ile Asp Thr
    210                 215                 220

Ile Val Gly Ile Leu Lys Thr Tyr Ser Asp Ile Arg Thr Ile Leu Val
225                 230                 235                 240

Ile Glu Pro Asp Ser Leu Ala Asn Leu Val Thr Asn Leu Ser Val Ala
                245                 250                 255

Lys Cys Ser Asn Ala Gln Ala Ala Tyr Leu Glu Cys Ile Asn Tyr Ala
            260                 265                 270

Ile Thr Gln Leu Asn Leu Pro Asn Val Ala Met Tyr Leu Asp Ala Gly
        275                 280                 285

His Ala Gly Trp Leu Gly Trp Pro Ala Asn Gln Gln Pro Ala Ala Gln
    290                 295                 300

Leu Phe Ala Ser Val Tyr Lys Asn Ala Ser Ser Pro Arg Ala Val Arg
305                 310                 315                 320

Gly Leu Ala Thr Asn Val Ala Asn Tyr Asn Gly Trp Asn Ile Thr Ser
                325                 330                 335

Ala Pro Ser Tyr Thr Gln Gly Asn Ser Val Tyr Asn Glu Gln Leu Tyr
            340                 345                 350

Ile His Ala Ile Ser Pro Leu Leu Thr Gln Gln Gly Trp Ser Asn Thr
        355                 360                 365

Tyr Phe Ile Thr Asp Gln Gly Arg Ser Gly Lys Gln Pro Thr Gly Gln
    370                 375                 380

Gln Ala Trp Gly Asp Trp Cys Asn Val Ile Gly Thr Gly Phe Gly Ile
385                 390                 395                 400

Arg Pro Ser Ser Asn Thr Gly Asp Ser Leu Leu Asp Ala Phe Thr Trp
                405                 410                 415

Ile Lys Pro Gly Gly Glu Cys Asp Gly Thr Ser Asn Thr Ser Ala Thr
            420                 425                 430
```

```
Arg Tyr Asp Tyr His Cys Gly Leu Ser Asp Ala Leu Gln Pro Ala Pro
        435                 440                 445

Glu Ala Gly Ser Trp Phe Gln Ala Tyr Phe Val Gln Leu Leu Thr Asn
    450                 455                 460

Ala Asn Pro Ser Phe Leu
465                 470


<210> SEQ ID NO 111
<211> LENGTH: 1382
<212> TYPE: DNA
<213> ORGANISM: Corynascus thermophilus

<400> SEQUENCE: 111

atgaagctcg cgcaatctgc cgccgtggcg ttcgccgcca cggctctcgc tgccccctcg     60

cgcaccactc ccgaaaagcc ccgtcaggcg gcgggttgcg cgtcggccgt gacactggac    120

gccagcacca acgtgtggaa gcagtacaag ctgcacccca acaacttcta ccgtgccgag    180

gtcgaggctg ccgccgacgc catctccgac tccacgctgg ccgagaaggc ccgcaaggtt    240

gccgacatcg gtaccttcct ctggctcgac accatcgaga acatcaaccg gctggagccc    300

gcgctcgagg acgtgccgtg cgagaacatc ctgggtctcg tcatctacga cctcccgggc    360

cgtgactgcg cggccaaggc ctccaacggc gagctcaagg tcggcgagat cgacaggtac    420

aagaccgagt acatcgacag taagtaaacc ctttgtggcc gttcccccct ccacctcacc    480

cactcctccg agacgtcgtc gggagagaga gagagagaga gagagactga cgcgctggct    540

cgcagagatc gcctcgatcc tcaaggccca ccccaacacc gccttcgccc tcgtcatcga    600

gcccgactcg ctccccaacc tggtcaccaa catcgatcag caggcgtgcc agcagagcgc    660

ctccggctac cgcgagggcg tcgcctatgc ccttcagcag ctcaacctcc ccaacgtcgt    720

catgtacatc gatgccggcc acggtggctg gctcggctgg gacgacaacc tcaggcccgg    780

cgcccaggag ctcgccaacg tctacaaggc cgcaggctcg ccctcgcaag tccgtggtat    840

ctcgaccaac gtggctggct ggaactcctg gtaagacact ccattctctc cgcccctctt    900

tttttttttc ccgtggaatg caggaagctg acgtttcctt tttttttctc cactgcaaca    960

gggaccaaga gcccggtgag ttcgcgaacg acccggatgc tcagtggaat aagtgccaga   1020

acgagaagat ctacgtcaac accttcggcg ccgagctccg gaatgccggc atgccctacc   1080

acgccatcat cgacaccggc cgcaacggcg tcaccggtct ccgtcaggag tggggcaact   1140

ggtgcaacgt caacggtgcc ggcttcggtc tgcgcccgag tgccgacacc ggcgacgact   1200

tcgccgacgc cttcgtgtgg gtcaagcccg gcggcgagtc cgacggcacc agcgactcgt   1260

cggccacgcg ctacgacgag ttctgcggca agcccgacgc cttcaagccc agccctgagg   1320

ccggtacctg gcaccaggaa tacttcgaga tgctcgtcaa gaacgccaac cctccctct    1380

aa                                                                   1382


<210> SEQ ID NO 112
<211> LENGTH: 394
<212> TYPE: PRT
<213> ORGANISM: Corynascus thermophilus

<400> SEQUENCE: 112

Met Lys Leu Ala Gln Ser Ala Ala Val Ala Phe Ala Ala Thr Ala Leu
1               5                   10                  15

Ala Ala Pro Ser Arg Thr Thr Pro Glu Lys Pro Arg Gln Ala Ala Gly
            20                  25                  30
```

```
Cys Ala Ser Ala Val Thr Leu Asp Ala Ser Thr Asn Val Trp Lys Gln
        35                  40                  45

Tyr Lys Leu His Pro Asn Asn Phe Tyr Arg Ala Glu Val Glu Ala Ala
    50                  55                  60

Ala Asp Ala Ile Ser Asp Ser Thr Leu Ala Glu Lys Ala Arg Lys Val
65                  70                  75                  80

Ala Asp Ile Gly Thr Phe Leu Trp Leu Asp Thr Ile Glu Asn Ile Asn
                85                  90                  95

Arg Leu Glu Pro Ala Leu Glu Asp Val Pro Cys Glu Asn Ile Leu Gly
            100                 105                 110

Leu Val Ile Tyr Asp Leu Pro Gly Arg Asp Cys Ala Ala Lys Ala Ser
        115                 120                 125

Asn Gly Glu Leu Lys Val Gly Glu Ile Asp Arg Tyr Lys Thr Glu Tyr
    130                 135                 140

Ile Asp Lys Ile Ala Ser Ile Leu Lys Ala His Pro Asn Thr Ala Phe
145                 150                 155                 160

Ala Leu Val Ile Glu Pro Asp Ser Leu Pro Asn Leu Val Thr Asn Ile
                165                 170                 175

Asp Gln Gln Ala Cys Gln Gln Ser Ala Ser Gly Tyr Arg Glu Gly Val
            180                 185                 190

Ala Tyr Ala Leu Gln Gln Leu Asn Leu Pro Asn Val Val Met Tyr Ile
        195                 200                 205

Asp Ala Gly His Gly Gly Trp Leu Gly Trp Asp Asp Asn Leu Arg Pro
    210                 215                 220

Gly Ala Gln Glu Leu Ala Asn Val Tyr Lys Ala Ala Gly Ser Pro Ser
225                 230                 235                 240

Gln Val Arg Gly Ile Ser Thr Asn Val Ala Gly Trp Asn Ser Trp Asp
                245                 250                 255

Gln Glu Pro Gly Glu Phe Ala Asn Asp Pro Asp Ala Gln Trp Asn Lys
            260                 265                 270

Cys Gln Asn Glu Lys Ile Tyr Val Asn Thr Phe Gly Ala Glu Leu Arg
        275                 280                 285

Asn Ala Gly Met Pro Tyr His Ala Ile Ile Asp Thr Gly Arg Asn Gly
    290                 295                 300

Val Thr Gly Leu Arg Gln Glu Trp Gly Asn Trp Cys Asn Val Asn Gly
305                 310                 315                 320

Ala Gly Phe Gly Leu Arg Pro Ser Ala Asp Thr Gly Asp Asp Phe Ala
                325                 330                 335

Asp Ala Phe Val Trp Val Lys Pro Gly Gly Glu Ser Asp Gly Thr Ser
            340                 345                 350

Asp Ser Ser Ala Thr Arg Tyr Asp Glu Phe Cys Gly Lys Pro Asp Ala
        355                 360                 365

Phe Lys Pro Ser Pro Glu Ala Gly Thr Trp His Gln Glu Tyr Phe Glu
    370                 375                 380

Met Leu Val Lys Asn Ala Asn Pro Ser Leu
385                 390
```

<210> SEQ ID NO 113
<211> LENGTH: 1662
<212> TYPE: DNA
<213> ORGANISM: Corynascus thermophilus

<400> SEQUENCE: 113

```
atggccaaga agctcttcat caacgccgcg cttgcggccg tcgtgctggc tgctcccgtt      60
```

```
gtcgaggagc gccagaactg cgccggtctt tggtaagaga gaaagcctcg cgctgagcat    120

cccagaactg cctggtccaa gaacgggaca ctgaccgtgg aaattgacga acctaggggc    180

caatgcggcg gtaacgggtg gcagggcccg acatgctgcg tcgcgggctc gacctgcgtc    240

gcacagaacg agtggtactc tcagtgtttg cccggcggcg cctcctcgtc gtcgtcgacc    300

acctcgcagg gcatccccag caccaccgtc tcctccacct ccactacccc cccgccaatc    360

tcgacttcct ggagcagcat ccccggcggt gcgacctcga cggcgagcta cgccggtaac    420

cccttctcgg gcgtccggct ctgggccaac gactattacc ggtccgaggt ccacaacatc    480

gcgattccca gcctgaccgg tagtctggtc gccaaggctt ccgccgtcgc cgaagtcccg    540

agcttccagt ggctcgaccg caacgttacc gtcgacaccc tgatggtcga cactctgtca    600

aagatccggg ctgccaacga ggccggtgcc aaccctcctt atgctggtga gtcaacgacg    660

gaatgtcaac gcgaactcgt catatccacc ttcctctatc gcgtgacagg gaactctgct    720

gattacattg cctaacccgg gaaaccaaaa aataaacagc ccaacttgtc gtctacgacc    780

tccccgaccg tgactgtgcc gcggccgcgt ccaatggcga gtggtcgatt gcgaacggcg    840

gcgcggccaa ctacaggggc tacatcgaca ggatccgcca gctcctcatc caattctcgg    900

acatccggac catcctggtc atcgagcccg actcgatggc caacatggtg acaaacctga    960

acgttgccaa atgcagcaac gcccgctcga cgtaccatga gttgaccgtg tacgccctca   1020

agcaactcaa cctgccccat gtcgccatgt atctcgacgc cggccacgcc ggctggctcg   1080

gttggcccgc caacgtccaa ccggccgccg acctgtttgc cggcctctac aaagacgcgg   1140

gtagcccggc tgccgtccgc ggccttgcca caaatgttgc caactacaac gcctggagcc   1200

tctcctcggc cccgtcgtac acgtcgccga accccaacta cgacgagaag cactacatcg   1260

aggccttcag cccgctcctg aacgcggccg gcttcccggc acgcttcatc gtcgacaccg   1320

gccgcaacgg caagcaacct accggtatgt tcacacaatg tttctctctc tcacgcacaa   1380

acgactaaca attctacagg ccaactggag tggggcgact ggtgcaacgt gagggacacc   1440

ggctttggcg tccgcccgac ggccaacaca ggccacgagc tggtcgatgc cttcgtctgg   1500

atcaagcccg gcggcgagtc ggacggcacg agcgacacca gcgccgctcg ctacgactac   1560

cactgcggcc tgagcgatgc cctgaagcct gcccccgagg ccggtcagtg gttccaggcc   1620

tacttcgagc agctgctcat caacgccaac ccgccgtttt aa                      1662
```

<210> SEQ ID NO 114
<211> LENGTH: 469
<212> TYPE: PRT
<213> ORGANISM: Corynascus thermophilus

<400> SEQUENCE: 114

```
Met Ala Lys Lys Leu Phe Ile Asn Ala Ala Leu Ala Ala Val Val Leu
1               5                   10                  15

Ala Ala Pro Val Val Glu Glu Arg Gln Asn Cys Ala Gly Leu Trp Gly
            20                  25                  30

Gln Cys Gly Gly Asn Gly Trp Gln Gly Pro Thr Cys Cys Val Ala Gly
        35                  40                  45

Ser Thr Cys Val Ala Gln Asn Glu Trp Tyr Ser Gln Cys Leu Pro Gly
    50                  55                  60

Gly Ala Ser Ser Ser Ser Ser Thr Thr Ser Gln Gly Ile Pro Ser Thr
65                  70                  75                  80

Thr Val Ser Ser Thr Ser Thr Thr Pro Pro Pro Ile Ser Thr Ser Trp
                85                  90                  95
```

```
Ser Ser Ile Pro Gly Gly Ala Thr Ser Thr Ala Ser Tyr Ala Gly Asn
            100                 105                 110

Pro Phe Ser Gly Val Arg Leu Trp Ala Asn Asp Tyr Tyr Arg Ser Glu
        115                 120                 125

Val His Asn Ile Ala Ile Pro Ser Leu Thr Gly Ser Leu Val Ala Lys
    130                 135                 140

Ala Ser Ala Val Ala Glu Val Pro Ser Phe Gln Trp Leu Asp Arg Asn
145                 150                 155                 160

Val Thr Val Asp Thr Leu Met Val Asp Thr Leu Ser Lys Ile Arg Ala
                165                 170                 175

Ala Asn Glu Ala Gly Ala Asn Pro Pro Tyr Ala Ala Gln Leu Val Val
            180                 185                 190

Tyr Asp Leu Pro Asp Arg Asp Cys Ala Ala Ala Ala Ser Asn Gly Glu
        195                 200                 205

Trp Ser Ile Ala Asn Gly Gly Ala Ala Asn Tyr Arg Gly Tyr Ile Asp
    210                 215                 220

Arg Ile Arg Gln Leu Leu Ile Gln Phe Ser Asp Ile Arg Thr Ile Leu
225                 230                 235                 240

Val Ile Glu Pro Asp Ser Met Ala Asn Met Val Thr Asn Leu Asn Val
                245                 250                 255

Ala Lys Cys Ser Asn Ala Arg Ser Thr Tyr His Glu Leu Thr Val Tyr
            260                 265                 270

Ala Leu Lys Gln Leu Asn Leu Pro His Val Ala Met Tyr Leu Asp Ala
        275                 280                 285

Gly His Ala Gly Trp Leu Gly Trp Pro Ala Asn Val Gln Pro Ala Ala
    290                 295                 300

Asp Leu Phe Ala Gly Leu Tyr Lys Asp Ala Gly Ser Pro Ala Ala Val
305                 310                 315                 320

Arg Gly Leu Ala Thr Asn Val Ala Asn Tyr Asn Ala Trp Ser Leu Ser
                325                 330                 335

Ser Ala Pro Ser Tyr Thr Ser Pro Asn Pro Asn Tyr Asp Glu Lys His
            340                 345                 350

Tyr Ile Glu Ala Phe Ser Pro Leu Leu Asn Ala Ala Gly Phe Pro Ala
        355                 360                 365

Arg Phe Ile Val Asp Thr Gly Arg Asn Gly Lys Gln Pro Thr Gly Gln
    370                 375                 380

Leu Glu Trp Gly Asp Trp Cys Asn Val Arg Asp Thr Gly Phe Gly Val
385                 390                 395                 400

Arg Pro Thr Ala Asn Thr Gly His Glu Leu Val Asp Ala Phe Val Trp
                405                 410                 415

Ile Lys Pro Gly Gly Glu Ser Asp Gly Thr Ser Asp Thr Ser Ala Ala
            420                 425                 430

Arg Tyr Asp Tyr His Cys Gly Leu Ser Asp Ala Leu Lys Pro Ala Pro
        435                 440                 445

Glu Ala Gly Gln Trp Phe Gln Ala Tyr Phe Glu Gln Leu Leu Ile Asn
    450                 455                 460

Ala Asn Pro Pro Phe
465
```

<210> SEQ ID NO 115
<211> LENGTH: 1898
<212> TYPE: DNA
<213> ORGANISM: Talaromyces leycettanus

<400> SEQUENCE: 115

```
atgcggtctc tcctggctct tgcccctacc ctgctcgcgc ctgttgttca ggctcagcaa     60
accatgtggg gtcaatgtaa gttcttttca ctgcttacca tgtataatct ttgatatcaa    120
gcatcatatc tgactcacgt tttaggcggt ggtcagggct ggaccggacc taccatctgt    180
gtagcaggcg cgacatgcag cacacagaac ccttgtaagt cgggccttca tcaaaacttc    240
aacatcacca cctcgatgga gcaggagttg acctgatctt tacccttagg gtatgcgcag    300
tgcaccccag cacctaccgc gccgacgacc ttgcaaacaa caactacgac gagctcgaaa    360
tcgtccacga ccacgagctc gaagtcgtcc acgaccacag gtggaagtgg cggtggaact    420
acgacctcaa cgtcagccac catcaccgcg gctccatctg gtaacccata ctccggatac    480
cagctctatg tgaaccagga atactcgtcc gaggtgtacg cgtctgctat tccttccctt    540
accggcactc tggtcgcgaa ggcaagcgcc gcggcagagg tgccatcttt cctgtggctg    600
taagtttttt tgaccttgaa tgaacgccct gtcctctacg agtggccgca ggagctaatt    660
gagatgccaa tgaacaggga cactgcctcc aaggtgccac tgatgggcac ttacttgcag    720
gatatccagg cgaagaacgc tgctggcgcc aacccccat atgccggtca attcgtggtt     780
tacgacttgc cggatcgtga ttgcgctgca ttggccagca atggagagta ctccattgct    840
aacaatggtg ttgccaacta caaggcttac atcgactcca tccgcgcgct tcttgttcaa    900
tactcgaacg tccatgtcat ccttgtgatc ggtgagctat tgcagtctcg ctttaaagca    960
tttgactaga tcaatgtcgc taatggtacc taccgcacag agcccgacag cttggccaac   1020
cttgtcacca acctgaatgt tcagaagtgt gctaatgctc agagtgctta cctggagtgc   1080
atcaactatg ccctcactca gttgaacctc aagaacgttg ctatgtacat cgatgctggt   1140
gcgtgaacct tccctagtca gcccaaaata actgaaataa agagacggag tgtactgatt   1200
gtcatgcagg tcatgctgga tggctcggct ggcccgccaa ccttagcccg gccgctcaac   1260
tctttgcttc cgtataccag aatgcaagct ccccagctgc cgttcgcggc ctggcaacca   1320
acgtggccaa ctataatgcc tggtcgatcg ccacttgccc atcttacacc caaggcgacc   1380
ccaactgcga cgagcagaaa tacatcaacg ctctggctcc attgcttcag caacagggat   1440
ggtcatcagt tcactttatc accgataccg gtaagtctgc ctgtcctgcc aaccatgcgt   1500
tcaagagcgt tgcaatccta accatgctgg tatcttccag gccgtaacgg tgtccagcct   1560
accaagcaga atgcctgggg tgactggtgc aacgttatcg gaaccggctt cggtgtccgt   1620
cccaccacca acactggcga tccattggag gatgctttcg tctgggtcaa gcctggtggt   1680
gagagtgatg gtacttccaa ctccacttcg cctcgctacg acgcccactg cggttacagt   1740
gatgctcttc agcctgctcc tgaggctggt acctggttcg aggtaagctt ctgcatactg   1800
agatcgagaa tcctgaaagg gttaacctgc taatgcttcg gtgtttgata taggcttact   1860
ttgagcaact ccttaccaac gccaacccct ctttctaa                           1898
```

<210> SEQ ID NO 116
<211> LENGTH: 464
<212> TYPE: PRT
<213> ORGANISM: Talaromyces leycettanus

<400> SEQUENCE: 116

```
Met Arg Ser Leu Leu Ala Leu Ala Pro Thr Leu Leu Ala Pro Val Val
1               5                   10                  15

Gln Ala Gln Gln Thr Met Trp Gly Gln Cys Gly Gly Gln Gly Trp Thr
            20                  25                  30

Gly Pro Thr Ile Cys Val Ala Gly Ala Thr Cys Ser Thr Gln Asn Pro
        35                  40                  45

Trp Tyr Ala Gln Cys Thr Pro Ala Pro Thr Ala Pro Thr Thr Leu Gln
    50                  55                  60

Thr Thr Thr Thr Thr Ser Ser Lys Ser Ser Thr Thr Thr Ser Ser Lys
65                  70                  75                  80

Ser Ser Thr Thr Thr Gly Gly Ser Gly Gly Gly Thr Thr Thr Ser Thr
                85                  90                  95

Ser Ala Thr Ile Thr Ala Ala Pro Ser Gly Asn Pro Tyr Ser Gly Tyr
            100                 105                 110

Gln Leu Tyr Val Asn Gln Glu Tyr Ser Ser Glu Val Tyr Ala Ser Ala
        115                 120                 125

Ile Pro Ser Leu Thr Gly Thr Leu Val Ala Lys Ala Ser Ala Ala Ala
    130                 135                 140

Glu Val Pro Ser Phe Leu Trp Leu Asp Thr Ala Ser Lys Val Pro Leu
145                 150                 155                 160

Met Gly Thr Tyr Leu Gln Asp Ile Gln Ala Lys Asn Ala Ala Gly Ala
                165                 170                 175

Asn Pro Pro Tyr Ala Gly Gln Phe Val Val Tyr Asp Leu Pro Asp Arg
            180                 185                 190

Asp Cys Ala Ala Leu Ala Ser Asn Gly Glu Tyr Ser Ile Ala Asn Asn
        195                 200                 205

Gly Val Ala Asn Tyr Lys Ala Tyr Ile Asp Ser Ile Arg Ala Leu Leu
    210                 215                 220

Val Gln Tyr Ser Asn Val His Val Ile Leu Val Ile Glu Pro Asp Ser
225                 230                 235                 240

Leu Ala Asn Leu Val Thr Asn Leu Asn Val Gln Lys Cys Ala Asn Ala
                245                 250                 255

Gln Ser Ala Tyr Leu Glu Cys Ile Asn Tyr Ala Leu Thr Gln Leu Asn
            260                 265                 270

Leu Lys Asn Val Ala Met Tyr Ile Asp Ala Gly His Ala Gly Trp Leu
        275                 280                 285

Gly Trp Pro Ala Asn Leu Ser Pro Ala Ala Gln Leu Phe Ala Ser Val
    290                 295                 300

Tyr Gln Asn Ala Ser Ser Pro Ala Ala Val Arg Gly Leu Ala Thr Asn
305                 310                 315                 320

Val Ala Asn Tyr Asn Ala Trp Ser Ile Ala Thr Cys Pro Ser Tyr Thr
                325                 330                 335

Gln Gly Asp Pro Asn Cys Asp Glu Gln Lys Tyr Ile Asn Ala Leu Ala
            340                 345                 350

Pro Leu Leu Gln Gln Gln Gly Trp Ser Ser Val His Phe Ile Thr Asp
        355                 360                 365

Thr Gly Arg Asn Gly Val Gln Pro Thr Lys Gln Asn Ala Trp Gly Asp
    370                 375                 380

Trp Cys Asn Val Ile Gly Thr Gly Phe Gly Val Arg Pro Thr Thr Asn
385                 390                 395                 400

Thr Gly Asp Pro Leu Glu Asp Ala Phe Val Trp Val Lys Pro Gly Gly
```

-continued

```
            405                 410                 415

Glu Ser Asp Gly Thr Ser Asn Ser Thr Ser Pro Arg Tyr Asp Ala His
        420                 425                 430

Cys Gly Tyr Ser Asp Ala Leu Gln Pro Ala Pro Glu Ala Gly Thr Trp
    435                 440                 445

Phe Glu Ala Tyr Phe Glu Gln Leu Leu Thr Asn Ala Asn Pro Ser Phe
    450                 455                 460
```